US006121029A

United States Patent [19]
Schupp et al.

[11] Patent Number: 6,121,029
[45] Date of Patent: Sep. 19, 2000

[54] GENES FOR THE BIOSYNTHESIS OF EPOTHILONES

[75] Inventors: Thomas Schupp, Mohlin, Switzerland; James Madison Ligon, Apex, N.C.; Istvan Molnar, Durham, N.C.; Ross Zirkle, Raleigh, N.C.; Devon Dawn Cyr, Fuquay-Varina, N.C.; Jörn Görlach, Durham, N.C.

[73] Assignee: Novartis AG, Basel, Switzerland

[21] Appl. No.: 09/335,409

[22] Filed: Jun. 17, 1999

Related U.S. Application Data

[60] Provisional application No. 60/155,183, Jun. 18, 1998, provisional application No. 60/101,631, Sep. 24, 1998, and provisional application No. 60/118,906, Feb. 5, 1999.

[51] Int. Cl.$^7$ ............... C12N 9/00; C12N 1/20; C07H 21/04
[52] U.S. Cl. ............ 435/183; 435/232; 435/193; 435/189; 435/252.3; 435/252.35; 435/320.1; 530/300; 536/23.2; 536/23.7; 536/23.1
[58] Field of Search ............... 536/23.2, 23.7, 536/23.1; 435/183, 252.3, 232, 193, 189, 252.35, 320.1; 530/300

[56] References Cited

U.S. PATENT DOCUMENTS

| | | | |
|---|---|---|---|
| 5,496,804 | 3/1996 | Reed et al. | 514/12 |
| 5,565,478 | 10/1996 | Kohn et al. | 514/359 |
| 5,641,803 | 6/1997 | Caretta et al. | 514/449 |
| 5,672,491 | 9/1997 | Khosla et al. | 435/148 |
| 5,686,295 | 11/1997 | Jaoua et al. | 435/252.3 |
| 5,712,146 | 1/1998 | Khosla et al. | 435/252.35 |
| 5,716,849 | 2/1998 | Ligon et al. | 435/419 |
| 5,876,991 | 3/1999 | DeHoff et al. | 435/183 |

FOREIGN PATENT DOCUMENTS

| | | |
|---|---|---|
| 93/10121 | 5/1993 | WIPO . |
| 98/07868 | 2/1998 | WIPO . |
| 98/25929 | 6/1998 | WIPO . |

OTHER PUBLICATIONS

Molnar et al. "The biosynthetic gene cluster for the microtubule–stabilizing agent epothilones A and B . . . " Chem. Biol. 7, 97–109, Jan. 5, 2000.

Tang et al. "Cloning heterologous expression of epothilone gene cluster" Science 287, 640–642, Jan. 28, 2000.

Bollag, et al., Epothilones, A New Class of Micro–Tubule––stabilizing Agents with a Taxol–like Mechanism of Action, Cancer Research, 55, 2325–2333, Jun. 1995.

Gerth et al., Epothilons A and B: Antifungal and Cytotoxic Compounds from *Sorangium cellulosum* (Myxobacteria), The Journal of Antibiotics, 49:6, 560–563, Jun. 1996.

Nicolaou, et al., Chemical Biology of Epothilones, Angew. Chem. Int. Ed., 1998, 37, 2014–2045.

Schupp, et al., Cloning and sequence analysis of the putative rifamycin polyketide synthase gene cluster from *Amycolatopsis mediterranei*, FEMS Microbiology Letters, 159, 1998, 201–207.

Kealey et al., PNAS USA 95:505–509 (1998).

Caffrey et al., Eur. J. Biochem. 195:823–830 (1991).

Marsden et al., Science 279:199–202 (1998).

Kao et al., Science 265:509–512 (1994).

McDaniel et al., Science 262:1546–1550 (1993).

Beyer et al., Biochimica et Biophysica Acta 1445(2):185–195 (1999).

Molnar et al., Gene 169(1):1–7 (1996).

Aparicio et al., Gene 169(1)9–16 (1996).

Swan et al., Mol. Gen. Genet. 242(3):358–362 (1994).

Kakavas et al., J. Bacteriol. 179(23):7515–7522 (1997).

Schwecke et al., PNAS USA 92(17):7839–7843 (1995).

*Primary Examiner*—Nashaat T. Nashed
*Attorney, Agent, or Firm*—J. Timothy Meigs

[57] ABSTRACT

Nucleic acid molecules are isolated from *Sorangium cellulosum* that encode polypeptides necessary for the biosynthesis of epothilone. Disclosed are methods for the production of epothilone in recombinant hosts transformed with the genes of the invention. In this manner, epothilone can be produced in quantities large enough to enable their purification and use in pharmaceutical formulations such as those for the treatment of cancer.

115 Claims, No Drawings

GENES FOR THE BIOSYNTHESIS OF EPOTHILONES

CROSS REFERENCE TO RELATED APPLICATIONS

This application claims the benefit of U.S. Provisional Application No. 60/155,183, filed Jun. 18, 1998 [Schupp et al.; Attorney Docket No. CGC2012/PROV]; U.S. Provisional Application No. 60/101,631, filed Sep. 24, 1998; and U.S. Provisional Application No. 60/118,906, filed Feb. 5, 1999. The full disclosure of each of these provisional applications is incorporated herein by reference.

FIELD OF THE INVENTION

The present invention relates generally to polyketides and genes for their synthesis. In particular, the present invention relates to the isolation and characterization of novel polyketide synthase and nonribosomal peptide synthetase genes from *Sorangium cellulosum* that are necessary for the biosynthesis of epothilones A and B.

BACKGROUND OF THE INVENTION

Polyketides are compounds synthesized from two-carbon building blocks, the β-carbon of which always carries a keto group, thus the name polyketide. These compounds include many important antibiotics, immunosuppressants, cancer chemotherapeutic agents, and other compounds possessing a broad range of biological properties. The tremendous structural diversity derives from the different lengths of the polyketide chain, the different side-chains introduced (either as part of the two-carbon building blocks or after the polyketide backbone is formed), and the stereochemistry of such groups. The keto groups may also be reduced to hydroxyls, enoyls, or removed altogether. Each round of two-carbon addition is carried out by a complex of enzymes called the polyketide synthase (PKS) in a manner similar to fatty acid biosynthesis.

The biosynthetic genes for an increasing number of polyketides have been isolated and sequenced. For example, see U.S. Pat. Nos. 5,639,949, 5,693,774, and 5,716,849, all of which are incorporated herein by reference, which describe genes for the biosynthesis of soraphen. See also, Schupp et al., *FEMS Microbiology Letters* 159: 201–207 (1998) and WO 98/07868, which describe genes for the biosynthesis of rifamycin, and U.S. Pat. No. 5,876,991, which describes genes for the biosynthesis of tylactone, all of which are incorporated herein by reference. The encoded proteins generally fall into two types: type I and type II. Type I proteins are polyfunctional, with several catalytic domains carrying out different enzymatic steps covalently linked together (e.g. PKS for erythromycin, soraphen, rifamycin, and avermectin (MacNeil et al., in Industrial Microorganisms: Basic and Applied Molecular Genetics, (ed.: Baltz et al.), American Society for Microbiology, Washington D.C. pp. 245–256 (1993)); whereas type II proteins are monofunctional (Hutchinson et al., in Industrial Microorganisms: Basic and Applied Molecular Genetics, (ed.: Baltz et al.), American Society for Microbiology, Washington D.C. pp. 203–216 (1993)).

For the simpler polyketides such as actinorhodin (produced by Streptomyces coelicolor), the several rounds of two-carbon additions are carried out iteratively on PKS enzymes encoded by one set of PKS genes. In contrast, synthesis of the more complicated compounds such as erythromycin and soraphen involves PKS enzymes that are organized into modules, whereby each module carries out one round of two-carbon addition (for review, see Hopwood et al., in Industrial Microorganisms: Basic and Applied Molecular Genetics, (ed.: Baltz et al.), American Society for Microbiology, Washington D.C., pp. 267–275 (1993)).

Complex polyketides and secondary metabolites in general may contain substructures that are derived from amino acids instead of simple carboxylic acids. Incorporations of these building blocks are accomplished by non-ribosomal polypeptide synthetases (NRPSs). NRPSs are multienzymes that are organized in modules. Each module is responsible for the addition (and the additional processing, if required) of one amino acid building block. NRPSs activate amino acids by forming aminoacyl-adenylates, and capture the activated amino acids on thiol groups of phophopantheteinyl prosthetic groups on peptidyl carrier protein domains. Further, NRPSs modify the amino acids by epimerization, N-methylation, or cyclization if necessary, and catalyse the formation of peptide bonds between the enzyme-bound amino acids. NRPSs are responsible for the biosynthesis of peptide secondary metabolites like cyclosporin, could provide polyketide chain terminator units as in rapamycin, or form mixed systems with PKSs as in yersiniabactin biosynthesis.

Epothilones A and B are 16-membered macrocyclic polyketides with an acylcysteine-derived starter unit that are produced by the bacterium *Sorangium cellulosum* strain So ce90 (Gerth et al., *J. Antibiotics* 49: 560–563 (1996), incorporated herein by reference). The structure of epothilone A and B wherein R signifies hydrogen (epothilone A) or methyl (epothilone B) is:

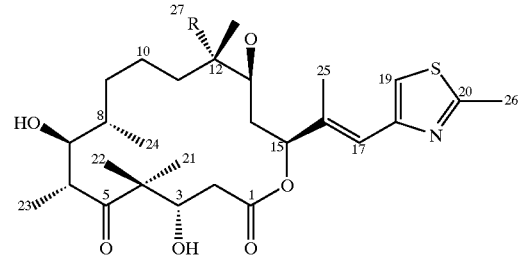

The epothilones have a narrow antifungal spectrum and especially show a high cytotoxicity in animal cell cultures (see, Höfle et al., Patent DE 4,138,042 (1993), incorporated herein by reference). Of significant importance, epothilones mimic the biological effects of taxol, both in vivo and in cultured cells (Bollag et al., *Cancer Research* 55: 2325–2333 (1995), incorporated herein by reference). Taxol and taxotere, which stabilize cellular microtubules, are cancer chemotherapeutic agents with significant activity against various human solid tumors (Rowinsky et al., *J. Nat. Cancer Inst.* 83: 1778–1781 (1991)). Competition studies have revealed that epothilones act as competitive inhibitors of taxol binding to microtubules, consistent with the interpretation that they share the same microtubule-binding site and possess a similar microtubule affinity as taxol. However, epothilones enjoy a significant advantage over taxol in that epothilones exhibit a much lower drop in potency compared to taxol against a multiple drug-resistant cell line (Bollag et al. (1995)). Furthermore, epothilones are considerably less efficiently exported from the cells by P-glycoprotein than is taxol (Gerth et al. (1996)). In addition, several epothilone analogs have been synthesized that have a superior cytotoxic activity as compared to epothilone A or epothilone B as demonstrated by their enhanced ability to induce the polymerization and stabilization of microtubules (WO 98/25929, incorporated herein by reference).

Despite the promise shown by the epothilones as anticancer agents, problems pertaining to the production of these compounds presently limit their commercial potential. The compounds are too complex for industrial-scale chemical synthesis and so must be produced by fermentation. Techniques for the genetic manipulation of myxobacteria such as *Sorangium cellulosum* are described in U.S. Pat. No. 5,686, 295, incorporated herein by reference. However, *Sorangium cellulosum* is notoriously difficult to ferment and production levels of epothilones are therefore low. Recombinant production of epothilones in heterologous hosts that are more amenable to fermentation could solve current production problems. However, the genes that encode the polypeptides responsible for epothilone biosynthesis have heretofore not been isolated. Furthermore, the strain that produces epothilones, i.e. So ce90, also produces at least one additional polyketide, spirangien, which would be expected to greatly complicate the isolation of the genes particularly responsible for epothilone biosynthesis.

Therefore, in view of the foregoing, one object of the present invention is to isolate the genes that are involved in the synthesis of epothilones, particularly the genes that are involved in the synthesis of epothilones A and B in myxobacteria of the Sorangium/Polyangium group, i.e., *Sorangium cellulosum* strain So ce90. A further object of the invention is to provide a method for the recombinant production of epothilones for application in anticancer formulations.

SUMMARY OF THE INVENTION

In furtherance of the aforementioned and other objects, the present invention unexpectedly overcomes the difficulties set forth above to provide for the first time a nucleic acid molecule comprising a nucleotide sequence that encodes at least one polypeptide involved in the biosynthesis of epothilone. In a preferred embodiment, the nucleotide sequence is isolated from a species belonging to Myxobacteria, most preferably *Sorangium cellulosum*.

In another preferred embodiment, the present invention provides an isolated nucleic acid molecule comprising a nucleotide sequence that encodes at least one polypeptide involved in the biosynthesis of an epothilone, wherein said polypeptide comprises an amino acid sequence substantially similar to an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, amino acids 1314–1385 of SEQ ID NO:2, SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, amino acids 1344–1351 of SEQ ID NO:3, SEQ ID NO:4, amino acids 7–432 of SEQ ID NO:4, amino acids 539–859 of SEQ ID NO:4, amino acids 869–1037 of SEQ ID NO:4, amino acids 1439–1684 of SEQ ID NO:4, amino acids 1722–1792 of SEQ ID NO:4, SEQ ID NO:5, amino acids 39–457 of SEQ ID NO:5, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, amino acids 7140–7211 of SEQ ID NO:5, SEQ ID NO:6, amino acids 35–454 of SEQ ID NO:6, amino acids 561–881 of SEQ ID NO:6, amino acids 1143–1393 of SEQ ID NO:6, amino acids 1430–1503 of SEQ ID NO:6, amino acids 1522–1946 of SEQ ID NO: 6, amino acids 2053–2373 of SEQ ID NO:6, amino acids 2383–2551 of SEQ ID NO:6, amino acids 2671–3045 of SEQ ID NO:6, amino acids 3392–3636 of SEQ ID NO:6, amino acids 3673–3745 of SEQ ID NO:6, SEQ ID NO:7, amino acids 32–450 of SEQ ID NO:7, amino acids 556–877 of SEQ ID NO:7, amino acids 887–1051 of SEQ ID NO:7, amino acids 1478–1790 of SEQ ID NO:7, amino acids 1810–2055 of SEQ ID NO:7, amino acids 2093–2164 of SEQ ID NO:7, amino acids 2165–2439 of SEQ ID NO:7, SEQ ID NO:8, SEQ ID NO:10, SEQ ID NO:11, and SEQ ID NO:22.

In a more preferred embodiment, the present invention provides an isolated nucleic acid molecule comprising a nucleotide sequence that encodes at least one polypeptide involved in the biosynthesis of an epothilone, wherein said polypeptide comprises an amino acid sequence selected from the group consisting of: SEQ ID NO:2, amino acids 11–437 of SEQ ID NO:2, amino acids 543–864 of SEQ ID NO:2, amino acids 974–1273 of SEQ ID NO:2, amino acids 1314–1385 of SEQ ID NO:2, SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, amino acids 1344–1351 of SEQ ID NO:3, SEQ ID NO:4, amino acids 7–432 of SEQ ID NO:4, amino acids 539–859 of SEQ ID NO:4, amino acids 869–1037 of SEQ ID NO:4, amino acids 1439–1684 of SEQ ID NO:4, amino acids 1722–1792 of SEQ ID NO:4, SEQ ID NO:5, amino acids 39–457 of SEQ ID NO:5, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, amino acids 7140–7211 of SEQ ID NO:5, SEQ ID NO:6, amino acids 35–454 of SEQ ID NO:6, amino acids 561–881 of SEQ ID NO:6, amino acids 1143–1393 of SEQ ID NO:6, amino acids 1430–1503 of SEQ ID NO:6, amino acids 1522–1946 of SEQ ID NO: 6, amino acids 2053–2373 of SEQ ID NO:6, amino acids 2383–2551 of SEQ ID NO:6, amino acids 2671–3045 of SEQ ID NO:6, amino acids 3392–3636 of SEQ ID NO:6, amino acids 3673–3745 of SEQ ID NO:6, SEQ ID NO:7, amino acids 32–450 of SEQ ID NO:7, amino acids 556–877 of SEQ ID NO:7, amino acids 887–1051 of SEQ ID NO:7, amino acids 1478–1790 of SEQ ID NO:7, amino acids 1810–2055 of SEQ ID NO:7, amino acids 2093–2164 of SEQ ID NO:7, amino acids 2165–2439 of SEQ ID NO:7, SEQ ID NO:8, SEQ ID NO:10 SEQ ID NO:11, and SEQ ID NO:22.

In yet another preferred embodiment, the present invention provides an isolated nucleic acid molecule comprising a nucleotide sequence that encodes at least one polypeptide involved in the biosynthesis of an epothilone, wherein said nucleotide sequence is substantially similar to a nucleotide sequence selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

In an especially preferred embodiment, the present invention provides a nucleic acid molecule comprising a nucleotide sequence that encodes at least one polypeptide involved in the biosynthesis of an epothilone, wherein said nucleotide sequence is selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

In yet another preferred embodiment, the present invention provides an isolated nucleic acid molecule comprising a nucleotide sequence that encodes at least one polypeptide involved in the biosynthesis of an epothilone, wherein said nucleotide sequence comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: the complement of nucleotides 1900–3171 of SEQ ID NO:1, nucleotides 3415–5556 of SEQ ID NO:1, nucleotides 7610–11875 of SEQ ID NO:1, nucleotides 7643–8920 of SEQ ID NO:1, nucleotides 9236–10201 of SEQ ID NO:1, nucleotides 10529–11428 of SEQ ID NO:1, nucleotides 11549–11764 of SEQ ID NO:1, nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, nucleotides 15901–15924 of SEQ ID NO:1, nucleotides 16251–21749 of SEQ ID NO:1, nucleotides 16269–17546 of SEQ ID NO:1, nucleotides 17865–18827 of SEQ ID NO:1, nucleotides 18855–19361 of SEQ ID NO:1, nucleotides 20565–21302 of SEQ ID NO:1, nucleotides 21414–21626 of SEQ ID NO:1, nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, nucleotides 43163–43378 of SEQ ID NO:1, nucleotides 43524–54920 of SEQ ID NO:1, nucleotides 43626–44885 of SEQ ID NO:1, nucleotides 45204–46166 of SEQ ID NO:1, nucleotides 46950–47702 of SEQ ID NO:1, nucleotides 47811–48032 of SEQ ID NO:1, nucleotides 48087–49361 of SEQ ID NO:1, nucleotides 49680–50642 of SEQ ID NO:1, nucleotides 50670–51176 of SEQ ID NO:1, nucleotides 51534–52657 of SEQ ID NO:1, nucleotides 53697–54431 of SEQ ID NO:1, nucleotides 54540–54758 of SEQ ID NO:1, nucleotides 54935–62254 of SEQ ID NO:1, nucleotides 55028–56284 of SEQ ID NO:1, nucleotides 56600–57565 of SEQ ID NO:1, nucleotides 57593–58087 of SEQ ID NO:1, nucleotides 59366–60304 of SEQ ID NO:1, nucleotides 60362–61099 of SEQ ID NO:1, nucleotides 61211–61426 of SEQ ID NO:1, nucleotides 61427–62254 of SEQ ID NO:1, nucleotides 62369–63628 of SEQ ID NO:1, nucleotides 67334–68251 of SEQ ID NO:1, and nucleotides 1–68750 SEQ ID NO:1.

The present invention also provides a chimeric gene comprising a heterologous promoter sequence operatively linked to a nucleic acid molecule of the invention. Further, the present invention provides a recombinant vector comprising such a chimeric gene, wherein the vector is capable of being stably transformed into a host cell. Still further, the present invention provides a recombinant host cell comprising such a chimeric gene, wherein the host cell is capable of expressing the nucleotide sequence that encodes at least one polypeptide necessary for the biosynthesis of an epothilone. In a preferred embodiment, the recombinant host cell is a bacterium belonging to the order Actinomycetales, and in a more preferred embodiment the recombinant host cell is a strain of Streptomyces. In other embodiments, the recombinant host cell is any other bacterium amenable to fermentation, such as a pseudomonad or E. coli. Even further, the present invention provides a Bac clone comprising a nucleic acid molecule of the invention, preferably Bac clone pEPO15.

In another aspect, the present invention provides an isolated nucleic acid molecule comprising a nucleotide sequence that encodes an epothilone synthase domain.

According to one embodiment, the epothilone synthase domain is a β-ketoacyl-synthase (KS) domain comprising an amino acid sequence substantially similar to an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO:6, and amino acids 32–450 of SEQ ID NO:7. According to this embodiment, said KS domain preferably comprises an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO:6, and amino acids 32–450 of SEQ ID NO:7. Also, according to this embodiment, said nucleotide sequence preferably is substantially similar to a nucleotide sequence selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1. In addition, according to this embodiment, said nucleotide sequence most preferably is selected from the group consisting of: nucleotides 7643–8920 of SEQ ID NO:1, nucleotides 16269–17546 of SEQ ID NO:1, nucleotides 21860–23116 of SEQ ID NO:1, nucleotides 26318–27595 of SEQ ID NO:1, nucleotides 30815–32092 of SEQ ID NO:1, nucleotides 37052–38320 of SEQ ID NO:1, nucleotides 43626–44885 of SEQ ID NO:1, nucleotides 48087–49361 of SEQ ID NO:1, and nucleotides 55028–56284 of SEQ ID NO:1.

According to another embodiment, the epothilone synthase domain is an acyltransferase (AT) domain comprising an amino acid sequence substantially similar to an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. According to this embodiment, said AT domain preferably comprises an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. Also, according to this embodiment, said nucleotide sequence preferably is substantially similar to a nucleotide sequence selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1. In addition, according to this embodiment, said nucleotide sequence most preferably is selected from the group consisting of: nucleotides 9236–10201 of SEQ ID NO:1, nucleotides 17865–18827 of SEQ ID NO:1, nucleotides 23431–24397 of SEQ ID NO:1, nucleotides 27911–28876 of SEQ ID NO:1, nucleotides 32408–33373 of SEQ ID NO:1, nucleotides 38636–39598 of SEQ ID NO:1, nucleotides 45204–46166 of SEQ ID NO:1, nucleotides 49680–50642 of SEQ ID NO:1, and nucleotides 56600–57565 of SEQ ID NO:1.

According to still another embodiment, the epothilone synthase domain is an enoyl reductase (ER) domain comprising an amino acid sequence substantially similar to an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. According to this embodiment, said ER domain preferably comprises an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. Also, according to this embodiment, said nucleotide sequence preferably is substantially similar to a nucleotide sequence selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1. In addition, according to this embodiment, said nucleotide sequence most preferably is selected from the group consisting of: nucleotides 10529–11428 of SEQ ID NO:1, nucleotides 35042–35902 of SEQ ID NO:1, nucleotides 41369–42256 of SEQ ID NO:1, and nucleotides 59366–60304 of SEQ ID NO:1.

According to another embodiment, the epothilone synthase domain is an acyl carrier protein (ACP) domain, wherein said polypeptide comprises an amino acid sequence substantially similar to an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. According to this embodiment, said ACP domain preferably comprises an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. Also, according to this embodiment, said nucleotide sequence preferably is substantially similar to a nucleotide sequence selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1. In addition, according to this embodiment, said nucleotide sequence most preferably is selected from the group consisting of: nucleotides 11549–11764 of SEQ ID NO:1, nucleotides 21414–21626 of SEQ ID NO:1, nucleotides 26045–26263 of SEQ ID NO:1, nucleotides 30539–30759 of SEQ ID NO:1, nucleotides 36773–36991 of SEQ ID NO:1, nucleotides 43163–43378 of SEQ ID NO:1, nucleotides 47811–48032 of SEQ ID NO:1, nucleotides 54540–54758 of SEQ ID NO:1, and nucleotides 61211–61426 of SEQ ID NO:1.

According to another embodiment, the epothilone synthase domain is a dehydratase (DH) domain comprising an amino acid sequence substantially similar to an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. According to this embodiment, said DH domain preferably comprises an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. Also, according to this embodiment, said nucleotide sequence preferably is substantially similar to a nucleotide sequence selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1. In addition, according to this embodiment, said nucleotide sequence most preferably is selected from the group consisting of: nucleotides 18855–19361 of SEQ ID NO:1, nucleotides 33401–33889 of SEQ ID NO:1, nucleotides 39635–40141 of SEQ ID NO:1, nucleotides 50670–51176 of SEQ ID NO:1, and nucleotides 57593–58087 of SEQ ID NO:1.

According to yet another embodiment, the epothilone synthase domain is a β-ketoreductase (KR) domain comprising an amino acid sequence substantially similar to an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. According to this embodiment, said KR domain preferably comprises an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. Also, according to this embodiment, said nucleotide sequence preferably is substantially similar to a nucleotide sequence selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1. In addition, according to this embodiment, said nucleotide sequence most preferably is selected from the group consisting of: nucleotides 20565–21302 of SEQ ID NO:1, nucleotides 25184–25942 of SEQ ID NO:1, nucleotides 29678–30429 of SEQ ID NO:1, nucleotides 35930–36667 of SEQ ID NO:1, nucleotides 42314–43048 of SEQ ID NO:1, nucleotides 46950–47702 of SEQ ID NO:1, nucleotides 53697–54431 of SEQ ID NO:1, and nucleotides 60362–61099 of SEQ ID NO:1.

According to an additional embodiment, the epothilone synthase domain is a methyltransferase (MT) domain comprising an amino acid sequence substantially similar to amino acids 2671–3045 of SEQ ID NO:6. According to this embodiment, said MT domain preferably comprises amino acids 2671–3045 of SEQ ID NO:6. Also, according to this embodiment, said nucleotide sequence preferably is substantially similar to nucleotides 51534–52657 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of nucleotides 51534–52657 of SEQ ID NO:1. In addition, according to this embodiment, said nucleotide sequence most preferably is nucleotides 51534–52657 of SEQ ID NO:1.

According to another embodiment, the epothilone synthase domain is a thioesterase (TE) domain comprising an amino acid sequence substantially similar to amino acids 2165–2439 of SEQ ID NO:7. According to this embodiment, said TE domain preferably comprises amino acids 2165–2439 of SEQ ID NO:7. Also, according to this embodiment, said nucleotide sequence preferably is substantially similar to nucleotides 61427–62254 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of nucleotides 61427–62254 of SEQ ID NO:1. In addition, according to this embodiment, said nucleotide sequence most preferably is nucleotides 61427–62254 of SEQ ID NO:1.

In still another aspect, the present invention provides an isolated nucleic acid molecule comprising a nucleotide sequence that encodes a non-ribosomal peptide synthetase, wherein said non-ribosomal peptide synthetase comprises an amino acid sequence substantially similar to an amino acid sequence selected from the group consisting of: SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, and amino acids 1344–1351 of SEQ ID NO:3. According to this embodiment, said non-ribosomal peptide synthetase preferably comprises an amino acid sequence selected from the group consisting of: SEQ ID NO:3, amino acids 72–81 of SEQ ID NO:3, amino acids 118–125 of SEQ ID NO:3, amino acids 199–212 of SEQ ID NO:3, amino acids 353–363 of SEQ ID NO:3, amino acids 549–565 of SEQ ID NO:3, amino acids 588–603 of SEQ ID NO:3, amino acids 669–684 of SEQ ID NO:3, amino acids 815–821 of SEQ ID NO:3, amino acids 868–892 of SEQ ID NO:3, amino acids 903–912 of SEQ ID NO:3, amino acids 918–940 of SEQ ID NO:3, amino acids 1268–1274 of SEQ ID NO:3, amino acids 1285–1297 of SEQ ID NO:3, amino acids 973–1256 of SEQ ID NO:3, and amino acids 1344–1351 of SEQ ID NO:3. Also, according to this embodiment, said nucleotide sequence preferably is substantially similar to a nucleotide sequence selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1. According to this embodiment, said nucleotide sequence more preferably comprises a consecutive 20, 25, 30, 35, 40, 45, or 50 (preferably 20) base pair nucleotide portion identical in sequence to a respective consecutive 20, 25, 30, 35, 40, 45, or 50 (preferably 20) base pair portion of a nucleotide sequence selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1. In addition, according to this embodiment, said nucleotide sequence most preferably is selected from the group consisting of: nucleotides 11872–16104 of SEQ ID NO:1, nucleotides 12085–12114 of SEQ ID NO:1, nucleotides 12223–12246 of SEQ ID NO:1, nucleotides 12466–12507 of SEQ ID NO:1, nucleotides 12928–12960 of SEQ ID NO:1, nucleotides 13516–13566 of SEQ ID NO:1, nucleotides 13633–13680 of SEQ ID NO:1, nucleotides 13876–13923 of SEQ ID NO:1, nucleotides 14313–14334 of SEQ ID NO:1, nucleotides 14473–14547 of SEQ ID NO:1, nucleotides 14578–14607 of SEQ ID NO:1, nucleotides 14623–14692 of SEQ ID NO:1, nucleotides 15673–15693 of SEQ ID NO:1, nucleotides 15724–15762 of SEQ ID NO:1, nucleotides 14788–15639 of SEQ ID NO:1, and nucleotides 15901–15924 of SEQ ID NO:1.

The present invention further provides an isolated nucleic acid molecule comprising a nucleotide sequence that encodes a polypeptide comprising an amino acid sequence selected from the group consisting of SEQ ID NOs:2–23.

In accordance with another aspect, the present invention also provides methods for the recombinant production of polyketides such as epothilones in quantities large enough to enable their purification and use in pharmaceutical formulations such as those for the treatment of cancer. A specific advantage of these production methods is the chirality of the molecules produced; production in transgenic organisms avoids the generation of populations of racemic mixtures, within which some enantiomers may have reduced activity. In particular, the present invention provides a method for heterologous expression of epothilone in a recombinant host, comprising: (a) introducing into a host a chimeric gene comprising a heterologous promoter sequence operatively linked to a nucleic acid molecule of the invention that comprises a nucleotide sequence that encodes at least one polypeptide involved in the biosynthesis of epothilone; and (b) growing the host in conditions that allow biosynthesis of epothilone in the host. The present invention also provides a method for producing epothilone, comprising: (a) expressing epothilone in a recombinant host by the aforementioned method; and (b) extracting epothilone from the recombinant host.

According to still another aspect, the present invention provides an isolated polypeptide comprising an amino acid sequence that consists of an epothilone synthase domain.

According to one embodiment, the epothilone synthase domain is a β-ketoacyl-synthase (KS) domain comprising an amino acid sequence substantially similar to an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO: 6, and amino acids 32–450 of SEQ ID NO:7. According to this embodiment, said KS domain preferably comprises an amino acid sequence selected from the group consisting of: amino acids 11–437 of SEQ ID NO:2, amino acids 7–432 of SEQ ID NO:4, amino acids 39–457 of SEQ ID NO:5, amino acids 1524–1950 of SEQ ID NO:5, amino acids 3024–3449 of SEQ ID NO:5, amino acids 5103–5525 of SEQ ID NO:5, amino acids 35–454 of SEQ ID NO:6, amino acids 1522–1946 of SEQ ID NO:6, and amino acids 32–450 of SEQ ID NO:7.

According to another embodiment, the epothilone synthase domain is an acyltransferase (AT) domain comprising an amino acid sequence substantially, similar to an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7. According to this embodiment, said AT domain preferably comprises an amino acid sequence selected from the group consisting of: amino acids 543–864 of SEQ ID NO:2, amino acids 539–859 of SEQ ID NO:4, amino acids 563–884 of SEQ ID NO:5, amino acids 2056–2377 of SEQ ID NO:5, amino acids 3555–3876 of SEQ ID NO:5, amino acids 5631–5951 of SEQ ID NO:5, amino acids 561–881 of SEQ ID NO:6, amino acids 2053–2373 of SEQ ID NO:6, and amino acids 556–877 of SEQ ID NO:7.

According to still another embodiment, the epothilone synthase domain is an enoyl reductase (ER) domain comprising an amino acid sequence substantially similar to an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7. According to this embodiment, said ER domain preferably comprises an amino acid sequence selected from the group consisting of: amino acids 974–1273 of SEQ ID NO:2, amino acids 4433–4719 of SEQ ID NO:5, amino acids 6542–6837 of SEQ ID NO:5, and amino acids 1478–1790 of SEQ ID NO:7.

According to another embodiment, the epothilone synthase domain is an acyl carrier protein (ACP) domain, wherein said polypeptide comprises an amino acid sequence substantially similar to an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7. According to this embodiment, said ACP domain preferably comprises an amino acid sequence selected from the group consisting of: amino acids 1314–1385 of SEQ ID NO:2, amino acids 1722–1792 of SEQ ID NO:4, amino acids 1434–1506 of SEQ ID NO:5, amino acids 2932–3005 of SEQ ID NO:5, amino acids 5010–5082 of SEQ ID NO:5, amino acids 7140–7211 of SEQ ID NO:5, amino acids 1430–1503 of SEQ ID NO:6, amino acids 3673–3745 of SEQ ID NO:6, and amino acids 2093–2164 of SEQ ID NO:7.

According to another embodiment, the epothilone synthase domain is a dehydratase (DH) domain comprising an amino acid sequence substantially similar to an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7. According to this embodiment, said DH domain preferably comprises an amino acid sequence selected from the group consisting of: amino acids 869–1037 of SEQ ID NO:4, amino acids 3886–4048 of SEQ ID NO:5, amino acids 5964–6132 of SEQ ID NO:5, amino acids 2383–2551 of SEQ ID NO:6, and amino acids 887–1051 of SEQ ID NO:7.

According to yet another embodiment, the epothilone synthase domain is a β-ketoreductase (KR) domain comprising an amino acid sequence substantially similar to an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7. According to this embodiment, said KR domain preferably comprises an amino acid sequence selected from the group consisting of: amino acids 1439–1684 of SEQ ID NO:4, amino acids 1147–1399 of SEQ ID NO:5, amino acids 2645–2895 of SEQ ID NO:5, amino acids 4729–4974 of SEQ ID NO:5, amino acids 6857–7101 of SEQ ID NO:5, amino acids 1143–1393 of SEQ ID NO:6, amino acids 3392–3636 of SEQ ID NO:6, and amino acids 1810–2055 of SEQ ID NO:7.

According to an additional embodiment, the epothilone synthase domain is a methyltransferase (MT) domain comprising an amino acid sequence substantially similar to amino acids 2671–3045 of SEQ ID NO:6. According to this embodiment, said MT domain preferably comprises amino acids 2671–3045 of SEQ ID NO:6.

According to another embodiment, the epothilone synthase domain is a thioesterase (TE) domain comprising an amino acid sequence substantially similar to amino acids 2165–2439 of SEQ ID NO:7. According to this embodiment, said TE domain preferably comprises amino acids 2165–2439 of SEQ ID NO:7.

Other aspects and advantages of the present invention will become apparent to those skilled in the art from a study of the following description of the invention and non-limiting examples.

DEFINITIONS

In describing the present invention, the following terms will be employed, and are intended to be defined as indicated below.

Associated With/Operatively Linked: Refers to two DNA sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

Chimeric Gene: A recombinant DNA sequence in which a promoter or regulatory DNA sequence is operatively linked to, or associated with, a DNA sequence that codes for an mRNA or which is expressed as a protein, such that the regulator DNA sequence is able to regulate transcription or expression of the associated DNA sequence. The regulator DNA sequence of the chimeric gene is not normally operatively linked to the associated DNA sequence as found in nature.

Coding DNA Sequence: A DNA sequence that is translated in an organism to produce a protein.

Domain: That part of a polyketide synthase necessary for a given distinct activity. Examples include acyl carrier protein (ACP), β-ketosynthase (KS), acyltransferase (AT), β-ketoreductase (KR), dehydratase (DH), enoylreductase (ER), and thioesterase (TE) domains.

Epothilones: 16-membered macrocyclic polyketides naturally produced by the bacterium *Sorangium cellulosum* strain So ce90, which mimic the biological effects of taxol. In this application, "epothilone" refers to the class of polyketides that includes epothilone A and epothilone B, as well as analogs thereof such as those described in WO 98/25929.

Epothilone Synthase: A polyketide synthase responsible for the biosynthesis of epothilone.

Gene: A defined region that is located within a genome and that, besides the aforementioned coding DNA sequence, comprises other, primarily regulatory, DNA sequences responsible for the control of the expression, that is to say the transcription and translation, of the coding portion.

Heterologous DNA Sequence: A DNA sequence not naturally associated with a host cell into which it is introduced, including non-naturally occurring multiple copies of a naturally occurring DNA sequence.

Homologous DNA Sequence: A DNA sequence naturally associated with a host cell into which it is introduced.

Homologous Recombination: Reciprocal exchange of DNA fragments between homologous DNA molecules.

Isolated: In the context of the present invention, an isolated nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

Module: A genetic element encoding all of the distinct activities required in a single round of polyketide biosynthesis, i.e., one condensation step and all the β-carbonyl processing steps associated therewith. Each module encodes an ACP, a KS, and an AT activity to accomplish the condensation portion of the biosynthesis, and selected post-condensation activities to effect the β-carbonyl processing.

NRPS: A non-ribosomal polypeptide synthetase, which is a complex of enzymatic activities responsible for the incorporation of amino acids into secondary metabolites including, for example, amino acid adenylation, epimerization, N-methylation, cyclization, peptidyl carrier protein, and condensation domains. A functional NRPS is one that catalyzes the incorporation of an amino acid into a secondary metabolite.

NRPS gene: One or more genes encoding NRPSs for producing functional secondary metabolites, e.g., epothilones A and B, when under the direction of one or more compatible control elements.

Nucleic Acid Molecule: A linear segment of single- or double-stranded DNA or RNA that can be isolated from any source. In the context of the present invention, the nucleic acid molecule is preferably a segment of DNA.

ORF: Open Reading Frame.

PKS: A polyketide synthase, which is a complex of enzymatic activities (domains) responsible for the biosynthesis of polyketides including, for example, ketoreductase, dehydratase, acyl carrier protein, enoylreductase, ketoacyl ACP synthase, and acyltransferase. A functional PKS is one that catalyzes the synthesis of a polyketide.

PKS Genes: One or more genes encoding various polypeptides required for producing functional polyketides, e.g., epothilones A and B, when under the direction of one or more compatible control elements.

Substantially Similar: With respect to nucleic acids, a nucleic acid molecule that has at least 60 percent sequence identity with a reference nucleic acid molecule. In a preferred embodiment, a substantially similar DNA sequence is at least 80% identical to a reference DNA sequence; in a more preferred embodiment, a substantially similar DNA sequence is at least 90% identical to a reference DNA sequence; and in a most preferred embodiment, a substantially similar DNA sequence is at least 95% identical to a reference DNA sequence. A substantially similar DNA sequence preferably encodes a protein or peptide having substantially the same activity as the protein or peptide encoded by the reference DNA sequence. A substantially similar nucleotide sequence typically hybridizes to a reference nucleic acid molecule, or fragments thereof, under the following conditions: hybridization at 7% sodium dodecyl sulfate (SDS), 0.5 M $NaPO_4$ pH 7.0, 1 mM EDTA at 50° C.; wash with 2×SSC, 1% SDS, at 50° C. With respect to proteins or peptides, a substantially similar amino acid sequence is an amino acid sequence that is at least 90% identical to the amino acid sequence of a reference protein or peptide and has substantially the same activity as the reference protein or peptide.

Transformation: A process for introducing heterologous nucleic acid into a host cell or organism.

Transformed/Transgenic/Recombinant: Refers to a host organism such as a bacterium into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, i.e., a bacterium, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DESCRIPTION OF THE SEQUENCES IN THE SEQUENCE LISTING

SEQ ID NO:1 is the nucleotide sequence of a 68750 bp contig containing 22 open reading frames (ORFs), which comprises the epothilone biosynthesis genes.

SEQ ID NO:2 is the protein sequence of a type I polyketide synthase (EPOS A) encoded by epoA (nucleotides 7610–11875 of SEQ ID NO:1).

SEQ ID NO:3 is the protein sequence of a non-ribosomal peptide synthetase (EPOS P) encoded by epoP (nucleotides 11872–16104 of SEQ ID NO:1).

SEQ ID NO:4 is the protein sequence of a type I polyketide synthase (EPOS B) encoded by epoB (nucleotides 16251–21749 of SEQ ID NO:1).

SEQ ID NO:5 is the protein sequence of a type I polyketide synthase (EPOS C) encoded by epoc (nucleotides 21746–43519 of SEQ ID NO:1).

SEQ ID NO:6 is the protein sequence of a type I polyketide synthase (EPOS D) encoded by epoD (nucleotides 43524–54920 of SEQ ID NO:1).

SEQ ID NO:7 is the protein sequence of a type I polyketide synthase (EPOS E) encoded by epoE (nucleotides 54935–62254 of SEQ ID NO:1).

SEQ ID NO:8 is the protein sequence of a cytochrome P450 oxygenase homologue (EPOS F) encoded by epoF (nucleotides 62369–63628 of SEQ ID NO:1).

SEQ ID NO:9 is a partial protein sequence (partial Orf 1) encoded by orf1 (nucleotides 1–1826 of SEQ ID NO:1).

SEQ ID NO:10 is a protein sequence (Orf 2) encoded by orf2 (nucleotides 3171–1900 on the reverse complement strand of SEQ ID NO:1).

SEQ ID NO:11 is a protein sequence (Orf 3) encoded by orf3 (nucleotides 3415–5556 of SEQ ID NO:1).

SEQ ID NO:12 is a protein sequence (Orf 4) encoded by orf4 (nucleotides 5992–5612 on the reverse complement strand of SEQ ID NO:1).

SEQ ID NO:13 is a protein sequence (Orf 5) encoded by orf5 (nucleotides 6226–6675 of SEQ ID NO:1).

SEQ ID NO:14 is a protein sequence (Orf 6) encoded by orf6 (nucleotides 63779–64333 of SEQ ID NO:1).

SEQ ID NO:15 is a protein sequence (Orf 7) encoded by orf7 (nucleotides 64290–63853 on the reverse complement strand of SEQ ID NO:1).

SEQ ID NO:16 is a protein sequence (Orf 8) encoded by orf8 (nucleotides 64363–64920 of SEQ ID NO:1).

SEQ ID NO:17 is a protein sequence (Orf 9) encoded by orf9 (nucleotides 64727–64287 on the reverse complement strand of SEQ ID NO:1).

SEQ ID NO:18 is a protein sequence (Orf 10) encoded by orf10 (nucleotides 65063–65767 of SEQ ID NO:1).

SEQ ID NO:19 is a protein sequence (Orf 11) encoded by orf11 (nucleotides 65874–65008 on the reverse complement strand of SEQ ID NO:1).

SEQ ID NO:20 is a protein sequence (Orf 12) encoded by orf12 (nucleotides 66338–65871 on the reverse complement strand of SEQ ID NO:1).

SEQ ID NO:21 is a protein sequence (Orf 13) encoded by orf13 (nucleotides 66667–67137 of SEQ ID NO:1).

SEQ ID NO:22 is a protein sequence (Orf 14) encoded by orf14 (nucleotides 67334–68251 of SEQ ID NO:1).

SEQ ID NO:23 is a partial protein sequence (partial Orf 15) encoded by orf15 (nucleotides 68346–68750 of SEQ ID NO:1).

SEQ ID NO:24 is the universal reverse PCR primer sequence.

SEQ ID NO:25 is the universal forward PCR primer sequence.

SEQ ID NO:26 is the NH24 end "B" PCR primer sequence.

SEQ ID NO:27 is the NH2 end "A" PCR primer sequence.

SEQ ID NO:28 is the NH2 end "B" PCR primer sequence.

SEQ ID NO:29 is the pEPO15-NH6 end "B" PCR primer sequence.

SEQ ID NO:30 is the pEPO15-H2.7 end "A" PCR primer sequence.

DEPOSIT INFORMATION

The following material has been deposited with the Agricultural Research Service, Patent Culture Collection (NRRL), 1815 North University Street, Peoria, Ill. 61604, under the Budapest Treaty on the International Recognition of the Deposit of Microorganisms for the Purposes of Patent Procedure. All restrictions on the availability of the deposited material will be irrevocably removed upon the granting of a patent.

| Deposited Material | Accession Number | Deposit Date |
|---|---|---|
| pEPO15 | NRRL B-30033 | June 11, 1998 |
| pEPO32 | NRRL B-30119 | April 16, 1999 |

DETAILED DESCRIPTION OF THE INVENTION

The genes involved in the biosynthesis of epothilones can be isolated using the techniques according to the present invention. The preferable procedure for the isolation of epothilone biosynthesis genes requires the isolation of genomic DNA from an organism identified as producing epothilones A and B, and the transfer of the isolated DNA on a suitable plasmid or vector to a host organism that does not normally produce the polyketide, followed by the identification of transformed host colonies to which the epothilone-producing ability has been conferred. Using a technique such as $\lambda$::Tn5 transposon mutagenesis (de Bruijn & Lupski, *Gene* 27: 131–149 (1984)), the exact region of the transforming epothilone-conferring DNA can be more precisely defined. Alternatively or additionally, the transforming epothilone-conferring DNA can be cleaved into smaller fragments and the smallest that maintains the epothilone-conferring ability further characterized. Whereas the host organism lacking the ability to produce epothilone may be a different species from the organism from which the polyketide derives, a variation of this technique involves the transformation of host DNA into the same host that has had its epothilone-producing ability disrupted by mutagenesis. In this method, an epothilone-producing organism is mutated and non-epothilone-producing mutants are isolated. These are then complemented by genomic DNA isolated from the epothilone-producing parent strain.

A further example of a technique that can be used to isolate genes required for epothilone biosynthesis is the use of transposon mutagenesis to generate mutants of an epothilone-producing organism that, after mutagenesis, fails to produce the polyketide. Thus, the region of the host genome responsible for epothilone production is tagged by the transposon and can be recovered and used as a probe to isolate the native genes from the parent strain. PKS genes that are required for the synthesis of polyketides and that are similar to known PKS genes may be isolated by virtue of their sequence homology to the biosynthetic genes for which the sequence is known, such as those for the biosynthesis of rifamycin or soraphen. Techniques suitable for isolation by homology include standard library screening by DNA hybridization.

Preferred for use as a probe molecule is a DNA fragment that is obtainable from a gene or another DNA sequence that plays a part in the synthesis of a known polyketide. A preferred probe molecule comprises a 1.2 kb SmaI DNA fragment encoding the ketosynthase domain of the fourth module of the soraphen PKS (U.S. Pat. No. 5,716,849), and a more preferred probe molecule comprises the $\beta$-ketoacyl synthase domains from the first and second modules of the rifamycin PKS (Schupp et al., *FEMS Microbiology Letters* 159: 201–207 (1998)). These can be used to probe a gene library of an epothilone-producing microorganism to isolate the PKS genes responsible for epothilone biosynthesis.

Despite the well-known difficulties with PKS gene isolation in general and despite the difficulties expected to be encountered with the isolation of epothilone biosynthesis genes in particular, by using the methods described in the instant specification, biosynthetic genes for epothilones A and B can surprisingly be cloned from a microorganism that produces that polyketide. Using the methods of gene manipulation and recombinant production described in this specification, the cloned PKS genes can be modified and expressed in transgenic host organisms.

The isolated epothilone biosynthetic genes can be expressed in heterologous hosts to enable the production of the polyketide with greater efficiency than might be possible from native hosts. Techniques for these genetic manipulations are specific for the different available hosts and are known in the art. For example, heterologous genes can be expressed in Streptomyces and other actinomycetes using techniques such as those described in McDaniel et al., *Science* 262: 1546–1550 (1993) and Kao et al., *Science* 265: 509–512 (1994), both of which are incorporated herein by reference. See also, Rowe et al., *Gene* 216: 215–223 (1998); Holmes et al., *EMBO Journal* 12(8): 3183–3191 (1993) and Bibb et al., *Gene* 38: 215–226 (1985), all of which are incorporated herein by reference.

Alternately, genes responsible for polyketide biosynthesis, i.e., epothilone biosynthetic genes, can also be expressed in other host organisms such as pseudomonads and *E. coli*. Techniques for these genetic manipulations are specific for the different available hosts and are known in the art. For example, PKS genes have been successfully expressed in *E. coli* using the pT7-7 vector, which uses the T7 promoter. See, Tabor et al., *Proc. Natl. Acad. Sci. USA* 82: 1074–1078 (1985), incorporated herein by reference. In addition, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al., in: Industrial Microorganisms: Basic and Applied Molecular Genetics, Eds. Baltz et al., American Society for Microbiology. Washington (1993)).

Other expression systems that may be used with the epothilone biosynthetic genes of the invention include yeast and baculovirus expression systems. See, for example, "The Expression of Recombinant Proteins in Yeasts," Sudbery, P. E., Curr. *Opin. Biotechnol.* 7(5): 517–524 (1996); "Methods for Expressing Recombinant Proteins in Yeast," Mackay, et al., Editor(s): Carey, Paul R., *Protein Eng. Des.* 105–153, Publisher: Academic, San Diego, Calif. (1996); "Expression of heterologous gene products in yeast," Pichuantes, et al., Editor(s): Cleland, J. L., Craik, C. S., *Protein Eng.* 129–161, Publisher: Wiley-Liss, New York, N.Y. (1996); WO 98/27203; Kealey et al., *Proc. Natl. Acad. Sci. USA* 95: 505–509 (1998); "Insect Cell Culture: Recent Advances, Bioengineering Challenges And Implications In Protein Production," Palomares, et al., Editor(s): Galindo, Enrique; Ramirez, Octavio T., *Adv. Bioprocess Eng.* Vol. II, Invited Pap. Int. Symp., 2nd (1998) 25–52, Publisher: Kluwer, Dordrecht, Neth; "Baculovirus Expression Vectors," Jarvis, Donald L., Editor(s): Miller, Lois K., *Baculoviruses* 389–431, Publisher: Plenum, New York, N.Y. (1997); "Production Of Heterologous Proteins Using The Baculovirus/ Insect Expression System," Grittiths, et al., *Methods Mol. Biol.* (Totowa, N.J.) 75 (Basic Cell Culture Protocols (2nd Edition)) 427–440 (1997); and "Insect Cell Expression Technology," Luckow, Verne A., *Protein Eng.* 183–218, Publisher: Wiley-Liss, New York, N.Y. (1996); all of which are incorporated herein by reference.

Another consideration for expression of PKS genes in heterologous hosts is the requirement of enzymes for post-translational modification of PKS enzymes by phosphopantetheinylation before they can synthesize polyketides. However, the enzymes responsible for this modification of type I PKS enzymes, phosphopantetheinyl (P-pant) transferases are not normally present in many hosts such as *E. coli*. This problem can be solved by coexpression of a P-pant transferase with the PKS genes in the heterologous host, as described by Kealey et al., *Proc. Natl. Acad. Sci. USA* 95: 505–509 (1998), incorporated herein by reference.

Therefore, for the purposes of polyketide production, the significant criteria in the choice of host organism are its ease of manipulation, rapidity of growth (i.e. fermentation), possession or the proper molecular machinery for processes such as posttranslational modification, and its lack of susceptibility to the polyketide being overproduced. Most preferred host organisms are actinomycetes such as strains of Streptomyces. Other preferred host organisms are pseudomonads and *E. coli*. The above-described methods of polyketide production have significant advantages over the technology currently used in the preparation of the compounds. These advantages include the cheaper cost of production, the ability to produce greater quantities of the compounds, and the ability to produce compounds of a preferred biological enantiomer, as opposed to racemic mixtures inevitably generated by organic synthesis. Compounds produced by heterologous hosts can be used in medical (e.g. cancer treatment in the case of epothilones) as well as agricultural applications.

EXPERIMENTAL

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), *Current Protocols in Molecular Biology*, John Wiley and Sons, Inc. (1994); T. Maniatis, E. F. Fritsch and J. Sambrook, *Molecular Cloning*: A Laboratory Manual, Cold Spring Harbor laboratory, Cold Spring Harbor, N.Y. (1989); and by T. J. Silhavy, M. L. Berman, and L. W. Enquist, *Experiments with Gene Fusions*, Cold Spring Harbor Laboratory, Cold Spring Harbor, N.Y. (1984).

EXAMPLE 1

Cultivation of an Epothilone-Producing Strain of *Sorangium cellulosum*

*Sorangium cellulosum* strain 90 (DSM 6773, Deutsche Sammlung von Mikroorganismen und Zellkulturen, Braunschweig) is streaked out and grown (30° C.) on an agar plate of SolE medium (0.35% glucose, 0.05% tryptone, 0.15% $MgSO_4 \times 7H_2O$, 0.05% ammonium sulfate, 0.1% $CaCl_2$, 0.006% $K_2HPO_4$, 0.01% sodium dithionite, 0.0008% Fe-EDTA, 1.2% HEPES, 3.5% [vol/vol] supernatant of sterilized stationary *S. cellulosum* culture) pH ad. 7.4. Cells from about 1 square cm are picked and inoculated into 5 mls of G51t liquid medium (0.2% glucose, 0.5% starch, 0.2% tryptone, 0.1% probion S, 0.05% $CaCl_2 \times 2H_2O$, 0.05% $MgSO_4 \times 7H_2O$, 1.2% HEPES, pH ad. 7.4) and incubated at 30° C. with shaking at 225 rpm. After 4 days, the culture is transferred into 50 mls of G51t and incubated as above for 5 days. This culture is used to inoculate 500 mls of G51t and incubated as above for 6 days. The culture is centrifuged for 10 minutes at 4000 rpm and the cell pellet is resuspended in 50 mls of G51t.

EXAMPLE 2

Generation of a Bacterial Artificial Chromosome (Bac) Library

To generate a Bac library, S. cellulosum cells cultivated as described in Example 1 above are embedded into agarose blocks, lysed, and the liberated genomic DNA is partially digested by the restriction enzyme HindIII. The digested DNA is separated on an agarose gel by pulsed-field electrophoresis. Large (approximately 90–150 kb) DNA fragments are isolated from the agarose gel and ligated into the vector pBelobacII. pBelobacII contains a gene encoding chloramphenicol resistance, a multiple cloning site in the lacZ gene providing for blue/white selection on appropriate medium, as well as the genes required for the replication and maintenance of the plasmid at one or two copies per cell. The ligation mixture is used to transform Escherichia coli DH10B electrocompetent cells using standard electroporation techniques. Chloramphenicol-resistant recombinant (white, lacZ mutant) colonies are transferred to a positively charged nylon membrane filter in 384 3×3 grid format. The clones are lysed and the DNA is cross-linked to the filters. The same clones are also preserved as liquid cultures at −80° C.

EXAMPLE 3

Screening the Bac Library of Sorangium cellulosum 90 for the Presence of Type I Polyketide Synthase-Related Sequences The Bac library filters are probed by standard Southern hybridization procedures. The DNA probes used encode β-ketoacyl synthase domains from the first and second modules of the rifamycin polyketide synthase (Schupp et al., FEMS Microbiology Letters 159: 201–207 (1998)). The probe DNAs are generated by PCR with primers flanking each ketosynthase domain using the plasmid pNE95 as the template (pNE95 equals cosmid 2 described in Schupp et al. (1998)). 25 ng of PCR-amplified DNA is isolated from a 0.5% agarose gel and labeled with $^{32}$P-dCTP using a random primer labeling kit (Gibco-BRL, Bethesda Md., USA) according to the manufacturer's instructions. Hybridization is at 65° C. for 36 hours and membranes are washed at high stringency (3 times with 0.1×SSC and 0.5% SDS for 20 min at 65° C.). The labeled blot is exposed on a phosphorescent screen and the signals are detected on a Phospholmager 445SI (screen and 445SI from Molecular Dynamics). This results in strong hybridization of certain Bac clones to the probes. These clones are selected and cultured overnight in 5 mls of Luria broth (LB) at 37° C. Bac DNA from the Bac clones of interest is isolated by a typical miniprep procedure. The cells are resuspended in 200 μl lysozyme solution (50 mM glucose, 10 mM EDTA, 25 mM Tris-HCl, 5 mg/ml lysozyme), lysed in 400 μl lysis solution (0.2 N NaOH and 2% SDS), the proteins are precipitated (3.0 M potassium acetate, adjusted to pH5.2 with acetic acid), and the Bac DNA is precipitated with isopropanol. The DNA is resuspended in 20 μl of nuclease-free distilled water, restricted with BamHI (New England Biolabs, Inc.) and separated on a 0.7% agarose gel. The gel is blotted by Southern hybridization as described above and probed under conditions described above, with a 1.2 kb SmaI DNA fragment encoding the ketosynthase domain of the fourth module of the soraphen polyketide synthase as the probe (see, U.S. Pat. No. 5,716,849). Five different hybridization patterns are observed. One clone representing each of the five patterns is selected and named pEPO15, pEPO20, pEPO30, pEPO31, and pEPO33, respectively.

EXAMPLE 4

Subcloning of BamHI Fragments from pEPO15, pEPO20, pEPO30, pEPO31, and pEPO33

The DNA of the five selected Bac clones is digested with BamHI and random fragments are subcloned into pBluescript II SK+(Stratagene) at the BamHI site. Subclones carrying inserts between 2 and 10 kb in size are selected for sequencing of the flanking ends of the inserts and also probed with the 1.2 SmaI probe as described above. Subclones that show a high degree of sequence homology to known polyketide synthases and/or strong hybridization to the soraphen ketosynthase domain are used for gene disruption experiments.

EXAMPLE 5

Preparation of Streptomycin-Resistant Spontaneous Mutants of Sorangium cellulosum strain So ce90

0.1 ml of a three day old culture of Sorangium cellulosum strain So ce90, which is raised in liquid medium G52-H (0.2% yeast extract, 0.2% soyameal defatted, 0.8% potato starch, 0.2% glucose, 0.1% MgSO4×7H2O, 0.1% CaCl2× 2H2O, 0.008% Fe-EDTA, pH ad 7.4 with KOH), is plated out on agar plates with SolE medium supplemented with 100 μg/ml streptomycin. The plates are incubated at 30° C. for 2 weeks. The colonies growing on this medium are streptomycin-resistant mutants, which are streaked out and cultivated once more on the same agar medium with streptomycin for purification. One of these streptomycin-resistant mutants is selected and is called BCE28/2.

EXAMPLE 6

Gene Disruptions in Sorangium cellulosum BCE28/ 2 Using the Subcloned BamHI Fragments The BamHI inserts of the subclones generated from the five selected Bac clones as described above are isolated and ligated into the unique BamHI site of plasmid pCIB132 (see, U.S. Pat. No. 5,716,849). The pCIB132 derivatives carrying the inserts are transformed into Escherichia coli ED8767 containing the helper plasmid pUZ8 (Hedges and Matthew, Plasmid2: 269–278 (1979). The transformants are used as donors in conjugation experiments with Sorangium cellulosum BCE28/2 as recipient. For the conjugation, 5–10× $10^9$cells of Sorangium cellulosum BCE28/2 from an early stationary phase culture (reaching about 5×10$^8$ cells/ml) grown at 30° C. in liquid medium G51b (G51b equals medium G51t with tryptone replaced by peptone) are mixed in a 1:1 cellular ratio with a late-log phase culture (in LB liquid medium) of E. coli ED8767 containing pCIB132 derivatives carrying the subcloned BamHI fragments and the helper plasmid pUZ8. The mixed cells are then centrifuged at 4000 rpm for 10 minutes and resuspended in 0.5 ml G51b medium. This cell suspension is then plated as a drop in the center of a plate with SolE agar containing 50 mg/l kanamycin. The cells obtained after incubation for 24 hours at 30° C. are harvested and resuspended in 0.8 ml of G51b medium, and 0.1 to 0.3 ml of this suspension is plated out on a selective So1E solid medium containing phleomycin (30 mg/l), streptomycin (300 mg/l), and kanamycin (50mg/l). The counterselection of the donor *Escherichia coli* strain takes place with the aid of streptomycin. The colonies that grow on this selective medium after an incubation time of 8–12 days at a temperature of 30° C. are isolated with a plastic loop and streaked out and cultivated on the same agar medium for a second round of selection and purification. The colony-derived cultures that grow on this selective agar medium after 7 days at a temperature of 30° C. are transconjugants of *Sorangium cellulosum* BCE28/2 that have acquired phleomycin resistance by conjugative transfer of the pCIB132 derivatives carrying the subcloned BamHI fragments.

Integration of the pCIB132-derived plasmids into the chromosome of *Sorangium cellulosum* BCE28/2 by homologous recombination is verified by Southern hybridization. For this experiment, complete DNA from 5–10 transconjugants per transferred BamHI fragment is isolated (from 10 ml cultures grown in medium G52-H for three days) applying the method described by Pospiech and Neumann, *Trends Genet.* 11: 217 (1995). For the Southern blot, the DNA isolated as described above is cleaved either with the restriction enzymes Bg/II, ClaI, or NotI, and the respective BamHI inserts or pCIB132 are used as 32P labelled probes.

EXAMPLE 7

Analysis of the Effect of the Integrated BamHI Fragments on Epothilone Production by *Sorangium cellulosum* After Gene Disruption Transconjugant cells grown on about 1 square cm surface of the selective So1E plates of the second round of selection (see Example 6) are transferred by a sterile plastic loop into 10 ml of medium G52-H in an 50 ml Erlenmeyer flask. After incubation at 30° C. and 180 rpm for 3 days, the culture is transferred into 50 ml of medium G52-H in an 200 ml Erlenmeyer flask. After incubation at 30° C. and 180 rpm for 4–5 days, 10 ml of this culture is transferred into 50 ml of medium 23B3 (0.2% glucose, 2% potato starch, 1.6% soya meal defatted, 0.0008% Fe-EDTA Sodium salt, 0.5% HEPES (4-(2-hydroxyethyl)-piperazine-1-ethane-sulfonic-acid), 2% vol/vol polysterole resin XAD16 (Rohm & Haas), pH adjusted to 7.8 with NaOH) in an 200 ml Erlenmeyer flask.

Quantitative determination of the epothilone produced takes place after incubation of the cultures at 30° C. and 180 rpm for 7 days. The complete culture broth is filtered by suction through a 150 µm nylon filter. The resin remaining on the filter is then resuspended in 10 ml isopropanol and extracted by shaking the suspension at 180 rpm for 1 hour. 1 ml is removed from this suspension and centrifuged at 12,000 rpm in an Eppendorff Microfuge. The amount of epothilones A and B therein is determined by means of an HPLC and detection at 250 nm with a UV_DAD detector (HPLC with Waters-Symetry C18 column and a gradient of 0.02% phosphoric acid 60%–0% and acetonitril 40%–100%).

Transconjugants with three different integrated BamHI fragments subcloned from pEPO15, namely transconjugants with the BamHI fragment of plasmid pEPO15-21, transconjugants with the BamHI fragment of plasmid pEPO15-4-5, and transconjugants with the BamHI fragment of plasmid pEPO15-4-1, are tested in the manner described above.

HPLC analysis reveals that all transconjugants no longer produce epothilone A or B. By contrast, epothilone A and B are detectable in a concentration of 2–4 mg/l in transconjugants with BamHI fragments integrated that are derived from pEPO20, pEPO30, pEPO31, pEPO33, and in the parental strain BCE28/2.

EXAMPLE 8

Nucleotide Sequence Determination of the Cloned Fragments and Construction of Contigs A. BamHI Insert of Plasmid pEPO15-21

Plasmid DNA is isolated from the strain *Escherichia coli* DH10B [pEPO15-21], and the nucleotide sequence of the 2.3-kb BamHI insert in pEPO15-21 is determined. Automated DNA sequencing is done on the double-stranded DNA template by the dideoxynucleotide chain termination method, using Applied Biosystems model 377 sequencers. The primers used are the universal reverse primer (5' GGA AAC AGC TAT GAC CAT G 3' (SEQ ID NO:24)) and the universal forward primer (5' GTA AAA CGA CGG CCA GT 3' (SEQ ID NO:25)). In subsequent rounds of sequencing reactions, custom-synthesized oligonucleotides, designed for the 3' ends of the previously determined sequences, are used to extend and join contigs. Both strands are entirely sequenced, and every nucleotide is sequenced at least two times. The nucleotide sequence is compiled using the program Sequencher vers. 3.0 (Gene Codes Corporation), and analyzed using the University of Wisconsin Genetics Computer Group programs. The nucleotide sequence of the 2213-bp insert corresponds to nucleotides 20779–22991 of SEQ ID NO:1.

B. BamHI Insert of Plasmid pEPO15-4-1

Plasmid DNA is isolated from the strain *Escherichia coli* DH10B [pEPO15-4-1], and the nucleotide sequence of the 3.9-kb BamHI insert in pEPO15-4-1 is determined as described in (A) above. The nucleotide sequence of the 3909-bp insert corresponds to nucleotides 16876–20784 of SEQ ID NO:1.

C. BamHI Insert of Plasmid pEPO15-4-5

Plasmid DNA is isolated from the strain *Escherichia coli* DH10B [pEPO15-4-5], and the nucleotide sequence of the 2.3-kb BamHI insert in pEPO15-4-5 is determined as described in (A) above. The nucleotide sequence of the 2233-bp insert corresponds to nucleotides 42528–44760 of SEQ ID NO:1.

EXAMPLE 9

Subcloning and Ordering of DNA Fragments from pEPO15 Containing Epothilone Biosynthesis Genes pEPO15 is digested to completion with the restriction enzyme HindIII and the resulting fragments are subcloned into pBluescript II SK– or pNEB193 (New England Biolabs) that has been cut with HindIII and dephosphorylated with calf intestinal alkaline phosphatase. Six different clones are generated and named pEPO15-NH1, pEPO15-NH2, pEPO15-NH6, pEPO15-NH24 (all based on pNEB193), and pEPO15-H2.7 and pEPO15-H3.0 (both based on pBluescript II SK–).

The BamHI insert of pEPO15-21 is isolated and DIG-labeled (Non-radioactive DNA labeling and detection system, Boehringer Mannheim), and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signal is detected for pEPO15-NH24, indicating that pEPO15-21 is contained within pEPO15-NH24.

The BamHI insert of pEPO15-4-1 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signals are detected for pEPO15-NH24 and pEPO15-H2.7. Nucleotide sequence data generated from one end each of pEPO15-NH24 and pEPO15-H2.7 are also in complete agreement with the previously determined sequence of the BamHI insert of pEPO15-4-1. These experiments demonstrate that pEPO15-4-1 (which contains one internal HindIII site) overlaps pEPO15-H2.7 and pEPO15-NH24, and that pEPO15-H2.7 and pEPO15-NH24, in this order, are contiguous.

The BamHI insert of pEPO15-4-5 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signal is detected for pEPO15-NH2, indicating that pEPO15-21 is contained within pEPO15-NH2.

Nucleotide sequence data is generated from both ends of pEPO15-NH2 and from the end of pEPO15-NH24 that does not overlap with pEPO15-4-1. PCR primers NH24 end "B": GTGACTGGCGCCTGGAATCTGCATGAGC (SEQ ID NO:26), NH2 end "A": AGCGGGAGCTTGCTAGACAT-TCTGTTTC (SEQ ID NO:27), and NH2 end "B": GACGCGCCTCGGGCAGCGCCCCAA (SEQ ID NO:28), pointing towards the HindIII sites, are designed based on these sequences and used in amplification reactions with pEPO15 and, in separate experiments, with *Sorangium cellulosum* So ce90 genomic DNA as the templates. Specific amplification is found with primer pair NH24 end "B" and NH2 end "A" with both templates. The amplimers are cloned into pBluescript II SK– and completely sequenced. The sequences of the amplimers are identical, and also agree completely with the end sequences of pEPO15-NH24 and pEPO15-NH2, fused at the HindIII site, establishing that the HindIII fragments of pEPO15-NH2 and pEPO15-NH24 are, in this order, contiguous.

The HindIII insert of pEPO15-H2.7 is isolated and DIG-labeled as above, and used as a probe in a DNA hybridization experiment at high stringency against pEPO15 digested by NotI. A NotI fragment of about 9 kb in size shows a strong a hybridization, and is further subcloned into pBluescript II SK– that has been digested with NotI and dephosphorylated with calf intestinal alkaline phosphatase, to yield pEPO15-N9-16. The NotI insert of pEPO15-N9-16 is isolated and DIG-labeled as above, and used as a probe in DNA hybridization experiments at high stringency against pEPO15-NH1, pEPO15-NH2, pEPO15-NH6, pEPO15-NH24, pEPO15-H2.7 and pEPO15-H3.0. Strong hybridization signals are detected for pEPO15-NH6, and also for the expected clones pEPO15-H2.7 and pEPO15-NH24. Nucleotide sequence data is generated from both ends of pEPO15-NH6 and from the end of pEPO15-H2.7 that does not overlap with pEPO15-4-1. PCR primers are designed pointing towards the HindIII sites and used in amplification reactions with pEPO15 and, in separate experiments, with *Sorangium cellulosum* So ce90 genomic DNA as the templates. Specific amplification is found with primer pair pEPO15-NH6 end "B": CACCGAAGCGTCGATCTG-GTCCATC (SEQ ID NO:29) and pEPO15-H2.7 end "A": CGGTCAGATCGACGACGGGCTTTCC (SEQ ID NO:30) with both templates. The amplimers are cloned into pBluescript II SK– and completely sequenced. The sequences of the amplimers are identical, and also agree completely with the end sequences of pEPO15-NH6 and pEPO15-H2.7, fused at the HindIII site, establishing that the HindIII fragments of pEPO15-NH6 and pEPO15-H2.7 are, in this order, contiguous.

All of these experiments, taken together, establish a contig of HindIII fragments covering a region of about 55 kb and consisting of the HindIII inserts of pEPO15-NH6, pEPO15-H2.7, pEPO15-NH24, and pEPO15-NH2, in this order. The inserts of the remaining two HindIII subclones, namely pEPO15-NH1 and pEPO15-H3.0, are not found to be parts of this contig.

EXAMPLE 10

Further Extension of the Subclone Contig Covering the Epothilone Biosynthesis Genes An approximately 2.2 kb BamHI—HindIII fragment derived from the downstream end of the insert of pEPO15-NH2 and thus representing the downstream end of the subclone contig described in Example 9 is isolated, DIG-labeled, and used in Southern hybridization experiments against pEPO15 and pEPO15-NH2 DNAs digested with several enzymes. The strongly hybridizing bands are always found to be the same in size between the two target DNAs indicating that the *Sorangium cellulosum* So ce90 genomic DNA fragment cloned into pEPO15 ends with the HindIII site at the downstream end of pEPO15-NH2.

A cosmid DNA library of *Sorangium cellulosum* So ce90 is generated, using established procedures, in pScosTriplex-II (Ji, et al., *Genomics* 31: 185–192 (1996)). Briefly, high-molecular weight genomic DNA of *Sorangium cellulosum* So ce90 is partially digested with the restriction enzyme Sau3AI to provide fragments with average sizes of about 40 kb, and ligated to BamHI and XbaI digested pScosTriplex-II. The ligation mix is packaged with Gigapack III XL (Stratagene) and used to transfect *E. coli* XL1 Blue MR cells.

The cosmid library is screened with the approximately 2.2 kb BamHI—HindIII fragment, derived from the downstream end of the insert of pEPO15-NH2, used as a probe in colony hybridization. A strongly hybridizing clone, named pEPO4E7 is selected.

pEPO4E7 DNA is isolated, digested with several restriction endonucleases, and probed in Southern hybridization experiments with the 2.2 kb BamHI—HindIII fragment. A strongly hybridizing NotI fragment of approximately 9 kb in size is selected and subcloned into pBluescript II SK– to yield pEPO4E7-N9-8. Further Southern hybridization experiments reveal that the approximately 9 kb NotI insert of pEPO4E7-N9-8 overlaps pEPO15-NH2 over 6 kb in a NotI—HindIII fragment, while the remaining approximately 3 kb HindIII—NotI fragment would extend the subclone contig described in Example 9. End sequencing reveals, however, that the downstream end of the insert of pEPO4E7-N9-8 contains the BamHI—NotI polylinker of pScosTriplex-II, thereby indicating that the genomic DNA insert of pEPO4E7 ends at a Sau3AI site within the extending HindIII—NotI fragment and that the NotI site is derived from pScosTriplex-II.

An approximately 1.6 kb PstI—SalI fragment derived from the approximately 3 kb extending HindIII—NotI subfragment of pEPO4E7-N9-8, containing only *Sorangium cellulosum* So ce90—derived sequences free of vector, is used as a probe against the bacterial artificial chromosome library described in Example 2. Besides the previously-isolated EPO15, a Bac clone, named EPO32, is found to strongly hybridize to the probe. pEPO32 is isolated, digested with several restriction endonucleases, and hybridized with the approximately 1.6 kb PstI—SalI probe. A HindIII—EcoRV fragment of about 13 kb in size is found to strongly hybridize to the probe, and is subcloned into pBluescript II SK− digested with HindIII and HincII to yield pEPO32-HEV15.

Oligonucleotide primers are designed based on the downstream end sequence of pEPO15-NH2 and on the upstream (HindIII) end sequence derived from pEPO32-HEV15, and used in sequencing reactions with pEPO4E7-N9-8 as the template. The sequences reveal the existence of a small HindIII fragment (EPO4E7-H0.02) of 24 bp, undetectable in standard restriction analysis, separating the HindIII site at the downstream end of pEPO15-NH2 from the HindIII site at the upstream end of pEPO32-HEV15.

Thus, the subclone contig described in Example 9 is extended to include the HindIII fragment EPO4E7-H0.02 and the insert of pEPO32-HEV15, and constitutes the inserts of: pEPO15-NH6, pEPO15-H2.7, pEPO15-NH24, pEPO15-NH2, EPO4E7-H0.02 and pEPO32-HEV15, in this order.

EXAMPLE 11

Nucleotide Sequence Determination of the Subclone Contig Covering the Epothilone Biosynthesis Genes The nucleotide sequence of the subclone contig described in Example 10 is determined as follows.

pEPO15-H2.7. Plasmid DNA is isolated from the strain *Escherichia coli* DH10B [pEPO15-H2.7], and the nucleotide sequence of the 2.7-kb BamHI insert in pEPO15-H2.7 is determined. Automated DNA sequencing is done on the double-stranded DNA template by the dideoxynucleotide chain termination method, using Applied Biosystems model 377 sequencers. The primers used are the universal reverse primer (5' GGA AAC AGC TAT GAC CAT G 3' (SEQ ID NO:24)) and the universal forward primer (5' GTA AAA CGA CGG CCA GT 3' (SEQ ID NO:25)). In subsequent rounds of sequencing reactions, custom-synthesized oligonucleotides, designed for the 3' ends of the previously determined sequences, are used to extend and join contigs.

pEPO15-NH6, pEPO15-NH24 and pEPO15-NH2. The HindIII inserts of these plasmids are isolated, and subjected to random fragmentation using a Hydroshear apparatus (Genomic Instrumentation Services, Inc.) to yield an average fragment size of 1–2 kb. The fragments are end-repaired using T4 DNA Polymerase and Klenow DNA Polymerase enzymes in the presence of desoxynucleotide triphosphates, and phosphorylated with T4 DNA Kinase in the presence of ribo-ATP. Fragments in the size range of 1.5–2.2 kb are isolated from agarose gels, and ligated into pBluescript II SK− that has been cut with EcoRV and dephosphorylated. Random subclones are sequenced using the universal reverse and the universal forward primers.

pEPO32-HEV15. pEPO32-HEV15 is digested with HindIII and SspI, the approximately 13.3 kb fragment containing the ~13 kb HindIII—EcoRV insert from *So. cellulosum* So ce90 and a 0.3 kb HincII—SspI fragment from pBluescript II SK− is isolated, and partially digested with HaeIII to yield fragments with an average size of 1–2 kb. Fragments in the size range of 1.5–2.2 kb are isolated from agarose gels, and ligated into pBluescript II SK− that has been cut with EcoRV and dephosphorylated. Random subclones are sequenced using the universal reverse and the universal forward primers.

The chromatograms are analyzed and assembled into contigs with the Phred, Phrap and Consed programs (Ewing, et al., *Genome Res.* 8(3): 175–185 (1998); Ewing, et al., *Genome Res.* 8(3): 186–194 (1998); Gordon, et al., *Genome Res.* 8(3): 195–202 (1998)). Contig gaps are filled, sequence discrepancies are resolved, and low-quality regions are resequenced using custom-designed oligonucleotide primers for sequencing on either the original subclones or selected clones from the random subclone libraries. Both strands are completely sequenced, and every basepair is covered with at least a minimum aggregated Phred score of 40 (confidence level of 99.99%).

The nucleotide sequence of the 68750 bp contig is shown as SEQ ID NO:1.

EXAMPLE 12

Nucleotide Sequence Analysis of the Epothilone Biosynthesis Genes

SEQ ID NO:1 is found to contain 22 ORFs as detailed below in Table 1:

TABLE 1

| ORF | Start codon | Stop codon | Homology of deduced protein | Proposed function of deduced protein |
| --- | --- | --- | --- | --- |
| orf1 | outside of sequenced range | 1826 | | |
| orf2* | 3171 | 1900 | Hypothetical protein SP: Q11037; DD-peptidase SP:P15555 | |
| orf3 | 3415 | 5556 | Na/H antiporter PID:D1017724 | Transport |
| orf4* | 5992 | 5612 | | |
| orf5 | 6226 | 6675 | | |
| epoA | 7610 | 11875 | Type I polyketide synthase | Epothilone synthase: Thiazole ring formation |
| epoP | 11872 | 16104 | Non-ribosomal peptide synthetase | Epothilone synthase: Thiazole ring formation |
| epoB | 16251 | 21749 | Type I polyketide synthase | Epothilone synthase: Polyketide backbone formation |
| epoC | 21746 | 43519 | Type I polyketide synthase | Epothilone synthase: Polyketide backbone formation |
| epoD | 43524 | 54920 | Type I polyketide synthase | Epothilone synthase: Polyketide backbone formation |
| epoE | 54935 | 62254 | Type I polyketide synthase | Epothilone synthase: Polyketide backbone formation |
| epoF | 62369 | 63628 | Cytochrome P450 | Epothilone macrolactone oxidase |

TABLE 1-continued

| ORF | Start codon | Stop codon | Homology of deduced protein | Proposed function of deduced protein |
|---|---|---|---|---|
| orf6 | 63779 | 64333 | | |
| orf7* | 64290 | 63853 | | |
| orf8 | 64363 | 64920 | | |
| orf9* | 64727 | 64287 | | |
| orf10 | 65063 | 65767 | | |
| orf11* | 65874 | 65008 | | |
| orf12* | 66338 | 65871 | | |
| orf13 | 66667 | 67137 | | |
| orf14 | 67334 | 68251 | Hypothetical protein GI:3293544; Cation efflux system protein GI:2623026 | Transport |
| orf15 | 68346 | outside of sequenced range | | |

*On the reverse complementer strand. Numbering according to SEQ ID NO: 1.

epoA (nucleotides 7610–11875 of SEQ ID NO:1) codes for EPOS A (SEQ ID NO:2), a type I polyketide synthase consisting of a single module, and harboring the following domains: β-ketoacyl-synthase (KS) (nucleotides 7643–8920 of SEQ ID NO:1, amino acids 11–437 of SEQ ID NO:2); acyltransferase (AT) (nucleotides 9236–10201 of SEQ ID NO:1, amino acids 543–864 of SEQ ID NO:2); enoyl reductase (ER) (nucleotides 10529–11428 of SEQ ID NO:1, amino acids 974–1273 of SEQ ID NO:2); and acyl carrier protein homologous domain (ACP) (nucleotides 11549–11764 of SEQ ID NO:1, amino acids 1314–1385 of SEQ ID NO:2). Sequence comparisons and motif analysis (Haydock, et al. *FEBS Lett*. 374: 246–248 (1995); Tang, et al., *Gene* 216: 255–265 (1998)) reveal that the AT encoded by EPOS A is specific for malonyl-CoA. EPOS A should be involved in the initiation of epothilone biosynthesis by loading the acetate unit to the multienzyme complex that will eventually form part of the 2-methylthiazole ring (C26 and C20).

epoP (nucleotides 11872–16104 of SEQ ID NO:1) codes for EPOS P (SEQ ID NO:3), a non-ribosomal peptide synthetase containing one module. EPOS P harbors the following domains:

peptide bond formation domain, as delineated by motif K (amino acids 72–81 [FPLTDIQESY] of SEQ ID NO:3, corresponding to nucleotide positions 12085–12114 of SEQ ID NO:1); motif L (amino acids 118–125 [VVARHDML] of SEQ ID NO:3, corresponding to nucleotide positions 12223–12246 of SEQ ID NO:1); motif M (amino acids 199–212 [SIDLINVDLGSLSI] of SEQ ID NO:3, corresponding to nucleotide positions 12466–12507 of SEQ ID NO:1); and motif O (amino acids 353–363 [GDFTSMVLLDI] of SEQ ID NO:3, corresponding to nucleotide positions 12928–12960 of SEQ ID NO:1);

aminoacyl adenylate formation domain, as delineated by motif A (amino acids 549–565 [LTYEELSRRSRRLGARL] of SEQ ID NO:3, corresponding to nucleotide positions 13516–13566 of SEQ ID NO:1); motif B (amino acids 588–603 [VAVLAVLESGAAYVPI] of SEQ ID NO:3, corresponding to nucleotide positions 13633–13680 of SEQ ID NO:1); motif C (amino acids 669–684 [AYVIYTSGSTGLPKGV] of SEQ ID NO:3, corresponding to nucleotide positions 13876–13923 of SEQ ID NO:1); motif D (amino acids 815–821 [SLGGATE] of SEQ ID NO:3, corresponding to nucleotide positions 14313–14334 of SEQ ID NO:1); motif E (amino acids 868–892 [GQLYIGGVGLALGYWRDEEKTRKSF] of SEQ ID NO:3, corresponding to nucleotide positions 14473–14547 of SEQ ID NO:1); motif F (amino acids 903–912 [YKTGDLGRYL] of SEQ ID NO:3, corresponding to nucleotide positions 14578–14607 of SEQ ID NO:1); motif G (amino acids 918–940 [EFMGREDNQIKLRGYRVELGEIE] of SEQ ID NO:3, corresponding to nucleotide positions 14623–14692 of SEQ ID NO:1); motif H (amino acids 1268–1274 [LPEYMVP] of SEQ ID NO:3, corresponding to nucleotide positions 15673–15693 of SEQ ID NO:1); and motif I (amino acids 1285–1297 [LTSNGKVDRKALR] of SEQ ID NO:3, corresponding to nucleotide positions 15724–15762 of SEQ ID NO:1);

an unknown domain, inserted between motifs G and H of the aminoacyl adenylate formation domain (amino acids 973–1256 of SEQ ID NO:3, corresponding to nucleotide positions 14788–15639 of SEQ ID NO:1); and a peptidyl carrier protein homologous domain (PCP), delineated by motif J (amino acids 1344–1351 [GATSIHIV] of SEQ ID NO:3, corresponding to nucleotide positions 15901–15924 of SEQ ID NO:1).

It is proposed that EPOS P is involved in the activation of a cysteine by adenylation, binding the activated cysteine as an aminoacyl-S-PCP, forming a peptide bond between the enzyme-bound cysteine and the acetyl-S-ACP supplied by EPOS A, and the formation of the initial thiazoline ring by intramolecular heterocyclization. The unknown domain of EPOS P displays very weak homologies to NAD(P)H oxidases and reductases from Bacillus species. Thus, this unknown domain and/or the ER domain of EPOS A may be involved in the oxidation of the initial 2-methylthiazoline ring to a 2-methylthiazole.

epoB (nucleotides 16251–21749 of SEQ ID NO:1) codes for EPOS B (SEQ ID NO:4), a type I polyketide synthase consisting of a single module, and harboring the following domains: KS (nucleotides 16269–17546 of SEQ ID NO:1, amino acids 7–432 of SEQ ID NO:4); AT (nucleotides 17865–18827 of SEQ ID NO:1, amino acids 539–859 of SEQ ID NO:4); dehydratase (DH) (nucleotides 18855–19361 of SEQ ID NO:1, amino acids 869–1037 of SEQ ID NO:4); β-ketoreductase (KR) (nucleotides 20565–21302 of SEQ ID NO:1, amino acids 1439–1684 of SEQ ID NO:4); and ACP (nucleotides 21414–21626 of SEQ ID NO:1, amino acids 1722–1792 of SEQ ID NO:4). Sequence comparisons and motif analysis reveal that the AT encoded by EPOS B is specific for methylmalonyl-CoA. EPOS A should be involved in the first polyketide chain extension by catalysing the Claisen-like condensation of the 2-methyl-4-thiazolecarboxyl-S-PCP starter group with the methylmalonyl-S-ACP, and the concomitant reduction of the b-keto group of C17 to an enoyl.

epoC (nucleotides 21746–43519 of SEQ ID NO:1) codes for EPOS C (SEQ ID NO:5), a type I polyketide synthase consisting of 4 modules. The first module harbors a KS (nucleotides 21860–23116 of SEQ ID NO:1, amino acids 39–457 of SEQ ID NO:5); a malonyl CoA-specific AT (nucleotides 23431–24397 of SEQ ID NO:1, amino acids 563–884 of SEQ ID NO:5); a KR (nucleotides 25184–25942 of SEQ ID NO:1, amino acids 1147–1399 of SEQ ID NO:5); and an ACP (nucleotides 26045–26263 of SEQ ID NO:1, amino acids 1434–1506 of SEQ ID NO:5). This module incorporates an acetate extender unit (C14-C13) and reduces the β-keto group at C15 to the hydroxyl group that takes part in the final lactonization of the epothilone macrolactone ring. The second module of EPOS C harbors a KS (nucleotides 26318–27595 of SEQ ID NO:1, amino acids 1524–1950 of SEQ ID NO-5); a malonyl CoA-specific AT (nucleotides 27911–28876 of SEQ ID NO:1, amino acids 2056–2377 of SEQ ID NO:5); a KR (nucleotides 29678–30429 of SEQ ID NO:1, amino acids 2645–2895 of SEQ ID NO:5); and an ACP (nucleotides 30539–30759 of SEQ ID NO:1, amino acids 2932–3005 of SEQ ID NO:5). This module incorporates an acetate extender unit (C12-C11) and reduces the β-keto group at C13 to a hydroxyl group. Thus, the nascent polyketide chain of epothilone corresponds to epothilone A, and the incorporation of the methyl side chain at C12 in epothilone B would require a post-PKS C-methyltransferase activity. The formation of the epoxi ring at C13-C12 would also require a post-PKS oxidation step. The third module of EPOS C harbors a KS (nucleotides 30815–32092 of SEQ ID NO:1, amino acids 3024–3449 of SEQ ID NO:5); a malonyl CoA-specific AT (nucleotides 32408–33373 of SEQ ID NO:1, amino acids 3555–3876 of SEQ ID NO:5); a DH (nucleotides 33401–33889 of SEQ ID NO:1, amino acids 3886–4048 of SEQ ID NO:5); an ER (nucleotides 35042–35902 of SEQ ID NO:1, amino acids 4433–4719 of SEQ ID NO:5); a KR (nucleotides 35930–36667 of SEQ ID NO:1, amino acids 4729–4974 of SEQ ID NO:5); and an ACP (nucleotides 36773–36991 of SEQ ID NO:1, amino acids 5010–5082 of SEQ ID NO:5). This module incorporates an acetate extender unit (C10-C9) and fully reduces the β-keto group at C11. The fourth module of EPOS C harbors a KS (nucleotides 37052–38320 of SEQ ID NO:1, amino acids 5103–5525 of SEQ ID NO:5); a methylmalonyl CoA-specific AT (nucleotides 38636–39598 of SEQ ID NO:1, amino acids 5631–5951 of SEQ ID NO:5); a DH (nucleotides 39635–40141 of SEQ ID NO:1, amino acids 5964–6132 of SEQ ID NO:5); an ER (nucleotides 41369–42256 of SEQ ID NO:1, amino acids 6542–6837 of SEQ ID NO:5); a KR (nucleotides 42314–43048 of SEQ ID NO:1, amino acids 6857–7101 of SEQ ID NO:5); and an ACP (nucleotides 43163–43378 of SEQ ID NO:1, amino acids 7140–7211 of SEQ ID NO:5). This module incorporates a propionate extender unit (C24 and C8-C7) and fully reduces the β-keto group at C9.

epoD (nucleotides 43524–54920 of SEQ ID NO:1) codes for EPOS D (SEQ ID NO:6), a type I polyketide synthase consisting of 2 modules. The first module harbors a KS (nucleotides 43626–44885 of SEQ ID NO:1, amino acids 35–454 of SEQ ID NO:6); a methylmalonyl CoA-specific AT (nucleotides 45204–46166 of SEQ ID NO:1, amino acids 561–881 of SEQ ID NO:6); a KR (nucleotides 46950–47702 of SEQ ID NO:1, amino acids 1143–1393 of SEQ ID NO:6); and an ACP (nucleotides 47811–48032 of SEQ ID NO:1, amino acids 1430–1503 of SEQ ID NO:6). This module incorporates a propionate extender unit (C23 and C6-C5) and reduces the β-keto group at C7 to a hydoxyl group. The second module harbors a KS (nucleotides 48087–49361 of SEQ ID NO:1, amino acids 1522–1946 of SEQ ID NO: 6); a methylmalonyl CoA-specific AT (nucleotides 49680–50642 of SEQ ID NO:1, amino acids 2053–2373 of SEQ ID NO:6); a DH (nucleotides 50670–51176 of SEQ ID NO:1, amino acids 2383–2551 of SEQ ID NO:6); a methyltransferase (MT, nucleotides 51534–52657 of SEQ ID NO:1, amino acids 2671–3045 of SEQ ID NO:6); a KR (nucleotides 53697–54431 of SEQ ID NO:1, amino acids 3392–3636 of SEQ ID NO:6); and an ACP (nucleotides 54540–54758 of SEQ ID NO:1, amino acids 3673–3745 of SEQ ID NO:6). This module incorporates a propionate extender unit (C21 or C22 and C4-C3) and reduces the β-keto group at C5 to a hydoxyl group. This reduction is somewhat unexpected, since epothilones contain a keto group at C5. Discrepancies of this kind between the deduced reductive capabilities of PKS modules and the redox state of the corresponding positions in the final polyketide products have been, however, reported in the literature (see, for example, Schwecke, et al., *Proc. Natl. Acad. Sci. USA* 92: 7839–7843 (1995) and Schupp, et al., *FEMS Microbiology Letters* 159: 201–207 (1998)). An important feature of epothilones is the presence of gem-methyl side groups at C4 (C21 and C22). The second module of EPOS D is predicted to incorporate a propionate unit into the growing polyketide chain, providing one methyl side chain at C4. This module also contains a methyltransferase domain integrated into the PKS between the DH and the KR domains, in an arrangement similar to the one seen in the HMWP1 yersiniabactin synthase (Gehring, A. M., DeMoll, E., Fetherston, J. D., Mori, I., Mayhew, G. F., Blattner, F. R., Walsh, C. T., and Perry, R. D.: Iron acquisition in plague: modular logic in enzymatic biogenesis of yersiniabactin by Yersinia pestis. *Chem. Biol.* 5, 573–586, 1998). This MT domain in EPOS D is proposed to be responsible for the incorporation of the second methyl side group (C21 or C22) at C4.

epoE (nucleotides 54935–62254 of SEQ ID NO:1) codes for EPOS E (SEQ ID NO:7), a type I polyketide synthase consisting of one module, harboring a KS (nucleotides 55028–56284 of SEQ ID NO:1, amino acids 32–450 of SEQ ID NO:7); a malonyl CoA-specific AT (nucleotides 56600–57565 of SEQ ID NO:1, amino acids 556–877 of SEQ ID NO:7); a DH (nucleotides 57593–58087 of SEQ ID NO:1, amino acids 887–1051 of SEQ ID NO:7); a probably nonfunctional ER (nucleotides 59366–60304 of SEQ ID NO:1, amino acids 1478–1790 of SEQ ID NO:7); a KR (nucleotides 60362–61099 of SEQ ID NO:1, amino acids 1810–2055 of SEQ ID NO:7); an ACP (nucleotides 61211–61426 of SEQ ID NO:1, amino acids 2093–2164 of SEQ ID NO:7); and a thioesterase (TE) (nucleotides 61427–62254 of SEQ ID NO:1, amino acids 2165–2439 of SEQ ID NO:7). The ER domain in this module harbors an active site motif with some highly unusual amino acid substitutions that probably render this domain inactive. The module incorporates an acetate extender unit (C2-C1), and reduces the β-keto at C3 to an enoyl group. Epothilones contain a hydroxyl group at C3, so this reduction also appears to be excessive as discussed for the second module of EPOS D. The TE domain of EPOS E takes part in the release and cyclization of the grown polyketide chain via lactonization between the carboxyl group of C1 and the hydroxyl group of C15.

Five ORFs are detected upstream of epoA in the sequenced region. The partially sequenced orf1 has no homologues in the sequence databanks. The deduced protein product (Orf 2, SEQ ID NO:10) of orf2 (nucleotides 3171–1900 on the reverse complement strand of SEQ ID NO:1) shows strong similarities to hypothetical ORFs from *Mycobacterium* and *Streptomyces coelicolor*, and more distant similarities to carboxypeptidases and DD-peptidases of different bacteria. The deduced protein product of orf3 (nucleotides 3415–5556 of SEQ ID NO:1), Orf 3 (SEQ ID NO:11), shows homologies to Na/H antiporters of different bacteria. Orf 3 might take part in the export of epothilones from the producer strain. orf4 and orf5 have no homologues in the sequence databanks.

Eleven ORFs are found downstream of epoE in the sequenced region. epoF (nucleotides 62369–63628 of SEQ ID NO:1) codes for EPOS F (SEQ ID NO:8), a deduced protein with strong sequence similarities to cytochrome P450 oxygenases. EPOS F may take part in the adjustment of the redox state of the carbons C12, C5, and/or C3. The deduced protein product of orf14 (nucleotides 67334–68251 of SEQ ID NO:1), Orf 14 (SEQ ID NO:22) shows strong similarities to GI:3293544, a hypothetic protein with no proposed function from *Streptomyces coelicolor*, and also to GI:2654559, the human embrionic lung protein. It is also more distantly related to cation efflux system proteins like GI:2623026 from *Methano bacterium thermoautotrophicum*, so it might also take part in the export of epothilones from the producing cells. The remaining ORFs (orf6-orf13 and orf15) show no homologies to entries in the sequence databanks.

EXAMPLE 13

Recombinant Expression of Epothilone Biosynthesis Genes

Epothilone synthase genes according to the present invention are expressed in heterologous organisms for the purposes of epothilone production at greater quantities than can be accomplished by fermentation of *Sorangium cellulosum*. A preferable host for heterologous expression is Streptomyces, e.g. *Streptomyces coelicolor*, which natively produces the polyketide actinorhodin. Techniques for recombinant PKS gene expression in this host are described in McDaniel et al., *Science* 262: 1546–1550 (1993) and Kao et al., *Science* 265: 509–512 (1994). See also, Holmes et al., *EMBO Journal* 12(8): 3183–3191 (1993) and Bibb et al., *Gene* 38: 215–226 (1985), as well as U.S. Pat. Nos. 5,521,077, 5,672,491, and 5,712,146, which are incorporated herein by reference.

According to one method, the heterologous host strain is engineered to contain a chromosomal deletion of the actinorhodin (act) gene cluster. Expression plasmids containing the epothilone synthase genes of the invention are constructed by transferring DNA from a temperature-sensitive donor plasmid to a recipient shuttle vector in *E. coli* (McDaniel et al. (1993) and Kao et al. (1994)), such that the synthase genes are built-up by homologous recombination within the vector. Alternatively, the epothilone synthase gene cluster is introduced into the vector by restriction fragment ligation. Following selection, e.g. as described in Kao et al. (1994), DNA from the vector is introduced into the act-minus *Streptomyces coelicolor* strain according to protocols set forth in Hopwood et al., Genetic Manipulation of Streptomyces. *A Laboratory Manual* (John Innes Foundation, Norwich, United Kingdom, 1985), incorporated herein by reference. The recombinant Streptomyces strain is grown on R2YE medium (Hopwood et al. (1985)) and produces epothilones. Alternatively, the epothilone synthase genes according to the present invention are expressed in other host organisms such as pseudomonads, Bacillus, yeast, insect cells and/or *E. coli*. PKS and NRPS genes are preferably expressed in *E. coli* using the pT7-7 vector, which uses the T7 promoter. See, Tabor et al., *Proc. Natl. Acad. Sci. USA* 82: 1074–1078 (1985). In another embodiment, the expression vectors pKK223-3 and pKK223-2 are used to express PKS and NRPS genes in *E. coli*, either in transcriptional or translational fusion, behind the tac or trc promoter. Expression of PKS and NRPS genes in heterologous hosts, which do not naturally have the phosphopantetheinyl (P-pant) transferases needed for post-translational modification of PKS enzymes, requires the coexpression in the host of a P-pant transferase, as described by Kealey et al., *Proc. Natl. Acad. Sci. USA* 95: 505–509 (1998).

EXAMPLE 14

Isolation of Epothilones from Producing Strains

Examples of cultivation, fermentation, and extraction procedures for polyketide isolation, which are useful for extracting epothilones from both native and recombinant hosts according to the present invention, are given in WO 93/10121, incorporated herein by reference, in Example 57 of U.S. Pat. No. 5,639,949, in Gerth et al., *J. Antibiotics* 49: 560–563 (1996), and in Swiss patent application no. 396/98, filed Feb. 19, 1998, and U.S. patent application Ser. No. 09/248,910 (that discloses also preferred mutant strains of *Sorangium cellulosum*), both of which are incorporated herein by reference. The following are procedures that are useful for isolating epothilones from cultured *Sorangium cellulosum* strains, e.g., So ce90, and may also be used for the isolation of epothilone from recombinant hosts.

A: Cultivation of Epothilone-Producing Strains:

| | | |
|---|---|---|
| Strain: | *Sorangium cellulosum* Soce-90 or a recombinant host strain according to the present invention. | |
| Preservation of the strain: | In liquid $N_2$. | |
| Media: | Precultures and intermediate cultures: G52 Main culture: 1B12 | |
| G52 Medium: | | |
| | yeast extract, low in salt (BioSpringer, Maison Alfort, France) | 2 g/l |
| | $MgSO_4$ ($7H_2O$) | 1 g/l |
| | $CaCl_2$ ($2H_2O$) | 1 g/l |
| | soya meal defatted Soyamine 50T (Lucas Meyer, Hamburg, Germany) | 2 g/l |
| | potato starch Noredux A-150 (Blattmann, Waedenswil, Switzerland) | 8 g/l |
| | glucose anhydrous | 2 g/l |
| | EDTA-Fe(III)-Na salt (8 g/l) | 1 ml/l |
| | pH 7.4, corrected with KOH Sterilisation: 20 mins. 120° C. | |
| 1B12 Medium: | | |
| | potato starch Noredux A-150 (Blattmann, Waedenswil, Switzerland) | 20 g/l |
| | soya meal defatted Soyamine 50T (Lucas Meyer, Hamburg, Germany) | 11 g/l |
| | EDTA-Fe(III)-Na salt | 8 mg/l |
| | pH 7.8, corrected with KOH Sterilisation: 20 mins. 120° C. | |
| Addition of cyclodextrins and cyclodextrin | Cyclodextrins (Fluka, Buchs, Switzerland, or Wacker Chemie, | |

| derivatives: | Munich, Germany) in different concentrations are sterilised separately and added to the 1B12 medium prior to seeding. |
|---|---|

Cultivation: 1 ml of the suspension of *Sorangium cellulosum* Soce-90 from a liquid $N_2$ ampoule is transferred to 10 ml of G52 medium (in a 50 ml Erlenmeyer flask) and incubated for 3 days at 180 rpm in an agitator at 30° C., 25 mm displacement. 5 ml of this culture is added to 45 ml of G52 medium (in a 200 ml Erlenmeyer flask) and incubated for 3 days at 180 rpm in an agitator at 30° C., 25 mm displacement. 50 ml of this culture is then added to 450 ml of G52 medium (in a 2 litre Erlenmeyer flask) and incubated for 3 days at 180 rpm in an agitator at 30° C., 50 mm displacement.

Maintenance culture: The culture is overseeded every 3–4 days, by adding 50 ml of culture to 450 ml of G52 medium (in a 2 liter Erlenmeyer flask). All experiments and fermentations are carried out by starting with this maintenance culture.

Tests in a Flask:

(I) Preculture in an Agitating Flask:
Starting with the 500 ml of maintenance culture, 1×450 ml of G52 medium are seeded with 50 ml of the maintenance culture and incubated for 4 days at 180 rpm in an agitator at 30° C., 50 mm displacement.

(ii) Main Culture in the Agitating Flask:
40 ml of 1B12 medium plus 5 g/l 4-morpholine-propane-sulfonic acid (=MOPS) powder (in a 200 ml Erlenmeyer flask) are mixed with 5 ml of a 10×concentrated cyclodextrin solution, seeded with 10 ml of preculture and incubated for 5 days at 180 rpm in an agitator at 30° C., 50 mm displacement.

Fermentation: Fermentations are carried out on a scale of 10 liters, 100 litres and 500 liters. 20 liter and 100 litre fermentations serve as an intermediate culture step. Whereas the precultures and intermediate cultures are seeded as the maintenance culture 10% (v/v), the main cultures are seeded with 20% (v/v) of the intermediate culture. In contrast to the agitating cultures, ingredients of the fermentation media are calculated on the final culture volume including the inoculum. If, for example, 18 liters of medium +2 liters of inoculum are combined, then substances for 20 liters are weighed in, but are only mixed with 18 liters.

Preculture in an Agitating Flask:
Starting with the 500 ml maintenance culture, 4×450 ml of G52 medium (in a 2 litre Erlenmeyer flask) are each seeded with 50 ml thereof, and incubated for 4 days at 180 rpm in an agitator at 30° C., 50 mm displacement.

Intermediate Culture, 20 Litres or 100 Litres:
20 liters: 18 liters of G52 medium in a fermenter having a total volume of 30 liters are seeded with 2 liters of preculture. Cultivation lasts for 3–4 days, and the conditions are: 30° C., 250 rpm, 0.5 liters of air per litre liquid per min, 0.5 bars excess pressure, no pH control. 100 liters: 90 liters of G52 medium in a fermenter having a total volume of 150 liters are seeded with 10 liters of the 20 litre intermediate culture. Cultivation lasts for 3–4 days, and the conditions are: 30° C., 150 rpm, 0.5 liters of air per litre liquid per min, 0.5 bars excess pressure, no pH control.

Main Culture, 10 Litres, 100 Litres or 500 Litres:
10 liters: The media substances for 10 liters of 1 B12 medium are sterilised in 7 liters of water, then 1 litre of a sterile 10% 2-(hydroxypropyl)-β-cyclodextrin solution are added, and seeded with 2 liters of a 20 litre intermediate culture. The duration of the main culture is 6–7 days, and the conditions are: 30° C., 250 rpm, 0.5 liters of air per litre of liquid per min, 0.5 bars excess pressure, pH control with $H_2SO_4$/KOH to pH 7.6+/−0.5 (i.e. no control between pH 7.1 and 8.1).

100 liters: The media substances for 100 liters of 1B12 medium are sterilised in 70 liters of water, then 10 liters of a sterile 10% 2-(hydroxypropyl)-β-cyclodextrin solution are added, and seeded with 20 liters of a 20 litre intermediate culture. The duration of the main culture is 6–7 days, and the conditions are: 30° C., 200 rpm, 0.5 liters air per litre liquid per min., 0.5 bars excess pressure, pH control with $H_2SO_4$/KOH to pH 7.6+/−0.5. The chain of seeding for a 100 litre fermentation is shown schematically as follows:

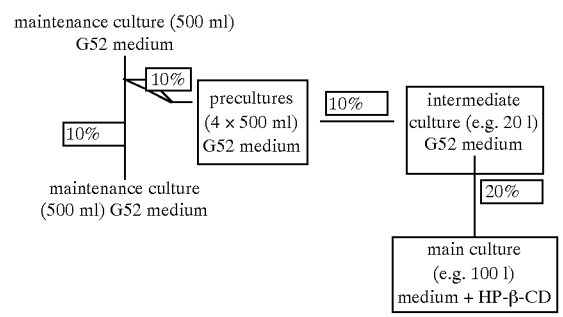

500 liters: The media substances for 500 liters of 1B12 medium are sterilised in 350 liters of water, then 50 liters of a sterile 10% 2-(hydroxypropyl)-β-cyclodextrin solution are added, and seeded with 100 liters of a 100 litre intermediate culture. The duration of the main culture is 6–7 days, and the conditions are: 30° C., 120 rpm, 0.5 liters air per litre liquid per min., 0.5 bars excess pressure, pH control with $H_2SO_4$/KOH to pH 7.6+/−0.5.

Product Analysis:

Preparation of the Sample:
50 ml samples are mixed with 2 ml of polystyrene resin Amberlite XAD16 (Rohm+Haas, Frankfurt, Germany) and shaken at 180 rpm for one hour at 30° C. The resin is subsequently filtered using a 150 μm nylon sieve, washed with a little water and then added together with the filter to a 15 ml Nunc tube.

Elution of the Product from the Resin:
10 ml of isopropanol (>99%) are added to the tube with the filter and the resin. Afterwards, the sealed tube is shaken for 30 minutes at room temperature on a Rota-Mixer (Labinco BV, Netherlands). Then, 2 ml of the liquid are centrifuged off and the supernatant is added using a pipette to HPLC tubes.

HPLC Analysis:

| Column: | Waters-Symetry C18, 100 × 4 mm, 3.5 μm WAT066220 + preliminary column 3.9 × 20 mm WAT054225 |
|---|---|
| Solvents: | A: 0.02% phosphoric acid |
| | B: Acetonitrile (HPLC-Quality) |
| Gradient: | 41% B from 0 to 7 min. |
| | 100% B from 7.2 to 7.8 min. |
| | 41% B from 8 to 12 min. |
| Oven temp.: | 30° C. |
| Detection: | 250 nm, UV-DAD detection |
| Injection vol.: | 10 μl |
| Retention time: | Epo A: 4.30 min Epo B: 5.38 min |

B: Effect of the Addition of Cyclodextrin and Cyclodextrin Derivatives to the Epothilone Concentrations Attained.

Cyclodextrins are cyclic (α-1,4)-linked oligosaccharides of α-D-glucopyranose with a relatively hydrophobic central cavity and a hydrophilic external surface area.

The following are distinguished in particular (the figures in parenthesis give the number of glucose units per molecule): α-cyclodextrin (6), β-cyclodextrin (7), γ-cyclodextrin (8), δ-cyclodextrin (9), ε-cyclodextrin (10), ζ-cyclodextrin (11), η-cyclodextrin (12), and θ-cyclodextrin (13). Especially preferred are δ-cyclodextrin and in particular α-cyclodextrin, β-cyclodextrin or γ-cyclodextrin, or mixtures thereof.

Cyclodextrin derivatives are primarily derivatives of the above-mentioned cyclodextrins, especially of α-cyclodextrin, β-cyclodextrin or γ-cyclodextrin, primarily those in which one or more up to all of the hydroxy groups (3 per glucose radical) are etherified or esterified. Ethers are primarily alkyl ethers, especially lower alkyl, such as methyl or ethyl ether, also propyl or butyl ether; the arylhydroxyalkyl ethers, such as phenyl-hydroxy-lower-alkyl, especially phenyl-hydroxyethyl ether; the hydroxyalkyl ethers, in particular hydroxy-lower-alkyl ethers, especially 2-hydroxyethyl, hydroxypropyl such as 2-hydroxypropyl or hydroxybutyl such as 2-hydroxybutyl ether; the carboxyalkyl ethers, in particular carboxy-lower-alkyl ethers, especially carboxymethyl or carboxyethyl ether; derivatised carboxyalkyl ethers, in particular derivatised carboxy-lower-alkyl ether in which the derivatised carboxy is etherified or amidated carboxy (primarily aminocarbonyl, mono- or di-lower-alkyl-aminocarbonyl, morpholino-, piperidino-, pyrrolidino- or piperazino-carbonyl, or alkyloxycarbonyl), in particular lower alkoxycarbonyl-lower-alkyl ether, for example methyloxycarbonylpropyl ether or ethyloxycarbonylpropyl ether; the sulfoalkyl ethers, in particular sulfolower-alkyl ethers, especially sulfobutyl ether; cyclodextrins in which one or more OH groups are etherified with a radical of formula

—O—[alk-O—]$_n$—H wherein alk is alkyl, especially lower alkyl, and n is a whole number from 2 to 12, especially 2 to 5, in particular 2 or 3; cyclodextrins in which one or more OH groups are etherified with a radical of formula

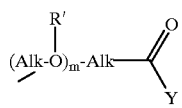

wherein R' is hydrogen, hydroxy, —O—(alk-O)$_z$—H, —O—(alk(—R)—O—)$_p$—H or —O—(alk(—R)—O—)$_q$—alk-CO—Y; alk in all cases is alkyl, especially lower alkyl; m, n, p, q and z are a whole number from 1 to 12, preferably 1 to 5, in particular 1 to 3; and Y is OR$_1$ or NR$_2$R$_3$, wherein R$_1$, R$_2$ and R$_3$ independently of one another, are hydrogen or lower alkyl, or R$_2$ and R$_3$ combined together with the linking nitrogen signify morpholino, piperidino, pyrrolidino or piperazino; or branched cyclodextrins, in which etherifications or acetals with other sugar molecules are present, especially glucosyl-, diglucosyl- (G$_2$-β-cyclodextrin), maltosyl- or dimaltosyl-cyclodextrin, or N-acetylglucosaminyl-, glucosaminyl-, N-acetylgalactosaminyl- or galactosaminyl-cyclodextrin.

Esters are primarily alkanoyl esters, in particular lower alkanoyl esters, such as acetyl esters of cyclodextrins.

It is also possible to have cyclodextrins in which two or more different said ether and ester groups are present at the same time.

Mixtures of two or more of the said cyclodextrins and/or cyclodextrin derivatives may also exist.

Preference is given in particular to α-, β-, or γ-cyclodextrins or the lower alkyl ethers thereof, such as methyl-β-cyclodextrin or in particular 2,6-di-O-methyl-β-cyclodextrin, or in particular the hydroxy lower alkyl ethers thereof, such as 2-hydroxypropyl-α-, 2-hydroxypropyl-β- or 2-hydroxypropyl-γ-cyclodextrin.

The cyclodextrins or cyclodextrin derivatives are added to the culture medium preferably in a concentration of 0.02 to 10, preferably 0.05 to 5, especially 0.1 to 4, for example 0.1 to 2 percent by weight (w/v).

Cyclodextrins or cyclodextrin derivatives are known or may be produced by known processes (see for example U.S. Pat. No. 3,459,731; U.S. Pat. No. 4,383,992; U.S. Pat. No. 4,535,152; U.S. Pat. No. 4,659,696; EP 0 094 157; EP 0 149 197; EP 0 197 571; EP 0 300 526; EP 0 320 032; EP 0 499 322; EP 0 503 710; EP 0 818 469; WO 90/12035; WO 91/11200; WO 93/19061; WO 95/08993; WO 96/14090; GB 2,189,245; DE 3,118,218; DE 3,317,064 and the references mentioned therein, which also refer to the synthesis of cyclodextrins or cyclodextrin derivatives, or also: T. Loftsson and M. E. Brewster (1996): Pharmaceutical Applications of Cyclodextrins: Drug Solubilization and Stabilisation: Journal of Pharmaceutical Science 85 (10):1017–1025; R. A. Rajewski and V. J. Stella(1996): Pharmaceutical Applications of Cyclodextrins: In Vivo Drug Delivery: Journal of Pharmaceutical Science 85 (11): 1142–1169).

All the cyclodextrin derivatives tested here are obtainable from the company Fluka, Buchs, CH. The tests are carried out in 200 ml agitating flasks with 50 ml culture volume. As controls, flasks with adsorber resin Amberlite XAD-16 (Rohm & Haas, Frankfurt, Germany) and without any adsorber addition are used. After incubation for 5 days, the following epothilone titres can be determined by HPLC:

TABLE 2

| Addition | order No. | Conc [% w/v][1] | Epo A [mg/l] | Epo B [mg/l] |
| --- | --- | --- | --- | --- |
| Amberlite XAD-16 (v/v) | | 2.0 (% v/v) | 9.2 | 3.8 |
| 2-hydroxypropyl-β-cyclodextrin | 56332 | 0.1 | 2.7 | 1.7 |
| 2-hydroxypropyl-β-cyclodextrin | " | 0.5 | 4.7 | 3.3 |
| 2-hydroxypropyl-β-cyclodextrin | " | 1.0 | 4.7 | 3.4 |
| 2-hydroxypropyl-β-cyclodextrin | " | 2.0 | 4.7 | 4.1 |
| 2-hydroxypropyl-β-cyclodextrin | " | 5.0 | 1.7 | 0.5 |
| 2-hydroxypropyl-α-cyclodextrin | 56330 | 0.5 | 1.2 | 1.2 |
| 2-hydroxypropyl-α-cyclodextrin | " | 1.0 | 1.2 | 1.2 |
| 2-hydroxypropyl-α-cyclodextrin | " | 5.0 | 2.5 | 2.3 |
| β-cyclodextrin | 28707 | 0.1 | 1.6 | 1.3 |
| β-cyclodextrin | " | 0.5 | 3.6 | 2.5 |
| β-cyclodextrin | " | 1.0 | 4.8 | 3.7 |
| β-cyclodextrin | " | 2.0 | 4.8 | 2.9 |
| β-cyclodextrin | " | 5.0 | 1.1 | 0.4 |
| methyl-β-cyclodextrin | 66292 | 0.5 | 0.8 | <0.3 |
| methyl-β-cyclodextrin | " | 1.0 | <0.3 | <0.3 |
| methyl-β-cyclodextrin | " | 2.0 | <0.3 | <0.3 |
| 2,6 di-o-methyl-β-cyclodextrin | 39915 | 1.0 | <0.3 | <0.3 |
| 2-hydroxypropyl-γ-cyclodextrin | 56334 | 0.1 | 0.3 | <0.3 |
| 2-hydroxypropyl-γ-cyclodextrin | " | 0.5 | 0.9 | 0.8 |
| 2-hydroxypropyl-γ-cyclodextrin | " | 1.0 | 1.1 | 0.7 |
| 2-hydroxypropyl-γ-cyclodextrin | " | 2.0 | 2.6 | 0.7 |
| 2-hydroxypropyl-γ-cyclodextrin | " | 5.0 | 5.0 | 1.1 |
| no addition | | | 0.5 | 0.5 |

[1]Apart from Amberlite (% v/v), all percentages are by weight (% w/v).

Few of the cyclodextrins tested (2,6-di-o-methyl-β-cyclodextrin, methyl-β-cyclodextrin) display no effect or a negative effect on epothilone production at the concentrations used. 1–2% 2-hydroxy-propyl-β-cyclodextrin and β-cyclodextrin increase epothilone production in the examples by 6 to 8 times compared with production using no cyclodextrins.

C: 10 Litre Fermentation with 1% 2-(hydroxypropyl)-β-Cyclodextrin):

Fermentation is carried out in a 15 liter glass fermenter. The medium contains 10 g/l of 2-(hydroxypropyl)-β-cyclodextrin from Wacker Chemie, Munich, Del. Fermentation progress is illustrated in Table 3. Fermentation is ended after 6 days and working up takes place.

TABLE 3

Progress of a 10 litre fermentation

| duration of culture [d] | Epothilone A [mg/l] | Epothilone B [mg/l] |
|---|---|---|
| 0 | 0 | 0 |
| 1 | 0 | 0 |
| 2 | 0.5 | 0.3 |
| 3 | 1.8 | 2.5 |
| 4 | 3.0 | 5.1 |
| 5 | 3.7 | 5.9 |
| 6 | 3.6 | 5.7 |

D: 100 Litre Fermentation with 1% 2-(hydroxypropyl)-β-Cyclodextrin):

Fermentation is carried out in a 150 liter fermenter. The medium contains 10 g/l of 2-(Hydroxypropyl)-β-cyclodextrin. The progress of fermentation is illustrated in Table 4. The fermentation is harvested after 7 days and worked up.

TABLE 4

Progress of a 100 litre fermentation

| duration of culture [d] | Epothilone A [mg/l] | Epothilone B [mg/l] |
|---|---|---|
| 0 | 0 | 0 |
| 1 | 0 | 0 |
| 2 | 0.3 | 0 |
| 3 | 0.9 | 1.1 |
| 4 | 1.5 | 2.3 |
| 5 | 1.6 | 3.3 |
| 6 | 1.8 | 3.7 |
| 7 | 1.8 | 3.5 |

E: 100 Litre Fermentation with 1% 2-(Hydroxypropyl)-β-Cyclodextrin):

Fermentation is carried out in a 750 liter fermenter. The medium contains 10 g/l of 2-(hydroxypropyl)-β-cyclodextrin. The progress of fermentation is illustrated in Table 5. The fermentation is harvested after 7 days and worked up.

TABLE 5

Progress of a 500 litre fermentation

| duration of culture [d] | Epothilone A [mg/l] | Epothilone B [mg/l] |
|---|---|---|
| 0 | 0 | 0 |
| 1 | 0 | 0 |
| 2 | 0 | 0 |
| 3 | 0.6 | 0.6 |
| 4 | 1.7 | 2.2 |
| 5 | 3.1 | 4.5 |
| 6 | 3.1 | 5.1 |

F: Comparison Example 10 Litre Fermentation Without Adding an Adsorber:

Fermentation is carried out in a 15 liter glass fermenter. The medium does not contain any cyclodextrin or other absorber. The progress of fermentation is illustrated in Table 6. The fermentation is not harvested and worked up.

TABLE 6

Progress of a 10 litre fermentation without adsorber.

| duration of culture [d] | Epothilone A [mg/l] | Epothilone B [mg/l] |
|---|---|---|
| 0 | 0 | 0 |
| 1 | 0 | 0 |
| 2 | 0 | 0 |
| 3 | 0 | 0 |
| 4 | 0.7 | 0.7 |
| 5 | 0.7 | 1.0 |
| 6 | 0.8 | 1.3 |

G: Working up of the Epothilones: Isolation from a 500 liter main culture:

The volume of harvest from the 500 liter main culture of example 2D is 450 liters and is separated using a Westfalia clarifying separator Type SA-20-06 (rpm=6500) into the liquid phase (centrifugate+rinsing water=650 liters) and solid phase (cells=ca. 15 kg). The main part of the epothilones are found in the centrifugate, The centrifuged cell pulp contains <15% of the determined epothilone portion and is not further processed. The 650 liter centrifugate is then placed in a 4000 liter stirring vessel, mixed with 10 liters of Amberlite XAD-16 (centrifugate:resin volume= 65:1) and stirred. After a period of contact of ca. 2 hours, the resin is centrifugate away in a Heine overflow centrifuge (basket content 40 liters; rpm=2800). The resin is discharged from the centrifuge and washed with 10–15 liters of deionised water. Desorption is effected by stirring the resin twice, each time in portions with 30 liters of isopropanol in 30 liter glass stirring vessels for 30 minutes. Separation of the isopropanol phase from the resin takes place using a suction filter. The isopropanol is then removed from the combined isopropanol phases by adding 15–20 liters of water in a vacuum-operated circulating evaporator (Schmid-Verdampfer) and the resulting water phase of ca. 10 liters is extracted 3×each time with 10 liters of ethyl acetate. Extraction is effected in 30 liter glass stirring vessels. The ethyl acetate extract is concentrated to 3–5 liters in a vacuum-operated circulating evaporator (Schmid-Verdampfer) and afterwards concentrated to dryness in a rotary evaporator (Büchi type) under vacuum. The result is an ethyl acetate extract of 50.2 g. The ethyl acetate extract is dissolved in 500 ml of methanol, the insoluble portions filtered off using a folder filter, and the solution added to a 10 kg Sephadex LH 20 column (Pharmacia, Uppsala, Sweden) (column diameter 20 cm, filling level ca. 1.2 m). Elution is effected with methanol as eluant. Epothilone A and B is present predominantly in fractions 21–23 (at a fraction size of 1 liter). These fractions are concentrated to dryness in a vacuum on a rotary evaporator (total weight 9.0 g). These Sephadex peak fractions (9.0 g) are thereafter dissolved in 92 ml of acetonitrile:-water:-methylene chloride=50:40:2, the solution filtered through a folded filter and added to a RP column (equipment Prepbar 200, Merck; 2.0 kg LiChrospher RP-18 Merck, grain size 12 µm, column diameter 10 cm, filling level 42 cm; Merck, Darmstadt, Germany). Elution is effected with acetonitrile:water=3:7 (flow rate=500 ml/min.; retention time of epothilone A=ca. 51–59 mins.; retention time of epothilone B=ca. 60–69 mins.). Fractionation is monitored with a UV detector at 250 nm. The fractions are concentrated to dryness under vacuum on a Büchi-Rotavapor rotary evaporator. The weight of the epothilone A peak fraction is 700 mg, and according to HPLC (external standard) it has a content of 75.1%. That of the epothilone B peak fraction is 1980 mg, and the content according to HPLC (external standard) is 86.6%. Finally, the epothilone A fraction (700 mg) is crystallised from 5 ml of ethyl acetate:toluene=2:3, and yields 170 mg of epothilone A pure crystallisate [content according to HLPC (% of area)=94.3%]. Crystallisation of the epothilone B fraction (1980 mg) is effected from 18 ml of methanol and yields 1440 mg of epothilone B pure crystallisate [content according to HPLC (% of area)= 99.2%]. m.p. (Epothilone B): e.g. 124–125° C.; $^1$H-NMR data for Epothilone B: 500 MHz-NMR, solvent: DMSO-d6. Chemical displacement δ in ppm relative to TMS. s=singlet; d=doublet; m=multiplet.

| δ (Multiplicity) | Integral (number of H) |
| --- | --- |
| 7.34 (s) | 1 |
| 6.50 (s) | 1 |
| 5.28 (d) | 1 |
| 5.08 (d) | 1 |
| 4.46 (d) | 1 |
| 4.08 (m) | 1 |
| 3.47 (m) | 1 |
| 3.11 (m) | 1 |
| 2.83 (dd) | 1 |
| 2.64 (s) | 3 |
| 2.36 (m) | 2 |
| 2.09 (s) | 3 |
| 2.04 (m) | 1 |
| 1.83 (m) | 1 |
| 1.61 (m) | 1 |
| 1.47–1.24 (m) | 4 |
| 1.18 (s) | 6 |
| 1.13 (m) | 2 |
| 1.06 (d) | 3 |
| 0.89 (d + s, overlapping) | 6 |
|  | Σ = 41 |

EXAMPLE 15

Medical Uses of Recombinantly Produced Epothilones

Pharmaceutical preparations or compositions comprising epothilones are used for example in the treatment of cancerous diseases, such as various human solid tumors. Such anticancer formulations comprise, for example, an active amount of an epothilone together with one or more organic or inorganic, liquid or solid, pharmaceutically suitable carrier materials. Such formulations are delivered, for example, enterally, nasally, rectally, orally, or parenterally, particularly intramuscularly or intravenously. The dosage of the active ingredient is dependent upon the weight, age, and physical and pharmacokinetical condition of the patient and is further dependent upon the method of delivery. Because epothilones mimic the biological effects of taxol, epothilones may be substituted for taxol in compositions and methods utilizing taxol in the treatment of cancer. See, for example, U.S. Pat. Nos. 5,496,804, 5,565,478, and 5,641,803, all of which are incorporated herein by reference.

For example, for treatments, epothilone B is supplied in individual 2 ml glass vials formulated as 1 mg/1 ml of clear, colorless intravenous concentrate. The substance is formulated in polyethylene glycol 300 (PEG 300) and diluted with 50 or 100 ml 0.9% Sodium Chloride Injection, USP, to achieve the desired final concentration of the drug for infusion. It is administered as a single 30-minute intravenous infusion every 21 days (treatment three-weekly) for six cycles, or as a single 30-minute intravenous infusion every 7 days (weekly treatment).

Preferably, for weekly treatment, the dose is between about 0.1 and about 6, preferably about 0.1 and about 5 mg/M$^2$, more preferably about 0.1 and about 3 mg/M$^2$, even more preferably 0.1 and 1.7 mg/m$^2$, most preferably about 0.3 and about 1 mg/m$^2$; for three-weekly treatment (treatment every three weeks or every third week) the dose is between about 0.3 and about 18 mg/M$^2$, preferably about 0.3 and about 15 mg/M$^2$, more preferably about 0.3 and about 12 mg/m$^2$, even more preferably about 0.3 and about 7.5 mg/m$^2$, still more preferably about 0.3 and about 5 mg/m$^2$, most preferably about 1.0 and about 3.0 mg/m$^2$. This dose is preferably administered to the human by intravenous (i.v.) administration during 2 to 180 min, preferably 2 to 120 min, more preferably during about 5 to about 30 min, most preferably during about 10 to about 30 min, e.g. during about 30 min.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. An isolated nucleic acid fragment comprising a nucleotide sequence that encodes at least one polypeptide required for the biosynthesis of epothilone, wherein the complement of said nucleotide sequence hybridizes to a sequence selected from the group consisting of: nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, and nucleotides 43163–43378 of SEQ ID NO:1, under conditions of hybridization at 65° C. for 36 hours and washing 3 times at high stringency with 0.1×SSC and 0.5% SDS for 20 minutes at 65° C.

2. A chimeric gene comprising a heterologous promoter sequence operatively linked to a nucleic acid fragment according to claim 1.

3. A recombinant vector comprising a chimeric gene according to claim 2.

4. A recombinant host cell comprising a chimeric gene according to claim 2.

5. The recombinant host cell of claim 4, which is a bacteria.

6. The recombinant host cell of claim 5, which is an Actinomycete.

7. The recombinant host cell of claim 6, which is Streptomyces.

8. An isolated nucleic acid fragment according to claim 1, wherein said polypeptide comprises a β-ketoacyl-synthase domain and wherein the complement of said nucleotide sequence hybridizes to a sequence selected from the group consisting of: nucleotides 21860–23116 of SEQ ID NO:1, nucleotides 26318–27595 of SEQ ID NO:1, nucleotides 30815–32092 of SEQ ID NO:1, and nucleotides 37052–38320 of SEQ ID NO:1, under conditions of hybridization at 65° C. for 36 hours and washing 3times at high stringency with 0.1×SSC and 0.5% SDS for 20 minutes at 65° C.

9. A chimeric gene comprising a heterologous promoter sequence operatively linked to a nucleic acid fragment according to claim 8.

10. A recombinant vector comprising a chimeric gene according to claim 9.

11. A recombinant host cell comprising a chimeric gene according to claim 9.

12. The recombinant host cell of claim 11, which is a bacteria.

13. The recombinant host cell of claim 12, which is an Actinomycete.

14. The recombinant host cell of claim 13, which is Streptomyces.

15. An isolated nucleic acid fragment according to claim 1, wherein said polypeptide comprises an acyltransferase domain and wherein the complement of said nucleotide sequence hybridizes to a sequence selected from the group consisting of: nucleotides 23431–24397 of SEQ ID NO:1, nucleotides 27911–28876 of SEQ ID NO:1, nucleotides 32408–33373 of SEQ ID NO:1, and nucleotides 38636–39598 of SEQ ID NO:1, under conditions of hybridization at 65° C. for 36 hours and washing 3 times at high stringency with 0.1×SSC and 0.5% SDS for 20 minutes at 65° C.

16. A chimeric gene comprising a heterologous promoter sequence operatively linked to a nucleic acid fragment according to claim 15.

17. A recombinant vector comprising a chimeric gene according to claim 16.

18. A recombinant host cell comprising a chimeric gene according to claim 17.

19. The recombinant host cell of claim 18, which is a bacteria.

20. The recombinant host cell of claim 19, which is an Actinomycete.

21. The recombinant host cell of claim 20, which is Streptomyces.

22. An isolated nucleic acid fragment according to claim 1, wherein said polypeptide comprises an enoyl reductase domain and wherein the complement of said nucleotide sequence hybridizes to a sequence selected from the group consisting of; nucleotides 35042–35902 of SEQ ID NO:1 and nucleotides 41369–42256 of SEQ ID NO:1, under conditions of hybridization at 65° C. for 36 hours and washing 3 times at high stringency with 0.1×SSC and 0.5% SDS for 20 minutes at 65° C.

23. A chimeric gene comprising a heterologous promoter sequence operatively linked to a nucleic acid fragment according to claim 22.

24. A recombinant vector comprising a chimeric gene according to claim 23.

25. A recombinant host cell comprising a chimeric gene according to claim 23.

26. The recombinant host cell of claim 25, which is a bacteria.

27. The recombinant host cell of claim 26, which is an Actinomycete.

28. The recombinant host cell of claim 27, which is Streptomyces.

29. An isolated nucleic acid fragment according to claim 1, wherein said polypeptide comprises an acyl carrier protein domain and wherein the complement of said nucleotide sequence hybridizes to a sequence selected from the group consisting of: nucleotides 26045–26263 of SEQ ID NO:1, nucleotides 30539–30759 of SEQ ID NO:1, nucleotides 36773–36991 of SEQ ID NO:1, and nucleotides 43163–43378 of SEQ ID NO:1, under conditions of hybridization at 65° C. for 36 hours and washing 3 times at high stringency with 0.1×SSC and 0.5% SDS for 20 minutes at 65° C.

30. A chimeric gene comprising a heterologous promoter sequence operatively linked to a nucleic acid fragment according to claim 29.

31. A recombinant vector comprising a chimeric gene according to claim 30.

32. A recombinant host cell comprising a chimeric gene according to claim 30.

33. The recombinant host cell of claim 32, which is a bacteria.

34. The recombinant host cell of claim 33, which is an Actinomycete.

35. The recombinant host cell of claim 34, which is Streptomyces.

36. An isolated nucleic acid fragment according to claim 1, wherein said polypeptide comprises a dehydratase domain and wherein the complement of said nucleotide sequence hybridizes to a sequence selected from the group consisting of: nucleotides 33401–33889 of SEQ ID NO:1 and nucleotides 39635–40141 of SEQ ID NO:1, under conditions of hybridization at 65° C. for 36 hours and washing 3 times at high stringency with 0.1×SSC and 0.5% SDS for 20 minutes at 65° C.

37. A chimeric gene comprising a heterologous promoter sequence operatively linked to a nucleic acid fragment according to claim 36.

38. A recombinant vector comprising a chimeric gene according to claim 37.

39. A recombinant host cell comprising a chimeric gene according to claim 37.

40. The recombinant host cell of claim 39, which is a bacteria.

41. The recombinant host cell of claim 40, which is an Actinomycete.

42. The recombinant host cell of claim 41, which is Streptomyces.

43. An isolated nucleic acid fragment according to claim 1, wherein said polypeptide comprises a β-ketoreductase domain and wherein the complement of said nucleotide sequence hybridizes to a sequence selected from the group consisting of: nucleotides 25184–25942 of SEQ ID NO:1, nucleotides 29678–30429 of SEQ ID NO:1, nucleotides 35930–36667 of SEQ ID NO:1, and nucleotides 42314–43048 of SEQ ID NO:1, under conditions of hybridization at 65° C. for 36 hours and washing 3 times at high stringency with 0.1×SSC and 0.5% SDS for 20 minutes at 65° C.

44. A chimeric gene comprising a heterologous promoter sequence operatively linked to a nucleic acid fragment according to claim 43.

45. A recombinant vector comprising a chimeric gene according to claim 44.

46. A recombinant host cell comprising a chimeric gene according to claim 44.

47. The recombinant host cell of claim 46, which is a bacteria.

48. The recombinant host cell of claim 47, which is an Actinomycete.

49. The recombinant host cell of claim 48, which is Streptomyces.

50. An isolated nucleic acid fragment comprising a nucleotide sequence that encodes a polypeptide comprising an amino acid sequence selected from the group consisting of: SEQ ID NO:5, amino acids 39–457 of SEQ ID NO:5, amino acids 563–884 of SEQ ID NO:5, amino acids 1147–1399 of SEQ ID NO:5, amino acids 1434–1506 of SEQ ID NO:5, amino acids 1524–1950 of SEQ ID NO:5, amino acids 2056–2377 of SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acid 4433–4719 of SEQ ID NO:5, amino acids 4729–4974 of SEQ ID NO:5, amino acids 5010–5082 of SEQ ID NO:5, amino acids 5103–5525 of SEQ ID NO5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, and amino acids 7140–7211 of SEQ ID NO:5.

51. A nucleic acid fragment according to claim 50, wherein said nucleotide sequence is selected from the group consisting of: nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1 nucleotides 26318–27595 of SEQ ID NO:1, nucleotides 27911–28876 of SEQ ID NO:1, nucleotides 29678–30429 of SEQ ID NO:1, nucleotides 30539–30159 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, and nucleotides 43163–43378 of SEQ ID NO:1.

52. An isolated nucleic acid fragment according to claim 50, wherein said polypeptide comprises a β-ketoacyl-synthase domain comprising an amino acid sequence selected from the group consisting of: amino acids 39–457 of SEQ ID NO:5, amino acids 1524–1950 of SEQ ID NO:5, amino acids 3024–3449 of SEQ ID NO:5, and amino acids 5103–5525 of SEQ ID NO:5.

53. An isolated nucleic acid fragment according to claim 52, wherein said nucleotide sequence is selected from the group consisting of: nucleotides 21860–23116 of SEQ ID NO:1, nucleotides 26318–27595 of SEQ ID NO:1, nucleotides 30815–32092 of SEQ ID NO:1, and nucleotides 37052–38320 of SEQ ID NO:1.

54. An isolated nucleic acid fragment according to claim 50, wherein said polypeptide comprises an acyltransferase domain comprising an amino acid sequence selected from the group consisting of: amino acids 563–884 of SEQ ID NO:5, amino acids 2056–2377 of SEQ ID NO:5, amino acids 3555–3876 of SEQ ID NO:5, and amino acids 5631–591 1 of SEQ ID NO:5.

55. An isolated nucleic acid fragment according to claim 54, wherein said nucleotide sequence is selected from the group consisting of: nucleotides 23431–24397 of SEQ ID NO:1, nucleotides 27911–28876 of SEQ ID NO:1, nucleotides 32408–33373 of SEQ ID NO:1, and nucleotides 38636–39598 of SEQ ID NO:1.

56. An isolated nucleic acid fragment according to claim 50, wherein said polypeptide comprises an enoyl reductase domain comprising an amino acid sequence selected from the group consisting of: amino acids 4433–4719 of SEQ ID NO:5 and amino acids 6542–6837 of SEQ ID NO:5.

57. An isolated nucleic acid fragment according to claim 56, wherein said nucleotide sequence is selected from the group consisting of: nucleotides 35042–35902 of SEQ ID NO:1 and nucleotides 41369–42256 of SEQ ID NO:1.

58. An isolated nucleic acid fragment according to claim 50, wherein said polypeptide comprises an acyl carrier protein domain comprising an amino acid sequence selected from the group consisting of: amino acids 1434–1506 of SEQ ID NO:5, amino acids 2932–3005 of SEQ ID NO:5, amino acids 5010–5082 of SEQ ID NO:5, and amino acids 7140–7211 of SEQ ID NO:5.

59. An isolated nucleic acid fragment according to claim 58, wherein said nucleotide sequence is selected from the group consisting of: nucleotides 26045–26263 of SEQ ID NO:1 nucleotides 30539–30759 of SEQ ID NO:1, nucleotides 36773–36991 of SEQ ID NO:1, and nucleotides 43163–43378 of SEQ ID NO:1.

60. An isolated nucleic acid fragment according to claim 50, wherein said polypeptide comprises a dehydratase domain comprising an amino acid sequence selected from the group consisting of: amino acids 3886–4048 of SEQ ID NO:5 and amino acids 5964–6132 of SEQ ID NO:5.

61. An isolated nucleic acid fragment according to claim 60, wherein said nucleotide sequence is selected from the group consisting of: nucleotides 33401–33889 of SEQ ID NO:1 and nucleotides 39635–40141 of SEQ ID NO:1.

62. An isolated nucleic acid fragment according to claim 50, wherein said polypeptide comprises a β-ketoreductase domain comprising an amino acid sequence selected from the group consisting of: amino acids 1147–1399 of SEQ ID NO:5, amino acids 2645–2895 of SEQ ID NO:5, amino acids 4729–4974 of SEQ ID NO:5, and amino acids 6857–7101 of SEQ ID NO:5.

63. An isolated nucleic acid fragment according to claim 62, wherein said nucleotide sequence is selected from the group consisting of: nucleotides 25184–25942 of SEQ ID NO:1, nucleotides 29678–30429 of SEQ ID NO:1, nucleotides 35930–36667 of SEQ ID NO:1, and nucleotides 42314–43048 of SEQ ID NO:1.

64. A chimeric gene comprising a heterologous promoter sequence operatively linked to a nucleic acid fragment according to claim 50.

65. A recombinant vector comprising a chimeric gene according to claim 64.

66. A recombinant host cell comprising a chimeric gene according to claim 64.

67. The recombinant host cell of claim 66, which is a bacteria.

68. The recombinant host cell of claim 67, which is an Actinomycete.

69. The recombinant host cell of claim 68, which is Streptomyces.

70. An isolated polypeptide required for the biosynthesis of epothilone, wherein said polypeptide comprises an amino acid sequence encoded by a nucleotide sequence whose complement hybridizes to a sequence selected from the group consisting of: nucleotides 21746–43519 of SEQ ID NO:1, nucleotides 21860–23116 of SEQ ID NO:1, nucleotides 23431–24397 of SEQ ID NO:1, nucleotides 25184–25942 of SEQ ID NO:1, nucleotides 26045–26263 of SEQ ID NO:1, nucleotides 26318–27595 of SEQ ID NO:1, nucleotides 27911–28876 of SEQ ID NO:1, nucleotides 29678–30429 of SEQ ID NO:1, nucleotides 30539–30759 of SEQ ID NO:1, nucleotides 30815–32092 of SEQ ID NO:1, nucleotides 32408–33373 of SEQ ID NO:1, nucleotides 33401–33889 of SEQ ID NO:1, nucleotides 35042–35902 of SEQ ID NO:1, nucleotides 35930–36667 of SEQ ID NO:1, nucleotides 36773–36991 of SEQ ID NO:1, nucleotides 37052–38320 of SEQ ID NO:1, nucleotides 38636–39598 of SEQ ID NO:1, nucleotides 39635–40141 of SEQ ID NO:1, nucleotides 41369–42256 of SEQ ID NO:1, nucleotides 42314–43048 of SEQ ID NO:1, and nucleotides 43163–43378 of SEQ ID NO:1, under conditions of hybridization at 65° C. for 36 hours and washing 3 times at high stringency with 0.1×SSC and 0.5% SDS for 20 minutes at 65° C.

71. A recombinant host cell comprising the polypeptide according to claim 70.

72. The recombinant host cell of claim 71, which is a bacteria.

73. The recombinant host cell of claim 72, which is an Actinomycete.

74. The recombinant host cell of claim 73, which is Streptomyces.

75. An isolated polypeptide according to claim 70, wherein said polypeptide comprises a β-ketoacyl-synthase domain and wherein the complement of said nucleotide sequence hybridizes to a sequence selected from the group consisting of: nucleotides 21860–23116 of SEQ ID NO:1, nucleotides 26318–27595 of SEQ ID NO:1, nucleotides 30815–32092 of SEQ ID NO:1, and nucleotides 37052–38320 of SEQ ID NO:1, under conditions of hybridization at 65° C. for 36 hours and washing 3 times at high stringency with 0.1×SSC and 0.5% SDS for 20 minutes at 65° C.

76. A recombinant host cell comprising the polypeptide according to claim 75.

77. The recombinant host cell of claim 76, which is a bacteria.

78. The recombinant host cell of claim 77, which is an Actinomycete.

79. The recombinant host cell of claim 78, which is Streptomyces.

80. An isolated polypeptide according to claim 70, wherein said polypeptide comprises an acyltransferase domain and wherein the complement of said nucleotide sequence hybridizes to a sequence selected from the group consisting of: nucleotides 23431–24397 of SEQ ID NO:1, nucleotides 27911–28876 of SEQ ID NO:1, nucleotides 32408–33373 of SEQ ID NO:1, and nucleotides 38636–39598 of SEQ ID NO:1, under conditions of hybridization at 65° C. for 36 hours and washing 3 times at high stringency with 0.1×SSC and 0.5% SDS for 20 minutes at 65° C.

81. A recombinant host cell comprising the polypeptide according to claim 80.

82. The recombinant host cell of claim 81, which is a bacteria.

83. The recombinant host cell of claim 82, which is an Actinomycete.

84. The recombinant host cell of claim 83, which is Streptomyces.

85. An isolated polypeptide according to claim 70, wherein said polypeptide comprises an enoyl reductase domain and wherein the complement of said nucleotide sequence hybridizes to a sequence selected from the group consisting of: nucleotides 35042–35902 of SEQ ID NO:1 and nucleotides 41369–42256 of SEQ ID NO:1, under conditions of hybridization at 65° C. for 36 hours and washing 3 times at high stringency with 0.1×SSC and 0.5% SDS for 20 minutes at 65° C.

86. A recombinant host cell comprising the polypeptide according to claim 85.

87. The recombinant host cell of claim 86, which is a bacteria.

88. The recombinant host cell of claim 87, which is an Actinomycete.

89. The recombinant host cell of claim 88, which is Streptomyces.

90. An isolated polypeptide according to claim 70, wherein said polypeptide comprises an acyl carrier protein domain and wherein the complement of said nucleotide sequence hybridizes to a sequence selected from the group consisting of: nucleotides 26045–26263 of SEQ ID NO:1, nucleotides 30539–30759 of SEQ ID NO:1, nucleotides 36773–36991 of SEQ ID NO:1, and nucleotides 43163–43378 of SEQ ID NO:1, under conditions of hybridization at 65° C. for 36 hours and washing 3 times at high stringency with 0.1×SSC and 0.5% SDS for 20 minutes at 65° C.

91. A recombinant host cell comprising the polypeptide according to claim 90.

92. The recombinant host cell of claim 91, which is a bacteria.

93. The recombinant host cell of claim 92, which is an Actinomycete.

94. The recombinant host cell of claim 93, which is Streptomyces.

95. An isolated polypeptide according to claim 70, wherein said polypeptide comprises a dehydratase domain and wherein the complement of said nucleotide sequence hybridizes to a sequence selected from the group consisting of: nucleotides 33401–33889 of SEQ ID NO:1 and nucleotides 39635–40141 of SEQ ID NO:1, under conditions of hybridization at 65° C. for 36 hours and washing 3 times at high stringency with 0.1×SSC and 0.5% SDS for 20 minutes at 65° C.

96. A recombinant host cell comprising the polypeptide according to claim 95.

97. The recombinant host cell of claim 96, which is a bacteria.

98. The recombinant host cell of claim 97, which is an Actinomycete.

99. The recombinant host cell of claim 98, which is Streptomyces.

100. An isolated polypeptide according to claim 70, wherein said polypeptide comprises a β-ketoreductase domain and wherein the complement of said nucleotide sequence hybridizes to a sequence selected from the group consisting of: nucleotides 25184–25942 of SEQ ID NO:1, nucleotides 29678–30429 of SEQ ID NO:1, nucleotides 35930–36667 of SEQ ID NO:1, and nucleotides 42314–43048 of SEQ ID NO:1, under conditions of hybridization at 65° C. for 36 hours and washing 3 times at high stringency with 0.1×SSC and 0.5% SDS for 20 minutes at 65° C.

101. A recombinant host cell comprising the polypeptide according to claim 100.

102. The recombinant host cell of claim 101, which is a bacteria.

103. The recombinant host cell of claim 102, which is an Actinomycete.

104. The recombinant host cell of claim 103, which is Streptomyces.

105. An isolated polypeptide comprising an amino acid sequence selected from the group consisting of: SEQ ID NO:5, amino acids 39–457 of SEQ ID NO:5, amino acids 563–894 of SEQ ID NO:5, amino acids 1147–1399 of SEQ ID NO:5, amino acids 14314–1506 of SEQ ID NO:5, amino acids 1524–1950 of SEQ ID NO:5, amino acids 2056–2377 or SEQ ID NO:5, amino acids 2645–2895 of SEQ ID NO:5, amino acids 2932–3005 of SEQ ID NO:5, amino acids 3024–3449 of SEQ ID NO:5, amino acids 3555–3876 of SEQ ID NO:5, amino acids 3886–4048 of SEQ ID NO:5, amino acids 4433–4719 of SEQ ID NO:5, amino acids 4729–4974 of SEQ ID NO:5, amino acids 5010–5082 of SEQ ID NO:5, amino acids 5103–5525 of SEQ ID NO:5, amino acids 5631–5951 of SEQ ID NO:5, amino acids 5964–6132 of SEQ ID NO:5, amino acids 6542–6837 of SEQ ID NO:5, amino acids 6857–7101 of SEQ ID NO:5, and amino acids 7140–7211 of SEQ ID NO:5.

106. An isolated polypeptide according to claim 105, wherein said polypeptide comprises a β-ketoacyl-synthase domain comprising an amino acid sequence selected from the group consisting of: amino acids 39–457 of SEQ ID NO:5, amino acids 1524–1950 of SEQ ID NO:5, amino acids 3024–3449 of SEQ ID NO:5, and amino acids 5103–5525 of SEQ ID NO:5.

107. An isolated polypeptide according to claim 105, wherein said polypeptide comprises an acyltransferase domain comprising all amino acid sequence selected from the group consisting of: amino acids 563–884 of SEQ ID NO:5, amino acids 2056–2377 of SEQ ID NO:5, amino acids 3555–3876 of SEQ ID NO:5, and amino acids 5631–5951 of SEQ ID NO:5.

108. An isolated polypeptide according to claim 105, wherein said polypeptide comprises an enoyl reductase domain comprising an amino acid sequence selected from the group consisting of: amino acids 4433–4719 of SEQ ID NO:5 and amino acids 6542–6837 of SEQ ID NO:5.

109. An isolated polypeptide according to claim 105, wherein said polypeptide comprises an acyl carrier protein domain comprising an amino acid sequence selected from the group consisting of amino acids 1434–1506 of SEQ ID NO:5, amino acids 2932–3005 of SEQ ID NO:5, amino acids 5010–5082 of SEQ ID NO:5, and amino acids 7140–7211 of SEQ ID NO:5.

110. An isolated polypeptide according to claim 105, wherein said polypeptide comprises a dehydratase domain comprising an amino acid sequence selected from the group consisting of: amino acids 3886–4048 of SEQ ID NO:5 and amino acids 5964–6132 of SEQ ID NO:5.

111. An isolated polypeptide according to claim 105, wherein said polypeptide comprises a β-ketoreductase domain comprising an amino acid sequence selected from the group consisting of: amino acids 1147–1399 of SEQ ID NO:5, amino acids 2645–2895 of SEQ ID NO:5, amino acids 4729–4974 of SEQ ID NO:5, and amino acids 6857–7101 of SEQ ID NO:5.

112. A recombinant host cell comprising the polypeptide according to claim 105.

113. The recombinant host cell of claim 112, which is a bacteria.

114. The recombinant host cell of claim 113, which is an Actinomycete.

115. The recombinant host cell of claim 114, which is Streptomyces.

\* \* \* \* \*

SEQUENCE LISTING

```
<160> NUMBER OF SEQ ID NOS: 30

<210> SEQ ID NO 1
<211> LENGTH: 68750
<212> TYPE: DNA
<213> ORGANISM: Sorangium cellulosum

<400> SEQUENCE: 1
aagcttcgct cgacgccctc ttcgcccgcg ccacctctgc ccgtgtgctc gatgatggcc      60
acggccgggc cacggagcgg catgtgctcg ccgaggcgcg cgggatcgag gacctccgcg     120
ccctccgaga gcacctccgc atccaggaag gggggccgtc ctttcactgc atgtgcctcg     180
gcgacctgac ggtggagctc ctcgcgcacg accagcccct cgcgtccatc agcttccacc     240
atgcccgcag cctgaggcac cccgactgga cctcggacgc gatgctcgtc gacggccccg     300
```

-continued

```
cgctcgtccg gtggctcgcc gcgcgcggcg cgccgggtcc cctccgcgag tacgaagagg    360
agcgcgagcg agcccgaacc gcgcaggagg cgaggcgcct gtggctcgcg ccgcgccgc     420
cctgcttcgc gcccgatctg ccccgcttcg aggacgacgc caacgggctg ccgctcggcc    480
cgatgtcgcc tgaagtcgcc gaggccgagc ggcgcctccg cgcctcgtac gcgactcctg    540
agctcgcctg tgccgcgctg ctcgcctggc tcgggacggg cgcgggtccc tggtccggat    600
atcccgccta cgagatgctg ccagagaatc tgctcctcgg gtttggcctc ccgaccgcga    660
tcgccgcggc tccgcgccc ggcacatcgg aggccgctct ccgcggcgca gcgcggctgt     720
tcgcctcctg ggaggtcgta tcgagcaaga agagccagct cggcaacatc cccgaagccc    780
tgtgggagcg gctccggacg atcgtccgcg cgatgggcaa tgccgacaac ctctctcgct    840
tcgagcgcgc cgaggcgatc gcggcggagg tgcgccgcct gcgcgcacag ccggcgccct    900
tcgcggcggg cgccggcctg gcggtcgctg gggtctcctc gagcggccgg ctctcgggcc    960
tcgtgaccga cggagacgca ttgtactccg gcgacggcaa cgacatcgtc atgttccaac   1020
ccggccggat ctcgcggtc gtgctgctcg ccggaaccga tcccttcttc gagctcgcac    1080
cgcccctcag ccagatgctc ttcgtcgcgc acgccaacgc gggcaccatc tccaaggtcc   1140
tgacggaagg cagccccctc atcgtgatgg caagaaacca ggcgcgaccg atgagcctcg   1200
tccacgctcg cgggttcatg gcgtgggtca accaggccat ggtgcccgac ccgagcgggg   1260
gcgcgccctt cgtcgtccag cgctcgacca tcatggaatt cgagcacccc acgcctcgtt   1320
gtctccacga gcccgccggc agcgctttct ccctcgcctg cgacgaggag cacctctact   1380
ggtgcgagct ttcggctggc cggctcgagc tatggcgcca cccgcaccac cgccccggcg   1440
ccccgagccg cttcgcgtac ctcggcgagc accccattgc ggcgacctgg taccctcgc    1500
tcaccctcaa tgcgacccac gtgctgtggg ccgaccctga tcgcagggcc atcctcgggg   1560
tcgacaagcg caccggcgta gagcccatcg tcctcgcgga gacgcgccat cccccggcgc   1620
acgtcgtgtc cgaggaccgg gacatcttcg cgcttaccgg acagcccgac tcccgcgact   1680
ggcacgtcga gcacatccgc tccggcgcct ccaccgtcgt ggccgactac cagcgccagc   1740
tatgggaccg ccctgacatg gtgctcaatc ggcgcggcct cttcttcacg acgaacgacc   1800
gcatcctgac gctcgcccgc agctgacatc gctcgacgcc gggccgctca tcgagggcgc   1860
ccggaccgag ctggcgaccc gccgctggcg ggccgcagct catgccgatt cggtggcgac   1920
gtagacgctg cgccagaaac gctcgagagc ccccgagaac aggaagccgg cggattgtgt   1980
catcacgatc ccgatcagct cgcggcccgg atcattgatc caggacgtcc cgaacccgcc   2040
gtcccaccca tagcgcccgg gcacctccga gaccgcgtcc ggcgccgtga ccacggccat   2100
cccataaccc cagccgtgcg tctcgaagaa gcccgggaaa acgaggacg ccgccttctg    2160
ggccggcgtg aggtgatcgg ccgtcatctc gcgcaccgag gcggcgctca agagccgccg   2220
gccctcgtgc acaccgccgt tcatgagcat gcgcgcgaac aggaggtagt cgtccaccgt   2280
cgacacgagc ccggcggcgc ccgaagggaa cgccggcggg ctggcatagg cgctctcggc   2340
cccgtcgcga tccatgcgcg tcttctcccc cgtctgctcg tcggtgaagt aaccgcagcc   2400
cgcgaaccga gcgagcttgt ccgccgggac gtgaaagtcg gtgtccgca tcccgagcgg    2460
cgcgaggatg cgctcgcgca cgaacgcatc gaagccctgc tcggccgcgc gccccacgag   2520
caccccctgc accaggctcc ccgtgttgta catccactgc gcccccggct gatgcatgag   2580
cggcagcgtc ccgagccgcc ggatccactc gtctggcccg tgcggcgtca tcggcaccgg   2640
ctgcgcgttg acgagcccga gctcgtcgat ggcccgctgg atcggcgacg atgcgtcgaa   2700
```

-continued

```
cgagattccg aagcccatcg tgaacgtcat caggtcgcgc accgtgatcg gccgctccgc    2760
gggcaccgtc tcgtcgatcg gaccatcgat gcgcgccagc accttccggt tcgcgagctc    2820
cggcaaccat cggtcgacgg gggagtcgag gtcgagcttg ccttcctcga cgagcatcat    2880
caccgccgtc gcggtgaccg ccttcgtcat cgaggcgatc cggaagatcg tgtcccgccg    2940
catgggcgcg ctgccgccga gctcggtcac gcccaccgcg tccacgtgca cgtcgtcgcc    3000
gcgcgcgacc agccagaccg ctcccggcat ctgccccgcc gccacctccg ccgccatcac    3060
ctcgcgcgcg ggcgccagcg cgccggcccc cgcgtcctgc cctggctgcc cctcctcctc    3120
ggccccaccc aacgcgcacc ccggcgccgc cacgctgatc aaagctccca taaactcccg    3180
ccttctcatg accgtcgatg cctctccgag cgggggcgcg tgccctgcc gagagcactg    3240 actgcccgcg cccgaaaaaa tcatcggtgc cccgtcacga tcgccgccgg gcgtggctcc    3300
gcccggccgc ccgctcgggc gcccgcccct ggacgagcaa agctcgcccg cccgcgctca    3360
gcacgccgct tgccatgtcc ggcctgcacc cacaccgagg agccacccac cctgatgcac    3420
ggcctcaccg agcggcaggt cctgctctcg ctcgtcaccc tcgcgctcat cctcgtgacc    3480
gcgcgcgcct ccggcgagct cgcgcggcgg ctgcgccagc ccgaggtgct cggggagctc    3540
ttcggcggcg tcgtgctggg cccctccgtc gtcggcgcgc tcgcgcccgg gttccatcga    3600
gccctcttcc aggagccggc ggtcgggtc gtgctctcgg gcatctcctg gataggcgcg    3660
ctcctcctgc tgctgatggc gggcatcgag gtcgacgtgg gcatcctgcg caaggaggcg    3720
cgccccgggg cgctctcggc gctcggcgcg atcgcgcccc cgctcgcggc gggcgccgcc    3780
ttctcggcgc tcgtgctcga tcggcccctt ccgagcggcc tcttcctcgg gatcgtgctc    3840
tcggtgacgg cggtcagcgt gatcgcgaag gtgctgatcg agcgcgagtc gatgcgccgc    3900
agctatcgcc aggtgacgct cgcggcgggg gtggtcagcg aggtcgctgc ctgggtgctc    3960
gtcgcgatga cgtcgtcgag ctacggcgcg tcgcccgcgc tggcggtcgc ccggagcgcg    4020
ctcctggcga gcggattctt gctgttcatg gtgctcgtcg gcggcggct cacccacctc    4080 gcgatgcgct gggtggccga cgcgacgcgc gtctccaagg gacaggtgtc gctcgtcctc    4140
gtcctcacgt tcctggccgc ggcgctgacg cagcggctcg gcctgcaccc gctgctcggc    4200
gcgttcgcgc tcggcgtgct gctcaacagc gctcctcgca ccaaccgccc tctcctcgac    4260
ggcgtgcaga cgctcgtggc gggcctcttc gcgcctgtgt tcttcgtcct cgcgggcatg    4320
cgcgtcgacg tgtcgcagct gcgcacgccg gcggcgtggg ggacggtcgc gttgctgctg    4380
gcgaccgcga cggcggcgaa ggtcgtcccc gccgcgctcg gcgcgcggct cggcgggctc    4440 agggggcagcg aggcggcgct cgtggcggtg ggcctgaaca tgaagggcgg cacggacctc    4500
atcgtcgcga tcgtcggcgt cgagctcggg ctcctctcca acgaggctta tacgatgtac    4560
gccgtcgtcg cgctggtcac ggtgaccgcc tcacccgcgc tcctcatctg gctcgagaaa    4620
agggcgcctc cgacgcagga ggagtcggct cgcctcgagc gcgaggaggc cgcgaggcgc    4680
gcgtacatcc ccggggtcga gcggatcctc gtcccgatcg tggcgcacgc cctgcccggg    4740
ttcgccacgg acatcgtgga gagcatcgtc gcctccaagc gaaagctcgg cgagacggtc    4800
gacatcacgg agctctccgt ggagcagcag gcgcccggcc catcgcgcgc gcgcggggag    4860
gcgagccggg ggctcgcgag gctcggcgcg cgcctccgcg tcggcatctg gcggcaaagg    4920
cgcgagctgc gcggctcgat ccaggcgatc ctgcgcgcct cgcgggatca cgatctgctc    4980
gtgatcggcg cgcgatcgcc ggcgcgcgcg cgcggaatgt cgttcggtcg cctgcaggac    5040
```

-continued

```
gcgatcgtcc agcgggccga gtccaacgtg ctcgtcgtgg tgggcgaccc tccggcggcg      5100
gagcgcgcct ccgcgcggcg gatcctcgtc ccgatcatcg gcctcgagta ctccttcgcc      5160
gccgccgatc tcgcggccca cgtggcgctg gcgtgggacg ccgagctcgt gctgctcagc      5220
agcgcgcaga ccgatccggg cgcggtcgtc tggcgcgatc gcgagccatc ccgggtgcgc      5280
gcggtggcgc ggagcgtcgt cgacgaggcg gtcttccggg ggcgccggct cggcgtgcgc      5340
gtctcgtcgc gcgtgcacgt gggcgcgcac ccgagcgacg agataacgcg ggagctcgcg      5400
cgcgccccgt acgatctgct cgtgctcgga tgctacgacc atgggccgct cggccggctc      5460
tacctcggca gcacggtcga gtcggtggtg gtccggagcc gggtgccggt cgcgttgctc      5520
gtcgcgcatg gagggactcg agagcaggtg aggtgaggct tccaccgcgc tcgcccgtga      5580
ggaagcgagc gcccggctct gccgacgatc gtcactcccg gtccgtgtag gcgatcgtgc      5640
tgagcagcgc gttctccgcc tgacgcgagt cgagccgggt atgctgcacg acgatggggg      5700
cgtccgattc gatcacgctg gcatagtccg tatcgcgcgg gatcggctcg ggttcggtca      5760
gatcgttgaa ccggacgtgc cgggtgcgcc tcgctggaac ggtcacccgg taaggcccgg      5820
cggggtcgcg gtcgctgaag taaacggtga tggcgacctg cgcgtcccgg tccgacgcat      5880
tcaacaggca ggccgtctca tggctcgtca tctgcggctc aggtccgttg ctcccgcctg      5940
ggatgtagcc ctctgcgatt gcacagcgcg tccgcccgat cggcttgtcc atgtgtcctc      6000
cctcctggct cctctttggc agcctccctc tgctgtccag gagcgatggc ctcttcgctc      6060
gacgcgctcg gggatccatg gctgaggatc ctcgccgagc gctccctgcc gaccggcgcg      6120
ccgagcgccg acgggctttg aaagcgcgcg accggccagc ccggacgcgg gcccgagagg      6180
gacagtgggt ccgccgtgaa gcagagaggc gatcgaggtg gtgagatgaa acacgtcgac      6240
acgggccgac gattcggccg ccggataggg cacacgctcg gtcttctcgc gagcatggcg      6300
ctcgccggct gcggcggtcc gagcgagaaa accgtgcagg gcacgcggct cgcgcccggc      6360
gccgatgcgc gcgtcaccgc cgacgtcgac cccgacgccg cgaccacgcg gctggcggtg      6420
gacgtcgttc acctctcgcc gcccgagcgg ctcgaggccg gcagcgagcg gttcgtcgtc      6480
tggcagcgtc cgagccccga gtccccgtgg cgacgggtcg gagtgctcga ctacaatgct      6540
gacagccgaa gaggcaagct ggccgagacg accgtgccgt atgccaactt cgagctgctc      6600
atcaccgccg agaagcagag cagccctcag tcgccatcgt ctgccgccgt catcgggccg      6660
acgtctgtcg ggtgacatcg cgctatcagc agcgctgagc ccgccagcag gccccagggc      6720
cctgcctcga tggccttccc catcacccct gcgcactcct ccagcgacgg ccgcgcagcg      6780
acggccgcgt ccaagcaacc gccgtgccgg cgcggctcca cgcgcgcgac aggcgagcgt      6840
cctggcgcgg cctgcgcatc gctggaagga tcggcggagc atggatagag aatcgaggat      6900
cgcgatcttt gttgccatcg cagccaacgt ggcgatcgcg gcggtcaagt tcatcgccgc      6960
cgccgtgacc ggcagctcgg cgaggcgttt gccgacttcg gcggcgtccc gcgcgtgctg      7020
ctctacgaca acctcaagag cgccgtcgtc gagcgccacg gcgacgcgat ccggttccac      7080
cccacgctgc tggctctgtc ggcgcattac gcttcgagc cgcgccccgt cgccgtcgcc      7140
cgcggcaacg agaagggccg cgtccagcgc gccatcacgg cgtggacgac atggcgcgga      7200
aacgtcgtcg taaccgccca gcaatgtcat gggaatggcc ccttgaaatg gcccttgag       7260 ggggctggcc ggggtcgacg atatcgcgcg atctccccgt caattcccga tggtaaaaga      7320
aaaatttgtc atagatcgta agctgtgata gtggtctgtc ttacgttgcg tcttccgcac      7380
ctcgagcgag ttctctcgga taactttcaa tttttccgag gggggcttgg tctctggttc      7440
```

```
ctcaggaagc ctgatcggga cgagctaatt cccatccatt tttttgaggc tctgctcaaa    7500
gggattagat cgagtgagac agttcttttg cagtgcgcga agaacctggg cctcgaccgg    7560
aggacgatcg acgtccgcga gcgggtcagc cgctgaggat gtgcccgtcg tggcggatcg    7620
tcccatcgag cgcgcagccg aagatccgat tgcgatcgtc ggagcgagtt gccgtctgcc    7680
cggtggcgtg atcgatctga gcgggttctg gacgctcctc gagggctcgc gcgacaccgt    7740
cgggcgagtc cccgccgaac gctgggatgc agcagcgtgg tttgatcccg accccgatgc    7800
cccggggaag acgcccgtta cgcgcgcatc tttcctgagc gacgtagcct gcttcgacgc    7860
ctccttcttc ggcatctcgc ctcgcgaagc gctgcggatg gaccctgcac atcgactctt    7920
gctggaggtg tgctgggagg cgctggagaa cgccgcgatc gctccatcgg cgctcgtcgg    7980
tacggaaacg ggagtgttca tcgggatcgg cccgtccgaa tatgaggccg cgctgccgca    8040
agcgacggcg tccgcagaga tcgacgctca tggcgggctg gggacgatgc ccagcgtcgg    8100
agcgggccga atctcgtatg ccctcgggct gcgagggccg tgtgtcgcgg tggatacggc    8160
ctattcgtcc tcgctggtgg ccgttcatct ggcctgtcag agcttgcgct ccggggaatg    8220
ctccacggcc ctggctggtg gggtatcgct gatgttgtcg ccgagcaccc tcgtgtggct    8280
ctcgaagacc cgggcgctgg ccagggacgg tcgctgcaag gcattttcgg cggaggccga    8340
tgggttcgga cgaggcgaag ggtgcgccgt cgtggtcctc aagcggctca gtggagcccg    8400
cgcggacggc gatcggatat tggcggtgat tcgaggatcc gcgatcaatc acgacggtgc    8460
gagcagcggt ctgaccgtgc cgaacgggag ctcccaagaa atcgtgctga acgggccct    8520 ggcggacgca ggctgcgccg cgtcttcggt gggttatgtc gaggcacacg gcacgggcac    8580
gacgcttggt gaccccatcg aaatccaagc tctgaatgcg gtatacggcc tcgggcgaga    8640
tgtcgccacg ccgctgctga tcgggtcggt gaagaccaac cttggccatc ctgagtatgc    8700
gtcggggatc actgggctgc tgaaggtcgt cttgtccctt cagcacgggc agattcctgc    8760
gcacctccac gcgcaggcgc tgaaccccg gatctcatgg ggtgatcttc ggctgaccgt    8820
cacgcgcgcc cggacaccgt ggccggactg gaatacgccg cgacgggcgg gggtgagctc    8880
gttcggcatg agcgggacca acgcgcacgt ggtgctggaa gaggcgccgg cggcgacgtg    8940
cacaccgccg gcgccggagc gaccggcaga gctgctggtg ctgtcggcaa ggaccgcgtc    9000
agccctggat gcacaggcgg cgcggctgcg cgaccatctg gagacctacc cttcgcagtg    9060
tctgggcgat gtggcgttca gtctggcgac gacgcgcagc gcgatggagc accggctcgc    9120
ggtggcggcg acgtcgaggg aggggctgcg ggcagccctg gacgctgcgg cgcagggaca    9180
gacgtcgccc ggtgcggtgc gcagtatcgc cgattcctca cgcggcaagc tcgcctttct    9240
cttcaccgga caggggcgc agacgctggg catggccgt gggctgtacg atgtatggtc    9300
cgcgttccgc gaggcgttcg acctgtgcgt gaggctgttc aaccaggagc tcgaccggcc    9360
gctccgcgag gtgatgtggg ccgaaccggc cagcgtcgac gccgcgctgc tcgaccagac    9420
agccttcacc cagccggcgc tgttcacctt cgaatatgcg ctcgccgcgc tgtggcggtc    9480
gtggggtgta gagccggagt tggtcgccgg ccatagcatc ggtgagctgg tggctgcctg    9540
cgtggcgggc gtgttctcgc ttgaggacgc ggtgttcctg gtggctgcgc gcgggcgcct    9600
gatgcaggcg ctgccggccg gcggggcgat ggtgtcgatc gaggcgccgg aggccgatgt    9660
ggctgctgcg gtgcgccgc acgcagcgtc ggtgtcgatc gccgcggtca acgctccgga    9720
ccaggtggtc atcgcgggcg ccgggcaacc cgtgcatgcg atcgcggcgg cgatggccgc    9780
```

-continued

```
gcgcggggcg cgaaccaagg cgctccacgt ctcgcatgcg ttccactcac cgctcatggc    9840
cccgatgctg gaggcgttcg ggcgtgtggc cgagtcggtg agctaccggc ggccgtcgat    9900
cgtcctggtc agcaatctga gcgggaaggc ttgcacagac gaggtgagct cgccgggcta    9960
ttgggtgcgc cacgcgcgag aggtggtgcg cttcgcggat ggagtgaagg cgctgcacgc    10020
ggccggtgcg ggcaccttcg tcgaggtcgg tccgaaatcg acgctgctcg gcctggtgcc    10080
tgcctgcatg ccggacgccc ggccggcgct gctcgcatcg tcgcgcgctg ggcgtgacga    10140
gccggcgacc gtgctcgagg cgctcggcgg gctctgggcc gtcggtggcc tggtctcctg    10200
ggccggcctc ttcccctcag gggggcggcg ggtgccgctg cccacgtacc cttggcagcg    10260
cgagcgctac tggatcgaca cgaaagccga cgacgcggcg cgtggcgacc gccgtgctcc    10320
gggagcgggt cacgacgagg tcgaggaggg gggcgcggtg cgcggcggcg accggcgcag    10380
cgctcggctc gaccatccgc cgcccgagag cggacgccgg gagaaggtcg aggccgccgg    10440
cgaccgtccg ttccggctcg agatcgatga gccaggcgtg cttgatcacc tcgtgcttcg    10500
ggtcacggag cggcgcgccc ctggtctggg cgaggtcgag atcgccgtcg acgcggcggg    10560
gctcagcttc aatgatgtcc agctcgcgct gggcatggtg cccgacgacc tgccgggaaa    10620
gcccaaccct ccgctgctgc tcggaggcga gtgcgccggg cgcatcgtcg ccgtgggcga    10680
gggcgtgaac ggcctcgtgg tgggccaacc ggtcatcgcc ctttcggcgg gagcgtttgc    10740
tacccacgtc accacgtcgg ctgcgctggt gctgcctcgg cctcaggcgc tctcggcgat    10800
cgaggcggcc gccatgcccg tcgcgtacct gacggcatgg tacgcgctcg acagaatagc    10860
ccgccttcag ccgggggagc gggtgctgat ccatgcggcg accggcgggg tcggtctcgc    10920
cgcggtgcag tgggcgcagc acgtgggagc cgaggtccat gcgacggccg gcacgcccga    10980
gaaacgcgcc tacctggagt cgctgggcgt gcggtatgtg agcgattccc gctcggaccg    11040
gttcgtcgcc gacgtgcgcg cgtggacggg cggcgaggga gtagacgtcg tgctcaactc    11100
gctctcgggc gagctgatcg acaagagttt caatctcctg cgatcgcacg gccggtttgt    11160
ggagctcggc aagcgcgact gttacgcgga taaccagctc gggctgcggc cgttcctgcg    11220
caatctctcc ttctcgctgg tggatctccg ggggatgatg ctcgagcggc cggcgcgggt    11280
ccgtgcgctc ttggaggagc tcctcggcct gatcgcggca ggcgtgttca ccctcccccc    11340
catcgcgacg ctcccgatcg cccgtgtcgc cgatgcgttc cggagcatgg cgcaggcgca    11400
gcatcttggg aagctcgtac tcacgctggg tgacccggag gtccagatcc gtattccaac    11460
ccacgcaggc gccggcccgt ccaccgggga tcgggacctg ctcgacaggc tcgcgtcagc    11520
tgcgccggcc gcgcgcgcgg cggcgctgga ggcgttcctc cgtacgcagg tctcgcaggt    11580
gctgcgcacg cccgaaatca aggtcggcgc ggaggcgctg ttcacccgcc tcggcatgga    11640
ctcgctcatg gccgtggagc tgcgcaatcg tatcgaggcg agcctcaagc tgaagctgtc    11700
gacgacgttc ctgtccacgt cccccaatat cgccttgttg gcccaaaacc tgttggatgc    11760
tctcgccaca gctctctcct tggagcgggt ggcggcggag aacctacggg caggcgtgca    11820
aaacgacttc gtctcatcgg gcgcagatca agactgggaa atcattgccc tatgacgatc    11880
aatcagcttc tgaacgagct cgagcaccag ggtatcaagc tggcggccga tggggagcgc    11940
ctccagatac aggcccccaa gaacgccctg aacccgaacc tgctcgctcg aatctccgag    12000
cacaaaagca cgatcctgac gatgctccgt cagagactcc ccgcagaatc catcgtgccc    12060
gccccagccg agcggcacgc tccgtttcct ctcacagaca tccaagaatc ctactggctg    12120
ggccggacag gagcgtttac ggtccccagc gggatccacg cctatcgcga atacgactgt    12180
```

```
acggatctcg acgtgccgag gctgagccgc gcctttcgga aagtcgtcgc gcggcacgac    12240
atgcttcggg cccacacgct gcccgacatg atgcaggtga tcgagcctaa agtcgacgcc    12300
gacatcgaga tcatcgatct gcgcgggctc gaccggagca cacgggaagc gaggctcgtg    12360
tcgttgcgag atgcgatgtc gcaccgcatc tatgacaccg agcgccctcc gctctatcac    12420
gtcgtcgccg ttcggctgga cgagcggcaa acccgtctcg tgctcagtat cgatctcatt    12480
aacgttgacc taggcagcct gtccatcatc ttcaaggact ggctcagctt ctacgaagat    12540
cccgagacct ctctccctgt cctggagctc tcgtaccgcg attatgtact cgcgctggag    12600
tctcgcaaga agtctgaggc gcatcaacga tcgatggatt actggaagcg gcgcatcgcc    12660
gagctcccac ctccgccgac gcttccgatg aaggccgatc catctaccct gaaggagatc    12720
cgcttccggc acacggagca atggctgccg tcggactcct ggggtcgatt gaagcggcgt    12780
gtcggggagc gcgggctgac cccgacgggc gtcatcctgg ctgcattttc cgaggtgatc    12840
gggcgctgga gcgcgagccc ccggtttacg ctcaacataa cgctcttcaa ccggctcccc    12900
gtccatccgc gcgtgaacga tatcaccggg gacttcacgt cgatggtcct cctggacatc    12960
gacaccactc gcgacaagag cttcgaacag cgcgctaagc gtattcaaga gcagctgtgg    13020
gaagcgatgg atcactgcga cgtaagcggt atcgaggtcc agcgagaggc cgcccgggtc    13080
ctggggatcc aacgaggcgc attgttcccc gtggtgctca cgagcgcgct taaccagcaa    13140
gtcgttggtg tcacctcgtt gcagaggctc ggaactccgg tgtacaccag cacgcagact    13200
cctcagctgc tgctggatca tcagctctac gagcacgatg gggacctcgt cctcgcgtgg    13260
gacatcgtcg acggagtgtt cccgcccgac cttctggacg acatgctcga agcgtacgtc    13320 gttttttctcc ggcggctcac tgaggaacca tggggtgaac aggtgcgctg ttcgcttccg    13380
cctgcccagc tagaagcgcg ggcgagcgca aacgcgacca acgcgctgct gagcgagcat    13440
acgctgcacg gcctgttcgc ggcgcgggtc gagcagctgc ccatgcagct cgccgtggtg    13500
tcggcgcgca agacgctcac gtacgaagag cttccgcgcc gttcgcggcg acttggcgcg    13560
cggctgcgcg agcaggggc acgcccgaac acattggtcg cggtggtgat ggagaaaggc    13620
tgggagcagg ttgtcgcggt tctcgcggtg ctcgagtcag gcgcggccta cgtgccgatc    13680
gatgccgacc taccggcgga gcgtatccac tacctcctcg atcatggtga ggtaaagctc    13740
gtgctgacgc agccatggct ggatggcaaa ctgtcatggc cgccggggat ccagcggctg    13800
ctcgtgagcg aggccggcgt cgaaggcgac ggcgaccagc ctccgatgat gcccattcag    13860
acaccttcgg atctcgcgta tgtcatctac acctcgggat ccacagggtt gcccaagggg    13920
gtgatgatcg atcatcgggg tgccgtcaac accatcctgg acatcaacga gcgcttcgaa    13980
ataggggccg gagacagggt gctggcgctc tcctcgctga gcttcgatct ctcggtctat    14040
gatgtgttcg ggatcctggc ggcgggcggt acgatcgtgg tgccggacgc gtccaagctg    14100
cgcgatccgg cgcattgggc agagttgatc gaacgagaga aggtgacggt gtggaactcg    14160
gtgccggcgc tgatgcggat gctcgtcgag cattttgagg tcgccccgga ttcgctcgct    14220
aggtctctgc ggctttcgct gctgagcggc gactggatcc cggtgggcct gcctggcgag    14280
ctccaggcca tcaggcccgg cgtgtcggtg atcagcctgg gcggggccac cgaagcgtcg    14340
atctggtcca tcgggtaccc cgtgaggaac gtcgacctat cgtgggcgag catcccctac    14400
ggccgtccgc tgcgcaacca gacgttccac gtgctcgatg aggcgctcga accgcgcccg    14460
gtctgggttc cggggcaact ctacattggc ggggtcgggc tggcactggg ctactggcgc    14520
```

-continued

```
gatgaagaga agacgcgcaa gagcttcctc gtgcaccccg agaccgggga gcgcctctac    14580
aagaccggcg atctgggccg ctacctgccc gatggaaaca tcgagttcat ggggcgtgag    14640
gacaaccaaa tcaagcttcg cggataccgc gttgagctcg gggaaatcga ggaaacgctc    14700
aagtcgcatc cgaacgtacg cgacgcggtg attgtgcccg tcgggaacga cgcggcgaac    14760
aagctccttc tagcctatgt ggtcccggag ggcacacgga gacgcgctgc cgagcaggac    14820
gcgagcctca agaccgagcg gatcgacgcg agagcacacg ccgccgaagc ggacggcttg    14880
agcgacggcg agagggtgca gttcaagctc gctcgacacg gactccggag ggacctggac    14940
ggaaagcccg tcgtcgatct gaccgggcag gatccgcggg aggcggggct ggacgtctac    15000
gcgcgtcgcc gtagcgtccg aacgttcctt gaggccccga ttccgtttgt tgagtttggt    15060
cgattcctga gctgcttgag cagcgtggag cccgacggcg cgacccttcc caaattccgt    15120
tatccatcgg cggcagcac gtacccggtg caaacctacg cgtatgtcaa atccggccgc    15180
atcgagggcg tggacgaggg cttctattat taccacccgt tcgagcaccg tttgctgaag    15240
ctctccgatc acgggatcga gcgcggagcg cacgttcggc aaaacttcga cgtgttcgat    15300
gaagcggcgt tcaacctcct gttcgtgggc aggatcgacg ccatcgagtc gctgtatgga    15360
tcgtcgtcgc gagaattttg cctgctggag gccggatata tggcgcagct cctgatggag    15420
caggcgcctt cctgcaacat cggcgtctgt ccggtggggc aattcaattt tgaacaggtt    15480
cggccggttc tcgacctgcg acattcggac gtttacgtgc acggcatgct gggcgggcgg    15540
gtagacccgc ggcagttcca ggtctgtacg ctcggtcagg attcctcacc gaggcgcgcc    15600
acgacgcgcg gcgcccctcc cggccgcgag cagcacttcg ccgatatgct tcgcgacttc    15660
ttgaggacca aactacccga gtacatggtg cctacagtct tcgtggagct cgatgcgttg    15720
ccgctgacgt ccaacggcaa ggtcgatcgt aaggccctgc gcgagcggaa ggatacctcg    15780
tcgccgcggc attcggggca cacgcgcca cgggacgcct tggaggagat cctcgtcgcg    15840
gtcgtacggg aggtgctcgg gctggaggtg gtcgggctcc agcagagctt cgtcgatctt    15900
ggtgcgacat cgattcacat cgttcgcatg aggagcctgt tgcagaagag gctggatagg    15960
gagatcgcca tcaccgagtt gttccagtac ccgaacctcg gctcgctggc gtccggtttg    16020
cgccgagact cgagagatct agatcagcgg ccgaacatgc aggaccgagt ggaggttcgg    16080
cgcaagggca ggagacgtag ctaagagcgc cgaacaaaac caggccgagc gggccgatga    16140
gccgcaagcc cgcctgcgtc accctgggac tcatctgatc tgatcgcggg tacgcgtcgc    16200
gggtgtgcgc gttgagccgt gttgttcgaa cgctgaggaa cggtgagctc atggaagaac    16260
aagagtcctc cgctatcgca gtcatcggca tgtcgggccg ttttccgggg gcgcgggatc    16320
tggacgaatt ctggaggaac cttcgagacg gcacggaggc cgtgcagcgc ttctccgagc    16380
aggagctcgc ggcgtccgga gtcgaccccg cgctggtgct ggacccgagc tacgtccggg    16440
cgggcagcgt gctggaagac gtcgaccggt tcgacgctgc tttcttcggc atcagcccgc    16500
gcgaggcaga gctcatggat ccgcagcacc ggatcttcat ggaatgcgcc tgggaggcgc    16560
tggagaacgc cggatacgac ccgacggctt acgagggctc tatcggcgtg tacgccggcg    16620
ccaacatgag ctcgtacttg acgtcgaacc tccacgagca cccagcgatg atgcggtggc    16680
ccggctggtt tcagacgttg atcggcaacg acaaggatta cctcgcgacc cacgtctcct    16740
acaggctgaa tctgagaggg ccgagcatct ccgttcaaac tgcctgctcc acctcgctcg    16800
tggcggttca cttggcgtgc atgagcctcc tggaccgcga gtgcgacatg gcgctggccg    16860
gcgggattac cgtccggatc ccccatcgag ccggctatgt atatgctgag gggggcatct    16920
```

-continued

```
tctctcccga cggccattgc cgggccttcg acgccaaggc gaacggcacg atcatgggca  16980
acggctgcgg cgttgtcctc ctgaagccgc tggaccgggc gctctccgat ggtgatcccg  17040
tccgcgcggt tatccttggg tctgccacaa acaacgacgg agcgaggaag atcgggttca  17100
ctgcgcccag tgaggtgggc caggcgcaag cgatcatgga ggcgctggcg ctggcagggg  17160
tcgaggcccg gtccatccaa tacatcgaga cccacggac cggcacgctg ctcggagacg  17220
ccatcgagac ggcggcgctg cggcgggtgt tcggtcgcga cgcttcggcc cggaggtctt  17280
gcgcgatcgg ctccgtgaag accggcatcg acacctcga atcggcggct ggcatcgccg  17340
gtttgatcaa gacggtcttg gcgctggagc accggcagct gccgcccagc ctgaacttcg  17400
agtctcctaa cccatcgatc gatttcgcga gcagcccgtt ctacgtcaat acctctctta  17460
aggattggaa taccggctcg actccgcggc gggccggcgt cagctcgttc gggatcggcg  17520
gcaccaacgc ccatgtcgtg ctggaggaag cgcccgcggc gaagcttcca gccgcggcgc  17580
cggcgcgctc tgccgagctc ttcgtcgtct cggccaagag cgcagcggcg ctggatgccg  17640
cggcggcacg gctacgagat catctgcagg cgcaccaggg gatttcgttg ggcgacgtcg  17700
ccttcagcct ggcgacgacg cgcagcccca tggagcaccg gctcgcgatg gcggcgccgt  17760
cgcgcgaggc gttgcgagag gggctcgacg cagcggcgcg aggccagacc ccgccggggcg  17820 ccgtgcgtgg ccgctgctcc ccaggcaacg tgccgaaggt ggtcttcgtc tttcccggcc  17880
agggctctca gtgggtcggc atgggccggc agctcctggc tgaggaaccc gtcttccacg  17940
cggcgctttc ggcgtgcgac cgggccatcc aggccgaagc tggttggtcg ctgctcgcgg  18000
agctcgccgc cgacgaaggg tcctcccagc tcgagcgcat cgacgtggtg cagccggtgc  18060
tgttcgccct cgcggtggca tttgcggcgc tgtggcggtc gtggggtgtc gcgcccgacg  18120
tcgtgatcgg ccacagcatg ggcgaggtag ccgccgcgca tgtggccggg gcgctgtcgc  18180
tcgaggatgc ggtggcgatc atctgccggc gcagccggct gctccggcgc atcagcggtc  18240
agggcgagat ggcggtgacc gagctgtcgc tggccgaggc cgaggcggcg ctccgaggct  18300
acgaggatcg ggtgagcgtg gccgtgagca acagcccgcg ctcgacggtg ctctcgggcg  18360
agccggcagc gatcggcgag gtgctgtcgt ccctgaacgc gaaggggtg ttctgccgtc  18420 gggtgaaggt ggatgtcgcc agccacagcc cgcaggtcga cccgctgcgc gaggacctct  18480
tggcagccct gggcgggctc cggccgggtg cggctgcggt gccgatgcgc tcgacggtga  18540
cgggcgccat ggtagcgggc ccggagctcg gagcgaatta ctggatgaac aacctcaggc  18600
agccagtgcg cttcgccgag gtagtccagg cgcagctcca aggcggccac ggtctgttcg  18660
tggagatgag cccgcatccg atcctaacga cttcggtcga ggagatgcgg cgcgcggccc  18720
agcggcgggg cgcagcggtg ggctcgctgc ggcggggggca ggacgagcgc ccggcgatgc  18780
tggaggcgct gggcacgctg tgggcgcagg gctaccctgt accctggggg cggctgtttc  18840
ccgcgggggg gcggcgggta ccgctgccga cctatccctg gcagcgcgag cggtactgga  18900
tcgaagcgcc ggccaagagc gccgcgggcg atcgccgcg cgtgcgtgcg gcggtcacc  18960 cgctcctcgg tgaaatgcag accctgtcaa cccagacgag cacgcggctg tgggagacga  19020
cgctggatct caagcggctg ccgtggctcg cgaccaccg ggtgcaggga gcggtcgtgt  19080
ttccgggcgc ggcgtacctg gagatggcga tttcgtcggg ggccgaggct ttgggcgatg  19140 gcccttttgca gataactgac gtggtgctcg ccgaggcgct ggccttcgcg ggcgacgcgg  19200
cggtgttggt ccaggtggtg acgacggagc agccgtcggg gcggctgcag ttccagatcg  19260
```

-continued

```
cgagccgggc gccgggcgct ggccacgcgt ccttccgggt ccacgctcgc ggcgcgttgc   19320
tccgagtgga gcgcaccgag gtcccggctg ggcttacgct ttccgctgtg cgcgcgcggc   19380
tccaggccag catacccgcc gcggccacct acgcggagct gaccgagatg gggctgcagt   19440
acggccctgc cttccagggg attgctgagc tatggcgggg tgaaggcgag gcgctgggac   19500
gggtacgcct gcccgacgcg gccggctcgg cagcggagta tcggttgcat cctgcgctgc   19560
tggacgcgtg cttccagatc gtcggcagcc tcttcgcccg cagtggcgag gcgacgccgt   19620
gggtgcccgt ggagttgggc tcgctgcggc tcttgcagcg gccttcgggg gagctgtggt   19680
gccatgcgcg cgtcgtgaac catgggcacc aaaccccga tcggcagggc gccgactttt    19740
gggtggtcga cagctcgggt gcagtggtcg ccgaagtttg cgggctcgtg gcgcagcggc   19800
ttccgggagg ggtgcgccgg cgcgaagaag acgattggtt cctggagctc gagtgggaac   19860
ccgcagcggt cggcacagcc aaggtcaacg cgggccggtg gctgctcctc ggcggcggcg   19920
gtgggctcgg cgccgcgttg cgcgcgatgc tggaggccgg cggccatgcc gtcgtgcatg   19980
cggcagagaa caacacgagc gctgccggcg tacgcgcgct cctggcaaag gcctttgacg   20040
gccaggctcc gacggcggtg gtgcacctcg gcagcctcga tgggggtggc gagctcgacc   20100
cagggctcgg ggcgcaaggc gcattggacg cgccccggag cgccgacgtc agtcccgatg   20160
ccctcgatcc ggcgctggta cgtggctgcg acagcgtgct ctggaccgtg caggccctgg   20220
ccggcatggg ctttcgagac gccccgcgat tgtggctttt gacccgcggc gcacaggccg   20280
tcggcgccgg cgacgtctcc gtgacacagg caccgctgct ggggctgggc cgcgtcatcg   20340
ccatggagca cgcggatctg cgctgcgctc gggtcgacct cgatccagcc cggcccgagg   20400
gggagctcgc tgccctgctg gccgagctgc tggccgacga cgccgaagcg gaagtcgcgt   20460
tgcgcggtgg cgagcgatgc gtcgctcgga tcgtccgccg gcagcccgag acccggcccc   20520
gggggaggat cgagagctgc gttccgaccg acgtcaccat ccgcgcggac agcacctacc   20580
ttgtgaccgg cggtctgggt gggctcggtc tgagcgtggc cggatggctg ccgagcgcg    20640 gcgctggtca cctggtgctg gtgggccgct ccggcgcggc gagcgtggag caacgggcag   20700
ccgtcgcggc gctcgaggcc cgcggcgcgc gcgtcaccgt ggcgaaggcg gatgtcgccg   20760
atcgggcgca gctcgagcgg atcctccgcg aggttaccac gtcggggatg ccgctgcggg   20820
gcgtcgtcca tgcggccggc atcttggacg acgggctgct gatgcagcag actcccgcgc   20880
ggtttcgtaa ggtgatggcg cccaaggtcc agggggcctt gcacctgcac gcgttgacgg   20940
gcgaagcgcc gctttccttc ttcgtgctgt acgcttcggg agtagggctc ttgggctcgc   21000
cgggccaggg caactacgcc gcggccaaca cgttcctcga cgctctggcg caccaccgga   21060
gggcgcaggg gctgccagcg ttgagcgtcg actgggcct gttcgcggag gtgggcatgg    21120
cggccgcgca ggaagatcgc ggcgcgcggc tggtctcccg cggaatgcgg agcctccaccc  21180 ccgacgaggg gctgtccgct ctggcacggc tgctcgaaag cggccgcgct caggtggggg   21240
tgatgccggt gaaccgcgg ctgtgggtgg agctctaccc cgcggcggcg tcttcgcgaa    21300
tgttgtcgcg cctggtgacg gcgcatcgcg cgagcgccgc cgggccagcc ggggacgggg   21360
acctgctccg ccgcctcgcc gctgccgagc cgagcgcgcg gagcgcgctc ctggagccgc   21420
tcctccgcgc gcagatctcg caggtgctgc gcctccccga gggcaagatc gaggtggacg   21480
ccccgctcac gagcctgggc atgaactcgc tgatgggggct cgagctgcgc aaccgcatcg   21540
aggccatgct gggcatcacc gtaccggcaa cgctgttgtg gacctatccc acggtggcgg   21600
cgctgagcgg gcatctggcg cgggaggcat gcgaagccgc tcctgtggag tcaccgcaca   21660
```

```
ccaccgccga ctctgccgtc gagatcgagg agatgtcgca ggacgatctg acgcagttga   21720
tcgcagcaaa attcaaggcg cttacatgac tactcgcggt cctacggcac agcagaatcc   21780
gctgaaacaa gcggccatca tcattcagcg gctggaggag cggctcgctg ggctcgcaca   21840
ggcggagctg gaacggaccg agccgatcgc catcgtcggt atcggctgcc gcttccctgg   21900
cggtgcggac gctccggaag cgttttggga gctgctcgac gcggagcgcg acgcggtcca   21960
gccgctcgac atgcgctggg cgctggtggg tgtcgctccc gtcgaggccg tgccgcactg   22020
ggcggggctg ctcaccgagc cgatagattg cttcgatgct gcgttcttcg gcatctcgcc   22080
tcgggaggcg cgatcgctcg acccgcagca tcgtctgttg ctggaggtcg cttgggaggg   22140
gctcgaggac gccggtatcc cgccccggtc catcgacggg agccgcaccg gtgtgttcgt   22200
cggcgctttc acggcggact acgcgcgcac ggtcgctcgg ctgccgcgcg aggagcgaga   22260 ccgtacagc gccaccggca acatgctcag catcgccgcc ggacggctgt cgtacacgct   22320 gggggttgcag ggaccttgcc tgaccgtcga cacggcgtgc tcgtcatcgc tggtggcgat   22380
tcacctcgcc tgccgcagcc tgcgcgcagg agagagcgat ctcgcgttgg cgggaggggt   22440
cagcgcgctc ctctcccccg acatgatgga agccgcggcg cgcacgcaag cgctgtcgcc   22500
cgatggtcgt tgccggacct tcgatgcttc ggccaacggg ttcgtccgtg gcgagggctg   22560
tggcctggtc gtcctcaaac ggctctccga cgcgcaacgg gatggcgacc gcatctgggc   22620
gctgatccgg ggctcggcca tcaaccatga tggccggtcg accgggttga ccgcgcccaa   22680
cgtgctggct caggagacgg tcttgcgcga ggcgctgcgg agcgcccacg tcgaagctgg   22740
ggccgtcgat tacgtcgaga cccacggaac agggacctcg ctgggcgatc ccatcgaggt   22800
cgaggcgctg cgggcgacgg tggggccggc gcgctccgac ggcacacgct gcgtgctggg   22860
cgcggtgaag accaacatcg gccatctcga ggccgcggca ggcgtagcgg gcctgatcaa   22920
ggcagcgctt tcgctgacgc acgagcgcat cccgagaaac ctcaacttcc gcacgctcaa   22980
tccgcggatc cggctcgagg gcagcgcgct cgcgttggcg accgagccgg tgccgtggcc   23040
gcgcacggac cgcccgcgct tcgcggggt gagctcgttc gggatgagcg gaacgaacgc   23100
gcatgtggtg ctggaagagg cgccggcggt ggagctgtgg cctgccgcgc cggagcgctc   23160
ggcggagctt ttggtgctgt cgggcaagag cgaggggggcg ctcgatgcgc aggcggcgcg   23220
gctgcgcgag cacctggaca tgcacccgga gctcgggctc ggggacgtgg cgttcagcct   23280
ggcgacgacg cgcagcgcga tgagccaccg gctcgcggtg gcggtgacgt cgcgcgaggg   23340
gctgctggcg gcgctctcgg ccgtggcgca ggggcagacg ccggcggggg cggcgcgctg   23400
catcgcgagc tcctcgcgcg gcaagctggc gttcctgttc accggacagg gcgcgcagac   23460
gccgggcatg ggccgggggc tttgcgcggc gtggccagcg ttccgggagg cgttcgaccg   23520
gtgcgtggcg ctgttcgacc gggagctgga ccgcccgctg cgcgaggtga tgtgggcgga   23580
ggcggggagc gccgagtcgt tgttgctcga ccagacggcg ttcacccagc ccgcgctctt   23640
cgcggtggag tacgcgctga cggcgctgtg gcggtcgtgg ggcgtagagc cggagctcct   23700
ggttgggcat agcatcgggg agctggtggc ggcgtgcgtg gcgggggtgt tctcgctgga   23760
agatggggtg aggctcgtgg cggcgcgcgg cggctgatg caggggctct cggcgggcgg   23820
cgcgatggtg tcgctcggag cgccggaggc ggaggtggcg gcgcggtgg cgccgcacgc   23880 ggcgtcggtg tcgatcgcgg cggtcaatgg gccggagcag gtggtgatcg cgggcgtgga   23940
gcaagcggtg caggcgatcg cggcgggggtt cgcggcgcgc ggcgcgcgca ccaagcggct   24000
```

```
gcatgtctcg cacgcgttcc actcgccgct gatggaaccg atgctggagg agttcgggcg    24060
ggtggcggcg tcggtgacgt accggcggcc aagcgtttcg ctggtgagca acctgagcgg    24120
gaaggtggtc acggacgagc tgagcgcgcc ggggtactgg gtgcggcacg tgcgggaggc    24180
ggtgcgcttc gcggacgggg tgaaggcgct gcacgaagcc ggcgcgggga cgttcgtcga    24240
agtgggcccg aagccgacgc tgctcgggct gttgccagcc tgcctgccgg aggcggagcc    24300
gacgctgctg gcgtcgttgc gcgccgggcg cgaggaggct gcggggtgc tcgaggcgct    24360 gggcaggctg tgggccgccg gcggctcggt cagctggccg ggcgtcttcc ccacggctgg    24420
gcggcgggtg ccgctgccga cctatccgtg gcagcggcag cggtactgga tcgaggcgcc    24480
ggccgaaggg ctcggagcca cggccgccga tgcgctggcg cagtggttct accgggtgga    24540
ctggcccgag atgcctcgct catccgtgga ttcgcggcga gcccggtccg gcgggtggct    24600
ggtgctggcc gaccggggtg gagtcgggga ggcggccgcg gcggcgcttt cgtcgcaggg    24660
atgttcgtgc gccgtgctcc atgcgcccgc cgaggcctcc gcggttgccg agcaggtgac    24720
ccaggccctc ggtggccgca acgactggca ggggtgctg tacctgtggg gtctggacgc    24780
cgtcgtggag gcgggggcat cggccgaaga ggtcgccaaa gtcacccatc ttgccgcggc    24840
gccggtgctc gcgctgattc aggcgctcgg cacggggccg cgctcacccc ggctctggat    24900
cgtgacccga ggggcctgca cggtgggcgg cgagcctgac gctgcccct gtcaggcggc    24960 gctgtggggt atgggccggg tcgcggcgct agagcatccc ggctcctggg gcgggctcgt    25020
ggacctggat ccggaggaga gcccgacgga ggtcgaggcc ctggtggccg agctgctttc    25080
gccggacgcc gaggatcagc tggcattccg ccaggggcgc cggcgcgcag cgcggcttgt    25140
ggccgcccca ccggagggaa acgcagcgcc ggtgtcgctg tctgcggagg ggagttactt    25200
ggtgacgggt gggctgggcg cccttggcct cctcgttgcg cggtggttgg tggagcgcgg    25260
ggcggggcac cttgtgctga tcagccggca cggattgccc gaccgcgagg aatgggccg    25320 agatcagccg ccagaggtgc gcgcgcgcat tgcggcgatc gaggcgctgg aggcgcaggg    25380
cgcgcgggtc accgtggcgg cggtcgacgt ggccgatgcc gaaggcatgg cggcgctctt    25440
ggcggccgtc gagccgccgc tgcggggggt agtgcacgcc gcgggtctgc tcgacgacgg    25500
gctgctggcc caccaggacg ctggtcggct cgccgggtg ttgcgcccca aggtggaggg    25560
ggcatgggtg ctgcacaccc ttacccgcga gcagccgctg gacctcttcg tactgttttc    25620
ctcggcgtcg ggcgtcttcg gctcgatcgg ccagggcagc tacgcggcag gcaatgcctt    25680
tttggacgcg ctggcggacc tccgccgaac gcagggctc gccgccctga gcatcgcctg    25740
gggcctgtgg gcggagggg ggatgggctc gcaggcgcag cgccgggaac acgaggcatc    25800
gggaatctgg gcgatgccga cgagtcgggc cctggcggcg atggaatggc tgctcggtac    25860
gcgcgcgacg cagcgcgtgg tcatccagat ggattgggcc catgcgggag cggcgccgcg    25920
cgacgcgagc cgaggccgct tctgggatcg gctggtaact gccacgaaag aggcctcctc    25980
ctcggccgtg ccagctgtgg agcgctggcg caacgcgtct gttgtggaga cccgctcggc    26040
gctctacgag cttgtgcgcg gcgtggtcgc cggggtgatg ggctttaccg accagggcac    26100
gctcgacgtg cgacgaggct cgccgagca gggcctcgac tccctgatgg ccgtggagat    26160
ccgcaaacgg cttcagggtg agctgggtat gccgctgtcg gcgacgctag cgttcgacca    26220
tccgaccgtg gagcggctgg tggaatactt gctgagccag gcgctggagc tgcaggaccg    26280
caccgacgtg cggagcgttc ggttgccggc gacagaggac ccgatcgcca tcgtgggtgc    26340
cgcctgccgc ttcccgggcg gggtcgagga cctggagtcc tactggcagc tgttgaccga    26400
```

-continued

```
gggcgtggtg gtcagcaccg aggtgccggc cgaccggtgg aatggggcag acgggcgcgt    26460
ccccggctcg ggagaggcac agagacagac ctacgtgccc aggggtggct ttctgcgcga    26520
ggtggagacg ttcgatgcgg cgttcttcca catctcgcct cgggaggcga tgagcctgga    26580
cccgcaacag cggctgctgc tggaagtgag ctgggaggcg atcgagcgcg cgggccagga    26640
cccgtcggcg ctgcgcgaga gccccacggg cgtgttcgtg ggcgcgggcc ccaacgaata    26700
tgccgagcgg gtgcaggaac tcgccgatga ggcggcgggg ctctacagcg gcaccggcaa    26760
catgctcagc gttgcggcgg gacggctatc attttcctg ggcctgcacg ggccgaccct    26820
ggctgtggat acggcgtgct cctcgtcgct ggtggcgctg cacctcggct gccagagctt    26880
gcgacggggc gagtgcgacc aagccctggt tggcggggtc aacatgctgc tctcgccgaa    26940
gaccttcgcg ctgctctcac ggatgcacgc actttcgccc ggcgggcggt gcaagacgtt    27000
ctcggccgac gcgacggct acgcgcgggc cgagggctgc gccgtggtgg tgctcaagcg    27060
gctctccgac gcgcagcgcg accgcgaccc catcctggcg gtgatccggg gtacggcgat    27120
caatcatgat ggcccgagca gcgggctgac agtgcccagc ggccctgccc aggaggcgct    27180
gttacgccag gcgctggcgc acgcagggt ggttccggcc gacgtcgatt tcgtggaatg    27240
ccacgggacc gggacggcgc tgggcgaccc gatcgaggtg cgtgcgctga gcgacgtgta    27300
cgggcaagcc cgccctgcgg accgaccgct gatcctggga gccgccaagg ccaaccttgg    27360
gcacatggag cccgcggcgg gcctggccgg cttgctcaag gcggtgctcg cgctggggca    27420
agagcaaata ccagcccagc cggagctggg cgagctcaac ccgctcttgc cgtgggaggc    27480
gctgccggtg gcggtggccc gcgcagcggt gccgtggccg cgcacggacc gcccgcgctt    27540
cgcgggggtg agctcgttcg ggatgagcgg aacgaacgcg catgtggtgc tggaagaggc    27600
gccggcggtg gagctgtggc ctgccgcgcc ggagcgctcg gcggagcttt tggtgctgtc    27660
gggcaagagc gaggggggcgc tcgatgcgca ggcggcgcgg ctgcgcgagc acctggacat    27720
gcacccggag ctcgggctcg gggacgtggc gttcagcctg gcgacgacgc gcagcgcgat    27780
gaaccaccgg ctcgcggtgg cggtgacgtc gcgcgagggg ctgctggcgg cgctttcggc    27840
cgtggcgcag gggcagacgc cgccggggc ggcgcgctgc atcgcgagct cgtcgcgcgg    27900
caagctggcg ttcctgttca ccggacaggg cgcgcagacg ccgggcatgg gccgggggct    27960
ttgcgcggcg tggccagcgt tccgggaggc gttcgaccgg tgcgtggcgc tgttcgaccg    28020
ggagctggac cgcccgctgc gcgaggtgat gtgggcggag ccggggagcg ccgagtcgtt    28080
gttgctcgac cagacggcgt tcacccagcc cgcgctcttc acggtggagt acgcgctgac    28140
ggcgctgtgg cggtcgtggg gcgtagagcc ggagctggtg gctgggcata cgccggga    28200 gctggtggcg gcgtgcgtgg cggggtgtt ctcgctggaa gatggggtga ggctcgtggc    28260
ggcgcgcggg cggctgatgc aggggctctc ggcgggcggc gcgatggtgt cgctcggagc    28320
gccggaggcg gaggtggcgg cggcggtggc gccgcacgcg gcgtcggtgt cgatcgcggc    28380
ggtcaatggg ccggagcagg tggtgatcgc gggcgtggag caagcggtgc aggcgatcgc    28440
ggcggggttc gcggcgcgcg gcgcgcgcac caagcggctg catgtctcgc acgcgtccca    28500
ctcgccgctc atggaaccga tgctggagga gttcgggcgg gtggcggcgt cggtgacgta    28560
ccggcggcca agcgtttcgc tggtgagcaa cctgagcggg aaggtggtcg cggacgagct    28620
gagcgcgccg gggtactggg tgcggcacgt gcgggaggcg gtgcgcttcg cggacggggt    28680
gaaggcgctg cacgaagccg gtgcgggcac gttcgtcgaa gtgggcccga gccgacgct    28740
```

-continued

```
gctcgggctg ttgccagcct gcctgccgga ggcggagccg acgctgctgg cgtcgttgcg   28800
cgccgggcgc gaggaggctg cggggtgct cgaggcgctg ggcaggctgt gggccgccgg    28860
cggctcggtc agctggccgg gcgtcttccc cacggctggg cggcgggtgc cgctgccgac   28920
ctatccgtgg cagcggcagc ggtactggcc cgacatcgag cctgacagcc gtcgccacgc   28980
agccgcggat ccgacccaag gctggttcta tcgcgtggac tggccggaga tacctcgcag   29040
cctccagaaa tcagaggagg cgagccgcgg gagctggctg gtattggcgg ataagggtgg   29100
agtcggcgag gcggtcgctg cagcgctgtc gacacgtgga cttccatgcg tcgtgctcca   29160
tgcgccggca gagacatccg cgaccgccga gctggtgacc gaggctgccg gcggtcgaag   29220
cgattggcag gtagtgctct acctgtgggg tctggacgcc gtcgtcggtg cggaggcgtc   29280
gatcgatgag atcggcgacg cgacccgtcg tgctaccgcg ccggtgctcg gcttggctcg   29340
gtttctgagc accgtgtctt gttcgccccg actctgggtc gtgacccggg gggcatgcat   29400
cgttggcgac gagcctgcga tcgccccttg tcaggcggcg ttatggggca tgggccgggt   29460
ggcggcgctc gagcatcccg gggcctgggg cgggctcgtg gacctggatc cccgagcgag   29520
cccgccccaa gccagcccga tcgacggcga gatgctcgtc accgagctat tgtcgcagga   29580
gaccgaggat cagctcgcct tccgccatgg gcgccggcac gcggcacggc tggtggccgc   29640
cccgccacag gggcaagcgg caccggtgtc gctgtctgcg gaggcgagct acctggtgac   29700
gggaggcctc ggtgggctgg gcctgatcgt ggcccagtgg ctggtggagc tgggagcgcg   29760
gcacttggtg ctgaccagcc ggcgcgggtt gcccgaccgg caggcgtggt gcgagcagca   29820
gccgcctgag atccgcgcgc ggatcgcagc ggtcgaggcg ctggaggcgc ggggtgcacg   29880
ggtgaccgtg gcagcggtgg acgtggccga cgtcgaaccg atgacagcgc tggtttcgtc   29940
ggtcgagccc ccgctgcgag gggtggtgca cgccgctggc gtcagcgtca tgcgtccact   30000
ggcggagacg gacgagaccc tgctcgagtc ggtgctccgt cccaaggtgg ccgggagctg   30060
gctgctgcac cggctgctgc acggccggcc tctcgacctg ttcgtgctgt tctcgtcggg   30120
cgcagcggtg tggggtagcc atagccaggg tgcgtacgcg gcggccaacg ctttcctcga   30180
cgggctcgcg catcttcggc gttcgcaatc gctgcctgcg ttgagcgtcg cgtggggtct   30240
gtgggccgag ggaggcatgg cggacgcgga ggctcatgca cgtctgagcg acatcggggt   30300
tctgcccatg tcgacgtcgg cagcgttgtc ggcgctccag cgcctggtgg agaccggcgc   30360
ggctcagcgc acggtgaccc ggatggactg ggcgcgcttc gcgccggtgt acaccgctcg   30420
agggcgtcgc aacctgctttt cggcgctggt cgcagggcgc gacatcatcg cgccttcccc   30480
tccggcggca gcaaccccgga actggcgtgg cctgtccgtt gcggaagccc gcgtggctct   30540
gcacgagatc gtccatgggg ccgtcgctcg ggtgctgggc ttcctcgacc cgagcgcgct   30600
cgatcctggg atggggttca atgagcaggg cctcgactcg ttgatggcgg tggagatccg   30660
caacctcctt caggctgagc tggacgtgcg gctttcgacg acgctggcct ttgatcatcc   30720
gacggtacag cggctggtgg agcatctgct cgtcgatgta ctgaagctgg aggatcgcag   30780
cgacacccag catgttcggt cgttggcgtc agacgagccc atcgccatcg tgggagccgc   30840
ctgccgcttc ccggcggggg tggaggacct ggagtcctac tggcagctat tggccgaggg   30900
cgtggtggtc agcgccgagg tgccggccga ccggtgggat gcggcggact ggtacgaccc   30960
tgatccggag atcccaggcc ggacttacgt gaccaaaggc gccttcctgc gcgatttgca   31020
gagattggat gcgaccttct tccgcatctc gcctcgcgag gcgatgagcc tcgacccgca   31080
gcagcggttg ctcctggagg taagctggga agcgctcgag agcgcgggta tcgctccgga   31140
```

-continued

```
tacgctgcga gatagcccca ccggggtgtt cgtgggtgcg gggcccaatg agtactacac    31200
gcagcggctg cgaggcttca ccgacggagc ggcagggttg tacggcggca ccgggaacat    31260
gctcagcgtt acggctggac ggctgtcgtt tttcctgggt ctgcacggcc cgacgctggc    31320
catggatacg gcgtgctcgt catccctggt cgcgctgcac ctcgcctgcc agagcctgcg    31380
actgggcgag tgcgatcaag cgctggttgg cggggtcaac gtgctgctcg cgccggagac    31440
cttcgtgctg ctctcacgga tgcgcgcgct ttcgcccgac gggcggtgca agacgttctc    31500
ggccgacgcg gacggctacg cgcggggcga ggggtgcgcc gtggtggtgc tcaagcggct    31560
gcgcgatgcg cagcgcgccg gcgactccat cctggcgctg atccggggaa gcgcggtgaa    31620
ccacgacggc ccgagcagcg ggctgaccgt acccaacgga cccgcccagc aagcattgct    31680
gcgccaggcg ctttcgcaag caggcgtgtc tccggtcgac gttgattttg tggagtgtca    31740
cgggacaggg acgcgctggg cgacccgat cgaggtgcag gcgctgagcg aggtgtatgg    31800
tccagggcgc tccggggacc gaccgctggt gctgggggcc gccaaggcca acgtcgcgca    31860
tctggaggcg gcatctggct tggccagcct gctcaaggcc gtgcttgcgc tgcggcacga    31920
gcagatcccg gcccagccgg agctggggga gctcaacccg cacttgccgt ggaacacgct    31980
gccggtggcg gtgccacgta aggcggtgcc gtggggggcg ggcgcacgcc cgcgtcgggc    32040
cggcgtgagc gcgttcgggt tgagcggaac caacgtgcat gtcgtgctgg aggaggcacc    32100
ggaggtggag ccggcgcccg cggcgccggc gcgaccggtg gagctggtcg tgctatcggc    32160
caagagcgcg gcggcgctgg acgccgcggc ggcacggctc tcggcgcacc tgtccgcgca    32220
cccggagctg agcctcggcg acgtggcgtt cagcctggcg acgacgcgca gcccgatgga    32280
gcaccggctc gccatcgcga cgacctcgcg cgaggccctg cgaggcgcgc tggacgccgc    32340
ggcgcagcaa aagacgccgc agggcgcggt gcgcggcaag gccgtgtcct cacgcggtaa    32400
gctggctttc ctgttcaccg gacagggcgc gcaaatgccg ggcatgggcc gtgggctgta    32460
cgaaacgtgg cctgcgttcc gggaggcgtt cgaccggtgc gtggcgctct tcgatcggga    32520
gatcgaccag cctctgcgcg aggtgatgtg ggctgcgccg ggcctcgctc aggcggcgcg    32580
gctcgatcag accgcgtacg cgcagccggc tctctttgcg ctggagtacg cgctggctgc    32640
cctgtggcgt tcgtggggcg tggagccgca cgtactgctc ggtcatagca tcggcgagct    32700
ggtcgccgcc tgcgtggcgg gcgtgttctc gctcgaagat gcggtgaggt tggtggccgc    32760
gcgcgggcgg ctgatgcagg cgctacccgc cggcggtgcc atggtagcca tcgcagcgtc    32820
cgaggccgag gtggccgcct ccgtggcgcc ccacgccgcc acggtgtcga tcgccgcggt    32880
caacggtcct gacgccgtcg tgatcgccgg cgccgaggta caggtgctcg ccctcggcgc    32940
gacgttcgcg gcgcgtggga tacgcacgaa gaggctcgcc gtctcccatg cgttccactc    33000
gccgctcatg gatccgatgc tggaagactt ccagcgggtc gctgcgacga tcgcgtaccg    33060
cgcgccagac cgcccggtgg tgtcgaatgt caccggccac gtcgcaggcc ccgagatcgc    33120
cacgcccgag tattgggtcc ggcatgtgcg aagcgccgtg cgcttcggcg acggggcaaa    33180
ggcgttgcat gccgcgggtg ccgccacgtt cgtcgaggtt ggcccgaagc cggtcctgct    33240
cgggctgttg ccagcgtgcc tcggggaagc ggacgcggtc ctcgtgccgt cgctacgcgc    33300
ggaccgctcg gaatgcgagg tggtcctcgc ggcgctcggg gcttggtatg cctgggggg    33360 tgcgctcgac tggaagggcg tgttcccga tggcgcgcg cgcgtggctc tgcccatgta    33420
tccatggcag cgtgagcgcc attggatgga cctcaccccg cgaagcgccg cgcctgcagg    33480
```

```
gatcgcaggt cgctggccgc tggctggtgt cgggctctgc atgcccggcg ctgtgttgca    33540
ccacgtgctc tcgatcggac cacgccatca gcccttcctc ggtgatcacc tcgtgtttgg    33600
caaggtggtg gtgcccggcg cctttcatgt cgcggtgatc ctcagcatcg ccgccgagcg    33660
ctggcccgag cgggcgatcg agctgacagg cgtggagttc ctgaaggcca tcgcgatgga    33720
gcccgaccag gaggtcgagc tccacgccgt gctcaccccc gaagccgccg gggatggcta    33780
cctgttcgag ctggcgaccc tggcggcgcc ggagaccgaa cgccgatgga cgacccacgc    33840
ccgcggtcgg gtgcagccga cagacggcgc gcccggcgcg ttgccgcgcc tcgaggtgct    33900
ggaggaccgc gcgatccagc ccctcgactt cgccggattc ctcgacaggt tatcggcggt    33960
gcggatcggc tggggtccgc tttggcgatg gctgcaggac gggcgcgtcg gcgacgaggc    34020
ctcgcttgcc accctcgtgc cgacctatcc gaacgcccac gacgtggcgc ccttgcaccc    34080
gatcctgctg gacaacggct tgcggtgag cctgctgtca acccggagcg agccggagga    34140
cgacgggacg ccccgctgc cgttcgccgt ggaacgggtg cggtggtggc gggcgccggt    34200
tggaagggtg cggtgtggcg gcgtgccgcg gtcgcaggca ttcggtgtct cgagcttcgt    34260
gctggtcgac gaaactggcg aggtggtcgc cgaggtggag ggatttgttt gccgccgggc    34320
gccgcgagag gtgttcctgc ggcaggagtc gggcgcgtcg actgcagcct tgtaccgcct    34380
cgactggccc gaagcgccct tgcccgatgc gcctgcggaa cggatcgagg agagctgggc    34440
cgtggtggca gcacctggct cggagatggc cgcggcgctc gcaacacggc tcaaccgctg    34500
cgtcctcgcc gaacccaaag gcctcgaggc ggccctcgcg ggggtgtctc ccgcaggtgt    34560
gatctgcctc tgggaggctg gagcccacga ggaagctccg gcggcggcgc agcgtgtggc    34620
gaccgagggc ctctcggtgg tgcaggcgct cagggaccgc gcggtgcgcc tgtggtgggt    34680
gaccatgggc gcagtggccg tcgaggccgg tgagcgggtg caggtcgcca cagcgccggt    34740
atggggcctg gccggacag tgatgcagga gcgcccggga ctcagctgca ctctggtgga    34800
tttggagccg gaggccgatg cagcgcgctc agctgacgtt ctgttgcggg agctcggtcg    34860
cgctgacgac gagacacagg tggctttccg ttccggaaag cgccgcgtag cgcggctggt    34920
caaagcgacg accccgaag ggctcctggt ccctgacgca gagtcctatc gactggaggc    34980
tgggcagaag ggcacattgg accagctccg cctcgcgccg gcacagcgcc gggcacctgg    35040
cccgggcgag gtcgagatca aggtaaccgc ctcggggctc aacttccgga ccgtcctcgc    35100
tgtgctggga atgtatccgg gcgacgccgg gccgatgggc ggagattgtg ccggtgtcgc    35160
cacggcggtg ggccaggggg tgcgccacgt cgcggtcggc gatgctgtca tgacgctggg    35220
gacgttgcat cgattcgtca cggtcgacgc gcggctggtg gtccggcagc ctgcagggct    35280
gactccgcg caggcagcta cggtgccggt cgcgttcctg acggcctggc tcgctctgca    35340
cgacctgggg aatctgcggc gcggcagcg ggtgctgatc catgctgcgg ccggcggtgt    35400
gggcatggcc gcggtgcaaa tcgcccgatg datagggccc gaggtgttcg ccacggcgag    35460
cccgtccaag tgggcagcgg ttcaggccat gggcgtgccg cgcacgcaca tcgccagctc    35520
gcggacgctg gagtttgctg agacgttccg gcaggtcacc ggcggccggg gcgtggacgt    35580
ggtgctcaac gcgctggccg gcgagttcgt ggacgcgagc ctgtccctgc tgtcgacggg    35640
cgggcggttc ctcgagatgg gcaagaccga catacgggat cgagccgcgg tcgcggcggc    35700
gcatcccggt gttcgctatc gggtattcga catcctggag ctcgctccgg atcgaactcg    35760
agagatcctg gagcgcgtgg tcgagggctt tgctgcggga catctgcgcg cattgccggt    35820
gcatgcgttc gcgatcacca aggccgaggc agcgtttcgg ttcatggcgc aagcgcggca    35880
```

```
tcagggcaag gtcgtgctgc tgccggcgcc ctccgcagcg cccttggcgc cgacgggcac    35940
cgtactgctg accggtgggc tgggagcgtt ggggctccac gtggcccgct ggctcgccca    36000
gcagggcgtg ccgcacatgg tgctcacagg tcggcggggc ctggatacgc cgggcgctgc    36060
caaagccgtc gcggagatcg aagcgctcgg cgctcgggtg acgatcgcgg cgtcggatgt    36120
cgccgatcgg aatgcgctgg aggctgtgct ccaggccatt ccggcggagt ggccgttaca    36180
gggcgtgatc catgcagccg gagcgctcga tgatggtgtg cttgatgagc agaccaccga    36240
ccgcttctcg cgggtgctgg caccgaaggt gactggcgcc tggaatctgc atgagctcac    36300
ggcgggcaac gatctcgctt tcttcgtgct gttctcctcc atgtcggggc tcttgggctc    36360
ggccgggcag tccaactatg cggcggccaa caccttcctc gacgcgctgg ccgcgcatcg    36420
gcgggccgaa ggcctggcgg cgcagagcct cgcgtggggc ccatggtcgg acggaggcat    36480
ggcagcgggg ctcagcgcgg cgctgcaggc gcggctcgct cggcatggga tgggagctct    36540
gtcgccggct caggcaccg cgctgctcgg gcaggcgctg gctcggccgg aaacgcagct    36600
cggggcgatg tcgctcgacg tgcgtgcggc aagccaagct tcgggagcgg cagtgccgcc    36660
tgtgtggcgc gcgttggtgc gcgcggaggc gcgccatacg gcggctgggg cgcaggggc    36720 attggccgcg cgtcttgggg cgctgcccga ggcgcgtcgc gccgacgagg tgcgcaaggt    36780
cgtgcaggcc gagatcgcgc gcgtgctttc atggagcgcc gcgagcgccg tgcccgtcga    36840
tcggccgctg tcggacttgg gcctcgactc gctcacggcg gtggagctgc gcaacgtgct    36900
cggccagcgg gtgggtgcga cgctgccggc gacgctggca ttcgatcacc cgacggtcga    36960
cgcgctcacg cgctggctgc tcgataaggt cctggccgtg gccgagccga gcgtatcgtc    37020
cgcaaagtcg tcgccgcagg tcgccctcga cgagcccatt gccatcatcg gcatcggctg    37080
ccgtttccca ggcggcgtgg ccgatccgga gtcgttttgg cggctgctcg aagagggcag    37140
cgatgccgtc gtcgaggtgc cgcatgagcg atgggacatc gacgcgttct atgatccgga    37200
tccggatgtg cgcggcaaga tgacgacacg ctttggcggc ttcctgtccg atatcgaccg    37260
gttcgatccg gccttcttcg gcatctcgcc gcgcgaagcg acgaccatgg atccgcagca    37320
gcggctgctc ctggagacga gctgggaggc gttcgagcgc gccgggattt tgcccgagcg    37380
gctgatgggc agcgataccg cgtgttcgt ggggctcttc taccaggagt acgctgcgct    37440
cgccggcggc atcgaggcgt tcgatggcta tctaggcacc ggcaccacgg ccagcgtcgc    37500
ctcgggcagg atctcttatg tgctcgggct aaaggggccg agcctgacgg tggacaccgc    37560
gtgctcctcg tcgctggtcg cggtgcacct ggcctgccag gcgctgcggc ggggcgagtg    37620
ttcggtggcg ctgccggcg gcgtggcgct gatgctcacg ccggcgacgt tcgtggagtt    37680
cagccggctg cgaggcctgg ctcccgacgg acggtgcaag agcttctcgg ccgcagccga    37740
cggcgtgggg tggagcgaag gctgcgccat gctcctgctc aaaccgcttc gcgatgcgca    37800
gcgcgatggg gatccgatcc tggcggtgat ccgcggcacc gcggtgaacc aggatgggcg    37860
cagcaacggg ctgacggcgc ccaacgggtc gtcgcagcaa gaggtgatcc gtcgggccct    37920
ggagcaggcg gggctggctc cggcggacgt cagctacgtc gagtgccacg gcaccggcac    37980
gacgttgggc gaccccatcg aagtgcaggc cctgggcgcc gtgctggcac aggggcgacc    38040
ctcggaccgg ccgctcgtga tcgggtcggt gaagtccaat atcggacata cgcaggctgc    38100
ggcgggcgtg gccggtgtca tcaaggtggc gctggcgctc gagcgcgggc ttatcccgag    38160
gagcctgcat ttcgacgcgc ccaatccgca cattccgtgg tcggagctcg ccgtgcaggt    38220
```

-continued

| | |
|---|---|
| ggccgccaaa cccgtcgaat ggacgagaaa cggcgtgccg cgacgagccg gggtgagctc | 38280 |
| gtttggcgtc agcgggacca acgcgcacgt ggtgctggag gaggcgccag cggcggcgtt | 38340 |
| cgcgcccgcg gcgcgcgcgtt cagcggagct tttcgtgctg tcggcgaaga gcgccgcggc | 38400 |
| gctggacgcg caggcggcgc ggctttcggc gcacgtcgtt gcgcacccgg agctcggcct | 38460 |
| cggcgacctg gcgttcagcc tggcgacgac ccgcagcccg atgacgtacc ggctcgcggt | 38520 |
| ggcggcgacc tcgcgcgagg cgctgtctgc cgcgctcgac acagcggcgc aggggcaggc | 38580 |
| gccgcccgca gcgcgctcgcg gccacgcttc cacaggcagc gccccaaagg tggttttcgt | 38640 |
| ctttcctggc cagggctccc agtggctggg catgggccaa aagctcctct cggaggagcc | 38700 |
| cgtcttccgc gacgcgctct cggcgtgtga ccgagcgatt caggccgaag ccggctggtc | 38760 |
| gctgctcgcc gagctcgcgg ccgatgagac cacctcgcag ctcggccgca tcgacgtggt | 38820 |
| gcagccggc ctgttcgcga tcgaggtcgc gctgtcggcg ctgtggcggt cgtggggcgt | 38880 |
| cgagccggat gcagtggtag gccacagcat gggcgaagtg gcggccgcgc acgtcgccgg | 38940 |
| cgccctgtcg ctcgaggatg ctgtagcgat catctgccgg cgcagcctgc tgctgcggcg | 39000 |
| gatcagcggc caaggcgaga tggcggtcgt cgagcttttcc ctggccgagg ccgaggcagc | 39060 |
| gctcctgggc tacgaagacc ggctcagcgt ggcggtgagc aacagcccgc gctcgacgt | 39120 |
| gctggcgggc gagccggcag cgctcgcaga ggtgctggcg atccttgcgg caaagggggt | 39180 |
| gttctgccgt cgagtcaagg tggacgtcgc cagccacagc ccacagatcg acccgctgcg | 39240 |
| cgacgagcta ttggcagcat tgggcgagct cgagccgcga caagcgaccg tgtcgatgcg | 39300 |
| ctcgacggtg acgagcacga tcatggcggg cccggagctc gtggcgagct actgggcgga | 39360 |
| caacgttcga cagccggtgc gcttcgccga agcggtgcaa tcgttgatgg aagacggtca | 39420 |
| tgggctgttc gtggagatga gcccgcatcc gatcctgacg acatcggtcg aggagatccg | 39480 |
| acgggcgacg aagcgggagg gagtcgcggt gggctcgttg cggcgtggac aggacgagcg | 39540 |
| cctgtccatg ttggaggcgc tgggagcgct ctgggtacac ggccaggcgg tgggctggga | 39600 |
| gcggctgttc tccgcgggcg gcgcgggcct ccgtcgcgtg ccgctgccga cctatccctg | 39660 |
| gcagcgcgag cggtactggg tcgatgcgcc gaccggcggc gcggcgggcg gcagccgctt | 39720 |
| tgctcatgcg ggcagtcacc cgctcctggg tgaaatgcag accctgtcga cccagaggag | 39780 |
| cacgcgcgtg tgggagacga cgctggatct caaacggctg ccgtggctcg gcgatcaccg | 39840 |
| ggtgcagggg gcggtcgtgt tcccgggcgc ggcgtacctg gagatggcgc tttcgtccgg | 39900 |
| ggccgaggcc ttgggtgacg gtccgctcca ggtcagcgat gtggtgctcg ccgaggcgct | 39960 |
| ggccttcgcg gatgatacgc cggcggcggt gcaggtcatg gcgaccgagg agcgaccagg | 40020 |
| ccgcctgcaa ttccacgttg cgagccgggt gccgggccac ggcggtgctg cctttcgaag | 40080 |
| ccatgcccgc ggggtgctgc gccagatcga gcgcgccgag gtcccggcga ggctggatct | 40140 |
| ggccgcgctt cgtgcccggc ttcaggccag cgcacccgct gcggctacct atgcggcgct | 40200 |
| ggccgagatg gggctcgagt acggcccagc gttccagggg cttgtcgagc tgtggcgggg | 40260 |
| ggagggcgag gcgctgggac gtgtgcggct ccccgaggcc gccggctccc cagccgcgtg | 40320 |
| ccggctccac cccgcgctct tggatgcgtg cttccacgtg agcagcgcct tcgctgaccg | 40380 |
| cggcgaggcg acgccatggg tacccgtgga aatcggctcg ctgcggtggt tccagcggcc | 40440 |
| gtcgggggag ctgtggtgtc atgcgcgagt tgtgagccac ggaaagccaa cacccgaccg | 40500 |
| gcggagtacc gacttctggg tggtcgacag cacgggcgcg atcgtcgccg agatctccgg | 40560 |
| gctcgtggcg cagcggctcg cgggaggtgt acgccggcgc gaagaagacg actggttcat | 40620 |

```
ggagccggct tgggaaccga ccgcggtccc cggatccgag gtcatggcgg gccggtggct   40680
gctcatcggc tcgggcggcg ggctcggcgc tgcgctccac tcggcgctga cggaagctgg   40740
ccattccgtc gtccacgcga cagggcgcgg cacgagcgcc gccgggttgc aggcactctt   40800
gacggcgtcc ttcgacggcc aggccccgac gtcggtggtg cacctcggca gcctcgatga   40860
gcgtggcgtg ctcgacgcgg atgccccctt cgacgccgat gcgcttgagg agtcgctggt   40920
gcgcggctgc gacagcgtgc tctggaccgt gcaggccgtg gccggggcgg gcttccgaga   40980
tcctccgcgg ttgtggctcg tgacacgcgg cgctcaggcc atcggcgccg cgacgtctc    41040 tgtggcgcaa gcgccgctcc tggggctggg ccgcgttatc gccttggagc acgccgagct   41100
gcgctgcgct cggatcgacc tcgatccagc gcggcgcgac ggagaagtcg atgagctgct   41160
tgccgagctg ttggccgacg acgccgagga ggaagtcgcg tttcgcggcg gtgagcggcg   41220
cgtggcccgg ctcgtccgaa ggctgcccga daccgactgc cgagagaaaa tcgagcccgc   41280
ggaaggccgg ccgttccggc tggagatcga tgggtccggc gtgctcgacg acctggtgct   41340
ccgagccacg gagcggcgcc ctcctggccc ggcgaggtc gagatcgccg tcgaggcggc   41400
ggggctcaac tttctcgacg tgatgagggc catggggatc taccctgggc ccggggacgg   41460
tccggttgcg ctgggcgccg agtgctccgg ccgaattgtc gcgatgggcg aaggtgtcga   41520
gagccttcgt atcggccagg acgtcgtggc cgtcgcgccc ttcagtttcg gcacccacgt   41580
caccatcgac gcccggatgc tcgcacctcg ccccgcggcg ctgacggccg cgcaggcagc   41640
cgcgctgccc gtcgcattca tgacggcctg gtacggtctc gtccatctgg ggaggctccg   41700
ggccggcgag cgcgtgctca tccactcggc gacggggggc accgggctcg ctgctgtgca   41760
gatcgcccgc cacctcggcg cggagatatt tgcgaccgct ggtacaccgg agaagcgggc   41820
gtggctgcgc gagcagggga tcgcgcacgt gatggactcg cggtcgctgg acttcgccga   41880
gcaagtgctg gccgcgacga agggcgaggg ggtcgacgtc gtgttgaact cgctgtctgg   41940
cgccgcgatc gacgcgagcc tttcgaccct cgtgccggac ggccgcttca tcgagctcgg   42000
caagacggac atctatgcag atcgctcgct ggggctcgct cacttcagga agagcctgtc   42060
ctacagcgcc gtcgatcttg cgggcttggc cgtgcgtcgg cccgagcgcg tcgcagcgct   42120
gctggcggag gtggtggacc tgctcgcacg gggagcgctg cagccgcttc cggtagagat   42180
cttccccctc tcgcgggccg cggacgcgtt ccggaaaatg gcgcaagcgc agcatctcgg   42240
gaagctcgtg ctcgcgctgg aggacccgga cgtgcggatc cgcgttccgg gcgaatccgg   42300
cgtcgccatc cgcgcggacg gcgcctacct cgtgaccggc ggtctggggg gctcggtct    42360 gagcgtggct ggatggctgg ccgagcaggg ggctgggcat ctggtgctgg tgggccgctc   42420
cggcgcggtg agcgcggagc agcagacggc tgtcgccgcg ctcgaggcgc acggcgcgcg   42480
tgtcacggta gcgagggcag acgtcgccga tcgggcgcag atggagcgga tcctccgcga   42540
ggttaccgcg tcggggatgc cgctccgcgg cgtcgttcat gcggccggaa tcctggacga   42600
cgggctgctg atgcagcaaa ccccgcgcg gttccgcgcg gtcatggcgc caaggtccg    42660 aggggccttg cacctgcatg cgttgacacg cgaagcgccg ctctccttct tcgtgctgta   42720
cgcttcggga gcagggctct tggctcgcc gggccagggc aactacgccg cggccaacac   42780
gttcctcgac gcactggcac accaccggag ggcgcagggg ctgccagcat tgagcatcga   42840
ctggggcctg ttcgcggacg tgggtttggc cgccgggcag caaaatcgcg gcgcacggct   42900
ggtcacccgc gggacgcgga gcctcacccc cgacgaaggg ctgtgggcgc tcgagcgcct   42960
```

-continued

```
gctcgacggc gatcgcaccc aggccggggt catgccgttc gacgtgcggc agtgggtgga   43020
gttctacccg gcggcggcat cttcgcggag gttgtcgcgg ctcatgacgg cacggcgcgt   43080
ggcttccggt cggctcgccg gggatcggga cctgctcgaa cggctcgcca ccgccgaggc   43140
gggcgcgcgg gcaggatgc tgcaggaggt cgtgcgcgcg caggtctcgc aggtgctgcg    43200
cctctccgaa ggcaagctcg acgtggatgc gccgctcacg agcctgggaa tggactcgct   43260 gatgggcta gagctgcgca accgcatcga ggccgtgctc ggcatcacca tgccggcgac    43320
cctgctgtgg acctacccca cggtggcagc gctgagtgcg catctggctt ctcatgtcgt   43380
ctctacgggg gatggggaat ccgcgcgccc gccggataca gggagcgtgg ctccaacgac   43440
ccacgaagtc gcttcgctcg acgaagacgg gttgttcgcg ttgattgatg agtcactcgc   43500
gcgcgcggga aagaggtgat tgcgtgacag accgagaagg ccagctcctg gagcgcttgc   43560
gtgaggttac tctggcccgtt cgcaagacgc tgaacgagcg cgataccctg gagctcgaga   43620
agaccgagcc gatcgccatc gtggggatcg gctgccgctt ccccggcgga gcggcactc    43680 cggaggcgtt ctgggagctg ctcgacgacg ggcgcgacgc gatccggccg ctcgaggagc   43740
gctgggcgct cgtaggtgtc gacccaggcg acgacgtacc gcgctgggcg gggctgctca   43800
ccgaggccat cgacggcttc gacgccgcgt tcttcggtat cgccccccgg gaggcacggt   43860
cgctcgaccc gcagcatcgc ctgctgctgg aggtcgcctg ggaggggttc gaagacgccg   43920
gcatcccgcc caggtccctc gtcgggagcc gcaccggcgt gttcgtcggc gtctgcgcca   43980
cggagtacct ccacgccgcc gtcgcgcacc agccgcgcga agagcgggac gcgtacagca   44040
ccaccggcaa catgctcagc atcgccgccg gacggctatc gtacacgctg gggctgcagg   44100
gaccttgcct gaccgtcgat acggcgtgct cgtcatcgct ggtggccatt cacctcgcct   44160
gccgcagcct gcgcgctcga gagagcgatc tcgcgctggc gggaggggtc aacatgcttc   44220 tctccccga cacgatgcga gctctggcgc gcacccaggc gctgtcgccc aatgccgtt    44280 gccagacctt cgacgcgtcg gccaacgggt tcgtccgtgg ggagggctgc ggtctgatcg   44340
tgctcaagcg attgagcgac gcgcggcggg atggggaccg gatctggcg ctgatccgag    44400 gatcggccat caatcaggac ggccggtcga cggggttgac ggcgcccaac gtgctcgccc   44460 aggggcgct cttgcgcgag gcgctgcgga acgccgcgt cgaggccgag gccatcggtt     44520
acatcgagac ccacggggcg gcaacctcgc tgggcgaccc catcgagatc gaagcgctgc   44580
gcgctgtggt ggggccggcg cgagccgacg gagcgcgctg cgtgctgggc gcggtgaaga   44640
ccaacctcgg ccacctggag ggcgctgccg gcgtggcggg cctgatcaag gcgacgcttt   44700
cgctacatca cgagcgcatc ccgaggaacc tcaactttcg tacgctcaat ccgcggatcc   44760
ggatcgaggg gaccgcgctc gcgttggcga ccgaaccggt gccctggccg cggacgggcc   44820
ggacgcgctt cgcgggagtg agctcgttcg ggatgagcgg gaccaacgcg catgtggtgt   44880
tggaggaggc gccggcggtg gagcctgagg ccgcggcccc cgagcgcgca gcggagctgt   44940
tcgtcctgtc ggcgaagagc gcggcggcgc tggatgcgca ggcagcccgg ctgcgggacc   45000
acctggagaa gcacgtcgag cttggcctcg gcgatgtggc gttcagcctg gcgacgacgc   45060
gcagcgcgat ggagcaccgg ctgcggtgg ccgcgagctc gcgcgaggcg ctgcgagggg    45120
cgctttcggc cgcagcgcag gggcacacgc cgccgggagc cgtgcgtggg cgggcctcgg   45180
gcggcagcgc gccgaaggtg gtcttcgtgt ttcccggtca gggctcgcag tgggtgggca   45240
tgggccgaaa gctcatggcc gaagagccgg tcttccgggg ggcgctggag ggttgcgacc   45300
gggccatcga ggcggaagcg ggctggtcgc tgctcgggga gctctccgcc gacgaggccg   45360
```

```
cctcgcagct cgggcgcatc gacgtggttc agccggtgct cttcgccatg gaagtagcgc    45420
tttctgcgct gtggcggtcg tggggagtgg agccggaagc ggtggtgggc cacagcatgg    45480
gcgaggttgc ggcggcgcac gtggccggcg cgctgtcgct cgaggacgcg gtggcgatca    45540
tctgccggcg cagccggctg ctgcggcgga tcagcggtca gggggagatg gcgctggtcg    45600
agctgtcgct ggaggaggcc gaggcggcgc tgcgtggcca tgagggtcgg ctgagcgtgg    45660
cggtgagcaa cagcccgcgc tcgaccgtgc tcgccggcga gccggcggcg ctctcggagg    45720
tgctggcggc gctgacggcc aagggggtgt tctggcggca ggtgaaggtg gacgtcgcca    45780
gccatagccc gcaggtcgac ccgctgcgcg aagagctgat cgcggcgctg ggagcgatcc    45840
ggccgcgagc ggctgcggtg ccgatgcgct cgacggtgac gggcggggtg atcgcgggtc    45900
cggagctcgg tgcgagctac tggcggaca accttcggca gccggtgcgc ttcgctgcgg     45960
cggcgcaagc gctgctggag ggtggcccg cgctgttcat cgagatgagc ccgcacccga     46020
tcctggtgcc gcccctggac gagatccaga cggcggccga gcaaggggc gctgcggtgg     46080 gctcgctgcg gcgagggcag gacgagcgcg cgacgctgct ggaggcgctg gggacgctgt    46140
gggcgtccgg ctatccggtg agctgggctc ggctgttccc cgcgggcggc aggcgggttc    46200
cgctgccgac ctatccctgg cagcacgagc ggtgctggat cgaggtcgag cctgacgccc    46260
gccgcctcgc cgcagccgac cccaccaagg actggttcta ccgaacggac tggcccgagg    46320
tgccccgcgc cgccccgaaa tcggagacag ctcatgggag ctggctgctg ttggccgaca    46380
ggggtggggt cggtgaggcg gtcgctgcag cgctgtcgac gcgcggactt tcctgcaccg    46440
tgcttcatgc gtcggctgac gcctccaccg tcgccgagca ggtatccgaa gctgccagtc    46500
gccgaaacga ctgcaggga gtcctctacc tgtggggcct cgacgccgtc gtcgatgctg     46560
gggcatcggc cgacgaagtc agcgaggcta ccgccgtgc caccgcaccc gtccttgggc     46620
tggttcgatt cctgagcgct cgcccatc ctcctcgctt ctgggtggtg acccgcgggg      46680
catgcacggt gggcggcgag ccagaggcct ctctttgcca agcggcgttg tggggcctcg    46740
cgcgcgtcgc ggcgctggag caccccgctg cctggggtgg cctcgtggac ctggatcctc    46800
agaagagccc gacggagatc gagccctgg tggccgagct gctttcgccg gacgccgagg    46860
atcaactggc gttccgcagc ggtcgcaggc acgcagcacg ccttgtagcc gccccgccgg    46920
agggcgacgt cgcaccgata tcgctgtccg cggaggggag ctacctggtg acgggcgggc    46980
tgggtggcct tggtctgctc gtggctcggt ggctggtgga gcggggagct cgacatctgg    47040
tgctcaccag ccggcacggg ctgccagagc gacaggcgtc gggcggagag cagccgccgg    47100
aggcccgcgc gcgcatcgca gcggtcgagg ggctggaagc gcagggcgcg cgggtgaccg    47160
tggcagcggt ggatgtcgcc gaggccgatc ccatgacggc gctgctggcc gccatcgagc    47220
ccccgttgcg cggggtggtg cacgccgccg gcgtcttccc cgtgcgtcac ctggcggaga    47280
cggacgaggc cctgctggag tcggtgctcc gtcccaaggt ggccgggagc tggctgctgc    47340
accggctgct gcgcgaccgg cctctcgacc tgttcgtgct gttctcgtcg ggcgcggcgg    47400
tgtggggtgg caaaggccaa ggcgcatacg ccgcggccaa tgcgttcctc gacgggctcg    47460
cgcaccatcg ccgcgcgcac tcgctgccgg cgttgagcct cgcctgggc ttatgggccg     47520 agggaggcat ggttgatgca aaggctcatg cacgtctgag cgacatcggg gtcctgccca    47580
tggccacggg gccggccttg tcggcgctgg agcgcctggt gaacaccagc gctgtccagc    47640
gttcggtcac acggatggac tgggcgcgct tcgcgccggt ctatgccgcg cgagggcggc    47700
```

```
gcaacttgct tcggctctg gtcgcggagg acgagcgcgc tgcgtctccc ccggtgccga   47760
cggcaaaccg gatctggcgc ggcctgtccg ttgcggagag ccgctcagcc ctctacgagc   47820
tcgttcgcgg catcgtcgcc cggtgctgg gcttctccga cccggcgcg ctcgacgtcg    47880 gccgaggctt cgccgagcag gggctcgact ccctgatggc tctggagatc cgtaaccgcc   47940
ttcagcgcga gctgggcgaa cggctgtcgg cgactctggc cttcgaccac ccgacggtgg   48000
agcggctggt ggcgcatctc ctcaccgacg tgctgaagct ggaggaccgg agcgacaccc   48060
ggcacatccg gtcggtggcg gcggatgacg acatcgccat cgtcggtgcc gcctgccggt   48120
tcccaggtgg ggatgagggc ctggagacat actggcggca tctggccgag ggcatggtgg   48180
tcagcaccga ggtgccagcc gaccggtggc gcgcggcgga ctggtacgac cccgatccgg   48240
aggttccggg ccggacctat gtggccaagg gtgccttcct ccgcgatgtg cgcagcttgg   48300
atgcggcgtt cttcgccatt tccctcgtg aggcgatgag cctggacccg caacagcggc    48360
tgttgctgga ggtgagctgg gaggcgatcg agcgcgctgg ccaggacccg atggcgctgc   48420
gcgagagcgc cacgggcgtg ttcgtgggca tgatcgggag cgagcacgcc gagcgggtgc   48480
agggcctcga cgacgacgcg gcgttgctgt acggcaccac cggcaacctg ctcagcgtcg   48540
ccgctggacg gctgtcgttc ttcctgggtc tgcacggccc gacgatgacg gtggacaccg   48600
cctgctcgtc gtcgctggtg gcgttgcacc tcgcctgcca gagcctgcga ttgggcgagt   48660
gcgaccaggc cctggccggc gggtccagcg tgcttttgtc gccgcggtca ttcgtcgcgg   48720
cgtcgcgcat gcgtttgctt tcgccagatg ggcggtgcaa gacgttctcg gccgctgcag   48780
acggctttgc gcgggccgag ggctgcgccg tggtggtgct caagcggctc cgtgacgcgc   48840
agcgcgaccg cgaccccatc ctggcggtgg tcaggagcac ggcgatcaac cacgatggcc   48900
cgagcagcgg gctcacggtg cccagcggtc ctgcccagca ggcgttgcta cgccaggcgc   48960
tggcgcaagc gggcgtggcg ccggccgagg tcgatttcgt ggagtgccac gggacgggga   49020
cagcgctggg tgacccgatc gaggtgcagg cgctgggcgc ggtgtacggg cggggccgcc   49080
ccgcggagcg gccgctctgg ctgggcgctg tcaaggccaa cctcggccac ctggaggccg   49140
cggcgggctt ggccggcgtg ctcaaggtgc tcttggcgct ggagcacgag cagattccgg   49200
ctcaaccgga gctcgacgag ctcaacccgc acatcccgtg gcagagctg ccagtggccg    49260 ttgtccgcag ggcggtcccc tggccgcgcg gcgcgcgccc gcgtcgtgca ggcgtgagcg   49320
ctttcggcct gagcgggacc aacgcgcatg tggtgttgga ggaggcgccg gcggtggagc   49380
ctgtggccgc ggcccccgag cgcgcagcgg agctgttcgt cctgtcggcg aagagcgcgg   49440
cggcgctgga tgcgcaggca gcccggctgc gggaccacct ggagaagcat gtcgagcttg   49500
gcctcggcga tgtggcgttc agcctggcga cgacgcgcag cgcgatggag caccggctgg   49560
cggtggccgc gagctcgcgc gaggcgctgc gagggcgcgt ttcggccgca gcgcaggggc   49620
acacgccgcc gggagccgtg cgtgggcggg cctcggcgg cagcgcgccg aaggtggtct     49680
tcgtgtttcc cggccagggc tcgcagtggg tgggcatggg ccgaaagctc atggccgaag   49740
agccggtctt ccggcggcg ctgagggtt gcgaccggc catcgaggcg gaagcgggct       49800
ggtcgctgct cggggagctc tccgccgacg aggccgcctc gcagctcggg cgcatcgacg   49860
tggttcagcc ggtgctgttc gccatggaag tagcgctttc tgcgctgtgg cggtcgtggg   49920
gagtggagcc ggaagcggtg gtgggccaca gcatgggcga ggttgcggcg cgcacgtgg     49980 ccggcgcgct gtcgctcgag gacgcggtgg cgatcatctg ccggcgcagc cggctgctgc   50040
ggcggatcag cggtcagggg gagatggcgc tggtcgagct gtcgctggag gaggccgagg   50100
```

```
cggcgctgcg tggccatgag ggtcggctga gcgtggcggt gagcaacagc ccgcgctcga   50160
ccgtgctcgc cggcgagccg gcggcgctct cggaggtgct ggcggcgctg acggccaagg   50220
gggtgttctg gcggcaggtg aaggtggacg tcgccagcca tagcccgcag gtcgacccgc   50280
tgcgcgaaga gctgatcgcg gcgctgggag cgatccggcc gcgagcggct gcggtgccga   50340
tgcgctcgac ggtgacgggc ggggtgatcg cgggtccgga gctcggtgcg agctactggg   50400
cggacaacct tcggcagccg gtgcgcttcg ctgcggcggc gcaagcgctg ctggagggtg   50460
gccccgcgct gttcatcgag atgagcccgc acccgatcct ggtgccgccc ctggacgaga   50520
tccagacggc ggccgagcaa gggggcgctg cggtgggctc gctgcggcga gggcaggacg   50580
agcgcgcgac gctgctggag gcgctgggga cgctgtgggc gtccggctat ccggtgagct   50640
gggctcggct gttccccgcg ggcggcaggc gggttccgct gccgacctat ccctggcagc   50700
acgagcggta ctggatcgag gacagcgtgc atgggtcgaa gccctcgctg cggcttcggc   50760
agcttcgcaa cggcgccacg gaccatccgc tgctcggggc tccattgctc gtctcggcgc   50820
gacccggagc tcacttgtgg gagcaagcgc tgagcgacga gaggctatcc taccttcgg   50880 aacataggt ccatggcgaa gccgtgttgc ccagcgcggc gtatgtagag atggcgctcg   50940
ccgccggcgt agatctctat ggcacggcga cgctggtgct ggagcagctg gcgctcgagc   51000
gagccctcgc cgtgccctcc gaaggcggac gcatcgtgca agtggccctc agcgaagaag   51060
gtcccggtcg ggcctcattc caggtatcga gtcgtgagga ggcaggtagg agctgggtgc   51120
ggcacgccac ggggcacgtg tgtagcggcc agagctcagc ggtgggagcg ttgaaggaag   51180
ctccgtggga gattcaacgg cgatgtccga gcgtcctgtc gtcggaggcg ctctatccgc   51240
tgctcaacga gcacgccctc gactatggtc cctgcttcca gggcgtggag caggtgtggc   51300
tcggcacggg ggaggtgctc ggccgggtac gcttgccagg agacatggca tcctcaagtg   51360
gcgcctaccg gattcatccc gccttgttgg atgcatgttt tcaggtgctg acagcgctgc   51420
tcaccacgcc ggaatccatc gagattcgga ggcggctgac ggatctccac gaaccggatc   51480
tcccgcggtc cagggctccg gtgaatcaag cggtgagtga cacctggctg tgggacgccg   51540
cgctggacgt tggacggcgc cagagcgcga gcgtgcccgt cgacctggtg ctcggcagct   51600
tccatgcgaa gtgggaggtc atggagcgcc tcgcgcaggc gtacatcatc ggcactctcc   51660
gcatatggaa cgtcttctgc gctgctggag agcgtcacac gatagacgag ttgctcgtca   51720
ggcttcaaat ctctgtcgtc tacaggaagg tcatcaagcg atggatggaa caccttgtcg   51780
cgatcggcat ccttgtaggg gacggagagc attttgtgag ctctcagccg ctgccggagc   51840
ctgatttggc ggcggtgctc gaggaggccg ggagggtgtt cgccgacctc ccagtcctat   51900
ttgagtggtg caagtttgcc ggggaacggc tcgcggacgt attgaccggt aagacgctcg   51960
cgctcgagat cctcttccct ggtggctcgt tcgatatggc ggagcgaatc tatcgagatt   52020
cgcccatcgc ccgttactcg aacggcatcg tgcgcggtgt cgtcgagtcg cggcgcgggg   52080
tggtagcacc gtcgggaatg ttcagcatct tggagatcgg agcagggacg ggcgcgacca   52140
ccgccgccgt cctcccggtg ttgctgcctg accggacgga gtaccatttc accgatgttt   52200
ctccgctctt ccttgctcgc gcggagcaaa gatttcgaga ttatccattc ctgaagtatg   52260
gcattctgga tgtcgaccag gagccagctg gccagggata cgcacatcag aggtttgacg   52320
tcatcgtcgc ggccaatgtc atccatgcga cccgcgatat aagagccacg gcgaagcgtc   52380
tcctgtcgtt gctcgcgccc ggaggccttc tggtgctggt cgagggcaca gggcatccga   52440
```

```
tctggttcga tatcaccacg ggattgattg aggggtggca gaagtacgaa gatgatcttc    52500
gtatcgacca tccgctcctg cctgctcgga cctggtgtga cgtcctgcgc cgggtaggct    52560
ttgcggacgc cgtgagtctg ccaggcgacg gatctccggc ggggatcctc ggacagcacg    52620
tgatcctctc gcgcgcgccg ggcatagcag gagccgcttg tgacagctcc ggtgagtcgg    52680
cgaccgaatc gccggccgcg cgtgcagtac ggcaggaatg ggccgatggc tccgctgacg    52740
tcgtccatcg gatggcgttg gagaggatgt acttccaccg ccggccgggc cggcaggttt    52800
gggtccacgg tcgattgcgt accggtggag gcgcgttcac gaaggcgctc gctggagatc    52860
tgctcctgtt cgaagacacc gggcaggtcg tggcagaggt tcagggctc cgcctgccgc     52920 agctcgaggc ttctgctttc gcgccgcggg acccgcggga agagtggttg tacgctttgg    52980
aatggcagcg caaagaccct ataccagagg ctccggcagc cgcgtcttct tcctccgcgg    53040
gggcttggct cgtgctgatg gaccaggcg ggacaggcgc tgcgctcgta tcgctgctgg     53100
aagggcgagg cgaggcgtgc gtgcgcgtca tcgcgggtac ggcatacgcc tgcctcgcgc    53160
cggggctgta tcaagtcgat ccggcgcagc cagatggctt tcataccctg ctccgcgatg    53220
cattcggcga ggaccggatt tgtcgcgcgg tagtgcatat gtggagcctt gatgcgacgg    53280
cagcagggga gagggcgaca gcggagtcgc ttcaggccga tcaactcctg ggagcctga    53340 gcgcgctttc tctggtgcag gcgctggtgc ccggaggtg gcgcaacatg ccgcggcttt     53400
ggctcttgac ccgcgccgtg catgcggtgg gcgcggagga cgcagcggcc tcggtggcgc    53460
aggcgccggt gtggggcctc ggtcggacgc tcgcgctcga gcatccagag ctgcggtgca    53520
cgctcgtgga cgtgaacccg gcgccgtctc cagaggacgc agccgcactg gcggtggagc    53580
tcggggcgag cgacagagag gaccaggtcg cattgcgctc ggatggccgc tacgtggcgc    53640
gcctcgtgcg gagctccttt tccggcaagc ctgctacgga ttgcggcatc cgggcggacg    53700
gcagctatgt gatcaccgat ggcatgggga gagtgggct ctcggtcgcg caatggatgg     53760
tgatgcaggg ggcccgccat gtggtgctcg tggatcgcgg cggcgcttcc gaggcatccc    53820
gggatgccct ccgtccatg gccgaggctg gcgcggaggt gcagatcgtg gaggccgacg     53880
tggctcggcg cgacgatgtc gctcggctcc tctcgaagat cgaaccgtcg atgccgccgc    53940
ttcgggggat cgtgtacgtg gacgggacct tccaggcga ctcctcgatg ctggagctgg     54000
atgcccgtcg cttcaaggag tggatgtatc ccaaggtgct cggagcgtgg aacctgcacg    54060
cgctgaccag ggatagatcg ctggacttct tcgtcctgta ttcctcgggc acctcgcttc    54120
tgggcttgcc aggacagggg agccgcgccg ccggtgacgc cttcttggac gccatcgcgc    54180
atcaccggtg caaggtgggc cttacagcga tgagcatcaa ctgggggattg ctctccgaag    54240 catcatcgcc ggcgaccccg aacgacggcg gagcacggct cgaataccgg gggatggaag    54300
gcctcacgct ggagcaggga gcggcggcgc tcgggcgctt gctcgcacga cccagggcgc    54360
aggtaggggt gatgcggctg aatctgcgcc agtggttgga gttctatccc aacgcggccc    54420
gattggcgct gtgggcggag ctgctgaagg agcgtgaccg cgccgaccga ggcgcgtcga    54480
acgcgtcgaa cctgcgcgag gcgctgcaga gcgccaggcc cgaagatcgt cagttgattc    54540
tggagaagca cttgagcgag ctgttgggc gggggctgcg ccttccgccg gagaggatcg     54600
agcggcacgt gccgttcagc aatctcggca tggactcgct gataggcctg gagctccgca    54660
accgcatcga ggccgcgctc ggcatcaccg tgccggcgac cctgctatgg acctacccta    54720
acgtagcagc tctgagcggg agcttgctag acattctgtt tccgaatgcc ggcgcgaccc    54780
acgctccggc caccgagcgg gagaagagct tcgagaacga tgccgcagat ctcgaggctc    54840
```

```
tgcggggcat gacggacgag cagaaggacg cgttgctcgc cgaaaagctg gcgcagctcg    54900
cgcagatcgt tggtgagtaa gggaccgagg gagtatggcg accacgaatg ccgggaagct    54960
tgagcatgcc cttctgctca tggacaagct tgcgaaaaag aacgcgtctt tggagcaaga    55020
gcggaccgag ccgatcgcca tcgtaggcat tggctgccgc ttccccggcg gagcggacac    55080
tccggaggca ttctgggagc tgctcgactc aggccgagac gcggtccagc cgctcgaccg    55140
gcgctgggcg ctggtcggcg tccatcccag cgaggaggtg ccgcgctggg ccggactgct    55200
caccgaggcg gtggacggct tcgacgccgc gttctttggc acctcgcctc gggaggcgcg    55260
gtcgctcgat cctcagcaac gcctgctgct ggaggtcacc tgggaagggc tcgaggacgc    55320
cggcatcgca ccccagtccc tcgacggcag ccgcaccggg gtgttcctgg gcgcatgcag    55380
cagcgactac tcgcataccg ttgcgcaaca gcggcgcgag gagcaggacg catacgacat    55440
caccggcaat acgctcagcg tcgccgccgg acggttgtct tatacgctag ggctgcaggg    55500
accctgcctg accgtcgaca cggcctgctc gtcgtcgctc gtggccatcc accttgcctg    55560
ccgcagcctg cgcgctcgcg agagcgatct cgcgctgggc ggaggcgtca acatgctcct    55620
ttcgtccaag acgatgataa tgctggggcg catccaggcg ctgtcgcccg atggccactg    55680
ccggacattc gacgcctcgg ccaacggggtt cgtccgtggg gagggctgcg gtatggtcgt    55740
gctcaaacgg ctctccgacg cccagcgaca cggcgatcgg atctgggctc tgatccgggg    55800
ttcggccatg aatcaggatg gccggtcgac agggttgatg gcacccaatg tgctcgctca    55860
ggaggcgctc ttgcgcgagg cgctgcagag cgctcgcgtc gacgccgggg ccatcggtta    55920
tgtcgagacc cacggaacgg ggacctcgct cggcgacccg atcgaggtcg aggcgctgcg    55980
tgccgtgttg gggccggcgc gggccgatgg gagccgctgc gtgctgggcg cagtgaagac    56040
aaacctcggc cacctggagg gcgctgcagg cgtggcgggt ttgatcaagg cggcgctggc    56100
tctgcaccac gaactgatcc cgcgaaacct ccatttccac acgctcaatc cgcggatccg    56160
gatcgagggg accgcgctcg cgctggcgac ggagccggtg ccgtggccgc gggcgggccg    56220
accgcgcttc gcgggggtga gcgcgttcgg cctcagcggc accaacgtcc atgtcgtgct    56280
ggaggaggcg ccggccacgg tgctcgcacc ggcgacgccg gggcgctcag cggagctttt    56340
ggtgctgtcg gcgaagagcg ccgccgcgct ggacgcacag gcggcgcggc tctcagcgca    56400
catcgccgcg tacccggagc agggtctcgg agacgtcgcg ttcagcctgg tatcgacgcg    56460
tagcccgatg gagcaccggc tcgcggtggc ggcgacctcg cgcgaggcgc tgcgaagcgc    56520
gctggaggtt gcggcgcagg ggcagacccc ggcaggcgcg gcgcgcggca gggccgcttc    56580
ctcgcccggc aagctcgcct tcctgttcgc cgggcagggc gcgcaggtgc cggcatggg    56640 ccgtgggttg tgggaggcgt ggccggcgtt ccgcgagacc ttcgaccggt gcgtcacgct    56700
cttcgaccgg gagctccatc agccgctctg cgaggtgatg tgggccgagc cgggcagcag    56760
caggtcgtcg ttgctggacc agacggcgtt cacccagccg gcgctctttg cgctggagta    56820
cgcgctggcc gcgctcttcc ggtcgtgggg cgtggagccg gagctcgtcg ctggccatag    56880
cctcggcgag ctggtggccg cctgcgtggc gggtgtgttc tccctcgagg acgccgtgcg    56940
cttggtggtc gcgcgcggcc ggttgatgca ggcgctgccg gccggcggcg cgatggtatc    57000
gatcgccgcg ccggaggccg acgtggctgc cgcggtggcg ccgcacgcag cgttggtgtc    57060
gatcgcggca gtcaatgggc cggagcaggt ggtgatcgcg ggcgccgaga aattcgtgca    57120
gcagatcgcg gcggcgttcg cggcgcgggg ggcgcgaacc aaaccgctgc atgtctcgca    57180
```

```
cgcgttccac tcgccgctca tggatccgat gctggaggcg ttccggcggg tgactgagtc   57240
ggtgacgtac cggcggcctt cgatcgcgct ggtgagcaac ctgagcggga agccctgcac   57300
cgatgaggtg agcgcgccgg gttactgggt gcgtcacgcg cgagaggcgg tgcgcttcgc   57360
ggacggagtg aaggcgctgc acgcggccgg tgcgggcctc ttcgtcgagg tggggccgaa   57420
gccgacgctc tcggccttg tgccggcctg cctgccggat gccaggccgg tgctgctccc   57480
agcgtcgcgc gccgggcgtg acgaggctgc gagcgcgcta gaggcgctgg gtgggttctg   57540
ggtcgtcggt ggatcggtca cctggtcggg tgtcttccct tcgggcggac ggcgggtacc   57600
gctgccaacc tatccctggc agcgcgagcg ttactggatc gaagcgccgg tcgatcgtga   57660
ggcggacggc accggccgtg ctcggccggg gggccacccc cttctgggtg aagtcttttc   57720
cgtgtcgacc catgccggtc tgcgcctgtg ggagacgacg ctggaccgaa agcggctgcc   57780
gtggctcggc gagcaccggg cgcaggggga ggtcgtgttt cctggcgccg ggtacctgga   57840
gatggcgctg tcgtcggggg ccgagatctt gggcgatgga ccgatccagg tcacggatgt   57900
ggtgctcatc gagacgctga ccttcgcggg cgatacggcg gtaccggtcc aggtggtgac   57960
gaccgaggag cgaccgggac ggctgcggtt ccaggtagcg agtcgggagc cggggggaacg   58020 tcgcgcgccc ttccggatcc acgcccgcgg cgtgctgcgc cggatcgggc gcgtcgagac   58080
cccggcgagg tcgaacctcg ccgccctgcg cgcccggctt catgccgccg tgcccgctgc   58140
ggctatctat ggtgcgctcg ccgagatggg gcttcaatac ggcccggcgt tgcggggggct   58200 cgccgagctg tggcggggtg agggcgaggc gctgggcagg gtgagactgc ctgaggccga   58260
cggctccgcg acagcctacc agctgcatcc ggtgctgctg gacgcgtgcg tccaaatgat   58320
tgttggcgcg ttcgccgatc gcgatgaggc gacgccgtgg gcgccggtgg aggtgggctc   58380
ggtgcggctg ttccagcggt ctcctgggga gctatggtgc catgcgcgcg tcgtgagcga   58440
tggtcaacag gcctccagcc ggtggagcgc cgactttgag ttgatggacg gtacgggcgc   58500
ggtggtcgcc gagatctccc ggctggtggt ggagcggctt gcgagcggtg tacgccggcg   58560
cgacgcagac gactggttcc tggagctgga ttgggagccc gcggcgctcg gtgggcccaa   58620
gatcacagcc ggccggtggc tgctgctcgg cgagggtggt gggctcgggc gctcgttgtg   58680
ctcggcgctc aaggccgccg gccatgtcgt cgtccacgcc gcggggggacg acacgagcac   58740 tgcaggaatg cgcgcgctcc tggccaacgc gttcgacggc caggccccga cggccgtggt   58800
gcacctcagc agcctcgacg ggggcggcca gctcggcccg gggctcgggg cgcagggcgc   58860
gctcgacgcg ccccggagcc cagatgtcga tgccgatgcc ctcgaatcgg cgctgatgcg   58920
tggttgcgac agcgtgctct ccctggtgca agcgctggtc ggcatggacc tccgaaacgc   58980
gccgcggctg tggctcttga cccgcgggc tcaggcggcc gccgccggcg atgtctccgt   59040
ggtgcaagcg ccgctgttgg ggctgggccg caccatcgcc ttggagcacg ccgagctgcg   59100
ctgtatcagc gtcgacctcg atccagccga gcctgaaggg gaagccgatg ctttgctggc   59160
cgagctactt gcagatgatg ccgaggagga ggtcgcgctg cgcggtggcg accggctcgt   59220
tgcgcggctc gtccaccggc tgcccgacgc tcagcgccgg gagaaggtcg agcccgccgg   59280
tgacaggccg ttccggctag agatcgatga acccggcgcg ctggaccaac tggtgctccg   59340
agccacgggg cggcgcgctc ctggtccggg cgaggtcgag atctccgtcg aagcggcggg   59400
gctcgactcc atcgacatcc agctggcgtt gggcgttgct cccaatgatc tgcctggaga   59460
agaaatcgag ccgttggtgc tcggaagcga gtgcgccggg cgcatcgtcg ctgtgggcga   59520
gggcgtgaac ggccttgtgg tgggccagcc ggtgatcgcc cttgcggcgg gagtatttgc   59580
```

-continued

```
tacccatgtc accacgtcgg ccacgctggt gttgcctcgg cctctggggc tctcggcgac  59640
cgaggcggcc gcgatgcccc tcgcgtattt gacggcctgg tacgccctcg acaaggtcgc  59700
ccacctgcag gcgggggagc gggtgctgat ccatgcggag gccggtggtg tcggtctttg  59760
cgcggtgcga tgggcgcagc gcgtgggcgc cgaggtgtat gcgaccgccg acacgcccga  59820
gaaccgtgcc tacctggagt cgctgggcgt gcggtacgtg agcgattccc gctcgggccg  59880
gttcgtcaca gacgtgcatg catggacgga cggcgagggt gtggacgtcg tgctcgactc  59940
gctttcgggc gagcgcatcg acaagagcct catggtcctg cgcgcctgtg gtcgccttgt  60000
gaagctgggc aggcgcgacg actgcgccga cacgcagcct gggctgccgc cgctcctacg  60060 gaattttttcc ttctcgcagg tggacttgcg gggaatgatg ctcgatcaac cggcgaggat  60120
ccgtgcgctc ctcgacgagc tgttcgggtt ggtcgcagcc ggtgccatca gcccactggg  60180
gtcggggttg cgcgttggcg gatccctcac gccaccgccg tcgagacct tcccgatctc  60240 tcgcgcagcc gaggcattcc ggaggatggc gcaaggacag catctcggga agctcgtgct  60300
cacgctggac gacccggagg tgcggatccg cgctccggcc gaatccagcg tcgccgtccg  60360
cgcggacggc acctaccttg tgaccggcgg tctgggtggc ctcggtctgc gcgtggccgg  60420
atggctggcc gagcgggggcg cggggcaact ggtgctggtg ggccgctccg gtgcggcgag  60480
cgcagagcag cgagccgccg tggcggcgct ggaggcccac ggcgcgcgcg tcacggtggc  60540
gaaagcggac gtcgccgatc ggtcacagat cgagcgggtc ctccgcgagg ttaccgcgtc  60600
ggggatgccg ctgcggggtg tcgtgcatgc ggcaggtctc gtggatgacg ggctgctgat  60660
gcagcagact ccggcgcggt tccgcacggt gatgggacct aaggtccagg gggccttgca  60720
cttgcacacg ctgacacgcg aagcgcctct ttccttcttc gtgctgtacg cttctgcagc  60780
tgggcttttc ggctcgccag gccagggcaa ctatgccgca ccaacgcgt tcctcgacgc  60840 cctttcgcat caccgaaggg cgcagggcct gccggcgctg agcatcgact ggggcatgtt  60900
cacggaggtg gggatggccg ttgcgcaaga aaaccgtggc gcgcggcaga tctctcgcgg  60960 gatgcgggc atcaccccccg atgagggtct gtcagctctg gcgcgcttgc tcgagggtga  61020
tcgcgtgcag acggggggtga taccgatcac tccgcggcag tgggtggagt tctacccggc  61080
aacagcggcc tcacggaggt tgtcgcggct ggtgaccacg cagcgcgcgg tcgctgatcg  61140
gaccgccggg gatcgggacc tgctcgaaca gcttgcgtcg gctgagccga gcgcgcgggc  61200
ggggctgctg caggacgtcg tgcgcgtgca ggtctcgcat gtgctgcgtc tccctgaaga  61260
caagatcgag gtggatgccc cgctctcgag catgggcatg gactcgctga tgagcctgga  61320
gctgcgcaac cgcatcgagg ctgcgctggg cgtcgccgcg cctgcagcct ggggtggac  61380 gtacccaacg gtagcagcga taacgcgctg gctgctcgac gacgccctcg tcgtccggct  61440
tggcggcggg tcgacacgg acgaatcgac ggcgagcgcc ggttcgttcg tccacgtcct  61500
ccgctttcgt cctgtcgtca agccgcgggc tcgtctcttc tgttttcacg gttctggcgg  61560
ctcgcccgag ggcttccgtt cctggtcgga gaagtctgag tggagcgatc tggaaatcgt  61620
ggccatgtgg cacgatcgca gcctcgcctc cgaggacgcg cctggtaaga agtacgtcca  61680
agaggcggcc tcgctgattc agcactatgc agacgcaccg tttgcgttag tagggttcag  61740
cctgggtgtc cggttcgtca tggggacagc cgtggagctc gccagtcgtt ccggcgcacc  61800
ggctccgctg gccgtcttca cgttgggcgg cagcttgatc tcttcttcag agatcacccc  61860
ggagatggag accgatataa tagccaagct cttcttccga aatgccgcgg gtttcgtgcg  61920
```

```
atccacccaa caagtccagg ccgatgctcg cgcagacaag gtcatcacag acaccatggt    61980
ggctccggcc cccggggact cgaaggagcc gcccgtgaag atcgcggtcc ctatcgtcgc    62040
catcgccggc tcggacgatg tgatcgtgcc tccgagcgac gttcaggatc tacaatctcg    62100
caccacggag cgcttctata tgcatctcct tcccggagat cacgaatttc tcgtcgatcg    62160
agggcgcgag atcatgcaca tcgtcgactc gcatctcaat ccgctgctcg ccgcgaggac    62220
gacgtcgtca ggccccgcgt tcgaggcaaa atgatggcag cctccctcgg gcgcgcgaga    62280
tggttgggag cagcgtgggc gctggcggcc ggcggcaggc cgcggaggcg catgagcctt    62340
cctggacgtt tgcagtatag gagattttat gacacaggag caagcgaatc agagtgagac    62400
gaagcctgct ttcgacttca agccgttcgc gcctgggtac gcggaggacc cgttccccgc    62460
gatcgagcgc ctgagagagg caaccccccat cttctactgg gatgaaggcc gctcctgggt    62520
cctcacccga taccgacgcg tgtcggcggt gttccgcgac gaacgcttcg cggtcagtcg    62580
agaagagtgg gaatcgagcg cggagtactc gtcggccatt cccgagctca gcgatatgaa    62640
gaagtacgga ttgttcgggc tgccgccgga ggatcacgct cgggtccgca agctcgtcaa    62700
cccgtcgttt acgtcacgcg ccatcgacct gctgcgcgcc gaaatacagc gcaccgtcga    62760
ccagctgctc gatgctcgct ccggacaaga ggagttcgac gttgtgcggg attacgcgga    62820
gggaatcccg atgcgcgcga tcagcgctct gttgaaggtt ccggccgagt gtgacgagaa    62880
gttccgtcgc ttcggctcgg cgactgcgcg cgcgctcggc gtgggtttgg tgccccaggt    62940
cgatgaggag accaagaccc tggtcgcgtc cgtcaccgag gggctcgcgc tgctccatga    63000
cgtcctcgat gagcggcgca ggaacccgct cgaaaatgac gtcttgacga tgctgcttca    63060
ggccgaggcc gacggcagca ggctgagcac gaaggagctg gtcgcgctcg tgggtgcgat    63120
tatcgctgct ggcaccgata ccacgatcta ccttatcgcg ttcgctgtgc tcaacctgct    63180
gcggtcgccc gaggcgctcg agctggtgaa ggccgagccc gggctcatga ggaacgcgct    63240
cgatgaggtg ctccgcttcg acaatatcct cagaatagga actgtgcgtt tcgccaggca    63300
ggacctggag tactgcgggg catcgatcaa gaaaggggag atggtctttc tcctgatccc    63360
gagcgccctg agagatggga ctgtattctc caggccagac gtgtttgatg tgcgacggga    63420
cacgggcgcg agcctcgcgt acggtagagg ccccatgtc tgccccgggg tgtcccttgc    63480
tcgcctcgag gcggagatcg ccgtgggcac catcttccgt aggttccccg agatgaagct    63540
gaaagaaact cccgtgtttg gataccaccc cgcgttccgg aacatcgaat cactcaacgt    63600
catcttgaag ccctccaaag ctggatagct cgcggggta tcgcttcccg aacctcattc    63660
cctcatgata cagctcgcgc gcgggtgctg tctgccgcgg gtgcgattcg atccagcgga    63720
caagcccatt gtcagcgcgc gaagatcgaa tccacggccc ggagaagagc ccgtccgggt    63780
gacgtcggaa gaagtgccgg gcgccgccct gggagcgcaa agctcgctcg ttcgcgctca    63840
gcacgccgct cgtcatgtcc ggccctgcac ccgcgccgag gagccgcccg ccctgatgca    63900
cggcctcacc gagcggcagg ttctgctctc gctcgtcgcc ctcgcgctcg tcctcctgac    63960
cgcgcgcgcc ttcggcgagc tcgcgcggcg gctgcgccag cccgaggtgc tcggcgagct    64020
cttcggcggc gtggtgctgg gcccgtccgt cgtcggcgcg ctcgctcctg ggttccatcg    64080
agtcctcttc caggatccgg cggtcggggt cgtgctctcc ggcatctcct ggataggcgc    64140
gctcgtcctg ctgctcatgg cgggtatcga ggtcgatgtg agcatcctgc gcaaggaggc    64200
gcgcccgggg gcgctctcgg cgctcggcgc gatcgcgccc ccgctgcgca cgccggggcc    64260
gctggtgcag cgcatgcagg gcgcgttcac gtgggatctc gacgtctcgc cgcgacgctc    64320
```

```
tgcgcaagcc tgagcctcgg cgcctgctcg tacacctcgc cggtgctcgc tccgcccgcg    64380
gacatccggc cgcccgccgc ggcccagctc gagccggact cgccggatga cgaggccgac    64440
gaggccgacg aggcgctccg cccgttccgc gacgcgatcg ccgcgtactc ggaggccgtt    64500
cggtgggcgg aggcggcgca gcggccgcgg ctggagagcc tcgtgcggct cgcgatcgtg    64560
cggctgggca aggcgctcga caaggtccct ttcgcgcaca cgacggccgg cgtctcccag    64620
atcgccggca gactccagaa cgatgcggtc tggttcgatg tcgccgcccg gtacgcgagc    64680 ttccgcgcg cgacggagca cgcgctccgc gacgcggcgt cggccatgga ggcgctcgcg    64740
gccggcccgt accgcggatc gagccgcgtg tccgctgccg taggggagtt tcggggggag    64800
gcggcgcgcc ttcaccccgc ggaccgtgta cccgcgtccg accagcagat cctgaccgcg    64860
ctgcgcgcag ccgagcgggc gctcatcgcg ctctacactg cgttcgcccg tgaggagtga    64920
gcctctctcg ggcgcagccg agcggcggcg tgccggtggt tccctcttcg caaccatgac    64980
cggagccgcg ctcggtccgc gcagcggcta gcgcgcgtcg cggcagagat cgctggagcg    65040
acaggcgacg acccgcccga gggtgtcgaa cggattgccg cagccctcat tgcggatccc    65100
ctccagacac tcgttcagct gcttggcgtc gatgccgcct gggcactcgc cgaaggtcag    65160
ctcgtcgcgc cactcggatc ggatcttgtt cgagcacgcg tccttgctcg aatactcccg    65220
gtcttgtccg atgttgttgc accgcgcctc gcggtcgcac cgcgccgcca cgatgctatc    65280 gacgcgctg ccgactggca ccggcgcctc gccctgcgcg ccacccgggg tttgcgcctc    65340
cccgcctgac cgcttttcgc cgccgcacgc cgcgagcagg ctcattcccg acaccgagat    65400
caggcccacg accagcttcc cagcaatctt ttgcatggct tcccctccct cacgacacgt    65460
cacatcagag actctccgct cggctcgtcg gttcgacagc cggcgacggc cacgagcaga    65520
accgtccccg accagaacag ccgcatgcgg gtttctcgca acatgccccg acatccttgc    65580
gactagcgtg cctccgctcg tgccgagatc ggctgtcctg tgcgacggca atatcctgcg    65640 atcgccggg caggaggtac cgacacgggc gccgggcggg aggtgccgcc acgggctcga    65700
aatgtgctgc ggcaggcgcc tccatgcccg cagccgggaa cgcggcgccc ggccagcctc    65760
ggggtgacgc cgcaaacggg agatgctccc ggagaggcgc cgggcacagc cgagcgccgt    65820
caccaccgtg cgcactcgtg agctccagct cctcggcata gaagagaccg tcactcccgg    65880
tccgtgtagg cgatcgtgct gatcagcgcg ttctccgcct gacgcgagtc gagccgggta    65940
tgctgcacga caatgggaac gtccgattcg atcacgctgg catagtccgt atcgcgcggg    66000
atcggctcgg gttcggtcag atcgttgaac cggacgtgcc gggtgcgcct cgctgggacg    66060
gtcacccggt acgcccggc ggggtcgcgg tcgctgaagt agacggtgat ggcgacctgc    66120
gcgtcccggt ccgacgcatt caacaggcag gccgtctcat ggctcgtcat ctgcggctcg    66180
ggtccgttgc tccggcctgg gatgtagccc tctgcgattg cccagcgcgt ccgcccgatc    66240
ggcttctcca tatgtcctcc ctgctggctc ctctttggct gcctccctct gctgtccagg    66300
agcgacggcc tcttctcccg acgcgctcgg ggatccatgg ctgaggatcc tcgccgagcg    66360
ctccttgccg accggcgcgc cgagcgccga cgggctttga aagcacgcga ccggacacgt    66420
gatgccggcc cgacgaggcc gccccgcgtc tgatcccgat cgtgacatcg cgacgtccgc    66480
cggcgcctct gcaggccggc ctgagcgttg cgcggtcatg gtcgtcctcg cgtcaccgcc    66540
acccgccgat tcacatccca ccgcggcacg acgcttgctc aaaccgcggc gagacggccg    66600
ggcggctgtg gtaccggcca gcccggacgc gaggcccgag agggacagtg ggtccgccgt    66660
```

-continued

```
gaagcagtga ggcgatcgag gtggcagatg aaacacgttg acacgggccg acgagtcggc    66720
cgccggatag ggctcacgct cggtctcctc gcgagcatgg cgctcgccgg ctgtggcggc    66780
ccgagcgaga aaatcgtgca gggcacgcgg ctcgcgcccg gcgccgatgc gcacgtcgcc    66840
gccgacgtcg accccgacgc cgcgaccacg cggctggcgg tggacgtcgt tcacctctcg    66900
ccgcccgagc gcatcgaggc cggcagcgag cggttcgtcg tctggcagcg tccgagctcc    66960
gagtccccgt ggcaacgggt cggagtgctc gactacaacg ctgccagccg aagaggcaag    67020
ctggccgaga cgaccgtgcc gcatgccaac ttcgagctgc tcatcaccgt cgagaagcag    67080
agcagccctc agtctccatc ttctgccgcc gtcatcgggc cgacgtccgt cgggtaacat    67140
cgcgctatca gcagcgctga gcccgccagc aggcccagga gccctgcctc gatcgccttc    67200
tccatcatat catccctgcg tactcctcca gcgacggccg cgtcgaagca accgccgtgc    67260
cggcgcggct ctacgtgcgc gacaggagag cgtcctggcg cggcctgcgc atcgctggaa    67320
ggatcggcgg agcatggaga aagaatcgag gatcgcgatc tacggcgcca tcgcagccaa    67380
cgtggcgatc gcggcggtca agttcatcgc cgccgccgtg accggcagct cggcgatgct    67440
ctccgagggc gtgcactccc tcgtcgatac tgcagacggg ctcctcctcc tgctcggcaa    67500
gcaccggagc gcacgcccgc ccgacgccga gcatccgttc ggccacggca aggagctcta    67560
tttctggacg ctgatcgtcg ccatcatgat cttcgccgcg ggcggcggcg tctcgatcta    67620
cgaagggatc ttgcacctct tgcacccgcg ccagatcgag gatccgacgt ggaactacgt    67680
cgtcctcggc gcagcggccg tcttcgaggg gacgtcgctc atcatctcga tccacgagtt    67740
caagaagaag gacggacagg gctacctcgc ggcgatgcgg tccagcaagg acccgacgac    67800
gttcacgatc gtcctggagg actccgcggc gctcgccggg ctcaccatcg ccttcctcgg    67860
cgtctggctc gggcaccgcc tgggaaaccc ctacctcgac ggcgcggcgt cgatcggcat    67920
cggcctcgtg ctcgccgcgg tcgcggtctt cctcgccagc cagagccgtg ggctcctcgt    67980
gggggagagc gcggacaggg agctcctcgc cgcgatccgc gcgctcgcca gcgcagatcc    68040
tggcgtgtcg gcggtggggc ggcccctgac gatgcacttc ggtccgcacg aagtcctggt    68100
cgtgctgcgc atcgagttcg acgccgcgct cacggcgtcc ggggtcgcgg aggcgatcga    68160
gcgcatcgag acccggatac ggagcgagcg acccgacgtg aagcacatct acgtcgaggc    68220
caggtcgctc caccagcgcg cgagggcgtg acgcgccgtg gagagaccgc gcgcggcctc    68280
cgccatcctc cgcggcgccc gggctcaggt ggccctcgca gcagggcgcg cctggcgggc    68340
aaaccgtgca gacgtcgtcc ttcgacgcga ggtacgctgg ttgcaagtcg tcacgccgta    68400
tcgcgaggtc cggcagcgcc ggagcccggg cgggccgggc gcacgaaggc gcggcgagcg    68460
caggcttcga gggggggcgac gtcatgagga aggccagggc gcatggggcg atgctcggcg    68520
ggcgagatga cggctggcgt cgcggcctcc ccggcgccgg cgcgcttcgc gccgcgctcc    68580
agcgcggtcg ctcgcgcgat ctcgcccggc gccggctcat cgcctccgtg tccctcgccg    68640
gcggcgccag catggcggtc gtctcgctgt tccagctcgg gatcatcgag cgcctgcccg    68700
atcctccgct tccagggttc gattcggcca aggtgacgag ctccgatatc                68750
```

<210> SEQ ID NO 2
<211> LENGTH: 1421
<212> TYPE: PRT
<213> ORGANISM: Sorangium cellulosum

<400> SEQUENCE: 2

Val Ala Asp Arg Pro Ile Glu Arg Ala Ala Glu Asp Pro Ile Ala Ile

-continued

```
   1               5                  10                 15
Val Gly Ala Ser Cys Arg Leu Pro Gly Val Ile Asp Leu Ser Gly
                20                  25                 30

Phe Trp Thr Leu Leu Glu Gly Ser Arg Asp Thr Val Gly Arg Val Pro
            35                  40                  45

Ala Glu Arg Trp Asp Ala Ala Ala Trp Phe Asp Pro Asp Pro Asp Ala
        50                  55                  60

Pro Gly Lys Thr Pro Val Thr Arg Ala Ser Phe Leu Ser Asp Val Ala
65                  70                  75                  80

Cys Phe Asp Ala Ser Phe Phe Gly Ile Ser Pro Arg Glu Ala Leu Arg
                85                  90                  95

Met Asp Pro Ala His Arg Leu Leu Leu Glu Val Cys Trp Glu Ala Leu
            100                 105                 110

Glu Asn Ala Ala Ile Ala Pro Ser Ala Leu Val Gly Thr Glu Thr Gly
        115                 120                 125

Val Phe Ile Gly Ile Gly Pro Ser Glu Tyr Glu Ala Ala Leu Pro Gln
130                 135                 140

Ala Thr Ala Ser Ala Glu Ile Asp Ala His Gly Gly Leu Gly Thr Met
145                 150                 155                 160

Pro Ser Val Gly Ala Gly Arg Ile Ser Tyr Ala Leu Gly Leu Arg Gly
                165                 170                 175

Pro Cys Val Ala Val Asp Thr Ala Tyr Ser Ser Ser Leu Val Ala Val
            180                 185                 190

His Leu Ala Cys Gln Ser Leu Arg Ser Gly Glu Cys Ser Thr Ala Leu
        195                 200                 205

Ala Gly Gly Val Ser Leu Met Leu Ser Pro Ser Thr Leu Val Trp Leu
210                 215                 220

Ser Lys Thr Arg Ala Leu Ala Arg Asp Gly Arg Cys Lys Ala Phe Ser
225                 230                 235                 240

Ala Glu Ala Asp Gly Phe Gly Arg Gly Glu Gly Cys Ala Val Val Val
                245                 250                 255

Leu Lys Arg Leu Ser Gly Ala Arg Ala Asp Gly Asp Arg Ile Leu Ala
            260                 265                 270

Val Ile Arg Gly Ser Ala Ile Asn His Asp Gly Ala Ser Ser Gly Leu
        275                 280                 285

Thr Val Pro Asn Gly Ser Ser Gln Glu Ile Val Leu Lys Arg Ala Leu
290                 295                 300

Ala Asp Ala Gly Cys Ala Ala Ser Ser Val Gly Tyr Val Glu Ala His
305                 310                 315                 320

Gly Thr Gly Thr Thr Leu Gly Asp Pro Ile Glu Ile Gln Ala Leu Asn
                325                 330                 335

Ala Val Tyr Gly Leu Gly Arg Asp Val Ala Thr Pro Leu Leu Ile Gly
            340                 345                 350

Ser Val Lys Thr Asn Leu Gly His Pro Glu Tyr Ala Ser Gly Ile Thr
        355                 360                 365

Gly Leu Leu Lys Val Val Leu Ser Leu Gln His Gly Gln Ile Pro Ala
370                 375                 380

His Leu His Ala Gln Ala Leu Asn Pro Arg Ile Ser Trp Gly Asp Leu
385                 390                 395                 400

Arg Leu Thr Val Thr Arg Ala Arg Thr Pro Trp Pro Asp Trp Asn Thr
                405                 410                 415

Pro Arg Arg Ala Gly Val Ser Ser Phe Gly Met Ser Gly Thr Asn Ala
            420                 425                 430
```

-continued

His Val Val Leu Glu Glu Ala Pro Ala Ala Thr Cys Thr Pro Pro Ala
        435                 440                 445

Pro Glu Arg Pro Ala Glu Leu Leu Val Leu Ser Ala Arg Thr Ala Ser
450                 455                 460

Ala Leu Asp Ala Gln Ala Ala Arg Leu Arg Asp His Leu Glu Thr Tyr
465                 470                 475                 480

Pro Ser Gln Cys Leu Gly Asp Val Ala Phe Ser Leu Ala Thr Thr Arg
                485                 490                 495

Ser Ala Met Glu His Arg Leu Ala Val Ala Ala Thr Ser Arg Glu Gly
            500                 505                 510

Leu Arg Ala Ala Leu Asp Ala Ala Gln Gly Gln Thr Ser Pro Gly
        515                 520                 525

Ala Val Arg Ser Ile Ala Asp Ser Ser Arg Gly Lys Leu Ala Phe Leu
530                 535                 540

Phe Thr Gly Gln Gly Ala Gln Thr Leu Gly Met Gly Arg Gly Leu Tyr
545                 550                 555                 560

Asp Val Trp Ser Ala Phe Arg Glu Ala Phe Asp Leu Cys Val Arg Leu
                565                 570                 575

Phe Asn Gln Glu Leu Asp Arg Pro Leu Arg Glu Val Met Trp Ala Glu
            580                 585                 590

Pro Ala Ser Val Asp Ala Ala Leu Leu Asp Gln Thr Ala Phe Thr Gln
        595                 600                 605

Pro Ala Leu Phe Thr Phe Glu Tyr Ala Leu Ala Ala Leu Trp Arg Ser
    610                 615                 620

Trp Gly Val Glu Pro Glu Leu Val Ala Gly His Ser Ile Gly Glu Leu
625                 630                 635                 640

Val Ala Ala Cys Val Ala Gly Val Phe Ser Leu Glu Asp Ala Val Phe
                645                 650                 655

Leu Val Ala Ala Arg Gly Arg Leu Met Gln Ala Leu Pro Ala Gly Gly
            660                 665                 670

Ala Met Val Ser Ile Glu Ala Pro Glu Ala Asp Val Ala Ala Ala Val
        675                 680                 685

Ala Pro His Ala Ala Ser Val Ser Ile Ala Ala Val Asn Ala Pro Asp
    690                 695                 700

Gln Val Val Ile Ala Gly Ala Gly Gln Pro Val His Ala Ile Ala Ala
705                 710                 715                 720

Ala Met Ala Ala Arg Gly Ala Arg Thr Lys Ala Leu His Val Ser His
                725                 730                 735

Ala Phe His Ser Pro Leu Met Ala Pro Met Leu Glu Ala Phe Gly Arg
            740                 745                 750

Val Ala Glu Ser Val Ser Tyr Arg Arg Pro Ser Ile Val Leu Val Ser
        755                 760                 765

Asn Leu Ser Gly Lys Ala Cys Thr Asp Glu Val Ser Ser Pro Gly Tyr
    770                 775                 780

Trp Val Arg His Ala Arg Glu Val Val Arg Phe Ala Asp Gly Val Lys
785                 790                 795                 800

Ala Leu His Ala Ala Gly Ala Gly Thr Phe Val Glu Val Gly Pro Lys
                805                 810                 815

Ser Thr Leu Leu Gly Leu Val Pro Ala Cys Met Pro Asp Ala Arg Pro
            820                 825                 830

Ala Leu Leu Ala Ser Ser Arg Ala Gly Arg Asp Glu Pro Ala Thr Val
        835                 840                 845

-continued

```
Leu Glu Ala Leu Gly Gly Leu Trp Ala Val Gly Gly Leu Val Ser Trp
    850                 855                 860

Ala Gly Leu Phe Pro Ser Gly Gly Arg Arg Val Pro Leu Pro Thr Tyr
865                 870                 875                 880

Pro Trp Gln Arg Glu Arg Tyr Trp Ile Asp Thr Lys Ala Asp Asp Ala
                885                 890                 895

Ala Arg Gly Asp Arg Arg Ala Pro Gly Ala Gly His Asp Glu Val Glu
                900                 905                 910

Glu Gly Gly Ala Val Arg Gly Gly Asp Arg Arg Ser Ala Arg Leu Asp
            915                 920                 925

His Pro Pro Glu Ser Gly Arg Arg Glu Lys Val Glu Ala Ala Gly
            930                 935                 940

Asp Arg Pro Phe Arg Leu Glu Ile Asp Glu Pro Gly Val Leu Asp His
945                 950                 955                 960

Leu Val Leu Arg Val Thr Glu Arg Arg Ala Pro Gly Leu Gly Glu Val
                965                 970                 975

Glu Ile Ala Val Asp Ala Ala Gly Leu Ser Phe Asn Asp Val Gln Leu
                980                 985                 990

Ala Leu Gly Met Val Pro Asp Asp Leu Pro Gly Lys Pro Asn Pro Pro
            995                 1000                1005

Leu Leu Leu Gly Gly Glu Cys Ala Gly Arg Ile Val Ala Val Gly Glu
    1010                1015                1020

Gly Val Asn Gly Leu Val Val Gly Gln Pro Val Ile Ala Leu Ser Ala
1025                1030                1035                1040

Gly Ala Phe Ala Thr His Val Thr Thr Ser Ala Ala Leu Val Leu Pro
                1045                1050                1055

Arg Pro Gln Ala Leu Ser Ala Ile Glu Ala Ala Ala Met Pro Val Ala
                1060                1065                1070

Tyr Leu Thr Ala Trp Tyr Ala Leu Asp Arg Ile Ala Arg Leu Gln Pro
            1075                1080                1085

Gly Glu Arg Val Leu Ile His Ala Ala Thr Gly Gly Val Gly Leu Ala
    1090                1095                1100

Ala Val Gln Trp Ala Gln His Val Gly Ala Glu Val His Ala Thr Ala
1105                1110                1115                1120

Gly Thr Pro Glu Lys Arg Ala Tyr Leu Glu Ser Leu Gly Val Arg Tyr
                1125                1130                1135

Val Ser Asp Ser Arg Ser Asp Arg Phe Val Ala Asp Val Arg Ala Trp
                1140                1145                1150

Thr Gly Gly Glu Gly Val Asp Val Val Leu Asn Ser Leu Ser Gly Glu
            1155                1160                1165

Leu Ile Asp Lys Ser Phe Asn Leu Leu Arg Ser His Gly Arg Phe Val
    1170                1175                1180

Glu Leu Gly Lys Arg Asp Cys Tyr Ala Asp Asn Gln Leu Gly Leu Arg
1185                1190                1195                1200

Pro Phe Leu Arg Asn Leu Ser Phe Ser Leu Val Asp Leu Arg Gly Met
                1205                1210                1215

Met Leu Glu Arg Pro Ala Arg Val Arg Ala Leu Leu Glu Glu Leu Leu
            1220                1225                1230

Gly Leu Ile Ala Ala Gly Val Phe Thr Pro Pro Ile Ala Thr Leu
    1235                1240                1245

Pro Ile Ala Arg Val Ala Asp Ala Phe Arg Ser Met Ala Gln Ala Gln
    1250                1255                1260

His Leu Gly Lys Leu Val Leu Thr Leu Gly Asp Pro Glu Val Gln Ile
```

-continued

```
1265                1270                1275                1280

Arg Ile Pro Thr His Ala Gly Ala Gly Pro Ser Thr Gly Asp Arg Asp
                1285                1290                1295

Leu Leu Asp Arg Leu Ala Ser Ala Ala Pro Ala Ala Arg Ala Ala Ala
            1300                1305                1310

Leu Glu Ala Phe Leu Arg Thr Gln Val Ser Gln Val Leu Arg Thr Pro
        1315                1320                1325

Glu Ile Lys Val Gly Ala Glu Ala Leu Phe Thr Arg Leu Gly Met Asp
    1330                1335                1340

Ser Leu Met Ala Val Glu Leu Arg Asn Arg Ile Glu Ala Ser Leu Lys
1345                1350                1355                1360

Leu Lys Leu Ser Thr Thr Phe Leu Ser Thr Ser Pro Asn Ile Ala Leu
                1365                1370                1375

Leu Ala Gln Asn Leu Leu Asp Ala Leu Ala Thr Ala Leu Ser Leu Glu
            1380                1385                1390

Arg Val Ala Ala Glu Asn Leu Arg Ala Gly Val Gln Asn Asp Phe Val
        1395                1400                1405

Ser Ser Gly Ala Asp Gln Asp Trp Glu Ile Ile Ala Leu
    1410                1415                1420

<210> SEQ ID NO 3
<211> LENGTH: 1410
<212> TYPE: PRT
<213> ORGANISM: Sorangium cellulosum

<400> SEQUENCE: 3

Met Thr Ile Asn Gln Leu Leu Asn Glu Leu Glu His Gln Gly Ile Lys
  1               5                  10                  15

Leu Ala Ala Asp Gly Glu Arg Leu Gln Ile Gln Ala Pro Lys Asn Ala
             20                  25                  30

Leu Asn Pro Asn Leu Leu Ala Arg Ile Ser Glu His Lys Ser Thr Ile
         35                  40                  45

Leu Thr Met Leu Arg Gln Arg Leu Pro Ala Glu Ser Ile Val Pro Ala
     50                  55                  60

Pro Ala Glu Arg His Ala Pro Phe Pro Leu Thr Asp Ile Gln Glu Ser
 65                  70                  75                  80

Tyr Trp Leu Gly Arg Thr Gly Ala Phe Thr Val Pro Ser Gly Ile His
                 85                  90                  95

Ala Tyr Arg Glu Tyr Asp Cys Thr Asp Leu Asp Val Pro Arg Leu Ser
            100                 105                 110

Arg Ala Phe Arg Lys Val Val Ala Arg His Asp Met Leu Arg Ala His
        115                 120                 125

Thr Leu Pro Asp Met Met Gln Val Ile Glu Pro Lys Val Asp Ala Asp
    130                 135                 140

Ile Glu Ile Ile Asp Leu Arg Gly Leu Asp Arg Ser Thr Arg Glu Ala
145                 150                 155                 160

Arg Leu Val Ser Leu Arg Asp Ala Met Ser His Arg Ile Tyr Asp Thr
                165                 170                 175

Glu Arg Pro Pro Leu Tyr His Val Val Ala Val Arg Leu Asp Glu Arg
            180                 185                 190

Gln Thr Arg Leu Val Leu Ser Ile Asp Leu Ile Asn Val Asp Leu Gly
        195                 200                 205

Ser Leu Ser Ile Ile Phe Lys Asp Trp Leu Ser Phe Tyr Glu Asp Pro
    210                 215                 220
```

-continued

```
Glu Thr Ser Leu Pro Val Leu Glu Leu Ser Tyr Arg Asp Tyr Val Leu
225                 230                 235                 240

Ala Leu Glu Ser Arg Lys Lys Ser Gly Ala His Gln Arg Ser Met Asp
            245                 250                 255

Tyr Trp Lys Arg Arg Ile Ala Glu Leu Pro Pro Pro Thr Leu Pro
                260                 265                 270

Met Lys Ala Asp Pro Ser Thr Leu Lys Glu Ile Arg Phe Arg His Thr
        275                 280                 285

Glu Gln Trp Leu Pro Ser Asp Ser Trp Gly Arg Leu Lys Arg Arg Val
    290                 295                 300

Gly Glu Arg Gly Leu Thr Pro Thr Gly Val Ile Leu Ala Ala Phe Ser
305                 310                 315                 320

Glu Val Ile Gly Arg Trp Ser Ala Ser Pro Arg Phe Thr Leu Asn Ile
                325                 330                 335

Thr Leu Phe Asn Arg Leu Pro Val His Pro Arg Val Asn Asp Ile Thr
                340                 345                 350

Gly Asp Phe Thr Ser Met Val Leu Leu Asp Ile Asp Thr Thr Arg Asp
            355                 360                 365

Lys Ser Phe Glu Gln Arg Ala Lys Arg Ile Gln Glu Gln Leu Trp Glu
370                 375                 380

Ala Met Asp His Cys Asp Val Ser Gly Ile Glu Val Gln Arg Glu Ala
385                 390                 395                 400

Ala Arg Val Leu Gly Ile Gln Arg Gly Ala Leu Phe Pro Val Val Leu
                405                 410                 415

Thr Ser Ala Leu Asn Gln Gln Val Val Gly Val Thr Ser Leu Gln Arg
                420                 425                 430

Leu Gly Thr Pro Val Tyr Thr Ser Thr Gln Thr Pro Gln Leu Leu Leu
            435                 440                 445

Asp His Gln Leu Tyr Glu His Asp Gly Asp Leu Val Leu Ala Trp Asp
        450                 455                 460

Ile Val Asp Gly Val Phe Pro Pro Asp Leu Leu Asp Asp Met Leu Glu
465                 470                 475                 480

Ala Tyr Val Val Phe Leu Arg Arg Leu Thr Glu Pro Trp Gly Glu
                485                 490                 495

Gln Val Arg Cys Ser Leu Pro Pro Ala Gln Leu Glu Ala Arg Ala Ser
            500                 505                 510

Ala Asn Ala Thr Asn Ala Leu Leu Ser Glu His Thr Leu His Gly Leu
            515                 520                 525

Phe Ala Ala Arg Val Glu Gln Leu Pro Met Gln Leu Ala Val Val Ser
530                 535                 540

Ala Arg Lys Thr Leu Thr Tyr Glu Glu Leu Ser Arg Arg Ser Arg Arg
545                 550                 555                 560

Leu Gly Ala Arg Leu Arg Glu Gln Gly Ala Arg Pro Asn Thr Leu Val
                565                 570                 575

Ala Val Val Met Glu Lys Gly Trp Glu Gln Val Val Ala Val Leu Ala
                580                 585                 590

Val Leu Glu Ser Gly Ala Ala Tyr Val Pro Ile Asp Ala Asp Leu Pro
            595                 600                 605

Ala Glu Arg Ile His Tyr Leu Leu Asp His Gly Glu Val Lys Leu Val
        610                 615                 620

Leu Thr Gln Pro Trp Leu Asp Gly Lys Leu Ser Trp Pro Pro Gly Ile
625                 630                 635                 640

Gln Arg Leu Leu Val Ser Glu Ala Gly Val Glu Gly Asp Gly Asp Gln
```

-continued

```
                    645                 650                 655
    Pro Pro Met Met Pro Ile Gln Thr Pro Ser Asp Leu Ala Tyr Val Ile
                660                 665                 670
    Tyr Thr Ser Gly Ser Thr Gly Leu Pro Lys Gly Val Met Ile Asp His
                675                 680                 685
    Arg Gly Ala Val Asn Thr Ile Leu Asp Ile Asn Glu Arg Phe Glu Ile
                690                 695                 700
    Gly Pro Gly Asp Arg Val Leu Ala Leu Ser Ser Leu Ser Phe Asp Leu
    705                 710                 715                 720
    Ser Val Tyr Asp Val Phe Gly Ile Leu Ala Ala Gly Gly Thr Ile Val
                        725                 730                 735
    Val Pro Asp Ala Ser Lys Leu Arg Asp Pro Ala His Trp Ala Glu Leu
                    740                 745                 750
    Ile Glu Arg Glu Lys Val Thr Val Trp Asn Ser Val Pro Ala Leu Met
                755                 760                 765
    Arg Met Leu Val Glu His Phe Glu Gly Arg Pro Asp Ser Leu Ala Arg
                770                 775                 780
    Ser Leu Arg Leu Ser Leu Leu Ser Gly Asp Trp Ile Pro Val Gly Leu
    785                 790                 795                 800
    Pro Gly Glu Leu Gln Ala Ile Arg Pro Gly Val Ser Val Ile Ser Leu
                        805                 810                 815
    Gly Gly Ala Thr Glu Ala Ser Ile Trp Ser Ile Gly Tyr Pro Val Arg
                    820                 825                 830
    Asn Val Asp Leu Ser Trp Ala Ser Ile Pro Tyr Gly Arg Pro Leu Arg
                835                 840                 845
    Asn Gln Thr Phe His Val Leu Asp Glu Ala Leu Glu Pro Arg Pro Val
                850                 855                 860
    Trp Val Pro Gly Gln Leu Tyr Ile Gly Gly Val Gly Leu Ala Leu Gly
    865                 870                 875                 880
    Tyr Trp Arg Asp Glu Glu Lys Thr Arg Lys Ser Phe Leu Val His Pro
                        885                 890                 895
    Glu Thr Gly Glu Arg Leu Tyr Lys Thr Gly Asp Leu Gly Arg Tyr Leu
                    900                 905                 910
    Pro Asp Gly Asn Ile Glu Phe Met Gly Arg Glu Asp Asn Gln Ile Lys
                915                 920                 925
    Leu Arg Gly Tyr Arg Val Glu Leu Gly Glu Ile Glu Glu Thr Leu Lys
                930                 935                 940
    Ser His Pro Asn Val Arg Asp Ala Val Ile Val Pro Val Gly Asn Asp
    945                 950                 955                 960
    Ala Ala Asn Lys Leu Leu Leu Ala Tyr Val Val Pro Glu Gly Thr Arg
                        965                 970                 975
    Arg Arg Ala Ala Glu Gln Asp Ala Ser Leu Lys Thr Glu Arg Ile Asp
                    980                 985                 990
    Ala Arg Ala His Ala Ala Glu Ala Asp Gly Leu Ser Asp Gly Glu Arg
                995                 1000                1005
    Val Gln Phe Lys Leu Ala Arg His Gly Leu Arg Arg Asp Leu Asp Gly
        1010                1015                1020
    Lys Pro Val Val Asp Leu Thr Gly Gln Asp Pro Arg Glu Ala Gly Leu
    1025                1030                1035                1040
    Asp Val Tyr Ala Arg Arg Ser Val Arg Thr Phe Leu Glu Ala Pro
                    1045                1050                1055
    Ile Pro Phe Val Glu Phe Gly Arg Phe Leu Ser Cys Leu Ser Ser Val
                1060                1065                1070
```

-continued

```
Glu Pro Asp Gly Ala Thr Leu Pro Lys Phe Arg Tyr Pro Ser Ala Gly
    1075                1080                1085

Ser Thr Tyr Pro Val Gln Thr Tyr Ala Tyr Val Lys Ser Gly Arg Ile
    1090                1095                1100

Glu Gly Val Asp Glu Gly Phe Tyr Tyr Tyr His Pro Phe Glu His Arg
1105                1110                1115                1120

Leu Leu Lys Leu Ser Asp His Gly Ile Glu Arg Gly Ala His Val Arg
                1125                1130                1135

Gln Asn Phe Asp Val Phe Asp Glu Ala Ala Phe Asn Leu Leu Phe Val
            1140                1145                1150

Gly Arg Ile Asp Ala Ile Glu Ser Leu Tyr Gly Ser Ser Ser Arg Glu
        1155                1160                1165

Phe Cys Leu Leu Glu Ala Gly Tyr Met Ala Gln Leu Leu Met Glu Gln
    1170                1175                1180

Ala Pro Ser Cys Asn Ile Gly Val Cys Pro Val Gly Gln Phe Asn Phe
1185                1190                1195                1200

Glu Gln Val Arg Pro Val Leu Asp Leu Arg His Ser Asp Val Tyr Val
                1205                1210                1215

His Gly Met Leu Gly Gly Arg Val Asp Pro Arg Gln Phe Gln Val Cys
            1220                1225                1230

Thr Leu Gly Gln Asp Ser Ser Pro Arg Arg Ala Thr Thr Arg Gly Ala
        1235                1240                1245

Pro Pro Gly Arg Glu Gln His Phe Ala Asp Met Leu Arg Asp Phe Leu
    1250                1255                1260

Arg Thr Lys Leu Pro Glu Tyr Met Val Pro Thr Val Phe Val Glu Leu
1265                1270                1275                1280

Asp Ala Leu Pro Leu Thr Ser Asn Gly Lys Val Asp Arg Lys Ala Leu
                1285                1290                1295

Arg Glu Arg Lys Asp Thr Ser Ser Pro Arg His Ser Gly His Thr Ala
            1300                1305                1310

Pro Arg Asp Ala Leu Glu Glu Ile Leu Val Ala Val Arg Glu Val
        1315                1320                1325

Leu Gly Leu Glu Val Val Gly Leu Gln Gln Ser Phe Val Asp Leu Gly
    1330                1335                1340

Ala Thr Ser Ile His Ile Val Arg Met Arg Ser Leu Leu Gln Lys Arg
1345                1350                1355                1360

Leu Asp Arg Glu Ile Ala Ile Thr Glu Leu Phe Gln Tyr Pro Asn Leu
                1365                1370                1375

Gly Ser Leu Ala Ser Gly Leu Arg Arg Asp Ser Arg Asp Leu Asp Gln
            1380                1385                1390

Arg Pro Asn Met Gln Asp Arg Val Glu Val Arg Arg Lys Gly Arg Arg
        1395                1400                1405

Arg Ser
    1410

<210> SEQ ID NO 4
<211> LENGTH: 1832
<212> TYPE: PRT
<213> ORGANISM: Sorangium cellulosum

<400> SEQUENCE: 4

Met Glu Glu Gln Glu Ser Ser Ala Ile Ala Val Ile Gly Met Ser Gly
 1               5                  10                  15

Arg Phe Pro Gly Ala Arg Asp Leu Asp Glu Phe Trp Arg Asn Leu Arg
```

-continued

```
                20                  25                  30
Asp Gly Thr Glu Ala Val Gln Arg Phe Ser Glu Gln Glu Leu Ala Ala
                35                  40                  45
Ser Gly Val Asp Pro Ala Leu Val Leu Asp Pro Ser Tyr Val Arg Ala
 50                  55                  60
Gly Ser Val Leu Glu Asp Val Asp Arg Phe Asp Ala Ala Phe Phe Gly
 65                  70                  75                  80
Ile Ser Pro Arg Glu Ala Glu Leu Met Asp Pro Gln His Arg Ile Phe
                85                  90                  95
Met Glu Cys Ala Trp Glu Ala Leu Glu Asn Ala Gly Tyr Asp Pro Thr
                100                 105                 110
Ala Tyr Glu Gly Ser Ile Gly Val Tyr Ala Gly Ala Asn Met Ser Ser
                115                 120                 125
Tyr Leu Thr Ser Asn Leu His Glu His Pro Ala Met Met Arg Trp Pro
130                 135                 140
Gly Trp Phe Gln Thr Leu Ile Gly Asn Asp Lys Asp Tyr Leu Ala Thr
145                 150                 155                 160
His Val Ser Tyr Arg Leu Asn Leu Arg Gly Pro Ser Ile Ser Val Gln
                165                 170                 175
Thr Ala Cys Ser Thr Ser Leu Val Ala Val His Leu Ala Cys Met Ser
                180                 185                 190
Leu Leu Asp Arg Glu Cys Asp Met Ala Leu Ala Gly Gly Ile Thr Val
                195                 200                 205
Arg Ile Pro His Arg Ala Gly Tyr Val Tyr Ala Glu Gly Gly Ile Phe
                210                 215                 220
Ser Pro Asp Gly His Cys Arg Ala Phe Asp Ala Lys Ala Asn Gly Thr
225                 230                 235                 240
Ile Met Gly Asn Gly Cys Gly Val Val Leu Leu Lys Pro Leu Asp Arg
                245                 250                 255
Ala Leu Ser Asp Gly Asp Pro Val Arg Ala Val Ile Leu Gly Ser Ala
                260                 265                 270
Thr Asn Asn Asp Gly Ala Arg Lys Ile Gly Phe Thr Ala Pro Ser Glu
                275                 280                 285
Val Gly Gln Ala Gln Ala Ile Met Glu Ala Leu Ala Leu Ala Gly Val
                290                 295                 300
Glu Ala Arg Ser Ile Gln Tyr Ile Glu Thr His Gly Thr Gly Thr Leu
305                 310                 315                 320
Leu Gly Asp Ala Ile Glu Thr Ala Ala Leu Arg Arg Val Phe Gly Arg
                325                 330                 335
Asp Ala Ser Ala Arg Arg Ser Cys Ala Ile Gly Ser Val Lys Thr Gly
                340                 345                 350
Ile Gly His Leu Glu Ser Ala Ala Gly Ile Ala Gly Leu Ile Lys Thr
                355                 360                 365
Val Leu Ala Leu Glu His Arg Gln Leu Pro Pro Ser Leu Asn Phe Glu
370                 375                 380
Ser Pro Asn Pro Ser Ile Asp Phe Ala Ser Ser Pro Phe Tyr Val Asn
385                 390                 395                 400
Thr Ser Leu Lys Asp Trp Asn Thr Gly Ser Thr Pro Arg Arg Ala Gly
                405                 410                 415
Val Ser Ser Phe Gly Ile Gly Gly Thr Asn Ala His Val Val Leu Glu
                420                 425                 430
Glu Ala Pro Ala Ala Lys Leu Pro Ala Ala Ala Pro Ala Arg Ser Ala
                435                 440                 445
```

-continued

```
Glu Leu Phe Val Val Ser Ala Lys Ser Ala Ala Ala Leu Asp Ala Ala
    450                 455                 460
Ala Ala Arg Leu Arg Asp His Leu Gln Ala His Gln Gly Ile Ser Leu
465                 470                 475                 480
Gly Asp Val Ala Phe Ser Leu Ala Thr Thr Arg Ser Pro Met Glu His
                485                 490                 495
Arg Leu Ala Met Ala Ala Pro Ser Arg Glu Ala Leu Arg Glu Gly Leu
                500                 505                 510
Asp Ala Ala Ala Arg Gly Gln Thr Pro Pro Gly Ala Val Arg Gly Arg
                515                 520                 525
Cys Ser Pro Gly Asn Val Pro Lys Val Val Phe Val Phe Pro Gly Gln
                530                 535                 540
Gly Ser Gln Trp Val Gly Met Gly Arg Gln Leu Leu Ala Glu Glu Pro
545                 550                 555                 560
Val Phe His Ala Ala Leu Ser Ala Cys Asp Arg Ala Ile Gln Ala Glu
                565                 570                 575
Ala Gly Trp Ser Leu Leu Ala Glu Leu Ala Ala Asp Glu Gly Ser Ser
                580                 585                 590
Gln Leu Glu Arg Ile Asp Val Val Gln Pro Val Leu Phe Ala Leu Ala
                595                 600                 605
Val Ala Phe Ala Ala Leu Trp Arg Ser Trp Gly Val Ala Pro Asp Val
                610                 615                 620
Val Ile Gly His Ser Met Gly Glu Val Ala Ala Ala His Val Ala Gly
625                 630                 635                 640
Ala Leu Ser Leu Glu Asp Ala Val Ala Ile Ile Cys Arg Arg Ser Arg
                645                 650                 655
Leu Leu Arg Arg Ile Ser Gly Gln Gly Glu Met Ala Val Thr Glu Leu
                660                 665                 670
Ser Leu Ala Glu Ala Glu Ala Leu Arg Gly Tyr Glu Asp Arg Val
                675                 680                 685
Ser Val Ala Val Ser Asn Ser Pro Arg Ser Thr Val Leu Ser Gly Glu
                690                 695                 700
Pro Ala Ala Ile Gly Glu Val Leu Ser Ser Leu Asn Ala Lys Gly Val
705                 710                 715                 720
Phe Cys Arg Arg Val Lys Val Asp Val Ala Ser His Ser Pro Gln Val
                725                 730                 735
Asp Pro Leu Arg Glu Asp Leu Leu Ala Ala Leu Gly Gly Leu Arg Pro
                740                 745                 750
Gly Ala Ala Val Pro Met Arg Ser Thr Val Thr Gly Ala Met Val
                755                 760                 765
Ala Gly Pro Glu Leu Gly Ala Asn Tyr Trp Met Asn Asn Leu Arg Gln
770                 775                 780
Pro Val Arg Phe Ala Glu Val Val Gln Ala Gln Leu Gln Gly Gly His
785                 790                 795                 800
Gly Leu Phe Val Glu Met Ser Pro His Pro Ile Leu Thr Thr Ser Val
                805                 810                 815
Glu Glu Met Arg Arg Ala Ala Gln Arg Ala Gly Ala Ala Val Gly Ser
                820                 825                 830
Leu Arg Arg Gly Gln Asp Glu Arg Pro Ala Met Leu Glu Ala Leu Gly
                835                 840                 845
Thr Leu Trp Ala Gln Gly Tyr Pro Val Pro Trp Gly Arg Leu Phe Pro
850                 855                 860
```

-continued

```
Ala Gly Gly Arg Arg Val Pro Leu Pro Thr Tyr Pro Trp Gln Arg Glu
865                 870                 875                 880

Arg Tyr Trp Ile Glu Ala Pro Ala Lys Ser Ala Ala Gly Asp Arg Arg
                885                 890                 895

Gly Val Arg Ala Gly Gly His Pro Leu Leu Gly Glu Met Gln Thr Leu
                900                 905                 910

Ser Thr Gln Thr Ser Thr Arg Leu Trp Glu Thr Thr Leu Asp Leu Lys
                915                 920                 925

Arg Leu Pro Trp Leu Gly Asp His Arg Val Gln Gly Ala Val Val Phe
930                 935                 940

Pro Gly Ala Ala Tyr Leu Glu Met Ala Ile Ser Ser Gly Ala Glu Ala
945                 950                 955                 960

Leu Gly Asp Gly Pro Leu Gln Ile Thr Asp Val Val Leu Ala Glu Ala
                965                 970                 975

Leu Ala Phe Ala Gly Asp Ala Ala Val Leu Val Gln Val Val Thr Thr
                980                 985                 990

Glu Gln Pro Ser Gly Arg Leu Gln Phe Gln Ile Ala Ser Arg Ala Pro
                995                 1000                1005

Gly Ala Gly His Ala Ser Phe Arg Val His Ala Arg Gly Ala Leu Leu
    1010                1015                1020

Arg Val Glu Arg Thr Glu Val Pro Ala Gly Leu Thr Leu Ser Ala Val
1025                1030                1035                1040

Arg Ala Arg Leu Gln Ala Ser Ile Pro Ala Ala Thr Tyr Ala Glu
                1045                1050                1055

Leu Thr Glu Met Gly Leu Gln Tyr Gly Pro Ala Phe Gln Gly Ile Ala
                1060                1065                1070

Glu Leu Trp Arg Gly Glu Gly Glu Ala Leu Gly Arg Val Arg Leu Pro
                1075                1080                1085

Asp Ala Ala Gly Ser Ala Ala Glu Tyr Arg Leu His Pro Ala Leu Leu
                1090                1095                1100

Asp Ala Cys Phe Gln Ile Val Gly Ser Leu Phe Ala Arg Ser Gly Glu
1105                1110                1115                1120

Ala Thr Pro Trp Val Pro Val Glu Leu Gly Ser Leu Arg Leu Leu Gln
                1125                1130                1135

Arg Pro Ser Gly Glu Leu Trp Cys His Ala Arg Val Val Asn His Gly
                1140                1145                1150

His Gln Thr Pro Asp Arg Gln Gly Ala Asp Phe Trp Val Val Asp Ser
                1155                1160                1165

Ser Gly Ala Val Val Ala Glu Val Cys Gly Leu Val Ala Gln Arg Leu
                1170                1175                1180

Pro Gly Gly Val Arg Arg Arg Glu Glu Asp Asp Trp Phe Leu Glu Leu
1185                1190                1195                1200

Glu Trp Glu Pro Ala Ala Val Gly Thr Ala Lys Val Asn Ala Gly Arg
                1205                1210                1215

Trp Leu Leu Leu Gly Gly Gly Gly Leu Gly Ala Ala Leu Arg Ala
                1220                1225                1230

Met Leu Glu Ala Gly Gly His Ala Val Val His Ala Ala Glu Asn Asn
                1235                1240                1245

Thr Ser Ala Ala Gly Val Arg Ala Leu Leu Ala Lys Ala Phe Asp Gly
                1250                1255                1260

Gln Ala Pro Thr Ala Val Val His Leu Gly Ser Leu Asp Gly Gly Gly
                1265                1270                1275                1280

Glu Leu Asp Pro Gly Leu Gly Ala Gln Gly Ala Leu Asp Ala Pro Arg
```

-continued

```
                1285                1290                1295
Ser Ala Asp Val Ser Pro Asp Ala Leu Asp Pro Ala Leu Val Arg Gly
            1300                1305                1310
Cys Asp Ser Val Leu Trp Thr Val Gln Ala Leu Ala Gly Met Gly Phe
            1315                1320                1325
Arg Asp Ala Pro Arg Leu Trp Leu Leu Thr Arg Gly Ala Gln Ala Val
            1330                1335                1340
Gly Ala Gly Asp Val Ser Val Thr Gln Ala Pro Leu Leu Gly Leu Gly
1345                1350                1355                1360
Arg Val Ile Ala Met Glu His Ala Asp Leu Arg Cys Ala Arg Val Asp
            1365                1370                1375
Leu Asp Pro Ala Arg Pro Glu Gly Glu Leu Ala Ala Leu Leu Ala Glu
            1380                1385                1390
Leu Leu Ala Asp Asp Ala Glu Ala Glu Val Ala Leu Arg Gly Gly Glu
            1395                1400                1405
Arg Cys Val Ala Arg Ile Val Arg Arg Gln Pro Glu Thr Arg Pro Arg
            1410                1415                1420
Gly Arg Ile Glu Ser Cys Val Pro Thr Asp Val Thr Ile Arg Ala Asp
1425                1430                1435                1440
Ser Thr Tyr Leu Val Thr Gly Gly Leu Gly Gly Leu Gly Leu Ser Val
            1445                1450                1455
Ala Gly Trp Leu Ala Glu Arg Gly Ala Gly His Leu Val Leu Val Gly
            1460                1465                1470
Arg Ser Gly Ala Ala Ser Val Glu Gln Arg Ala Ala Val Ala Ala Leu
            1475                1480                1485
Glu Ala Arg Gly Ala Arg Val Thr Val Ala Lys Ala Asp Val Ala Asp
            1490                1495                1500
Arg Ala Gln Leu Glu Arg Ile Leu Arg Glu Val Thr Thr Ser Gly Met
1505                1510                1515                1520
Pro Leu Arg Gly Val Val His Ala Ala Gly Ile Leu Asp Asp Gly Leu
            1525                1530                1535
Leu Met Gln Gln Thr Pro Ala Arg Phe Arg Lys Val Met Ala Pro Lys
            1540                1545                1550
Val Gln Gly Ala Leu His Leu His Ala Leu Thr Arg Glu Ala Pro Leu
            1555                1560                1565
Ser Phe Phe Val Leu Tyr Ala Ser Gly Val Gly Leu Leu Gly Ser Pro
            1570                1575                1580
Gly Gln Gly Asn Tyr Ala Ala Ala Asn Thr Phe Leu Asp Ala Leu Ala
1585                1590                1595                1600
His His Arg Arg Ala Gln Gly Leu Pro Ala Leu Ser Val Asp Trp Gly
            1605                1610                1615
Leu Phe Ala Glu Val Gly Met Ala Ala Ala Gln Glu Asp Arg Gly Ala
            1620                1625                1630
Arg Leu Val Ser Arg Gly Met Arg Ser Leu Thr Pro Asp Glu Gly Leu
            1635                1640                1645
Ser Ala Leu Ala Arg Leu Leu Glu Ser Gly Arg Ala Gln Val Gly Val
            1650                1655                1660
Met Pro Val Asn Pro Arg Leu Trp Val Glu Leu Tyr Pro Ala Ala Ala
1665                1670                1675                1680
Ser Ser Arg Met Leu Ser Arg Leu Val Thr Ala His Arg Ala Ser Ala
            1685                1690                1695
Gly Gly Pro Ala Gly Asp Gly Asp Leu Leu Arg Arg Leu Ala Ala Ala
            1700                1705                1710
```

```
Glu Pro Ser Ala Arg Ser Ala Leu Leu Glu Pro Leu Leu Arg Ala Gln
    1715                1720                1725

Ile Ser Gln Val Leu Arg Leu Pro Gly Lys Ile Glu Val Asp Ala
    1730                1735                1740

Pro Leu Thr Ser Leu Gly Met Asn Ser Leu Met Gly Leu Glu Leu Arg
1745                1750                1755                1760

Asn Arg Ile Glu Ala Met Leu Gly Ile Thr Val Pro Ala Thr Leu Leu
            1765                1770                1775

Trp Thr Tyr Pro Thr Val Ala Ala Leu Ser Gly His Leu Ala Arg Glu
                1780                1785                1790

Ala Cys Glu Ala Ala Pro Val Glu Ser Pro His Thr Thr Ala Asp Ser
            1795                1800                1805

Ala Val Glu Ile Glu Glu Met Ser Gln Asp Asp Leu Thr Gln Leu Ile
    1810                1815                1820

Ala Ala Lys Phe Lys Ala Leu Thr
1825                1830

<210> SEQ ID NO 5
<211> LENGTH: 7257
<212> TYPE: PRT
<213> ORGANISM: Sorangium cellulosum

<400> SEQUENCE: 5

Met Thr Thr Arg Gly Pro Thr Ala Gln Gln Asn Pro Leu Lys Gln Ala
1               5                   10                  15

Ala Ile Ile Ile Gln Arg Leu Glu Glu Arg Leu Ala Gly Leu Ala Gln
            20                  25                  30

Ala Glu Leu Glu Arg Thr Glu Pro Ile Ala Ile Val Gly Ile Gly Cys
        35                  40                  45

Arg Phe Pro Gly Ala Asp Ala Pro Glu Ala Phe Trp Glu Leu Leu
    50                  55                  60

Asp Ala Glu Arg Asp Ala Val Gln Pro Leu Asp Met Arg Trp Ala Leu
65                  70                  75                  80

Val Gly Val Ala Pro Val Glu Ala Val Pro His Trp Ala Gly Leu Leu
                85                  90                  95

Thr Glu Pro Ile Asp Cys Phe Asp Ala Ala Phe Phe Gly Ile Ser Pro
            100                 105                 110

Arg Glu Ala Arg Ser Leu Asp Pro Gln His Arg Leu Leu Leu Glu Val
        115                 120                 125

Ala Trp Glu Gly Leu Glu Asp Ala Gly Ile Pro Pro Arg Ser Ile Asp
    130                 135                 140

Gly Ser Arg Thr Gly Val Phe Val Gly Ala Phe Thr Ala Asp Tyr Ala
145                 150                 155                 160

Arg Thr Val Ala Arg Leu Pro Arg Glu Glu Arg Asp Ala Tyr Ser Ala
                165                 170                 175

Thr Gly Asn Met Leu Ser Ile Ala Ala Gly Arg Leu Ser Tyr Thr Leu
            180                 185                 190

Gly Leu Gln Gly Pro Cys Leu Thr Val Asp Thr Ala Cys Ser Ser Ser
        195                 200                 205

Leu Val Ala Ile His Leu Ala Cys Arg Ser Leu Arg Ala Gly Glu Ser
    210                 215                 220

Asp Leu Ala Leu Ala Gly Gly Val Ser Ala Leu Leu Ser Pro Asp Met
225                 230                 235                 240

Met Glu Ala Ala Ala Arg Thr Gln Ala Leu Ser Pro Asp Gly Arg Cys
```

-continued

```
                245                 250                 255
Arg Thr Phe Asp Ala Ser Ala Asn Gly Phe Val Arg Gly Glu Gly Cys
                260                 265                 270

Gly Leu Val Val Leu Lys Arg Leu Ser Asp Ala Gln Arg Asp Gly Asp
            275                 280                 285

Arg Ile Trp Ala Leu Ile Arg Gly Ser Ala Ile Asn His Asp Gly Arg
290                 295                 300

Ser Thr Gly Leu Thr Ala Pro Asn Val Leu Ala Gln Glu Thr Val Leu
305                 310                 315                 320

Arg Glu Ala Leu Arg Ser Ala His Val Glu Ala Gly Ala Val Asp Tyr
                325                 330                 335

Val Glu Thr His Gly Thr Gly Thr Ser Leu Gly Asp Pro Ile Glu Val
            340                 345                 350

Glu Ala Leu Arg Ala Thr Val Gly Pro Ala Arg Ser Asp Gly Thr Arg
            355                 360                 365

Cys Val Leu Gly Ala Val Lys Thr Asn Ile Gly His Leu Glu Ala Ala
            370                 375                 380

Ala Gly Val Ala Gly Leu Ile Lys Ala Ala Leu Ser Leu Thr His Glu
385                 390                 395                 400

Arg Ile Pro Arg Asn Leu Asn Phe Arg Thr Leu Asn Pro Arg Ile Arg
                405                 410                 415

Leu Glu Gly Ser Ala Leu Ala Leu Ala Thr Glu Pro Val Pro Trp Pro
            420                 425                 430

Arg Thr Asp Arg Pro Arg Phe Ala Gly Val Ser Ser Phe Gly Met Ser
            435                 440                 445

Gly Thr Asn Ala His Val Val Leu Glu Glu Ala Pro Ala Val Glu Leu
450                 455                 460

Trp Pro Ala Ala Pro Glu Arg Ser Ala Glu Leu Leu Val Leu Ser Gly
465                 470                 475                 480

Lys Ser Glu Gly Ala Leu Asp Ala Gln Ala Ala Arg Leu Arg Glu His
                485                 490                 495

Leu Asp Met His Pro Glu Leu Gly Leu Gly Asp Val Ala Phe Ser Leu
            500                 505                 510

Ala Thr Thr Arg Ser Ala Met Ser His Arg Leu Ala Val Ala Val Thr
            515                 520                 525

Ser Arg Glu Gly Leu Leu Ala Ala Leu Ser Ala Val Ala Gln Gly Gln
530                 535                 540

Thr Pro Ala Gly Ala Ala Arg Cys Ile Ala Ser Ser Arg Gly Lys
545                 550                 555                 560

Leu Ala Phe Leu Phe Thr Gly Gln Gly Ala Gln Thr Pro Gly Met Gly
                565                 570                 575

Arg Gly Leu Cys Ala Ala Trp Pro Ala Phe Arg Glu Ala Phe Asp Arg
            580                 585                 590

Cys Val Ala Leu Phe Asp Arg Glu Leu Asp Arg Pro Leu Arg Glu Val
            595                 600                 605

Met Trp Ala Glu Ala Gly Ser Ala Glu Ser Leu Leu Leu Asp Gln Thr
            610                 615                 620

Ala Phe Thr Gln Pro Ala Leu Phe Ala Val Glu Tyr Ala Leu Thr Ala
625                 630                 635                 640

Leu Trp Arg Ser Trp Gly Val Glu Pro Glu Leu Leu Val Gly His Ser
                645                 650                 655

Ile Gly Glu Leu Val Ala Ala Cys Val Ala Gly Val Phe Ser Leu Glu
            660                 665                 670
```

-continued

```
Asp Gly Val Arg Leu Val Ala Ala Arg Gly Arg Leu Met Gln Gly Leu
            675                 680                 685

Ser Ala Gly Gly Ala Met Val Ser Leu Gly Ala Pro Glu Ala Glu Val
    690                 695                 700

Ala Ala Ala Val Ala Pro His Ala Ala Ser Val Ser Ile Ala Ala Val
705                 710                 715                 720

Asn Gly Pro Glu Gln Val Val Ile Ala Gly Val Gln Ala Val Gln
                725                 730                 735

Ala Ile Ala Ala Gly Phe Ala Ala Arg Gly Ala Arg Thr Lys Arg Leu
                740                 745                 750

His Val Ser His Ala Phe His Ser Pro Leu Met Glu Pro Met Leu Glu
            755                 760                 765

Glu Phe Gly Arg Val Ala Ala Ser Val Thr Tyr Arg Arg Pro Ser Val
    770                 775                 780

Ser Leu Val Ser Asn Leu Ser Gly Lys Val Val Thr Asp Glu Leu Ser
785                 790                 795                 800

Ala Pro Gly Tyr Trp Val Arg His Val Arg Glu Ala Val Arg Phe Ala
                805                 810                 815

Asp Gly Val Lys Ala Leu His Glu Ala Gly Ala Gly Thr Phe Val Glu
                820                 825                 830

Val Gly Pro Lys Pro Thr Leu Leu Gly Leu Leu Pro Ala Cys Leu Pro
            835                 840                 845

Glu Ala Glu Pro Thr Leu Leu Ala Ser Leu Arg Ala Gly Arg Glu Glu
    850                 855                 860

Ala Ala Gly Val Leu Glu Ala Leu Gly Arg Leu Trp Ala Ala Gly Gly
865                 870                 875                 880

Ser Val Ser Trp Pro Gly Val Phe Pro Thr Ala Gly Arg Arg Val Pro
                885                 890                 895

Leu Pro Thr Tyr Pro Trp Gln Arg Gln Arg Tyr Trp Ile Glu Ala Pro
            900                 905                 910

Ala Glu Gly Leu Gly Ala Thr Ala Ala Asp Ala Leu Ala Gln Trp Phe
            915                 920                 925

Tyr Arg Val Asp Trp Pro Glu Met Pro Arg Ser Ser Val Asp Ser Arg
930                 935                 940

Arg Ala Arg Ser Gly Gly Trp Leu Val Leu Ala Asp Arg Gly Gly Val
945                 950                 955                 960

Gly Glu Ala Ala Ala Ala Leu Ser Ser Gln Gly Cys Ser Cys Ala
                965                 970                 975

Val Leu His Ala Pro Ala Glu Ala Ser Ala Val Ala Glu Gln Val Thr
            980                 985                 990

Gln Ala Leu Gly Gly Arg Asn Asp Trp Gln Gly Val Leu Tyr Leu Trp
            995                 1000                1005

Gly Leu Asp Ala Val Val Glu Ala Gly Ala Ser Ala Glu Glu Val Ala
    1010                1015                1020

Lys Val Thr His Leu Ala Ala Ala Pro Val Leu Ala Leu Ile Gln Ala
1025                1030                1035                1040

Leu Gly Thr Gly Pro Arg Ser Pro Arg Leu Trp Ile Val Thr Arg Gly
                1045                1050                1055

Ala Cys Thr Val Gly Gly Glu Pro Asp Ala Ala Pro Cys Gln Ala Ala
                1060                1065                1070

Leu Trp Gly Met Gly Arg Val Ala Leu Glu His Pro Gly Ser Trp
            1075                1080                1085
```

-continued

```
Gly Gly Leu Val Asp Leu Asp Pro Glu Glu Ser Pro Thr Glu Val Glu
        1090                1095                1100

Ala Leu Val Ala Glu Leu Leu Ser Pro Asp Ala Glu Asp Gln Leu Ala
1105                1110                1115                1120

Phe Arg Gln Gly Arg Arg Ala Ala Arg Leu Val Ala Ala Pro Pro
            1125                1130                1135

Glu Gly Asn Ala Ala Pro Val Ser Leu Ser Ala Glu Gly Ser Tyr Leu
                1140                1145                1150

Val Thr Gly Gly Leu Gly Ala Leu Gly Leu Leu Val Ala Arg Trp Leu
        1155                1160                1165

Val Glu Arg Gly Ala Gly His Leu Val Leu Ile Ser Arg His Gly Leu
        1170                1175                1180

Pro Asp Arg Glu Glu Trp Gly Arg Asp Gln Pro Glu Val Arg Ala
1185                1190                1195                1200

Arg Ile Ala Ala Ile Glu Ala Leu Glu Ala Gln Gly Ala Arg Val Thr
            1205                1210                1215

Val Ala Ala Val Asp Val Ala Asp Ala Glu Gly Met Ala Ala Leu Leu
                1220                1225                1230

Ala Ala Val Glu Pro Pro Leu Arg Gly Val Val His Ala Ala Gly Leu
        1235                1240                1245

Leu Asp Asp Gly Leu Leu Ala His Gln Asp Ala Gly Arg Leu Ala Arg
        1250                1255                1260

Val Leu Arg Pro Lys Val Glu Gly Ala Trp Val Leu His Thr Leu Thr
1265                1270                1275                1280

Arg Glu Gln Pro Leu Asp Leu Phe Val Leu Phe Ser Ser Ala Ser Gly
            1285                1290                1295

Val Phe Gly Ser Ile Gly Gln Gly Ser Tyr Ala Ala Gly Asn Ala Phe
        1300                1305                1310

Leu Asp Ala Leu Ala Asp Leu Arg Arg Thr Gln Gly Leu Ala Ala Leu
        1315                1320                1325

Ser Ile Ala Trp Gly Leu Trp Ala Glu Gly Gly Met Gly Ser Gln Ala
        1330                1335                1340

Gln Arg Arg Glu His Glu Ala Ser Gly Ile Trp Ala Met Pro Thr Ser
1345                1350                1355                1360

Arg Ala Leu Ala Ala Met Glu Trp Leu Leu Gly Thr Arg Ala Thr Gln
            1365                1370                1375

Arg Val Val Ile Gln Met Asp Trp Ala His Ala Gly Ala Ala Pro Arg
        1380                1385                1390

Asp Ala Ser Arg Gly Arg Phe Trp Asp Arg Leu Val Thr Ala Thr Lys
        1395                1400                1405

Glu Ala Ser Ser Ser Ala Val Pro Ala Val Glu Arg Trp Arg Asn Ala
1410                1415                1420

Ser Val Val Glu Thr Arg Ser Ala Leu Tyr Glu Leu Val Arg Gly Val
1425                1430                1435                1440

Val Ala Gly Val Met Gly Phe Thr Asp Gln Gly Thr Leu Asp Val Arg
            1445                1450                1455

Arg Gly Phe Ala Glu Gln Gly Leu Asp Ser Leu Met Ala Val Glu Ile
        1460                1465                1470

Arg Lys Arg Leu Gln Gly Glu Leu Gly Met Pro Leu Ser Ala Thr Leu
        1475                1480                1485

Ala Phe Asp His Pro Thr Val Glu Arg Leu Val Glu Tyr Leu Leu Ser
    1490                1495                1500

Gln Ala Leu Glu Leu Gln Asp Arg Thr Asp Val Arg Ser Val Arg Leu
```

-continued

```
1505                1510                1515                1520

Pro Ala Thr Glu Asp Pro Ile Ala Ile Val Gly Ala Ala Cys Arg Phe
            1525                1530                1535

Pro Gly Gly Val Glu Asp Leu Glu Ser Tyr Trp Gln Leu Leu Thr Glu
        1540                1545                1550

Gly Val Val Ser Thr Glu Val Pro Ala Asp Arg Trp Asn Gly Ala
    1555                1560                1565

Asp Gly Arg Val Pro Gly Ser Gly Glu Ala Gln Arg Gln Thr Tyr Val
    1570                1575                1580

Pro Arg Gly Gly Phe Leu Arg Glu Val Glu Thr Phe Asp Ala Ala Phe
1585                1590                1595                1600

Phe His Ile Ser Pro Arg Glu Ala Met Ser Leu Asp Pro Gln Gln Arg
            1605                1610                1615

Leu Leu Leu Glu Val Ser Trp Glu Ala Ile Glu Arg Ala Gly Gln Asp
        1620                1625                1630

Pro Ser Ala Leu Arg Glu Ser Pro Thr Gly Val Phe Val Gly Ala Gly
        1635                1640                1645

Pro Asn Glu Tyr Ala Glu Arg Val Gln Glu Leu Ala Asp Glu Ala Ala
    1650                1655                1660

Gly Leu Tyr Ser Gly Thr Gly Asn Met Leu Ser Val Ala Ala Gly Arg
1665                1670                1675                1680

Leu Ser Phe Phe Leu Gly Leu His Gly Pro Thr Leu Ala Val Asp Thr
            1685                1690                1695

Ala Cys Ser Ser Ser Leu Val Ala Leu His Leu Gly Cys Gln Ser Leu
            1700                1705                1710

Arg Arg Gly Glu Cys Asp Gln Ala Leu Val Gly Gly Val Asn Met Leu
    1715                1720                1725

Leu Ser Pro Lys Thr Phe Ala Leu Leu Ser Arg Met His Ala Leu Ser
    1730                1735                1740

Pro Gly Gly Arg Cys Lys Thr Phe Ser Ala Asp Ala Asp Gly Tyr Ala
1745                1750                1755                1760

Arg Ala Glu Gly Cys Ala Val Val Val Leu Lys Arg Leu Ser Asp Ala
            1765                1770                1775

Gln Arg Asp Arg Asp Pro Ile Leu Ala Val Ile Arg Gly Thr Ala Ile
        1780                1785                1790

Asn His Asp Gly Pro Ser Ser Gly Leu Thr Val Pro Ser Gly Pro Ala
    1795                1800                1805

Gln Glu Ala Leu Leu Arg Gln Ala Leu Ala His Ala Gly Val Val Pro
    1810                1815                1820

Ala Asp Val Asp Phe Val Glu Cys His Gly Thr Gly Thr Ala Leu Gly
1825                1830                1835                1840

Asp Pro Ile Glu Val Arg Ala Leu Ser Asp Val Tyr Gly Gln Ala Arg
            1845                1850                1855

Pro Ala Asp Arg Pro Leu Ile Leu Gly Ala Ala Lys Ala Asn Leu Gly
        1860                1865                1870

His Met Glu Pro Ala Ala Gly Leu Ala Gly Leu Leu Lys Ala Val Leu
    1875                1880                1885

Ala Leu Gly Gln Glu Gln Ile Pro Ala Gln Pro Glu Leu Gly Glu Leu
    1890                1895                1900

Asn Pro Leu Leu Pro Trp Glu Ala Leu Pro Val Ala Val Ala Arg Ala
1905                1910                1915                1920

Ala Val Pro Trp Pro Arg Thr Asp Arg Pro Arg Phe Ala Gly Val Ser
            1925                1930                1935
```

-continued

```
Ser Phe Gly Met Ser Gly Thr Asn Ala His Val Val Leu Glu Glu Ala
            1940                1945                1950
Pro Ala Val Glu Leu Trp Pro Ala Ala Pro Glu Arg Ser Ala Glu Leu
            1955                1960                1965
Leu Val Leu Ser Gly Lys Ser Glu Gly Ala Leu Asp Ala Gln Ala Ala
            1970                1975                1980
Arg Leu Arg Glu His Leu Asp Met His Pro Glu Leu Gly Leu Gly Asp
1985                1990                1995                2000
Val Ala Phe Ser Leu Ala Thr Thr Arg Ser Ala Met Asn His Arg Leu
            2005                2010                2015
Ala Val Ala Val Thr Ser Arg Glu Gly Leu Leu Ala Ala Leu Ser Ala
            2020                2025                2030
Val Ala Gln Gly Gln Thr Pro Pro Gly Ala Ala Arg Cys Ile Ala Ser
            2035                2040                2045
Ser Ser Arg Gly Lys Leu Ala Phe Leu Phe Thr Gly Gln Gly Ala Gln
            2050                2055                2060
Thr Pro Gly Met Gly Arg Gly Leu Cys Ala Ala Trp Pro Ala Phe Arg
2065                2070                2075                2080
Glu Ala Phe Asp Arg Cys Val Ala Leu Phe Asp Arg Glu Leu Asp Arg
            2085                2090                2095
Pro Leu Arg Glu Val Met Trp Ala Glu Pro Gly Ser Ala Glu Ser Leu
            2100                2105                2110
Leu Leu Asp Gln Thr Ala Phe Thr Gln Pro Ala Leu Phe Thr Val Glu
            2115                2120                2125
Tyr Ala Leu Thr Ala Leu Trp Arg Ser Trp Gly Val Glu Pro Glu Leu
            2130                2135                2140
Val Ala Gly His Ser Ala Gly Glu Leu Val Ala Ala Cys Val Ala Gly
2145                2150                2155                2160
Val Phe Ser Leu Glu Asp Gly Val Arg Leu Val Ala Ala Arg Gly Arg
            2165                2170                2175
Leu Met Gln Gly Leu Ser Ala Gly Gly Ala Met Val Ser Leu Gly Ala
            2180                2185                2190
Pro Glu Ala Glu Val Ala Ala Ala Val Ala Pro His Ala Ala Ser Val
            2195                2200                2205
Ser Ile Ala Ala Val Asn Gly Pro Glu Gln Val Val Ile Ala Gly Val
            2210                2215                2220
Glu Gln Ala Val Gln Ala Ile Ala Ala Gly Phe Ala Ala Arg Gly Ala
2225                2230                2235                2240
Arg Thr Lys Arg Leu His Val Ser His Ala Ser His Ser Pro Leu Met
            2245                2250                2255
Glu Pro Met Leu Glu Glu Phe Gly Arg Val Ala Ala Ser Val Thr Tyr
            2260                2265                2270
Arg Arg Pro Ser Val Ser Leu Val Ser Asn Leu Ser Gly Lys Val Val
            2275                2280                2285
Ala Asp Glu Leu Ser Ala Pro Gly Tyr Trp Val Arg His Val Arg Glu
            2290                2295                2300
Ala Val Arg Phe Ala Asp Gly Val Lys Ala Leu His Glu Ala Gly Ala
2305                2310                2315                2320
Gly Thr Phe Val Glu Val Gly Pro Lys Pro Thr Leu Leu Gly Leu Leu
            2325                2330                2335
Pro Ala Cys Leu Pro Glu Ala Glu Pro Thr Leu Leu Ala Ser Leu Arg
            2340                2345                2350
```

```
Ala Gly Arg Glu Glu Ala Ala Gly Val Leu Glu Ala Leu Gly Arg Leu
    2355                2360                2365

Trp Ala Ala Gly Gly Ser Val Ser Trp Pro Gly Val Phe Pro Thr Ala
    2370                2375                2380

Gly Arg Arg Val Pro Leu Pro Thr Tyr Pro Trp Gln Arg Gln Arg Tyr
2385                2390                2395                2400

Trp Pro Asp Ile Glu Pro Asp Ser Arg Arg His Ala Ala Ala Asp Pro
        2405                2410                2415

Thr Gln Gly Trp Phe Tyr Arg Val Asp Trp Pro Glu Ile Pro Arg Ser
            2420                2425                2430

Leu Gln Lys Ser Glu Glu Ala Ser Arg Gly Ser Trp Leu Val Leu Ala
    2435                2440                2445

Asp Lys Gly Gly Val Gly Glu Ala Val Ala Ala Ala Leu Ser Thr Arg
    2450                2455                2460

Gly Leu Pro Cys Val Val Leu His Ala Pro Ala Glu Thr Ser Ala Thr
2465                2470                2475                2480

Ala Glu Leu Val Thr Glu Ala Ala Gly Gly Arg Ser Asp Trp Gln Val
            2485                2490                2495

Val Leu Tyr Leu Trp Gly Leu Asp Ala Val Val Gly Ala Glu Ala Ser
            2500                2505                2510

Ile Asp Glu Ile Gly Asp Ala Thr Arg Arg Ala Thr Ala Pro Val Leu
    2515                2520                2525

Gly Leu Ala Arg Phe Leu Ser Thr Val Ser Cys Ser Pro Arg Leu Trp
    2530                2535                2540

Val Val Thr Arg Gly Ala Cys Ile Val Gly Asp Glu Pro Ala Ile Ala
2545                2550                2555                2560

Pro Cys Gln Ala Ala Leu Trp Gly Met Gly Arg Val Ala Ala Leu Glu
        2565                2570                2575

His Pro Gly Ala Trp Gly Gly Leu Val Asp Leu Asp Pro Arg Ala Ser
            2580                2585                2590

Pro Pro Gln Ala Ser Pro Ile Asp Gly Glu Met Leu Val Thr Glu Leu
    2595                2600                2605

Leu Ser Gln Glu Thr Glu Asp Gln Leu Ala Phe Arg His Gly Arg Arg
    2610                2615                2620

His Ala Ala Arg Leu Val Ala Ala Pro Pro Gln Gly Gln Ala Ala Pro
2625                2630                2635                2640

Val Ser Leu Ser Ala Glu Ala Ser Tyr Leu Val Thr Gly Gly Leu Gly
            2645                2650                2655

Gly Leu Gly Leu Ile Val Ala Gln Trp Leu Val Glu Leu Gly Ala Arg
            2660                2665                2670

His Leu Val Leu Thr Ser Arg Arg Gly Leu Pro Asp Arg Gln Ala Trp
    2675                2680                2685

Cys Glu Gln Gln Pro Pro Glu Ile Arg Ala Arg Ile Ala Ala Val Glu
    2690                2695                2700

Ala Leu Glu Ala Arg Gly Ala Arg Val Thr Val Ala Ala Val Asp Val
2705                2710                2715                2720

Ala Asp Val Glu Pro Met Thr Ala Leu Val Ser Ser Val Glu Pro Pro
            2725                2730                2735

Leu Arg Gly Val Val His Ala Ala Gly Val Ser Val Met Arg Pro Leu
            2740                2745                2750

Ala Glu Thr Asp Glu Thr Leu Leu Glu Ser Val Leu Arg Pro Lys Val
    2755                2760                2765

Ala Gly Ser Trp Leu Leu His Arg Leu Leu His Gly Arg Pro Leu Asp
```

```
                2770                2775                2780
Leu Phe Val Leu Phe Ser Ser Gly Ala Ala Val Trp Gly Ser His Ser
2785                2790                2795                2800

Gln Gly Ala Tyr Ala Ala Ala Asn Ala Phe Leu Asp Gly Leu Ala His
                2805                2810                2815

Leu Arg Arg Ser Gln Ser Leu Pro Ala Leu Ser Val Ala Trp Gly Leu
            2820                2825                2830

Trp Ala Glu Gly Gly Met Ala Asp Ala Glu Ala His Ala Arg Leu Ser
        2835                2840                2845

Asp Ile Gly Val Leu Pro Met Ser Thr Ser Ala Ala Leu Ser Ala Leu
    2850                2855                2860

Gln Arg Leu Val Glu Thr Gly Ala Ala Gln Arg Thr Val Thr Arg Met
2865                2870                2875                2880

Asp Trp Ala Arg Phe Ala Pro Val Tyr Thr Ala Arg Gly Arg Arg Asn
                2885                2890                2895

Leu Leu Ser Ala Leu Val Ala Gly Arg Asp Ile Ile Ala Pro Ser Pro
            2900                2905                2910

Pro Ala Ala Ala Thr Arg Asn Trp Arg Gly Leu Ser Val Ala Glu Ala
        2915                2920                2925

Arg Val Ala Leu His Glu Ile Val His Gly Ala Val Ala Arg Val Leu
    2930                2935                2940

Gly Phe Leu Asp Pro Ser Ala Leu Asp Pro Gly Met Gly Phe Asn Glu
2945                2950                2955                2960

Gln Gly Leu Asp Ser Leu Met Ala Val Glu Ile Arg Asn Leu Leu Gln
                2965                2970                2975

Ala Glu Leu Asp Val Arg Leu Ser Thr Thr Leu Ala Phe Asp His Pro
            2980                2985                2990

Thr Val Gln Arg Leu Val Glu His Leu Leu Val Asp Val Leu Lys Leu
        2995                3000                3005

Glu Asp Arg Ser Asp Thr Gln His Val Arg Ser Leu Ala Ser Asp Glu
    3010                3015                3020

Pro Ile Ala Ile Val Gly Ala Ala Cys Arg Phe Pro Gly Gly Val Glu
3025                3030                3035                3040

Asp Leu Glu Ser Tyr Trp Gln Leu Leu Ala Glu Gly Val Val Val Ser
                3045                3050                3055

Ala Glu Val Pro Ala Asp Arg Trp Asp Ala Ala Asp Trp Tyr Asp Pro
            3060                3065                3070

Asp Pro Glu Ile Pro Gly Arg Thr Tyr Val Thr Lys Gly Ala Phe Leu
        3075                3080                3085

Arg Asp Leu Gln Arg Leu Asp Ala Thr Phe Phe Arg Ile Ser Pro Arg
    3090                3095                3100

Glu Ala Met Ser Leu Asp Pro Gln Gln Arg Leu Leu Leu Glu Val Ser
3105                3110                3115                3120

Trp Glu Ala Leu Glu Ser Ala Gly Ile Ala Pro Asp Thr Leu Arg Asp
                3125                3130                3135

Ser Pro Thr Gly Val Phe Val Gly Ala Gly Pro Asn Glu Tyr Tyr Thr
            3140                3145                3150

Gln Arg Leu Arg Gly Phe Thr Asp Gly Ala Ala Gly Leu Tyr Gly Gly
        3155                3160                3165

Thr Gly Asn Met Leu Ser Val Thr Ala Gly Arg Leu Ser Phe Phe Leu
    3170                3175                3180

Gly Leu His Gly Pro Thr Leu Ala Met Asp Thr Ala Cys Ser Ser Ser
3185                3190                3195                3200
```

-continued

```
Leu Val Ala Leu His Leu Ala Cys Gln Ser Leu Arg Leu Gly Glu Cys
            3205                3210                3215

Asp Gln Ala Leu Val Gly Gly Val Asn Val Leu Leu Ala Pro Glu Thr
            3220                3225                3230

Phe Val Leu Leu Ser Arg Met Arg Ala Leu Ser Pro Asp Gly Arg Cys
            3235                3240                3245

Lys Thr Phe Ser Ala Asp Ala Asp Gly Tyr Ala Arg Gly Glu Gly Cys
            3250                3255                3260

Ala Val Val Val Leu Lys Arg Leu Arg Asp Ala Gln Arg Ala Gly Asp
3265                3270                3275                3280

Ser Ile Leu Ala Leu Ile Arg Gly Ser Ala Val Asn His Asp Gly Pro
            3285                3290                3295

Ser Ser Gly Leu Thr Val Pro Asn Gly Pro Ala Gln Gln Ala Leu Leu
            3300                3305                3310

Arg Gln Ala Leu Ser Gln Ala Gly Val Ser Pro Val Asp Val Asp Phe
            3315                3320                3325

Val Glu Cys His Gly Thr Gly Thr Ala Leu Gly Asp Pro Ile Glu Val
            3330                3335                3340

Gln Ala Leu Ser Glu Val Tyr Gly Pro Gly Arg Ser Gly Asp Arg Pro
3345                3350                3355                3360

Leu Val Leu Gly Ala Ala Lys Ala Asn Val Ala His Leu Glu Ala Ala
            3365                3370                3375

Ser Gly Leu Ala Ser Leu Leu Lys Ala Val Leu Ala Leu Arg His Glu
            3380                3385                3390

Gln Ile Pro Ala Gln Pro Glu Leu Gly Glu Leu Asn Pro His Leu Pro
            3395                3400                3405

Trp Asn Thr Leu Pro Val Ala Val Pro Arg Lys Ala Val Pro Trp Gly
            3410                3415                3420

Arg Gly Ala Arg Pro Arg Arg Ala Gly Val Ser Ala Phe Gly Leu Ser
3425                3430                3435                3440

Gly Thr Asn Val His Val Val Leu Glu Glu Ala Pro Glu Val Glu Pro
            3445                3450                3455

Ala Pro Ala Ala Pro Ala Arg Pro Val Glu Leu Val Val Leu Ser Ala
            3460                3465                3470

Lys Ser Ala Ala Ala Leu Asp Ala Ala Ala Arg Leu Ser Ala His
            3475                3480                3485

Leu Ser Ala His Pro Glu Leu Ser Leu Gly Asp Val Ala Phe Ser Leu
            3490                3495                3500

Ala Thr Thr Arg Ser Pro Met Glu His Arg Leu Ala Ile Ala Thr Thr
3505                3510                3515                3520

Ser Arg Glu Ala Leu Arg Gly Ala Leu Asp Ala Ala Ala Gln Gln Lys
            3525                3530                3535

Thr Pro Gln Gly Ala Val Arg Gly Lys Ala Val Ser Ser Arg Gly Lys
            3540                3545                3550

Leu Ala Phe Leu Phe Thr Gly Gln Gly Ala Gln Met Pro Gly Met Gly
            3555                3560                3565

Arg Gly Leu Tyr Glu Thr Trp Pro Ala Phe Arg Glu Ala Phe Asp Arg
            3570                3575                3580

Cys Val Ala Leu Phe Asp Arg Glu Ile Asp Gln Pro Leu Arg Glu Val
3585                3590                3595                3600

Met Trp Ala Ala Pro Gly Leu Ala Gln Ala Ala Arg Leu Asp Gln Thr
            3605                3610                3615
```

```
Ala Tyr Ala Gln Pro Ala Leu Phe Ala Leu Glu Tyr Ala Leu Ala Ala
        3620                3625                3630

Leu Trp Arg Ser Trp Gly Val Glu Pro His Val Leu Gly His Ser
    3635                3640                3645

Ile Gly Glu Leu Val Ala Ala Cys Val Ala Gly Val Phe Ser Leu Glu
    3650                3655                3660

Asp Ala Val Arg Leu Val Ala Ala Arg Gly Arg Leu Met Gln Ala Leu
3665                3670                3675                3680

Pro Ala Gly Gly Ala Met Val Ala Ile Ala Ala Ser Glu Ala Glu Val
        3685                3690                3695

Ala Ala Ser Val Ala Pro His Ala Ala Thr Val Ser Ile Ala Ala Val
        3700                3705                3710

Asn Gly Pro Asp Ala Val Val Ile Ala Gly Ala Glu Val Gln Val Leu
        3715                3720                3725

Ala Leu Gly Ala Thr Phe Ala Ala Arg Gly Ile Arg Thr Lys Arg Leu
        3730                3735                3740

Ala Val Ser His Ala Phe His Ser Pro Leu Met Asp Pro Met Leu Glu
3745                3750                3755                3760

Asp Phe Gln Arg Val Ala Ala Thr Ile Ala Tyr Arg Ala Pro Asp Arg
        3765                3770                3775

Pro Val Val Ser Asn Val Thr Gly His Val Ala Gly Pro Glu Ile Ala
        3780                3785                3790

Thr Pro Glu Tyr Trp Val Arg His Val Arg Ser Ala Val Arg Phe Gly
        3795                3800                3805

Asp Gly Ala Lys Ala Leu His Ala Ala Gly Ala Ala Thr Phe Val Glu
        3810                3815                3820

Val Gly Pro Lys Pro Val Leu Leu Gly Leu Leu Pro Ala Cys Leu Gly
3825                3830                3835                3840

Glu Ala Asp Ala Val Leu Val Pro Ser Leu Arg Ala Asp Arg Ser Glu
        3845                3850                3855

Cys Glu Val Val Leu Ala Ala Leu Gly Ala Trp Tyr Ala Trp Gly Gly
        3860                3865                3870

Ala Leu Asp Trp Lys Gly Val Phe Pro Asp Gly Ala Arg Arg Val Ala
        3875                3880                3885

Leu Pro Met Tyr Pro Trp Gln Arg Glu Arg His Trp Met Asp Leu Thr
3890                3895                3900

Pro Arg Ser Ala Ala Pro Ala Gly Ile Ala Gly Arg Trp Pro Leu Ala
3905                3910                3915                3920

Gly Val Gly Leu Cys Met Pro Gly Ala Val Leu His His Val Leu Ser
        3925                3930                3935

Ile Gly Pro Arg His Gln Pro Phe Leu Gly Asp His Leu Val Phe Gly
        3940                3945                3950

Lys Val Val Pro Gly Ala Phe His Val Ala Val Ile Leu Ser Ile
        3955                3960                3965

Ala Ala Glu Arg Trp Pro Glu Arg Ala Ile Glu Leu Thr Gly Val Glu
        3970                3975                3980

Phe Leu Lys Ala Ile Ala Met Glu Pro Asp Gln Glu Val Glu Leu His
3985                3990                3995                4000

Ala Val Leu Thr Pro Glu Ala Ala Gly Asp Gly Tyr Leu Phe Glu Leu
        4005                4010                4015

Ala Thr Leu Ala Ala Pro Glu Thr Glu Arg Arg Trp Thr Thr His Ala
        4020                4025                4030

Arg Gly Arg Val Gln Pro Thr Asp Gly Ala Pro Gly Ala Leu Pro Arg
```

-continued

```
            4035                4040                4045
Leu Glu Val Leu Glu Asp Arg Ala Ile Gln Pro Leu Asp Phe Ala Gly
    4050                4055                4060
Phe Leu Asp Arg Leu Ser Ala Val Arg Ile Gly Trp Gly Pro Leu Trp
4065                4070                4075                4080
Arg Trp Leu Gln Asp Gly Arg Val Gly Asp Glu Ala Ser Leu Ala Thr
        4085                4090                4095
Leu Val Pro Thr Tyr Pro Asn Ala His Asp Val Ala Pro Leu His Pro
    4100                4105                4110
Ile Leu Leu Asp Asn Gly Phe Ala Val Ser Leu Leu Ser Thr Arg Ser
        4115                4120                4125
Glu Pro Glu Asp Asp Gly Thr Pro Pro Leu Pro Phe Ala Val Glu Arg
    4130                4135                4140
Val Arg Trp Trp Arg Ala Pro Val Gly Arg Val Arg Cys Gly Gly Val
4145                4150                4155                4160
Pro Arg Ser Gln Ala Phe Gly Val Ser Ser Phe Val Leu Val Asp Glu
        4165                4170                4175
Thr Gly Glu Val Val Ala Glu Val Glu Gly Phe Val Cys Arg Arg Ala
    4180                4185                4190
Pro Arg Glu Val Phe Leu Arg Gln Glu Ser Gly Ala Ser Thr Ala Ala
    4195                4200                4205
Leu Tyr Arg Leu Asp Trp Pro Glu Ala Pro Leu Pro Asp Ala Pro Ala
    4210                4215                4220
Glu Arg Ile Glu Glu Ser Trp Val Val Ala Ala Pro Gly Ser Glu
4225                4230                4235                4240
Met Ala Ala Ala Leu Ala Thr Arg Leu Asn Arg Cys Val Leu Ala Glu
        4245                4250                4255
Pro Lys Gly Leu Glu Ala Ala Leu Ala Gly Val Ser Pro Ala Gly Val
    4260                4265                4270
Ile Cys Leu Trp Glu Ala Gly Ala His Glu Glu Ala Pro Ala Ala Ala
        4275                4280                4285
Gln Arg Val Ala Thr Glu Gly Leu Ser Val Val Gln Ala Leu Arg Asp
    4290                4295                4300
Arg Ala Val Arg Leu Trp Trp Val Thr Met Gly Ala Val Ala Val Glu
4305                4310                4315                4320
Ala Gly Glu Arg Val Gln Val Ala Thr Ala Pro Val Trp Gly Leu Gly
        4325                4330                4335
Arg Thr Val Met Gln Glu Arg Pro Glu Leu Ser Cys Thr Leu Val Asp
        4340                4345                4350
Leu Glu Pro Glu Ala Asp Ala Ala Arg Ser Ala Asp Val Leu Leu Arg
    4355                4360                4365
Glu Leu Gly Arg Ala Asp Asp Glu Thr Gln Val Ala Phe Arg Ser Gly
    4370                4375                4380
Lys Arg Arg Val Ala Arg Leu Val Lys Ala Thr Thr Pro Glu Gly Leu
4385                4390                4395                4400
Leu Val Pro Asp Ala Glu Ser Tyr Arg Leu Glu Ala Gly Gln Lys Gly
            4405                4410                4415
Thr Leu Asp Gln Leu Arg Leu Ala Pro Ala Gln Arg Arg Ala Pro Gly
        4420                4425                4430
Pro Gly Glu Val Glu Ile Lys Val Thr Ala Ser Gly Leu Asn Phe Arg
        4435                4440                4445
Thr Val Leu Ala Val Leu Gly Met Tyr Pro Gly Asp Ala Gly Pro Met
    4450                4455                4460
```

-continued

```
Gly Gly Asp Cys Ala Gly Val Ala Thr Ala Val Gly Gln Gly Val Arg
4465                4470                4475                4480

His Val Ala Val Gly Asp Ala Val Met Thr Leu Gly Thr Leu His Arg
            4485                4490                4495

Phe Val Thr Val Asp Ala Arg Leu Val Val Arg Gln Pro Ala Gly Leu
        4500                4505                4510

Thr Pro Ala Gln Ala Ala Thr Val Pro Val Ala Phe Leu Thr Ala Trp
    4515                4520                4525

Leu Ala Leu His Asp Leu Gly Asn Leu Arg Arg Gly Glu Arg Val Leu
    4530                4535                4540

Ile His Ala Ala Ala Gly Gly Val Gly Met Ala Ala Val Gln Ile Ala
4545                4550                4555                4560

Arg Trp Ile Gly Ala Glu Val Phe Ala Thr Ala Ser Pro Ser Lys Trp
            4565                4570                4575

Ala Ala Val Gln Ala Met Gly Val Pro Arg Thr His Ile Ala Ser Ser
        4580                4585                4590

Arg Thr Leu Glu Phe Ala Glu Thr Phe Arg Gln Val Thr Gly Gly Arg
    4595                4600                4605

Gly Val Asp Val Val Leu Asn Ala Leu Ala Gly Glu Phe Val Asp Ala
    4610                4615                4620

Ser Leu Ser Leu Leu Ser Thr Gly Gly Arg Phe Leu Glu Met Gly Lys
4625                4630                4635                4640

Thr Asp Ile Arg Asp Arg Ala Ala Val Ala Ala Ala His Pro Gly Val
            4645                4650                4655

Arg Tyr Arg Val Phe Asp Ile Leu Glu Leu Ala Pro Asp Arg Thr Arg
        4660                4665                4670

Glu Ile Leu Glu Arg Val Val Glu Gly Phe Ala Ala Gly His Leu Arg
    4675                4680                4685

Ala Leu Pro Val His Ala Phe Ala Ile Thr Lys Ala Glu Ala Ala Phe
    4690                4695                4700

Arg Phe Met Ala Gln Ala Arg His Gln Gly Lys Val Val Leu Leu Pro
4705                4710                4715                4720

Ala Pro Ser Ala Ala Pro Leu Ala Pro Thr Gly Thr Val Leu Leu Thr
            4725                4730                4735

Gly Gly Leu Gly Ala Leu Gly Leu His Val Ala Arg Trp Leu Ala Gln
        4740                4745                4750

Gln Gly Val Pro His Met Val Leu Thr Gly Arg Arg Gly Leu Asp Thr
    4755                4760                4765

Pro Gly Ala Ala Lys Ala Val Ala Glu Ile Glu Ala Leu Gly Ala Arg
    4770                4775                4780

Val Thr Ile Ala Ala Ser Asp Val Ala Asp Arg Asn Ala Leu Glu Ala
4785                4790                4795                4800

Val Leu Gln Ala Ile Pro Ala Glu Trp Pro Leu Gln Gly Val Ile His
            4805                4810                4815

Ala Ala Gly Ala Leu Asp Asp Gly Val Leu Asp Glu Gln Thr Thr Asp
        4820                4825                4830

Arg Phe Ser Arg Val Leu Ala Pro Lys Val Thr Gly Ala Trp Asn Leu
    4835                4840                4845

His Glu Leu Thr Ala Gly Asn Asp Leu Ala Phe Phe Val Leu Phe Ser
    4850                4855                4860

Ser Met Ser Gly Leu Leu Gly Ser Ala Gly Gln Ser Asn Tyr Ala Ala
4865                4870                4875                4880
```

```
Ala Asn Thr Phe Leu Asp Ala Leu Ala Ala His Arg Arg Ala Glu Gly
            4885                4890                4895

Leu Ala Ala Gln Ser Leu Ala Trp Gly Pro Trp Ser Asp Gly Gly Met
        4900                4905                4910

Ala Ala Gly Leu Ser Ala Ala Leu Gln Ala Arg Leu Ala Arg His Gly
        4915                4920                4925

Met Gly Ala Leu Ser Pro Ala Gln Gly Thr Ala Leu Leu Gly Gln Ala
        4930                4935                4940

Leu Ala Arg Pro Glu Thr Gln Leu Gly Ala Met Ser Leu Asp Val Arg
4945                4950                4955                4960

Ala Ala Ser Gln Ala Ser Gly Ala Ala Val Pro Pro Val Trp Arg Ala
            4965                4970                4975

Leu Val Arg Ala Glu Ala Arg His Thr Ala Ala Gly Ala Gln Gly Ala
            4980                4985                4990

Leu Ala Ala Arg Leu Gly Ala Leu Pro Glu Ala Arg Arg Ala Asp Glu
            4995                5000                5005

Val Arg Lys Val Val Gln Ala Glu Ile Ala Arg Val Leu Ser Trp Ser
        5010                5015                5020

Ala Ala Ser Ala Val Pro Val Asp Arg Pro Leu Ser Asp Leu Gly Leu
5025                5030                5035                5040

Asp Ser Leu Thr Ala Val Glu Leu Arg Asn Val Leu Gly Gln Arg Val
            5045                5050                5055

Gly Ala Thr Leu Pro Ala Thr Leu Ala Phe Asp His Pro Thr Val Asp
            5060                5065                5070

Ala Leu Thr Arg Trp Leu Leu Asp Lys Val Leu Ala Val Ala Glu Pro
        5075                5080                5085

Ser Val Ser Ser Ala Lys Ser Ser Pro Gln Val Ala Leu Asp Glu Pro
        5090                5095                5100

Ile Ala Ile Ile Gly Ile Gly Cys Arg Phe Pro Gly Gly Val Ala Asp
5105                5110                5115                5120

Pro Glu Ser Phe Trp Arg Leu Leu Glu Glu Gly Ser Asp Ala Val Val
            5125                5130                5135

Glu Val Pro His Glu Arg Trp Asp Ile Asp Ala Phe Tyr Asp Pro Asp
            5140                5145                5150

Pro Asp Val Arg Gly Lys Met Thr Thr Arg Phe Gly Gly Phe Leu Ser
            5155                5160                5165

Asp Ile Asp Arg Phe Asp Pro Ala Phe Phe Gly Ile Ser Pro Arg Glu
        5170                5175                5180

Ala Thr Thr Met Asp Pro Gln Gln Arg Leu Leu Leu Glu Thr Ser Trp
5185                5190                5195                5200

Glu Ala Phe Glu Arg Ala Gly Ile Leu Pro Glu Arg Leu Met Gly Ser
            5205                5210                5215

Asp Thr Gly Val Phe Val Gly Leu Phe Tyr Gln Glu Tyr Ala Ala Leu
            5220                5225                5230

Ala Gly Gly Ile Glu Ala Phe Asp Gly Tyr Leu Gly Thr Gly Thr Thr
        5235                5240                5245

Ala Ser Val Ala Ser Gly Arg Ile Ser Tyr Val Leu Gly Leu Lys Gly
        5250                5255                5260

Pro Ser Leu Thr Val Asp Thr Ala Cys Ser Ser Ser Leu Val Ala Val
5265                5270                5275                5280

His Leu Ala Cys Gln Ala Leu Arg Arg Gly Glu Cys Ser Val Ala Leu
            5285                5290                5295

Ala Gly Gly Val Ala Leu Met Leu Thr Pro Ala Thr Phe Val Glu Phe
```

-continued

```
              5300                5305                5310
Ser Arg Leu Arg Gly Leu Ala Pro Asp Gly Arg Cys Lys Ser Phe Ser
            5315                5320                5325
Ala Ala Ala Asp Gly Val Gly Trp Ser Glu Gly Cys Ala Met Leu Leu
            5330                5335                5340
Leu Lys Pro Leu Arg Asp Ala Gln Arg Asp Gly Asp Pro Ile Leu Ala
5345                5350                5355                5360
Val Ile Arg Gly Thr Ala Val Asn Gln Asp Gly Arg Ser Asn Gly Leu
            5365                5370                5375
Thr Ala Pro Asn Gly Ser Ser Gln Gln Glu Val Ile Arg Arg Ala Leu
            5380                5385                5390
Glu Gln Ala Gly Leu Ala Pro Ala Asp Val Ser Tyr Val Glu Cys His
            5395                5400                5405
Gly Thr Gly Thr Thr Leu Gly Asp Pro Ile Glu Val Gln Ala Leu Gly
            5410                5415                5420
Ala Val Leu Ala Gln Gly Arg Pro Ser Asp Arg Pro Leu Val Ile Gly
5425                5430                5435                5440
Ser Val Lys Ser Asn Ile Gly His Thr Gln Ala Ala Gly Val Ala
            5445                5450                5455
Gly Val Ile Lys Val Ala Leu Ala Leu Glu Arg Gly Leu Ile Pro Arg
            5460                5465                5470
Ser Leu His Phe Asp Ala Pro Asn Pro His Ile Pro Trp Ser Glu Leu
            5475                5480                5485
Ala Val Gln Val Ala Ala Lys Pro Val Glu Trp Thr Arg Asn Gly Val
            5490                5495                5500
Pro Arg Arg Ala Gly Val Ser Ser Phe Gly Val Ser Gly Thr Asn Ala
5505                5510                5515                5520
His Val Val Leu Glu Glu Ala Pro Ala Ala Phe Ala Pro Ala Ala
            5525                5530                5535
Ala Arg Ser Ala Glu Leu Phe Val Leu Ser Ala Lys Ser Ala Ala Ala
            5540                5545                5550
Leu Asp Ala Gln Ala Ala Arg Leu Ser Ala His Val Val Ala His Pro
            5555                5560                5565
Glu Leu Gly Leu Gly Asp Leu Ala Phe Ser Leu Ala Thr Thr Arg Ser
            5570                5575                5580
Pro Met Thr Tyr Arg Leu Ala Val Ala Ala Thr Ser Arg Glu Ala Leu
5585                5590                5595                5600
Ser Ala Ala Leu Asp Thr Ala Ala Gln Gly Gln Ala Pro Pro Ala Ala
            5605                5610                5615
Ala Arg Gly His Ala Ser Thr Gly Ser Ala Pro Lys Val Val Phe Val
            5620                5625                5630
Phe Pro Gly Gln Gly Ser Gln Trp Leu Gly Met Gly Gln Lys Leu Leu
            5635                5640                5645
Ser Glu Glu Pro Val Phe Arg Asp Ala Leu Ser Ala Cys Asp Arg Ala
            5650                5655                5660
Ile Gln Ala Glu Ala Gly Trp Ser Leu Leu Ala Glu Leu Ala Ala Asp
5665                5670                5675                5680
Glu Thr Thr Ser Gln Leu Gly Arg Ile Asp Val Val Gln Pro Ala Leu
            5685                5690                5695
Phe Ala Ile Glu Val Ala Leu Ser Ala Leu Trp Arg Ser Trp Gly Val
            5700                5705                5710
Glu Pro Asp Ala Val Val Gly His Ser Met Gly Glu Val Ala Ala Ala
            5715                5720                5725
```

-continued

His Val Ala Gly Ala Leu Ser Leu Glu Asp Ala Val Ala Ile Ile Cys
    5730                5735                5740

Arg Arg Ser Leu Leu Leu Arg Arg Ile Ser Gly Gln Gly Glu Met Ala
5745                5750                5755                5760

Val Val Glu Leu Ser Leu Ala Glu Ala Glu Ala Ala Leu Leu Gly Tyr
        5765                5770                5775

Glu Asp Arg Leu Ser Val Ala Val Ser Asn Ser Pro Arg Ser Thr Val
            5780                5785                5790

Leu Ala Gly Glu Pro Ala Ala Leu Ala Glu Val Leu Ala Ile Leu Ala
            5795                5800                5805

Ala Lys Gly Val Phe Cys Arg Arg Val Lys Val Asp Val Ala Ser His
    5810                5815                5820

Ser Pro Gln Ile Asp Pro Leu Arg Asp Glu Leu Leu Ala Ala Leu Gly
5825                5830                5835                5840

Glu Leu Glu Pro Arg Gln Ala Thr Val Ser Met Arg Ser Thr Val Thr
            5845                5850                5855

Ser Thr Ile Met Ala Gly Pro Glu Leu Val Ala Ser Tyr Trp Ala Asp
            5860                5865                5870

Asn Val Arg Gln Pro Val Arg Phe Ala Glu Ala Val Gln Ser Leu Met
        5875                5880                5885

Glu Asp Gly His Gly Leu Phe Val Glu Met Ser Pro His Pro Ile Leu
        5890                5895                5900

Thr Thr Ser Val Glu Glu Ile Arg Arg Ala Thr Lys Arg Glu Gly Val
5905                5910                5915                5920

Ala Val Gly Ser Leu Arg Arg Gly Gln Asp Glu Arg Leu Ser Met Leu
            5925                5930                5935

Glu Ala Leu Gly Ala Leu Trp Val His Gly Gln Ala Val Gly Trp Glu
            5940                5945                5950

Arg Leu Phe Ser Ala Gly Gly Ala Gly Leu Arg Arg Val Pro Leu Pro
        5955                5960                5965

Thr Tyr Pro Trp Gln Arg Glu Arg Tyr Trp Val Asp Ala Pro Thr Gly
        5970                5975                5980

Gly Ala Ala Gly Gly Ser Arg Phe Ala His Ala Gly Ser His Pro Leu
5985                5990                5995                6000

Leu Gly Glu Met Gln Thr Leu Ser Thr Gln Arg Ser Thr Arg Val Trp
                6005                6010                6015

Glu Thr Thr Leu Asp Leu Lys Arg Leu Pro Trp Leu Gly Asp His Arg
            6020                6025                6030

Val Gln Gly Ala Val Val Phe Pro Gly Ala Ala Tyr Leu Glu Met Ala
        6035                6040                6045

Leu Ser Ser Gly Ala Glu Ala Leu Gly Asp Gly Pro Leu Gln Val Ser
    6050                6055                6060

Asp Val Val Leu Ala Glu Ala Leu Ala Phe Ala Asp Asp Thr Pro Ala
6065                6070                6075                6080

Ala Val Gln Val Met Ala Thr Glu Glu Arg Pro Gly Arg Leu Gln Phe
            6085                6090                6095

His Val Ala Ser Arg Val Pro Gly His Gly Gly Ala Ala Phe Arg Ser
        6100                6105                6110

His Ala Arg Gly Val Leu Arg Gln Ile Glu Arg Ala Glu Val Pro Ala
        6115                6120                6125

Arg Leu Asp Leu Ala Ala Leu Arg Ala Arg Leu Gln Ala Ser Ala Pro
    6130                6135                6140

```
Ala Ala Ala Thr Tyr Ala Ala Leu Ala Glu Met Gly Leu Glu Tyr Gly
6145                6150                6155                6160

Pro Ala Phe Gln Gly Leu Val Glu Leu Trp Arg Gly Glu Gly Glu Ala
            6165                6170                6175

Leu Gly Arg Val Arg Leu Pro Glu Ala Ala Gly Ser Pro Ala Ala Cys
        6180                6185                6190

Arg Leu His Pro Ala Leu Leu Asp Ala Cys Phe His Val Ser Ser Ala
        6195                6200                6205

Phe Ala Asp Arg Gly Glu Ala Thr Pro Trp Val Pro Val Glu Ile Gly
        6210                6215                6220

Ser Leu Arg Trp Phe Gln Arg Pro Ser Gly Glu Leu Trp Cys His Ala
6225                6230                6235                6240

Arg Ser Val Ser His Gly Lys Pro Thr Pro Asp Arg Arg Ser Thr Asp
        6245                6250                6255

Phe Trp Val Val Asp Ser Thr Gly Ala Ile Val Ala Glu Ile Ser Gly
        6260                6265                6270

Leu Val Ala Gln Arg Leu Ala Gly Gly Val Arg Arg Glu Glu Asp
        6275                6280                6285

Asp Trp Phe Met Glu Pro Ala Trp Glu Pro Thr Ala Val Pro Gly Ser
6290                6295                6300

Glu Val Met Ala Gly Arg Trp Leu Leu Ile Gly Ser Gly Gly Gly Leu
6305                6310                6315                6320

Gly Ala Ala Leu His Ser Ala Leu Thr Glu Ala Gly His Ser Val Val
        6325                6330                6335

His Ala Thr Gly Arg Gly Thr Ser Ala Ala Gly Leu Gln Ala Leu Leu
        6340                6345                6350

Thr Ala Ser Phe Asp Gly Gln Ala Pro Thr Ser Val Val His Leu Gly
        6355                6360                6365

Ser Leu Asp Glu Arg Gly Val Leu Asp Ala Asp Ala Pro Phe Asp Ala
        6370                6375                6380

Asp Ala Leu Glu Glu Ser Leu Val Arg Gly Cys Asp Ser Val Leu Trp
6385                6390                6395                6400

Thr Val Gln Ala Val Ala Gly Ala Gly Phe Arg Asp Pro Pro Arg Leu
        6405                6410                6415

Trp Leu Val Thr Arg Gly Ala Gln Ala Ile Gly Ala Gly Asp Val Ser
        6420                6425                6430

Val Ala Gln Ala Pro Leu Leu Gly Leu Gly Arg Val Ile Ala Leu Glu
        6435                6440                6445

His Ala Glu Leu Arg Cys Ala Arg Ile Asp Leu Asp Pro Ala Arg Arg
        6450                6455                6460

Asp Gly Glu Val Asp Glu Leu Leu Ala Glu Leu Leu Ala Asp Asp Ala
6465                6470                6475                6480

Glu Glu Glu Val Ala Phe Arg Gly Gly Glu Arg Arg Val Ala Arg Leu
        6485                6490                6495

Val Arg Arg Leu Pro Glu Thr Asp Cys Arg Glu Lys Ile Glu Pro Ala
        6500                6505                6510

Glu Gly Arg Pro Phe Arg Leu Glu Ile Asp Gly Ser Gly Val Leu Asp
        6515                6520                6525

Asp Leu Val Leu Arg Ala Thr Gly Arg Arg Pro Pro Gly Pro Gly Glu
        6530                6535                6540

Val Glu Ile Ala Val Glu Ala Ala Gly Leu Asn Phe Leu Asp Val Met
6545                6550                6555                6560

Arg Ala Met Gly Ile Tyr Pro Gly Pro Gly Asp Gly Pro Val Ala Leu
```

-continued

```
                6565                6570                6575
Gly Ala Glu Cys Ser Gly Arg Ile Val Ala Met Gly Glu Gly Val Glu
                6580                6585            6590
Ser Leu Arg Ile Gly Gln Asp Val Val Ala Val Ala Pro Phe Ser Phe
        6595                6600                6605
Gly Thr His Val Thr Ile Asp Ala Arg Met Leu Ala Pro Arg Pro Ala
    6610                6615                6620
Ala Leu Thr Ala Ala Gln Ala Ala Ala Leu Pro Val Ala Phe Met Thr
6625                6630                6635                6640
Ala Trp Tyr Gly Leu Val His Leu Gly Arg Leu Arg Ala Gly Glu Arg
            6645                6650                6655
Val Leu Ile His Ser Ala Thr Gly Gly Thr Gly Leu Ala Ala Val Gln
        6660                6665                6670
Ile Ala Arg His Leu Gly Ala Glu Ile Phe Ala Thr Ala Gly Thr Pro
        6675                6680                6685
Glu Lys Arg Ala Trp Leu Arg Glu Gln Gly Ile Ala His Val Met Asp
        6690                6695            6700
Ser Arg Ser Leu Asp Phe Ala Glu Gln Val Leu Ala Ala Thr Lys Gly
6705                6710                6715                6720
Glu Gly Val Asp Val Val Leu Asn Ser Leu Ser Gly Ala Ala Ile Asp
            6725                6730                6735
Ala Ser Leu Ser Thr Leu Val Pro Asp Gly Arg Phe Ile Glu Leu Gly
        6740                6745                6750
Lys Thr Asp Ile Tyr Ala Asp Arg Ser Leu Gly Leu Ala His Phe Arg
        6755                6760                6765
Lys Ser Leu Ser Tyr Ser Ala Val Asp Leu Ala Gly Leu Ala Val Arg
        6770                6775            6780
Arg Pro Glu Arg Val Ala Ala Leu Leu Ala Glu Val Val Asp Leu Leu
6785                6790                6795                6800
Ala Arg Gly Ala Leu Gln Pro Leu Pro Val Glu Ile Phe Pro Leu Ser
            6805                6810                6815
Arg Ala Ala Asp Ala Phe Arg Lys Met Ala Gln Ala Gln His Leu Gly
        6820                6825                6830
Lys Leu Val Leu Ala Leu Glu Asp Pro Asp Val Arg Ile Arg Val Pro
    6835                6840                6845
Gly Glu Ser Gly Val Ala Ile Arg Ala Asp Gly Ala Tyr Leu Val Thr
    6850                6855            6860
Gly Gly Leu Gly Gly Leu Gly Leu Ser Val Ala Gly Trp Leu Ala Glu
6865                6870                6875                6880
Gln Gly Ala Gly His Leu Val Leu Val Gly Arg Ser Gly Ala Val Ser
            6885                6890                6895
Ala Glu Gln Gln Thr Ala Val Ala Ala Leu Glu Ala His Gly Ala Arg
        6900                6905            6910
Val Thr Val Ala Arg Ala Asp Val Ala Asp Arg Ala Gln Met Glu Arg
        6915                6920                6925
Ile Leu Arg Glu Val Thr Ala Ser Gly Met Pro Leu Arg Gly Val Val
    6930                6935            6940
His Ala Ala Gly Ile Leu Asp Asp Gly Leu Leu Met Gln Gln Thr Pro
6945                6950                6955                6960
Ala Arg Phe Arg Ala Val Met Ala Pro Lys Val Arg Gly Ala Leu His
            6965                6970                6975
Leu His Ala Leu Thr Arg Glu Ala Pro Leu Ser Phe Phe Val Leu Tyr
    6980                6985                6990
```

-continued

```
Ala Ser Gly Ala Gly Leu Leu Gly Ser Pro Gln Gly Asn Tyr Ala
        6995                7000                7005
Ala Ala Asn Thr Phe Leu Asp Ala Leu Ala His His Arg Arg Ala Gln
    7010                7015                7020
Gly Leu Pro Ala Leu Ser Ile Asp Trp Gly Leu Phe Ala Asp Val Gly
7025                7030                7035                7040
Leu Ala Ala Gly Gln Gln Asn Arg Gly Ala Arg Leu Val Thr Arg Gly
            7045                7050                7055
Thr Arg Ser Leu Thr Pro Asp Glu Gly Leu Trp Ala Leu Glu Arg Leu
        7060                7065                7070
Leu Asp Gly Asp Arg Thr Gln Ala Gly Val Met Pro Phe Asp Val Arg
    7075                7080                7085
Gln Trp Val Glu Phe Tyr Pro Ala Ala Ser Ser Arg Arg Leu Ser
        7090                7095                7100
Arg Leu Met Thr Ala Arg Arg Val Ala Ser Gly Arg Leu Ala Gly Asp
7105                7110                7115                7120
Arg Asp Leu Leu Glu Arg Leu Ala Thr Ala Glu Ala Gly Ala Arg Ala
            7125                7130                7135
Gly Met Leu Gln Glu Val Val Arg Ala Gln Val Ser Gln Val Leu Arg
        7140                7145                7150
Leu Ser Glu Gly Lys Leu Asp Val Asp Ala Pro Leu Thr Ser Leu Gly
    7155                7160                7165
Met Asp Ser Leu Met Gly Leu Glu Leu Arg Asn Arg Ile Glu Ala Val
    7170                7175                7180
Leu Gly Ile Thr Met Pro Ala Thr Leu Leu Trp Thr Tyr Pro Thr Val
7185                7190                7195                7200
Ala Ala Leu Ser Ala His Leu Ala Ser His Val Val Ser Thr Gly Asp
            7205                7210                7215
Gly Glu Ser Ala Arg Pro Pro Asp Thr Gly Ser Val Ala Pro Thr Thr
        7220                7225                7230
His Glu Val Ala Ser Leu Asp Glu Asp Gly Leu Phe Ala Leu Ile Asp
    7235                7240                7245
Glu Ser Leu Ala Arg Ala Gly Lys Arg
    7250                7255
```

<210> SEQ ID NO 6
<211> LENGTH: 3798
<212> TYPE: PRT
<213> ORGANISM: Sorangium cellulosum

<400> SEQUENCE: 6

```
Val Thr Asp Arg Glu Gly Gln Leu Leu Glu Arg Leu Arg Glu Val Thr
  1               5                  10                  15
Leu Ala Leu Arg Lys Thr Leu Asn Glu Arg Asp Thr Leu Glu Leu Glu
            20                  25                  30
Lys Thr Glu Pro Ile Ala Ile Val Gly Ile Gly Cys Arg Phe Pro Gly
        35                  40                  45
Gly Ala Gly Thr Pro Glu Ala Phe Trp Glu Leu Leu Asp Asp Gly Arg
    50                  55                  60
Asp Ala Ile Arg Pro Leu Glu Glu Arg Trp Ala Leu Val Gly Val Asp
65                  70                  75                  80
Pro Gly Asp Asp Val Pro Arg Trp Ala Gly Leu Leu Thr Glu Ala Ile
                85                  90                  95
Asp Gly Phe Asp Ala Ala Phe Phe Gly Ile Ala Pro Arg Glu Ala Arg
```

```
                100                 105                 110
Ser Leu Asp Pro Gln His Arg Leu Leu Glu Val Ala Trp Glu Gly
            115                 120                 125

Phe Glu Asp Ala Gly Ile Pro Pro Arg Ser Leu Val Gly Ser Arg Thr
130                 135                 140

Gly Val Phe Val Gly Val Cys Ala Thr Glu Tyr Leu His Ala Ala Val
145                 150                 155                 160

Ala His Gln Pro Arg Glu Arg Asp Ala Tyr Ser Thr Thr Gly Asn
                165                 170                 175

Met Leu Ser Ile Ala Ala Gly Arg Leu Ser Tyr Thr Leu Gly Leu Gln
            180                 185                 190

Gly Pro Cys Leu Thr Val Asp Thr Ala Cys Ser Ser Leu Val Ala
                195                 200                 205

Ile His Leu Ala Cys Arg Ser Leu Arg Ala Arg Glu Ser Asp Leu Ala
        210                 215                 220

Leu Ala Gly Gly Val Asn Met Leu Leu Ser Pro Asp Thr Met Arg Ala
225                 230                 235                 240

Leu Ala Arg Thr Gln Ala Leu Ser Pro Asn Gly Arg Cys Gln Thr Phe
                245                 250                 255

Asp Ala Ser Ala Asn Gly Phe Val Arg Gly Glu Gly Cys Gly Leu Ile
            260                 265                 270

Val Leu Lys Arg Leu Ser Asp Ala Arg Arg Asp Gly Asp Arg Ile Trp
        275                 280                 285

Ala Leu Ile Arg Gly Ser Ala Ile Asn Gln Asp Gly Arg Ser Thr Gly
        290                 295                 300

Leu Thr Ala Pro Asn Val Leu Ala Gln Gly Ala Leu Leu Arg Glu Ala
305                 310                 315                 320

Leu Arg Asn Ala Gly Val Glu Ala Glu Ala Ile Gly Tyr Ile Glu Thr
                325                 330                 335

His Gly Ala Ala Thr Ser Leu Gly Asp Pro Ile Glu Ile Glu Ala Leu
                340                 345                 350

Arg Ala Val Val Gly Pro Ala Arg Ala Asp Gly Ala Arg Cys Val Leu
            355                 360                 365

Gly Ala Val Lys Thr Asn Leu Gly His Leu Glu Gly Ala Ala Gly Val
        370                 375                 380

Ala Gly Leu Ile Lys Ala Thr Leu Ser Leu His His Glu Arg Ile Pro
385                 390                 395                 400

Arg Asn Leu Asn Phe Arg Thr Leu Asn Pro Arg Ile Arg Ile Glu Gly
                405                 410                 415

Thr Ala Leu Ala Leu Ala Thr Glu Pro Val Pro Trp Pro Arg Thr Gly
            420                 425                 430

Arg Thr Arg Phe Ala Gly Val Ser Ser Phe Gly Met Ser Gly Thr Asn
        435                 440                 445

Ala His Val Val Leu Glu Glu Ala Pro Ala Val Glu Pro Glu Ala Ala
    450                 455                 460

Ala Pro Glu Arg Ala Ala Glu Leu Phe Val Leu Ser Ala Lys Ser Ala
465                 470                 475                 480

Ala Ala Leu Asp Ala Gln Ala Ala Arg Leu Arg Asp His Leu Glu Lys
                485                 490                 495

His Val Glu Leu Gly Leu Gly Asp Val Ala Phe Ser Leu Ala Thr Thr
            500                 505                 510

Arg Ser Ala Met Glu His Arg Leu Ala Val Ala Ala Ser Ser Arg Glu
        515                 520                 525
```

-continued

```
Ala Leu Arg Gly Ala Leu Ser Ala Ala Gln Gly His Thr Pro Pro
    530                 535                 540
Gly Ala Val Arg Gly Arg Ala Ser Gly Gly Ser Ala Pro Lys Val Val
545                 550                 555                 560
Phe Val Phe Pro Gly Gln Gly Ser Gln Trp Val Gly Met Gly Arg Lys
                565                 570                 575
Leu Met Ala Glu Glu Pro Val Phe Arg Ala Ala Leu Glu Gly Cys Asp
            580                 585                 590
Arg Ala Ile Glu Ala Glu Ala Gly Trp Ser Leu Leu Gly Glu Leu Ser
        595                 600                 605
Ala Asp Glu Ala Ala Ser Gln Leu Gly Arg Ile Asp Val Val Gln Pro
    610                 615                 620
Val Leu Phe Ala Met Glu Val Ala Leu Ser Ala Leu Trp Arg Ser Trp
625                 630                 635                 640
Gly Val Glu Pro Glu Ala Val Val Gly His Ser Met Gly Glu Val Ala
                645                 650                 655
Ala Ala His Val Ala Gly Ala Leu Ser Leu Glu Asp Ala Val Ala Ile
            660                 665                 670
Ile Cys Arg Arg Ser Arg Leu Leu Arg Arg Ile Ser Gly Gln Gly Glu
        675                 680                 685
Met Ala Leu Val Glu Leu Ser Leu Glu Glu Ala Glu Ala Ala Leu Arg
690                 695                 700
Gly His Glu Gly Arg Leu Ser Val Ala Val Ser Asn Ser Pro Arg Ser
705                 710                 715                 720
Thr Val Leu Ala Gly Glu Pro Ala Ala Leu Ser Glu Val Leu Ala Ala
                725                 730                 735
Leu Thr Ala Lys Gly Val Phe Trp Arg Gln Val Lys Val Asp Val Ala
            740                 745                 750
Ser His Ser Pro Gln Val Asp Pro Leu Arg Glu Glu Leu Ile Ala Ala
        755                 760                 765
Leu Gly Ala Ile Arg Pro Arg Ala Ala Ala Val Pro Met Arg Ser Thr
    770                 775                 780
Val Thr Gly Gly Val Ile Ala Gly Pro Glu Leu Gly Ala Ser Tyr Trp
785                 790                 795                 800
Ala Asp Asn Leu Arg Gln Pro Val Arg Phe Ala Ala Ala Gln Ala
                805                 810                 815
Leu Leu Glu Gly Gly Pro Ala Leu Phe Ile Glu Met Ser Pro His Pro
            820                 825                 830
Ile Leu Val Pro Pro Leu Asp Glu Ile Gln Thr Ala Ala Glu Gln Gly
        835                 840                 845
Gly Ala Ala Val Gly Ser Leu Arg Arg Gly Gln Asp Glu Arg Ala Thr
    850                 855                 860
Leu Leu Glu Ala Leu Gly Thr Leu Trp Ala Ser Gly Tyr Pro Val Ser
865                 870                 875                 880
Trp Ala Arg Leu Phe Pro Ala Gly Gly Arg Arg Val Pro Leu Pro Thr
                885                 890                 895
Tyr Pro Trp Gln His Glu Arg Cys Trp Ile Glu Val Glu Pro Asp Ala
            900                 905                 910
Arg Arg Leu Ala Ala Ala Asp Pro Thr Lys Asp Trp Phe Tyr Arg Thr
        915                 920                 925
Asp Trp Pro Glu Val Pro Arg Ala Ala Pro Lys Ser Glu Thr Ala His
    930                 935                 940
```

-continued

```
Gly Ser Trp Leu Leu Leu Ala Asp Arg Gly Val Gly Glu Ala Val
945                 950                 955                 960

Ala Ala Ala Leu Ser Thr Arg Gly Leu Ser Cys Thr Val Leu His Ala
            965                 970                 975

Ser Ala Asp Ala Ser Thr Val Ala Glu Gln Val Ser Glu Ala Ala Ser
        980                 985                 990

Arg Arg Asn Asp Trp Gln Gly Val Leu Tyr Leu Trp Gly Leu Asp Ala
    995                 1000                1005

Val Val Asp Ala Gly Ala Ser Ala Asp Glu Val Ser Glu Ala Thr Arg
1010                1015                1020

Arg Ala Thr Ala Pro Val Leu Gly Leu Val Arg Phe Leu Ser Ala Ala
1025                1030                1035                1040

Pro His Pro Pro Arg Phe Trp Val Val Thr Arg Gly Ala Cys Thr Val
                1045                1050                1055

Gly Gly Glu Pro Glu Ala Ser Leu Cys Gln Ala Ala Leu Trp Gly Leu
            1060                1065                1070

Ala Arg Val Ala Ala Leu Glu His Pro Ala Ala Trp Gly Gly Leu Val
        1075                1080                1085

Asp Leu Asp Pro Gln Lys Ser Pro Thr Glu Ile Glu Pro Leu Val Ala
    1090                1095                1100

Glu Leu Leu Ser Pro Asp Ala Glu Asp Gln Leu Ala Phe Arg Ser Gly
1105                1110                1115                1120

Arg Arg His Ala Ala Arg Leu Val Ala Ala Pro Pro Glu Gly Asp Val
                1125                1130                1135

Ala Pro Ile Ser Leu Ser Ala Glu Gly Ser Tyr Leu Val Thr Gly Gly
            1140                1145                1150

Leu Gly Gly Leu Gly Leu Leu Val Ala Arg Trp Leu Val Glu Arg Gly
        1155                1160                1165

Ala Arg His Leu Val Leu Thr Ser Arg His Gly Leu Pro Glu Arg Gln
    1170                1175                1180

Ala Ser Gly Gly Glu Gln Pro Pro Glu Ala Arg Ala Arg Ile Ala Ala
1185                1190                1195                1200

Val Glu Gly Leu Glu Ala Gln Gly Ala Arg Val Thr Val Ala Ala Val
                1205                1210                1215

Asp Val Ala Glu Ala Asp Pro Met Thr Ala Leu Leu Ala Ala Ile Glu
            1220                1225                1230

Pro Pro Leu Arg Gly Val Val His Ala Ala Gly Val Phe Pro Val Arg
        1235                1240                1245

His Leu Ala Glu Thr Asp Glu Ala Leu Leu Glu Ser Val Leu Arg Pro
    1250                1255                1260

Lys Val Ala Gly Ser Trp Leu Leu His Arg Leu Leu Arg Asp Arg Pro
1265                1270                1275                1280

Leu Asp Leu Phe Val Leu Phe Ser Ser Gly Ala Ala Val Trp Gly Gly
                1285                1290                1295

Lys Gly Gln Gly Ala Tyr Ala Ala Ala Asn Ala Phe Leu Asp Gly Leu
            1300                1305                1310

Ala His His Arg Arg Ala His Ser Leu Pro Ala Leu Ser Leu Ala Trp
        1315                1320                1325

Gly Leu Trp Ala Glu Gly Gly Met Val Asp Ala Lys Ala His Ala Arg
    1330                1335                1340

Leu Ser Asp Ile Gly Val Leu Pro Met Ala Thr Gly Pro Ala Leu Ser
1345                1350                1355                1360

Ala Leu Glu Arg Leu Val Asn Thr Ser Ala Val Gln Arg Ser Val Thr
```

-continued

```
                1365                1370                1375
Arg Met Asp Trp Ala Arg Phe Ala Pro Val Tyr Ala Ala Arg Gly Arg
            1380                1385                1390
Arg Asn Leu Leu Ser Ala Leu Val Ala Glu Asp Glu Arg Ala Ala Ser
        1395                1400                1405
Pro Pro Val Pro Thr Ala Asn Arg Ile Trp Arg Gly Leu Ser Val Ala
    1410                1415                1420
Glu Ser Arg Ser Ala Leu Tyr Glu Leu Val Arg Gly Ile Val Ala Arg
1425                1430                1435                1440
Val Leu Gly Phe Ser Asp Pro Gly Ala Leu Asp Val Gly Arg Gly Phe
                1445                1450                1455
Ala Glu Gln Gly Leu Asp Ser Leu Met Ala Leu Glu Ile Arg Asn Arg
            1460                1465                1470
Leu Gln Arg Glu Leu Gly Glu Arg Leu Ser Ala Thr Leu Ala Phe Asp
        1475                1480                1485
His Pro Thr Val Glu Arg Leu Val Ala His Leu Leu Thr Asp Val Leu
    1490                1495                1500
Lys Leu Glu Asp Arg Ser Asp Thr Arg His Ile Arg Ser Val Ala Ala
1505                1510                1515                1520
Asp Asp Asp Ile Ala Ile Val Gly Ala Ala Cys Arg Phe Pro Gly Gly
                1525                1530                1535
Asp Glu Gly Leu Glu Thr Tyr Trp Arg His Leu Ala Glu Gly Met Val
            1540                1545                1550
Val Ser Thr Glu Val Pro Ala Asp Arg Trp Arg Ala Ala Asp Trp Tyr
        1555                1560                1565
Asp Pro Asp Pro Glu Val Pro Gly Arg Thr Tyr Val Ala Lys Gly Ala
    1570                1575                1580
Phe Leu Arg Asp Val Arg Ser Leu Asp Ala Ala Phe Phe Ala Ile Ser
1585                1590                1595                1600
Pro Arg Glu Ala Met Ser Leu Asp Pro Gln Gln Arg Leu Leu Leu Glu
                1605                1610                1615
Val Ser Trp Glu Ala Ile Glu Arg Ala Gly Gln Asp Pro Met Ala Leu
            1620                1625                1630
Arg Glu Ser Ala Thr Gly Val Phe Val Gly Met Ile Gly Ser Glu His
        1635                1640                1645
Ala Glu Arg Val Gln Gly Leu Asp Asp Asp Ala Ala Leu Leu Tyr Gly
    1650                1655                1660
Thr Thr Gly Asn Leu Leu Ser Val Ala Ala Gly Arg Leu Ser Phe Phe
1665                1670                1675                1680
Leu Gly Leu His Gly Pro Thr Met Thr Val Asp Thr Ala Cys Ser Ser
                1685                1690                1695
Ser Leu Val Ala Leu His Leu Ala Cys Gln Ser Leu Arg Leu Gly Glu
            1700                1705                1710
Cys Asp Gln Ala Leu Ala Gly Gly Ser Ser Val Leu Leu Ser Pro Arg
        1715                1720                1725
Ser Phe Val Ala Ala Ser Arg Met Arg Leu Leu Ser Pro Asp Gly Arg
    1730                1735                1740
Cys Lys Thr Phe Ser Ala Ala Ala Asp Gly Phe Ala Arg Ala Glu Gly
1745                1750                1755                1760
Cys Ala Val Val Val Leu Lys Arg Leu Arg Asp Ala Gln Arg Asp Arg
                1765                1770                1775
Asp Pro Ile Leu Ala Val Val Arg Ser Thr Ala Ile Asn His Asp Gly
            1780                1785                1790
```

```
Pro Ser Ser Gly Leu Thr Val Pro Ser Gly Pro Ala Gln Gln Ala Leu
        1795                1800                1805
Leu Arg Gln Ala Leu Ala Gln Ala Gly Val Ala Pro Ala Glu Val Asp
    1810                1815                1820
Phe Val Glu Cys His Gly Thr Gly Thr Ala Leu Gly Asp Pro Ile Glu
1825                1830                1835                1840
Val Gln Ala Leu Gly Ala Val Tyr Gly Arg Gly Arg Pro Ala Glu Arg
                1845                1850                1855
Pro Leu Trp Leu Gly Ala Val Lys Ala Asn Leu Gly His Leu Glu Ala
            1860                1865                1870
Ala Ala Gly Leu Ala Gly Val Leu Lys Val Leu Ala Leu Glu His
        1875                1880                1885
Glu Gln Ile Pro Ala Gln Pro Glu Leu Asp Glu Leu Asn Pro His Ile
    1890                1895                1900
Pro Trp Ala Glu Leu Pro Val Ala Val Val Arg Arg Ala Val Pro Trp
1905                1910                1915                1920
Pro Arg Gly Ala Arg Pro Arg Arg Ala Gly Val Ser Ala Phe Gly Leu
                1925                1930                1935
Ser Gly Thr Asn Ala His Val Val Leu Glu Glu Ala Pro Ala Val Glu
            1940                1945                1950
Pro Val Ala Ala Ala Pro Glu Arg Ala Ala Glu Leu Phe Val Leu Ser
        1955                1960                1965
Ala Lys Ser Ala Ala Ala Leu Asp Ala Gln Ala Ala Arg Leu Arg Asp
    1970                1975                1980
His Leu Glu Lys His Val Glu Leu Gly Leu Gly Asp Val Ala Phe Ser
1985                1990                1995                2000
Leu Ala Thr Thr Arg Ser Ala Met Glu His Arg Leu Ala Val Ala Ala
                2005                2010                2015
Ser Ser Arg Glu Ala Leu Arg Gly Ala Leu Ser Ala Ala Gln Gly
            2020                2025                2030
His Thr Pro Pro Gly Ala Val Arg Gly Arg Ala Ser Gly Gly Ser Ala
        2035                2040                2045
Pro Lys Val Val Phe Val Phe Pro Gly Gln Gly Ser Gln Trp Val Gly
    2050                2055                2060
Met Gly Arg Lys Leu Met Ala Glu Glu Pro Val Phe Arg Ala Ala Leu
2065                2070                2075                2080
Glu Gly Cys Asp Arg Ala Ile Glu Ala Glu Ala Gly Trp Ser Leu Leu
                2085                2090                2095
Gly Glu Leu Ser Ala Asp Glu Ala Ala Ser Gln Leu Gly Arg Ile Asp
            2100                2105                2110
Val Val Gln Pro Val Leu Phe Ala Met Glu Val Ala Leu Ser Ala Leu
        2115                2120                2125
Trp Arg Ser Trp Gly Val Glu Pro Glu Ala Val Val Gly His Ser Met
    2130                2135                2140
Gly Glu Val Ala Ala Ala His Val Ala Gly Ala Leu Ser Leu Glu Asp
2145                2150                2155                2160
Ala Val Ala Ile Ile Cys Arg Arg Ser Arg Leu Leu Arg Arg Ile Ser
                2165                2170                2175
Gly Gln Gly Glu Met Ala Leu Val Glu Leu Ser Leu Glu Glu Ala Glu
            2180                2185                2190
Ala Ala Leu Arg Gly His Glu Gly Arg Leu Ser Val Ala Val Ser Asn
        2195                2200                2205
```

-continued

```
Ser Pro Arg Ser Thr Val Leu Ala Gly Glu Pro Ala Ala Leu Ser Glu
    2210                2215                2220

Val Leu Ala Ala Leu Thr Ala Lys Gly Val Phe Trp Arg Gln Val Lys
2225                2230                2235                2240

Val Asp Val Ala Ser His Ser Pro Gln Val Asp Pro Leu Arg Glu Glu
                2245                2250                2255

Leu Ile Ala Ala Leu Gly Ala Ile Arg Pro Arg Ala Ala Val Pro
            2260                2265                2270

Met Arg Ser Thr Val Thr Gly Gly Val Ile Ala Gly Pro Glu Leu Gly
    2275                2280                2285

Ala Ser Tyr Trp Ala Asp Asn Leu Arg Gln Pro Val Arg Phe Ala Ala
    2290                2295                2300

Ala Ala Gln Ala Leu Leu Glu Gly Gly Pro Ala Leu Phe Ile Glu Met
2305                2310                2315                2320

Ser Pro His Pro Ile Leu Val Pro Pro Leu Asp Glu Ile Gln Thr Ala
                2325                2330                2335

Ala Glu Gln Gly Gly Ala Ala Val Gly Ser Leu Arg Arg Gly Gln Asp
            2340                2345                2350

Glu Arg Ala Thr Leu Leu Glu Ala Leu Gly Thr Leu Trp Ala Ser Gly
        2355                2360                2365

Tyr Pro Val Ser Trp Ala Arg Leu Phe Pro Ala Gly Gly Arg Arg Val
    2370                2375                2380

Pro Leu Pro Thr Tyr Pro Trp Gln His Glu Arg Tyr Trp Ile Glu Asp
2385                2390                2395                2400

Ser Val His Gly Ser Lys Pro Ser Leu Arg Leu Arg Gln Leu Arg Asn
                2405                2410                2415

Gly Ala Thr Asp His Pro Leu Leu Gly Ala Pro Leu Leu Val Ser Ala
            2420                2425                2430

Arg Pro Gly Ala His Leu Trp Glu Gln Ala Leu Ser Asp Glu Arg Leu
        2435                2440                2445

Ser Tyr Leu Ser Glu His Arg Val His Gly Glu Ala Val Leu Pro Ser
    2450                2455                2460

Ala Ala Tyr Val Glu Met Ala Leu Ala Ala Gly Val Asp Leu Tyr Gly
2465                2470                2475                2480

Thr Ala Thr Leu Val Leu Glu Gln Leu Ala Leu Glu Arg Ala Leu Ala
            2485                2490                2495

Val Pro Ser Glu Gly Gly Arg Ile Val Gln Val Ala Leu Ser Glu Glu
        2500                2505                2510

Gly Pro Gly Arg Ala Ser Phe Gln Val Ser Ser Arg Glu Glu Ala Gly
    2515                2520                2525

Arg Ser Trp Val Arg His Ala Thr Gly His Val Cys Ser Gly Gln Ser
2530                2535                2540

Ser Ala Val Gly Ala Leu Lys Glu Ala Pro Trp Glu Ile Gln Arg Arg
2545                2550                2555                2560

Cys Pro Ser Val Leu Ser Ser Glu Ala Leu Tyr Pro Leu Leu Asn Glu
                2565                2570                2575

His Ala Leu Asp Tyr Gly Pro Cys Phe Gln Gly Val Glu Gln Val Trp
            2580                2585                2590

Leu Gly Thr Gly Glu Val Leu Gly Arg Val Arg Leu Pro Gly Asp Met
        2595                2600                2605

Ala Ser Ser Ser Gly Ala Tyr Arg Ile His Pro Ala Leu Leu Asp Ala
    2610                2615                2620

Cys Phe Gln Val Leu Thr Ala Leu Leu Thr Thr Pro Glu Ser Ile Glu
```

-continued

```
             2625              2630              2635              2640

Ile Arg Arg Arg Leu Thr Asp Leu His Glu Pro Asp Leu Pro Arg Ser
                     2645              2650              2655

Arg Ala Pro Val Asn Gln Ala Val Ser Asp Thr Trp Leu Trp Asp Ala
                     2660              2665              2670

Ala Leu Asp Gly Gly Arg Arg Gln Ser Ala Ser Val Pro Val Asp Leu
                     2675              2680              2685

Val Leu Gly Ser Phe His Ala Lys Trp Glu Val Met Glu Arg Leu Ala
                     2690              2695              2700

Gln Ala Tyr Ile Ile Gly Thr Leu Arg Ile Trp Asn Val Phe Cys Ala
    2705              2710              2715              2720

Ala Gly Glu Arg His Thr Ile Asp Glu Leu Leu Val Arg Leu Gln Ile
                     2725              2730              2735

Ser Val Val Tyr Arg Lys Val Ile Lys Arg Trp Met Glu His Leu Val
                     2740              2745              2750

Ala Ile Gly Ile Leu Val Gly Asp Gly Glu His Phe Val Ser Ser Gln
                     2755              2760              2765

Pro Leu Pro Glu Pro Asp Leu Ala Ala Val Leu Glu Glu Ala Gly Arg
                     2770              2775              2780

Val Phe Ala Asp Leu Pro Val Leu Phe Glu Trp Cys Lys Phe Ala Gly
    2785              2790              2795              2800

Glu Arg Leu Ala Asp Val Leu Thr Gly Lys Thr Leu Ala Leu Glu Ile
                     2805              2810              2815

Leu Phe Pro Gly Gly Ser Phe Asp Met Ala Glu Arg Ile Tyr Arg Asp
                     2820              2825              2830

Ser Pro Ile Ala Arg Tyr Ser Asn Gly Ile Val Arg Gly Val Val Glu
                     2835              2840              2845

Ser Ala Ala Arg Val Val Ala Pro Ser Gly Met Phe Ser Ile Leu Glu
                     2850              2855              2860

Ile Gly Ala Gly Thr Gly Ala Thr Thr Ala Ala Val Leu Pro Val Leu
    2865              2870              2875              2880

Leu Pro Asp Arg Thr Glu Tyr His Phe Thr Asp Val Ser Pro Leu Phe
                     2885              2890              2895

Leu Ala Arg Ala Glu Gln Arg Phe Arg Asp Tyr Pro Phe Leu Lys Tyr
                     2900              2905              2910

Gly Ile Leu Asp Val Asp Gln Glu Pro Ala Gly Gln Gly Tyr Ala His
                     2915              2920              2925

Gln Arg Phe Asp Val Ile Val Ala Ala Asn Val Ile His Ala Thr Arg
                     2930              2935              2940

Asp Ile Arg Ala Thr Ala Lys Arg Leu Leu Ser Leu Leu Ala Pro Gly
    2945              2950              2955              2960

Gly Leu Leu Val Leu Val Glu Gly Thr Gly His Pro Ile Trp Phe Asp
                     2965              2970              2975

Ile Thr Thr Gly Leu Ile Glu Gly Trp Gln Lys Tyr Glu Asp Asp Leu
                     2980              2985              2990

Arg Ile Asp His Pro Leu Leu Pro Ala Arg Thr Trp Cys Asp Val Leu
                     2995              3000              3005

Arg Arg Val Gly Phe Ala Asp Ala Val Ser Leu Pro Gly Asp Gly Ser
         3010              3015              3020

Pro Ala Gly Ile Leu Gly Gln His Val Ile Leu Ser Arg Ala Pro Gly
    3025              3030              3035              3040

Ile Ala Gly Ala Ala Cys Asp Ser Ser Gly Glu Ser Ala Thr Glu Ser
                     3045              3050              3055
```

-continued

```
Pro Ala Ala Arg Ala Val Arg Gln Glu Trp Ala Asp Gly Ser Ala Asp
        3060                3065                3070
Val Val His Arg Met Ala Leu Glu Arg Met Tyr Phe His Arg Arg Pro
        3075                3080                3085
Gly Arg Gln Val Trp Val His Gly Arg Leu Arg Thr Gly Gly Gly Ala
        3090                3095                3100
Phe Thr Lys Ala Leu Ala Gly Asp Leu Leu Leu Phe Glu Asp Thr Gly
3105                3110                3115                3120
Gln Val Val Ala Glu Val Gln Gly Leu Arg Leu Pro Gln Leu Glu Ala
                3125                3130                3135
Ser Ala Phe Ala Pro Arg Asp Pro Arg Glu Glu Trp Leu Tyr Ala Leu
        3140                3145                3150
Glu Trp Gln Arg Lys Asp Pro Ile Pro Glu Ala Pro Ala Ala Ala Ser
        3155                3160                3165
Ser Ser Ser Ala Gly Ala Trp Leu Val Leu Met Asp Gln Gly Gly Thr
        3170                3175                3180
Gly Ala Ala Leu Val Ser Leu Leu Glu Gly Arg Gly Glu Ala Cys Val
3185                3190                3195                3200
Arg Val Ile Ala Gly Thr Ala Tyr Ala Cys Leu Ala Pro Gly Leu Tyr
                3205                3210                3215
Gln Val Asp Pro Ala Gln Pro Asp Gly Phe His Thr Leu Leu Arg Asp
        3220                3225                3230
Ala Phe Gly Glu Asp Arg Ile Cys Arg Ala Val Val His Met Trp Ser
        3235                3240                3245
Leu Asp Ala Thr Ala Ala Gly Glu Arg Ala Thr Ala Glu Ser Leu Gln
        3250                3255                3260
Ala Asp Gln Leu Leu Gly Ser Leu Ser Ala Leu Ser Leu Val Gln Ala
3265                3270                3275                3280
Leu Val Arg Arg Arg Trp Arg Asn Met Pro Arg Leu Trp Leu Leu Thr
                3285                3290                3295
Arg Ala Val His Ala Val Gly Ala Glu Asp Ala Ala Ala Ser Val Ala
        3300                3305                3310
Gln Ala Pro Val Trp Gly Leu Gly Arg Thr Leu Ala Leu Glu His Pro
        3315                3320                3325
Glu Leu Arg Cys Thr Leu Val Asp Val Asn Pro Ala Pro Ser Pro Glu
        3330                3335                3340
Asp Ala Ala Ala Leu Ala Val Glu Leu Gly Ala Ser Asp Arg Glu Asp
3345                3350                3355                3360
Gln Val Ala Leu Arg Ser Asp Gly Arg Tyr Val Ala Arg Leu Val Arg
                3365                3370                3375
Ser Ser Phe Ser Gly Lys Pro Ala Thr Asp Cys Gly Ile Arg Ala Asp
        3380                3385                3390
Gly Ser Tyr Val Ile Thr Asp Gly Met Gly Arg Val Gly Leu Ser Val
        3395                3400                3405
Ala Gln Trp Met Val Met Gln Gly Ala Arg His Val Leu Val Asp
        3410                3415                3420
Arg Gly Gly Ala Ser Glu Ala Ser Arg Asp Ala Leu Arg Ser Met Ala
3425                3430                3435                3440
Glu Ala Gly Ala Glu Val Gln Ile Val Glu Ala Asp Val Ala Arg Arg
                3445                3450                3455
Asp Asp Val Ala Arg Leu Leu Ser Lys Ile Glu Pro Ser Met Pro Pro
        3460                3465                3470
```

```
Leu Arg Gly Ile Val Tyr Val Asp Gly Thr Phe Gln Gly Asp Ser Ser
            3475                3480                3485

Met Leu Glu Leu Asp Ala Arg Arg Phe Lys Glu Trp Met Tyr Pro Lys
        3490                3495                3500

Val Leu Gly Ala Trp Asn Leu His Ala Leu Thr Arg Asp Arg Ser Leu
3505                3510                3515                3520

Asp Phe Phe Val Leu Tyr Ser Ser Gly Thr Ser Leu Leu Gly Leu Pro
            3525                3530                3535

Gly Gln Gly Ser Arg Ala Ala Gly Asp Ala Phe Leu Asp Ala Ile Ala
        3540                3545                3550

His His Arg Cys Lys Val Gly Leu Thr Ala Met Ser Ile Asn Trp Gly
            3555                3560                3565

Leu Leu Ser Glu Ala Ser Ser Pro Ala Thr Pro Asn Asp Gly Gly Ala
        3570                3575                3580

Arg Leu Glu Tyr Arg Gly Met Glu Gly Leu Thr Leu Glu Gln Gly Ala
3585                3590                3595                3600

Ala Ala Leu Gly Arg Leu Leu Ala Arg Pro Arg Ala Gln Val Gly Val
            3605                3610                3615

Met Arg Leu Asn Leu Arg Gln Trp Leu Glu Phe Tyr Pro Asn Ala Ala
        3620                3625                3630

Arg Leu Ala Leu Trp Ala Glu Leu Leu Lys Glu Arg Asp Arg Ala Asp
            3635                3640                3645

Arg Gly Ala Ser Asn Ala Ser Asn Leu Arg Glu Ala Leu Gln Ser Ala
        3650                3655                3660

Arg Pro Glu Asp Arg Gln Leu Ile Leu Glu Lys His Leu Ser Glu Leu
3665                3670                3675                3680

Leu Gly Arg Gly Leu Arg Leu Pro Pro Glu Arg Ile Glu Arg His Val
            3685                3690                3695

Pro Phe Ser Asn Leu Gly Met Asp Ser Leu Ile Gly Leu Glu Leu Arg
        3700                3705                3710

Asn Arg Ile Glu Ala Ala Leu Gly Ile Thr Val Pro Ala Thr Leu Leu
            3715                3720                3725

Trp Thr Tyr Pro Asn Val Ala Ala Leu Ser Gly Ser Leu Leu Asp Ile
        3730                3735                3740

Leu Phe Pro Asn Ala Gly Ala Thr His Ala Pro Ala Thr Glu Arg Glu
3745                3750                3755                3760

Lys Ser Phe Glu Asn Asp Ala Ala Asp Leu Glu Ala Leu Arg Gly Met
            3765                3770                3775

Thr Asp Glu Gln Lys Asp Ala Leu Leu Ala Glu Lys Leu Ala Gln Leu
        3780                3785                3790

Ala Gln Ile Val Gly Glu
        3795

<210> SEQ ID NO 7
<211> LENGTH: 2439
<212> TYPE: PRT
<213> ORGANISM: Sorangium cellulosum

<400> SEQUENCE: 7

Met Ala Thr Thr Asn Ala Gly Lys Leu Glu His Ala Leu Leu Leu Met
 1               5                  10                  15

Asp Lys Leu Ala Lys Lys Asn Ala Ser Leu Glu Gln Glu Arg Thr Glu
            20                  25                  30

Pro Ile Ala Ile Val Gly Ile Gly Cys Arg Phe Pro Gly Gly Ala Asp
        35                  40                  45
```

-continued

```
Thr Pro Glu Ala Phe Trp Glu Leu Leu Asp Ser Gly Arg Asp Ala Val
 50                  55                  60

Gln Pro Leu Asp Arg Arg Trp Ala Leu Val Gly Val His Pro Ser Glu
 65                  70                  75                  80

Glu Val Pro Arg Trp Ala Gly Leu Leu Thr Glu Ala Val Asp Gly Phe
                 85                  90                  95

Asp Ala Ala Phe Phe Gly Thr Ser Pro Arg Glu Ala Arg Ser Leu Asp
                100                 105                 110

Pro Gln Gln Arg Leu Leu Leu Glu Val Thr Trp Glu Gly Leu Glu Asp
                115                 120                 125

Ala Gly Ile Ala Pro Gln Ser Leu Asp Gly Ser Arg Thr Gly Val Phe
130                 135                 140

Leu Gly Ala Cys Ser Ser Asp Tyr Ser His Thr Val Ala Gln Gln Arg
145                 150                 155                 160

Arg Glu Glu Gln Asp Ala Tyr Asp Ile Thr Gly Asn Thr Leu Ser Val
                165                 170                 175

Ala Ala Gly Arg Leu Ser Tyr Thr Leu Gly Leu Gln Gly Pro Cys Leu
                180                 185                 190

Thr Val Asp Thr Ala Cys Ser Ser Leu Val Ala Ile His Leu Ala
                195                 200                 205

Cys Arg Ser Leu Arg Ala Arg Glu Ser Asp Leu Ala Leu Ala Gly Gly
210                 215                 220

Val Asn Met Leu Leu Ser Ser Lys Thr Met Ile Met Leu Gly Arg Ile
225                 230                 235                 240

Gln Ala Leu Ser Pro Asp Gly His Cys Arg Thr Phe Asp Ala Ser Ala
                245                 250                 255

Asn Gly Phe Val Arg Gly Glu Gly Cys Gly Met Val Val Leu Lys Arg
                260                 265                 270

Leu Ser Asp Ala Gln Arg His Gly Asp Arg Ile Trp Ala Leu Ile Arg
                275                 280                 285

Gly Ser Ala Met Asn Gln Asp Gly Arg Ser Thr Gly Leu Met Ala Pro
290                 295                 300

Asn Val Leu Ala Gln Glu Ala Leu Leu Arg Glu Ala Leu Gln Ser Ala
305                 310                 315                 320

Arg Val Asp Ala Gly Ala Ile Gly Tyr Val Glu Thr His Gly Thr Gly
                325                 330                 335

Thr Ser Leu Gly Asp Pro Ile Glu Val Glu Ala Leu Arg Ala Val Leu
                340                 345                 350

Gly Pro Ala Arg Ala Asp Gly Ser Arg Cys Val Leu Gly Ala Val Lys
                355                 360                 365

Thr Asn Leu Gly His Leu Glu Gly Ala Ala Gly Val Ala Gly Leu Ile
370                 375                 380

Lys Ala Ala Leu Ala Leu His His Glu Leu Ile Pro Arg Asn Leu His
385                 390                 395                 400

Phe His Thr Leu Asn Pro Arg Ile Arg Ile Glu Gly Thr Ala Leu Ala
                405                 410                 415

Leu Ala Thr Glu Pro Val Pro Trp Pro Arg Ala Gly Arg Pro Arg Phe
                420                 425                 430

Ala Gly Val Ser Ala Phe Gly Leu Ser Gly Thr Asn Val His Val Val
                435                 440                 445

Leu Glu Glu Ala Pro Ala Thr Val Leu Ala Pro Ala Thr Pro Gly Arg
450                 455                 460
```

```
Ser Ala Glu Leu Leu Val Leu Ser Ala Lys Ser Ala Ala Leu Asp
465                 470                 475                 480

Ala Gln Ala Ala Arg Leu Ser Ala His Ile Ala Ala Tyr Pro Glu Gln
            485                 490                 495

Gly Leu Gly Asp Val Ala Phe Ser Leu Val Ser Thr Arg Ser Pro Met
                500                 505                 510

Glu His Arg Leu Ala Val Ala Ala Thr Ser Arg Glu Ala Leu Arg Ser
        515                 520                 525

Ala Leu Glu Val Ala Ala Gln Gly Gln Thr Pro Ala Gly Ala Ala Arg
    530                 535                 540

Gly Arg Ala Ala Ser Ser Pro Gly Lys Leu Ala Phe Leu Phe Ala Gly
545                 550                 555                 560

Gln Gly Ala Gln Val Pro Gly Met Gly Arg Gly Leu Trp Glu Ala Trp
                565                 570                 575

Pro Ala Phe Arg Glu Thr Phe Asp Arg Cys Val Thr Leu Phe Asp Arg
                580                 585                 590

Glu Leu His Gln Pro Leu Cys Glu Val Met Trp Ala Glu Pro Gly Ser
        595                 600                 605

Ser Arg Ser Ser Leu Leu Asp Gln Thr Ala Phe Thr Gln Pro Ala Leu
    610                 615                 620

Phe Ala Leu Glu Tyr Ala Leu Ala Ala Leu Phe Arg Ser Trp Gly Val
625                 630                 635                 640

Glu Pro Glu Leu Val Ala Gly His Ser Leu Gly Glu Leu Val Ala Ala
                645                 650                 655

Cys Val Ala Gly Val Phe Ser Leu Glu Asp Ala Val Arg Leu Val Val
                660                 665                 670

Ala Arg Gly Arg Leu Met Gln Ala Leu Pro Ala Gly Gly Ala Met Val
        675                 680                 685

Ser Ile Ala Ala Pro Glu Ala Asp Val Ala Ala Val Ala Pro His
    690                 695                 700

Ala Ala Leu Val Ser Ile Ala Ala Val Asn Gly Pro Glu Gln Val Val
705                 710                 715                 720

Ile Ala Gly Ala Glu Lys Phe Val Gln Gln Ile Ala Ala Ala Phe Ala
                725                 730                 735

Ala Arg Gly Ala Arg Thr Lys Pro Leu His Val Ser His Ala Phe His
        740                 745                 750

Ser Pro Leu Met Asp Pro Met Leu Glu Ala Phe Arg Arg Val Thr Glu
    755                 760                 765

Ser Val Thr Tyr Arg Arg Pro Ser Ile Ala Leu Val Ser Asn Leu Ser
    770                 775                 780

Gly Lys Pro Cys Thr Asp Glu Val Ser Ala Pro Gly Tyr Trp Val Arg
785                 790                 795                 800

His Ala Arg Glu Ala Val Arg Phe Ala Asp Gly Val Lys Ala Leu His
            805                 810                 815

Ala Ala Gly Ala Gly Leu Phe Val Glu Val Gly Pro Lys Pro Thr Leu
            820                 825                 830

Leu Gly Leu Val Pro Ala Cys Leu Pro Asp Ala Arg Pro Val Leu Leu
        835                 840                 845

Pro Ala Ser Arg Ala Gly Arg Asp Glu Ala Ala Ser Ala Leu Glu Ala
    850                 855                 860

Leu Gly Gly Phe Trp Val Val Gly Gly Ser Val Thr Trp Ser Gly Val
865                 870                 875                 880

Phe Pro Ser Gly Gly Arg Arg Val Pro Leu Pro Thr Tyr Pro Trp Gln
```

-continued

```
                885                 890                 895
Arg Glu Arg Tyr Trp Ile Glu Ala Pro Val Asp Arg Glu Ala Asp Gly
                900                 905                 910
Thr Gly Arg Ala Arg Ala Gly Gly His Pro Leu Leu Gly Glu Val Phe
                915                 920                 925
Ser Val Ser Thr His Ala Gly Leu Arg Leu Trp Glu Thr Thr Leu Asp
                930                 935                 940
Arg Lys Arg Leu Pro Trp Leu Gly Glu His Arg Ala Gln Gly Glu Val
945                 950                 955                 960
Val Phe Pro Gly Ala Gly Tyr Leu Glu Met Ala Leu Ser Ser Gly Ala
                965                 970                 975
Glu Ile Leu Gly Asp Gly Pro Ile Gln Val Thr Asp Val Val Leu Ile
                980                 985                 990
Glu Thr Leu Thr Phe Ala Gly Asp Thr Ala Val Pro Val Gln Val Val
                995                 1000                1005
Thr Thr Glu Glu Arg Pro Gly Arg Leu Arg Phe Gln Val Ala Ser Arg
    1010                1015                1020
Glu Pro Gly Glu Arg Arg Ala Pro Phe Arg Ile His Ala Arg Gly Val
1025                1030                1035                1040
Leu Arg Arg Ile Gly Arg Val Glu Thr Pro Ala Arg Ser Asn Leu Ala
                1045                1050                1055
Ala Leu Arg Ala Arg Leu His Ala Ala Val Pro Ala Ala Ala Ile Tyr
                1060                1065                1070
Gly Ala Leu Ala Glu Met Gly Leu Gln Tyr Gly Pro Ala Leu Arg Gly
                1075                1080                1085
Leu Ala Glu Leu Trp Arg Gly Glu Gly Glu Ala Leu Gly Arg Val Arg
                1090                1095                1100
Leu Pro Glu Ala Ala Gly Ser Ala Thr Ala Tyr Gln Leu His Pro Val
1105                1110                1115                1120
Leu Leu Asp Ala Cys Val Gln Met Ile Val Gly Ala Phe Ala Asp Arg
                1125                1130                1135
Asp Glu Ala Thr Pro Trp Ala Pro Val Glu Val Gly Ser Val Arg Leu
                1140                1145                1150
Phe Gln Arg Ser Pro Gly Glu Leu Trp Cys His Ala Arg Val Val Ser
                1155                1160                1165
Asp Gly Gln Gln Ala Ser Ser Arg Trp Ser Ala Asp Phe Glu Leu Met
    1170                1175                1180
Asp Gly Thr Gly Ala Val Val Ala Glu Ile Ser Arg Leu Val Val Glu
1185                1190                1195                1200
Arg Leu Ala Ser Gly Val Arg Arg Asp Ala Asp Asp Trp Phe Leu
                1205                1210                1215
Glu Leu Asp Trp Glu Pro Ala Ala Leu Gly Gly Pro Lys Ile Thr Ala
                1220                1225                1230
Gly Arg Trp Leu Leu Gly Glu Gly Gly Leu Gly Arg Ser Leu
                1235                1240                1245
Cys Ser Ala Leu Lys Ala Ala Gly His Val Val Val His Ala Ala Gly
    1250                1255                1260
Asp Asp Thr Ser Thr Ala Gly Met Arg Ala Leu Leu Ala Asn Ala Phe
1265                1270                1275                1280
Asp Gly Gln Ala Pro Thr Ala Val Val His Leu Ser Ser Leu Asp Gly
                1285                1290                1295
Gly Gly Gln Leu Gly Pro Gly Leu Gly Ala Gln Gly Ala Leu Asp Ala
                1300                1305                1310
```

-continued

```
Pro Arg Ser Pro Asp Val Asp Ala Asp Ala Leu Glu Ser Ala Leu Met
    1315                1320                1325
Arg Gly Cys Asp Ser Val Leu Ser Leu Val Gln Ala Leu Val Gly Met
    1330                1335                1340
Asp Leu Arg Asn Ala Pro Arg Leu Trp Leu Leu Thr Arg Gly Ala Gln
1345                1350                1355                1360
Ala Ala Ala Ala Gly Asp Val Ser Val Val Gln Ala Pro Leu Leu Gly
                1365                1370                1375
Leu Gly Arg Thr Ile Ala Leu Glu His Ala Glu Leu Arg Cys Ile Ser
            1380                1385                1390
Val Asp Leu Asp Pro Ala Glu Pro Glu Gly Glu Ala Asp Ala Leu Leu
    1395                1400                1405
Ala Glu Leu Leu Ala Asp Asp Ala Glu Glu Glu Val Ala Leu Arg Gly
    1410                1415                1420
Gly Asp Arg Leu Val Ala Arg Leu Val His Arg Leu Pro Asp Ala Gln
1425                1430                1435                1440
Arg Arg Glu Lys Val Glu Pro Ala Gly Asp Arg Pro Phe Arg Leu Glu
                1445                1450                1455
Ile Asp Glu Pro Gly Ala Leu Asp Gln Leu Val Leu Arg Ala Thr Gly
            1460                1465                1470
Arg Arg Ala Pro Gly Pro Gly Glu Val Glu Ile Ser Val Glu Ala Ala
    1475                1480                1485
Gly Leu Asp Ser Ile Asp Ile Gln Leu Ala Leu Gly Val Ala Pro Asn
    1490                1495                1500
Asp Leu Pro Gly Glu Glu Ile Glu Pro Leu Val Leu Gly Ser Glu Cys
1505                1510                1515                1520
Ala Gly Arg Ile Val Ala Val Gly Glu Gly Val Asn Gly Leu Val Val
                1525                1530                1535
Gly Gln Pro Val Ile Ala Leu Ala Ala Gly Val Phe Ala Thr His Val
            1540                1545                1550
Thr Thr Ser Ala Thr Leu Val Leu Pro Arg Pro Leu Gly Leu Ser Ala
    1555                1560                1565
Thr Glu Ala Ala Ala Met Pro Leu Ala Tyr Leu Thr Ala Trp Tyr Ala
    1570                1575                1580
Leu Asp Lys Val Ala His Leu Gln Ala Gly Glu Arg Val Leu Ile His
1585                1590                1595                1600
Ala Glu Ala Gly Gly Val Gly Leu Cys Ala Val Arg Trp Ala Gln Arg
                1605                1610                1615
Val Gly Ala Glu Val Tyr Ala Thr Ala Asp Thr Pro Glu Asn Arg Ala
            1620                1625                1630
Tyr Leu Glu Ser Leu Gly Val Arg Tyr Val Ser Asp Ser Arg Ser Gly
            1635                1640                1645
Arg Phe Val Thr Asp Val His Ala Trp Thr Asp Gly Glu Gly Val Asp
    1650                1655                1660
Val Val Leu Asp Ser Leu Ser Gly Glu Arg Ile Asp Lys Ser Leu Met
1665                1670                1675                1680
Val Leu Arg Ala Cys Gly Arg Leu Val Lys Leu Gly Arg Arg Asp Asp
                1685                1690                1695
Cys Ala Asp Thr Gln Pro Gly Leu Pro Pro Leu Leu Arg Asn Phe Ser
            1700                1705                1710
Phe Ser Gln Val Asp Leu Arg Gly Met Met Leu Asp Gln Pro Ala Arg
    1715                1720                1725
```

-continued

```
Ile Arg Ala Leu Leu Asp Glu Leu Phe Gly Leu Val Ala Ala Gly Ala
    1730                1735                1740

Ile Ser Pro Leu Gly Ser Gly Leu Arg Val Gly Gly Ser Leu Thr Pro
1745                1750                1755                1760

Pro Pro Val Glu Thr Phe Pro Ile Ser Arg Ala Ala Glu Ala Phe Arg
                1765                1770                1775

Arg Met Ala Gln Gly Gln His Leu Gly Lys Leu Val Leu Thr Leu Asp
            1780                1785                1790

Asp Pro Glu Val Arg Ile Arg Ala Pro Ala Glu Ser Ser Val Ala Val
        1795                1800                1805

Arg Ala Asp Gly Thr Tyr Leu Val Thr Gly Gly Leu Gly Gly Leu Gly
    1810                1815                1820

Leu Arg Val Ala Gly Trp Leu Ala Glu Arg Gly Ala Gly Gln Leu Val
1825                1830                1835                1840

Leu Val Gly Arg Ser Gly Ala Ala Ser Ala Glu Gln Arg Ala Ala Val
                1845                1850                1855

Ala Ala Leu Glu Ala His Gly Ala Arg Val Thr Val Ala Lys Ala Asp
            1860                1865                1870

Val Ala Asp Arg Ser Gln Ile Glu Arg Val Leu Arg Glu Val Thr Ala
        1875                1880                1885

Ser Gly Met Pro Leu Arg Gly Val Val His Ala Ala Gly Leu Val Asp
    1890                1895                1900

Asp Gly Leu Leu Met Gln Gln Thr Pro Ala Arg Phe Arg Thr Val Met
1905                1910                1915                1920

Gly Pro Lys Val Gln Gly Ala Leu His Leu His Thr Leu Thr Arg Glu
                1925                1930                1935

Ala Pro Leu Ser Phe Phe Val Leu Tyr Ala Ser Ala Ala Gly Leu Phe
            1940                1945                1950

Gly Ser Pro Gly Gln Gly Asn Tyr Ala Ala Ala Asn Ala Phe Leu Asp
        1955                1960                1965

Ala Leu Ser His His Arg Arg Ala Gln Gly Leu Pro Ala Leu Ser Ile
    1970                1975                1980

Asp Trp Gly Met Phe Thr Glu Val Gly Met Ala Val Ala Gln Glu Asn
1985                1990                1995                2000

Arg Gly Ala Arg Gln Ile Ser Arg Gly Met Arg Gly Ile Thr Pro Asp
                2005                2010                2015

Glu Gly Leu Ser Ala Leu Ala Arg Leu Leu Glu Gly Asp Arg Val Gln
            2020                2025                2030

Thr Gly Val Ile Pro Ile Thr Pro Arg Gln Trp Val Glu Phe Tyr Pro
        2035                2040                2045

Ala Thr Ala Ala Ser Arg Arg Leu Ser Arg Leu Val Thr Thr Gln Arg
    2050                2055                2060

Ala Val Ala Asp Arg Thr Ala Gly Asp Arg Asp Leu Leu Glu Gln Leu
2065                2070                2075                2080

Ala Ser Ala Glu Pro Ser Ala Arg Ala Gly Leu Leu Gln Asp Val Val
                2085                2090                2095

Arg Val Gln Val Ser His Val Leu Arg Leu Pro Glu Asp Lys Ile Glu
            2100                2105                2110

Val Asp Ala Pro Leu Ser Ser Met Gly Met Asp Ser Leu Met Ser Leu
        2115                2120                2125

Glu Leu Arg Asn Arg Ile Glu Ala Ala Leu Gly Val Ala Ala Pro Ala
    2130                2135                2140

Ala Leu Gly Trp Thr Tyr Pro Thr Val Ala Ala Ile Thr Arg Trp Leu
```

-continued

```
                2145                2150                2155                2160
Leu Asp Asp Ala Leu Val Val Arg Leu Gly Gly Gly Ser Asp Thr Asp
                    2165                2170                2175
Glu Ser Thr Ala Ser Ala Gly Ser Phe Val His Val Leu Arg Phe Arg
                2180                2185                2190
Pro Val Val Lys Pro Arg Ala Arg Leu Phe Cys Phe His Gly Ser Gly
            2195                2200                2205
Gly Ser Pro Glu Gly Phe Arg Ser Trp Ser Glu Lys Ser Glu Trp Ser
        2210                2215                2220
Asp Leu Glu Ile Val Ala Met Trp His Asp Arg Ser Leu Ala Ser Glu
2225                2230                2235                2240
Asp Ala Pro Gly Lys Lys Tyr Val Gln Glu Ala Ala Ser Leu Ile Gln
                2245                2250                2255
His Tyr Ala Asp Ala Pro Phe Ala Leu Val Gly Phe Ser Leu Gly Val
                2260                2265                2270
Arg Phe Val Met Gly Thr Ala Val Glu Leu Ala Ser Arg Ser Gly Ala
                2275                2280                2285
Pro Ala Pro Leu Ala Val Phe Thr Leu Gly Gly Ser Leu Ile Ser Ser
            2290                2295                2300
Ser Glu Ile Thr Pro Glu Met Glu Thr Asp Ile Ile Ala Lys Leu Phe
2305                2310                2315                2320
Phe Arg Asn Ala Ala Gly Phe Val Arg Ser Thr Gln Gln Val Gln Ala
                2325                2330                2335
Asp Ala Arg Ala Asp Lys Val Ile Thr Asp Thr Met Val Ala Pro Ala
                2340                2345                2350
Pro Gly Asp Ser Lys Glu Pro Pro Val Lys Ile Ala Val Pro Ile Val
            2355                2360                2365
Ala Ile Ala Gly Ser Asp Asp Val Ile Val Pro Pro Ser Asp Val Gln
        2370                2375                2380
Asp Leu Gln Ser Arg Thr Thr Glu Arg Phe Tyr Met His Leu Leu Pro
2385                2390                2395                2400
Gly Asp His Glu Phe Leu Val Asp Arg Gly Arg Glu Ile Met His Ile
                2405                2410                2415
Val Asp Ser His Leu Asn Pro Leu Leu Ala Ala Arg Thr Thr Ser Ser
            2420                2425                2430
Gly Pro Ala Phe Glu Ala Lys
        2435

<210> SEQ ID NO 8
<211> LENGTH: 419
<212> TYPE: PRT
<213> ORGANISM: Sorangium cellulosum

<400> SEQUENCE: 8

Met Thr Gln Glu Gln Ala Asn Gln Ser Glu Thr Lys Pro Ala Phe Asp
1               5                   10                  15
Phe Lys Pro Phe Ala Pro Gly Tyr Ala Glu Asp Pro Phe Pro Ala Ile
            20                  25                  30
Glu Arg Leu Arg Glu Ala Thr Pro Ile Phe Tyr Trp Asp Glu Gly Arg
        35                  40                  45
Ser Trp Val Leu Thr Arg Tyr His Asp Val Ser Ala Val Phe Arg Asp
    50                  55                  60
Glu Arg Phe Ala Val Ser Arg Glu Glu Trp Glu Ser Ser Ala Glu Tyr
65                  70                  75                  80
```

```
Ser Ser Ala Ile Pro Glu Leu Ser Asp Met Lys Lys Tyr Gly Leu Phe
            85                  90                  95

Gly Leu Pro Pro Glu Asp His Ala Arg Val Arg Lys Leu Val Asn Pro
            100                 105                 110

Ser Phe Thr Ser Arg Ala Ile Asp Leu Leu Arg Ala Glu Ile Gln Arg
            115                 120                 125

Thr Val Asp Gln Leu Leu Asp Ala Arg Ser Gly Gln Glu Glu Phe Asp
            130                 135                 140

Val Val Arg Asp Tyr Ala Glu Gly Ile Pro Met Arg Ala Ile Ser Ala
145                 150                 155                 160

Leu Leu Lys Val Pro Ala Glu Cys Asp Glu Lys Phe Arg Arg Phe Gly
            165                 170                 175

Ser Ala Thr Ala Arg Ala Leu Gly Val Gly Leu Val Pro Gln Val Asp
            180                 185                 190

Glu Glu Thr Lys Thr Leu Val Ala Ser Val Thr Glu Gly Leu Ala Leu
            195                 200                 205

Leu His Asp Val Leu Asp Glu Arg Arg Asn Pro Leu Glu Asn Asp
            210                 215                 220

Val Leu Thr Met Leu Leu Gln Ala Glu Ala Asp Gly Ser Arg Leu Ser
225                 230                 235                 240

Thr Lys Glu Leu Val Ala Leu Val Gly Ala Ile Ile Ala Ala Gly Thr
            245                 250                 255

Asp Thr Thr Ile Tyr Leu Ile Ala Phe Ala Val Leu Asn Leu Leu Arg
            260                 265                 270

Ser Pro Glu Ala Leu Glu Leu Val Lys Ala Glu Pro Gly Leu Met Arg
            275                 280                 285

Asn Ala Leu Asp Glu Val Leu Arg Phe Asp Asn Ile Leu Arg Ile Gly
            290                 295                 300

Thr Val Arg Phe Ala Arg Gln Asp Leu Glu Tyr Cys Gly Ala Ser Ile
305                 310                 315                 320

Lys Lys Gly Glu Met Val Phe Leu Leu Ile Pro Ser Ala Leu Arg Asp
            325                 330                 335

Gly Thr Val Phe Ser Arg Pro Asp Val Phe Asp Val Arg Arg Asp Thr
            340                 345                 350

Gly Ala Ser Leu Ala Tyr Gly Arg Gly Pro His Val Cys Pro Gly Val
            355                 360                 365

Ser Leu Ala Arg Leu Glu Ala Glu Ile Ala Val Gly Thr Ile Phe Arg
            370                 375                 380

Arg Phe Pro Glu Met Lys Leu Lys Glu Thr Pro Val Phe Gly Tyr His
385                 390                 395                 400

Pro Ala Phe Arg Asn Ile Glu Ser Leu Asn Val Ile Leu Lys Pro Ser
            405                 410                 415

Lys Ala Gly

<210> SEQ ID NO 9
<211> LENGTH: 607
<212> TYPE: PRT
<213> ORGANISM: Sorangium cellulosum

<400> SEQUENCE: 9

Ala Ser Leu Asp Ala Leu Phe Ala Arg Ala Thr Ser Ala Arg Val Leu
 1               5                  10                  15

Asp Asp Gly His Gly Arg Ala Thr Glu Arg His Val Leu Ala Glu Ala
            20                  25                  30
```

-continued

```
Arg Gly Ile Glu Asp Leu Arg Ala Leu Arg Glu His Leu Arg Ile Gln
         35                  40                  45

Glu Gly Gly Pro Ser Phe His Cys Met Cys Leu Gly Asp Leu Thr Val
     50                  55                  60

Glu Leu Leu Ala His Asp Gln Pro Leu Ala Ser Ile Ser Phe His His
 65                  70                  75                  80

Ala Arg Ser Leu Arg His Pro Asp Trp Thr Ser Asp Ala Met Leu Val
                 85                  90                  95

Asp Gly Pro Ala Leu Val Arg Trp Leu Ala Ala Arg Gly Ala Pro Gly
            100                 105                 110

Pro Leu Arg Glu Tyr Glu Glu Arg Glu Arg Ala Arg Thr Ala Gln
        115                 120                 125

Glu Ala Arg Arg Leu Trp Leu Ala Ala Pro Pro Cys Phe Ala Pro
        130                 135                 140

Asp Leu Pro Arg Phe Glu Asp Asp Ala Asn Gly Leu Pro Leu Gly Pro
145                 150                 155                 160

Met Ser Pro Glu Val Ala Glu Ala Glu Arg Arg Leu Arg Ala Ser Tyr
                165                 170                 175

Ala Thr Pro Glu Leu Ala Cys Ala Ala Leu Leu Ala Trp Leu Gly Thr
            180                 185                 190

Gly Ala Gly Pro Trp Ser Gly Tyr Pro Ala Tyr Glu Met Leu Pro Glu
        195                 200                 205

Asn Leu Leu Leu Gly Phe Gly Leu Pro Thr Ala Ile Ala Ala Ala Ser
210                 215                 220

Ala Pro Gly Thr Ser Glu Ala Ala Leu Arg Gly Ala Ala Arg Leu Phe
225                 230                 235                 240

Ala Ser Trp Glu Val Val Ser Ser Lys Lys Ser Gln Leu Gly Asn Ile
                245                 250                 255

Pro Glu Ala Leu Trp Glu Arg Leu Arg Thr Ile Val Arg Ala Met Gly
            260                 265                 270

Asn Ala Asp Asn Leu Ser Arg Phe Glu Arg Ala Glu Ala Ile Ala Ala
        275                 280                 285

Glu Val Arg Arg Leu Arg Ala Gln Pro Ala Pro Phe Ala Ala Gly Ala
290                 295                 300

Gly Leu Ala Val Ala Gly Val Ser Ser Ser Gly Arg Leu Ser Gly Leu
305                 310                 315                 320

Val Thr Asp Gly Asp Ala Leu Tyr Ser Gly Asp Gly Asn Asp Ile Val
                325                 330                 335

Met Phe Gln Pro Gly Arg Ile Ser Pro Val Val Leu Leu Ala Gly Thr
            340                 345                 350

Asp Pro Phe Phe Glu Leu Ala Pro Pro Leu Ser Gln Met Leu Phe Val
        355                 360                 365

Ala His Ala Asn Ala Gly Thr Ile Ser Lys Val Leu Thr Glu Gly Ser
        370                 375                 380

Pro Leu Ile Val Met Ala Arg Asn Gln Ala Arg Pro Met Ser Leu Val
385                 390                 395                 400

His Ala Arg Gly Phe Met Ala Trp Val Asn Gln Ala Met Val Pro Asp
                405                 410                 415

Pro Glu Arg Gly Ala Pro Phe Val Val Gln Arg Ser Thr Ile Met Glu
            420                 425                 430

Phe Glu His Pro Thr Pro Arg Cys Leu His Glu Pro Ala Gly Ser Ala
        435                 440                 445

Phe Ser Leu Ala Cys Asp Glu Glu His Leu Tyr Trp Cys Glu Leu Ser
```

```
                   450                 455                 460
Ala Gly Arg Leu Glu Leu Trp Arg His Pro His His Arg Pro Gly Ala
465                 470                 475                 480

Pro Ser Arg Phe Ala Tyr Leu Gly Glu His Pro Ile Ala Ala Thr Trp
                    485                 490                 495

Tyr Pro Ser Leu Thr Leu Asn Ala Thr His Val Leu Trp Ala Asp Pro
                500                 505                 510

Asp Arg Arg Ala Ile Leu Gly Val Asp Lys Arg Thr Gly Val Glu Pro
            515                 520                 525

Ile Val Leu Ala Glu Thr Arg His Pro Pro Ala His Val Val Ser Glu
        530                 535                 540

Asp Arg Asp Ile Phe Ala Leu Thr Gly Gln Pro Asp Ser Arg Asp Trp
545                 550                 555                 560

His Val Glu His Ile Arg Ser Gly Ala Ser Thr Val Val Ala Asp Tyr
                565                 570                 575

Gln Arg Gln Leu Trp Asp Arg Pro Asp Met Val Leu Asn Arg Arg Gly
                580                 585                 590

Leu Phe Phe Thr Thr Asn Asp Arg Ile Leu Thr Leu Ala Arg Ser
                595                 600                 605

<210> SEQ ID NO 10
<211> LENGTH: 423
<212> TYPE: PRT
<213> ORGANISM: Sorangium cellulosum

<400> SEQUENCE: 10

Met Gly Ala Leu Ile Ser Val Ala Ala Pro Gly Cys Ala Leu Gly Gly
1               5                   10                  15

Ala Glu Glu Glu Gly Gln Pro Gly Gln Asp Ala Gly Ala Gly Ala Leu
                20                  25                  30

Ala Pro Ala Arg Glu Val Met Ala Glu Val Ala Ala Gly Gln Met
            35                  40                  45

Pro Gly Ala Val Trp Leu Val Ala Arg Gly Asp Asp Val His Val Asp
        50                  55                  60

Ala Val Gly Val Thr Glu Leu Gly Gly Ser Ala Pro Met Arg Arg Asp
65                  70                  75                  80

Thr Ile Phe Arg Ile Ala Ser Met Thr Lys Ala Val Thr Ala Thr Ala
                85                  90                  95

Val Met Met Leu Val Glu Gly Lys Leu Asp Leu Asp Ser Pro Val
                100                 105                 110

Asp Arg Trp Leu Pro Glu Leu Ala Asn Arg Lys Val Leu Ala Arg Ile
            115                 120                 125

Asp Gly Pro Ile Asp Glu Thr Val Pro Ala Glu Arg Pro Ile Thr Val
        130                 135                 140

Arg Asp Leu Met Thr Phe Thr Met Gly Phe Gly Ile Ser Phe Asp Ala
145                 150                 155                 160

Ser Ser Pro Ile Gln Arg Ala Ile Asp Glu Leu Gly Leu Val Asn Ala
                165                 170                 175

Gln Pro Val Pro Met Thr Pro His Gly Pro Asp Glu Trp Ile Arg Arg
            180                 185                 190

Leu Gly Thr Leu Pro Leu Met His Gln Pro Gly Ala Gln Trp Met Tyr
        195                 200                 205

Asn Thr Gly Ser Leu Val Gln Gly Val Leu Val Gly Arg Ala Ala Asp
    210                 215                 220
```

-continued

```
Gln Gly Phe Asp Ala Phe Val Arg Glu Arg Ile Leu Ala Pro Leu Gly
225                 230                 235                 240

Met Arg Asp Thr Asp Phe His Val Pro Ala Asp Lys Leu Ala Arg Phe
            245                 250                 255

Ala Gly Cys Gly Tyr Phe Thr Asp Glu Gln Thr Gly Glu Lys Thr Arg
            260                 265                 270

Met Asp Arg Asp Gly Ala Glu Ser Ala Tyr Ala Ser Pro Pro Ala Phe
        275                 280                 285

Pro Ser Gly Ala Ala Gly Leu Val Ser Thr Val Asp Asp Tyr Leu Leu
    290                 295                 300

Phe Ala Arg Met Leu Met Asn Gly Gly Val His Glu Gly Arg Arg Leu
305                 310                 315                 320

Leu Ser Ala Ala Ser Val Arg Glu Met Thr Ala Asp His Leu Thr Pro
                325                 330                 335

Ala Gln Lys Ala Ala Ser Ser Phe Phe Pro Gly Phe Phe Glu Thr His
            340                 345                 350

Gly Trp Gly Tyr Gly Met Ala Val Val Thr Ala Pro Asp Ala Val Ser
        355                 360                 365

Glu Val Pro Gly Arg Tyr Gly Trp Asp Gly Gly Phe Gly Thr Ser Trp
    370                 375                 380

Ile Asn Asp Pro Gly Arg Glu Leu Ile Gly Ile Val Met Thr Gln Ser
385                 390                 395                 400

Ala Gly Phe Leu Phe Ser Gly Ala Leu Glu Arg Phe Trp Arg Ser Val
                405                 410                 415

Tyr Val Ala Thr Glu Ser Ala
            420

<210> SEQ ID NO 11
<211> LENGTH: 713
<212> TYPE: PRT
<213> ORGANISM: Sorangium cellulosum

<400> SEQUENCE: 11

Met His Gly Leu Thr Glu Arg Gln Val Leu Leu Ser Leu Val Thr Leu
1               5                   10                  15

Ala Leu Ile Leu Val Thr Ala Arg Ala Ser Gly Glu Leu Ala Arg Arg
            20                  25                  30

Leu Arg Gln Pro Glu Val Leu Gly Glu Leu Phe Gly Gly Val Val Leu
        35                  40                  45

Gly Pro Ser Val Val Gly Ala Leu Ala Pro Gly Phe His Arg Ala Leu
    50                  55                  60

Phe Gln Glu Pro Ala Val Gly Val Leu Ser Gly Ile Ser Trp Ile
65                  70                  75                  80

Gly Ala Leu Leu Leu Leu Met Ala Gly Ile Glu Val Asp Val Gly
                85                  90                  95

Ile Leu Arg Lys Glu Ala Arg Pro Gly Ala Leu Ser Ala Leu Gly Ala
            100                 105                 110

Ile Ala Pro Pro Leu Ala Ala Gly Ala Ala Phe Ser Ala Leu Val Leu
        115                 120                 125

Asp Arg Pro Leu Pro Ser Gly Leu Phe Leu Gly Ile Val Leu Ser Val
    130                 135                 140

Thr Ala Val Ser Val Ile Ala Lys Val Leu Ile Glu Arg Glu Ser Met
145                 150                 155                 160

Arg Arg Ser Tyr Ala Gln Val Thr Leu Ala Ala Gly Val Val Ser Glu
                165                 170                 175
```

```
Val Ala Ala Trp Val Leu Val Ala Met Thr Ser Ser Tyr Gly Ala
            180                 185                 190

Ser Pro Ala Leu Ala Val Ala Arg Ser Ala Leu Leu Ala Ser Gly Phe
        195                 200                 205

Leu Leu Phe Met Val Leu Val Gly Arg Arg Leu Thr His Leu Ala Met
        210                 215                 220

Arg Trp Val Ala Asp Ala Thr Arg Val Ser Lys Gly Gln Val Ser Leu
225                 230                 235                 240

Val Leu Val Leu Thr Phe Leu Ala Ala Leu Thr Gln Arg Leu Gly
                245                 250                 255

Leu His Pro Leu Leu Gly Ala Phe Ala Leu Gly Val Leu Leu Asn Ser
            260                 265                 270

Ala Pro Arg Thr Asn Arg Pro Leu Leu Asp Gly Val Gln Thr Leu Val
            275                 280                 285

Ala Gly Leu Phe Ala Pro Val Phe Phe Val Leu Ala Gly Met Arg Val
            290                 295                 300

Asp Val Ser Gln Leu Arg Thr Pro Ala Ala Trp Gly Thr Val Ala Leu
305                 310                 315                 320

Leu Leu Ala Thr Ala Thr Ala Ala Lys Val Val Pro Ala Ala Leu Gly
                325                 330                 335

Ala Arg Leu Gly Gly Leu Arg Gly Ser Glu Ala Ala Leu Val Ala Val
                340                 345                 350

Gly Leu Asn Met Lys Gly Gly Thr Asp Leu Ile Val Ala Ile Val Gly
                355                 360                 365

Val Glu Leu Gly Leu Leu Ser Asn Glu Ala Tyr Thr Met Tyr Ala Val
        370                 375                 380

Val Ala Leu Val Thr Val Thr Ala Ser Pro Ala Leu Leu Ile Trp Leu
385                 390                 395                 400

Glu Lys Arg Ala Pro Pro Thr Gln Glu Glu Ser Ala Arg Leu Glu Arg
                405                 410                 415

Glu Glu Ala Ala Arg Arg Ala Tyr Ile Pro Gly Val Glu Arg Ile Leu
                420                 425                 430

Val Pro Ile Val Ala His Ala Leu Pro Gly Phe Ala Thr Asp Ile Val
                435                 440                 445

Glu Ser Ile Val Ala Ser Lys Arg Lys Leu Gly Glu Thr Val Asp Ile
        450                 455                 460

Thr Glu Leu Ser Val Glu Gln Gln Ala Pro Gly Pro Ser Arg Ala Ala
465                 470                 475                 480

Gly Glu Ala Ser Arg Gly Leu Ala Arg Leu Gly Ala Arg Leu Arg Val
                485                 490                 495

Gly Ile Trp Arg Gln Arg Arg Glu Leu Arg Gly Ser Ile Gln Ala Ile
                500                 505                 510

Leu Arg Ala Ser Arg Asp His Asp Leu Leu Val Ile Gly Ala Arg Ser
            515                 520                 525

Pro Ala Arg Ala Arg Gly Met Ser Phe Gly Arg Leu Gln Asp Ala Ile
            530                 535                 540

Val Gln Arg Ala Glu Ser Asn Val Leu Val Val Gly Asp Pro Pro
545                 550                 555                 560

Ala Ala Glu Arg Ala Ser Ala Arg Arg Ile Leu Val Pro Ile Ile Gly
                565                 570                 575

Leu Glu Tyr Ser Phe Ala Ala Ala Asp Leu Ala Ala His Val Ala Leu
            580                 585                 590
```

-continued

```
Ala Trp Asp Ala Glu Leu Val Leu Leu Ser Ser Ala Gln Thr Asp Pro
            595                 600                 605

Gly Ala Val Trp Arg Asp Arg Glu Pro Ser Arg Val Arg Ala Val
            610                 615                 620

Ala Arg Ser Val Val Asp Glu Ala Val Phe Arg Gly Arg Arg Leu Gly
625                 630                 635                 640

Val Arg Val Ser Ser Arg Val His Val Gly Ala His Pro Ser Asp Glu
                645                 650                 655

Ile Thr Arg Glu Leu Ala Arg Ala Pro Tyr Asp Leu Val Leu Gly
            660                 665                 670

Cys Tyr Asp His Gly Pro Leu Gly Arg Leu Tyr Leu Gly Ser Thr Val
            675                 680                 685

Glu Ser Val Val Arg Ser Arg Val Pro Val Ala Leu Leu Val Ala
        690                 695                 700

His Gly Gly Thr Arg Glu Gln Val Arg
705                 710

<210> SEQ ID NO 12
<211> LENGTH: 126
<212> TYPE: PRT
<213> ORGANISM: Sorangium cellulosum

<400> SEQUENCE: 12

Met Asp Lys Pro Ile Gly Arg Thr Arg Cys Ala Ile Ala Glu Gly Tyr
1               5                   10                  15

Ile Pro Gly Gly Ser Asn Gly Pro Glu Pro Gln Met Thr Ser His Glu
            20                  25                  30

Thr Ala Cys Leu Leu Asn Ala Ser Asp Arg Asp Ala Gln Val Ala Ile
        35                  40                  45

Thr Val Tyr Phe Ser Asp Arg Asp Pro Ala Gly Pro Tyr Arg Val Thr
    50                  55                  60

Val Pro Ala Arg Arg Thr Arg His Val Arg Phe Asn Asp Leu Thr Glu
65                  70                  75                  80

Pro Glu Pro Ile Pro Arg Asp Thr Asp Tyr Ala Ser Val Ile Glu Ser
                85                  90                  95

Asp Ala Pro Ile Val Val Gln His Thr Arg Leu Asp Ser Arg Gln Ala
            100                 105                 110

Glu Asn Ala Leu Leu Ser Thr Ile Ala Tyr Thr Asp Arg Glu
        115                 120                 125

<210> SEQ ID NO 13
<211> LENGTH: 149
<212> TYPE: PRT
<213> ORGANISM: Sorangium cellulosum

<400> SEQUENCE: 13

Met Lys His Val Asp Thr Gly Arg Arg Phe Gly Arg Arg Ile Gly His
1               5                   10                  15

Thr Leu Gly Leu Leu Ala Ser Met Ala Leu Ala Gly Cys Gly Gly Pro
            20                  25                  30

Ser Glu Lys Thr Val Gln Gly Thr Arg Leu Ala Pro Gly Ala Asp Ala
        35                  40                  45

Arg Val Thr Ala Asp Val Asp Pro Asp Ala Ala Thr Thr Arg Leu Ala
    50                  55                  60

Val Asp Val Val His Leu Ser Pro Pro Glu Arg Leu Glu Ala Gly Ser
65                  70                  75                  80
```

-continued

```
Glu Arg Phe Val Val Trp Gln Arg Pro Ser Pro Glu Ser Pro Trp Arg
                85                  90                  95

Arg Val Gly Val Leu Asp Tyr Asn Ala Asp Ser Arg Arg Gly Lys Leu
            100                 105                 110

Ala Glu Thr Thr Val Pro Tyr Ala Asn Phe Glu Leu Leu Ile Thr Ala
        115                 120                 125

Glu Lys Gln Ser Ser Pro Gln Ser Pro Ser Ser Ala Ala Val Ile Gly
    130                 135                 140

Pro Thr Ser Val Gly
145

<210> SEQ ID NO 14
<211> LENGTH: 184
<212> TYPE: PRT
<213> ORGANISM: Sorangium cellulosum

<400> SEQUENCE: 14

Val Thr Ser Glu Glu Val Pro Gly Ala Ala Leu Gly Ala Gln Ser Ser
  1               5                  10                  15

Leu Val Arg Ala Gln His Ala Ala Arg His Val Arg Pro Cys Thr Arg
             20                  25                  30

Ala Glu Glu Pro Pro Ala Leu Met His Gly Leu Thr Glu Arg Gln Val
         35                  40                  45

Leu Leu Ser Leu Val Ala Leu Ala Leu Val Leu Leu Thr Ala Arg Ala
     50                  55                  60

Phe Gly Glu Leu Ala Arg Arg Leu Arg Gln Pro Glu Val Leu Gly Glu
 65                  70                  75                  80

Leu Phe Gly Gly Val Val Leu Gly Pro Ser Val Val Gly Ala Leu Ala
                85                  90                  95

Pro Gly Phe His Arg Val Leu Phe Gln Asp Pro Ala Val Gly Val Val
            100                 105                 110

Leu Ser Gly Ile Ser Trp Ile Gly Ala Leu Val Leu Leu Leu Met Ala
        115                 120                 125

Gly Ile Glu Val Asp Val Ser Ile Leu Arg Lys Glu Ala Arg Pro Gly
    130                 135                 140

Ala Leu Ser Ala Leu Gly Ala Ile Ala Pro Pro Leu Arg Thr Pro Gly
145                 150                 155                 160

Pro Leu Val Gln Arg Met Gln Gly Ala Phe Thr Trp Asp Leu Asp Val
                165                 170                 175

Ser Pro Arg Arg Ser Ala Gln Ala
            180

<210> SEQ ID NO 15
<211> LENGTH: 145
<212> TYPE: PRT
<213> ORGANISM: Sorangium cellulosum

<400> SEQUENCE: 15

Val Asn Ala Pro Cys Met Arg Cys Thr Ser Gly Pro Gly Val Arg Ser
  1               5                  10                  15

Gly Gly Ala Ile Ala Pro Ser Ala Glu Ser Ala Pro Gly Arg Ala Ser
             20                  25                  30

Leu Arg Arg Met Leu Thr Ser Thr Ser Ile Pro Ala Met Ser Ser Arg
         35                  40                  45

Thr Ser Ala Pro Ile Gln Glu Met Pro Glu Ser Thr Thr Pro Thr Ala
     50                  55                  60
```

-continued

Gly Ser Trp Lys Arg Thr Arg Trp Asn Pro Gly Ala Ser Ala Pro Thr
65 70 75 80

Thr Asp Gly Pro Ser Thr Thr Pro Pro Lys Ser Ser Pro Ser Thr Ser
85 90 95

Gly Trp Arg Ser Arg Arg Ala Ser Ser Pro Lys Ala Arg Ala Val Arg
100 105 110

Arg Thr Ser Ala Arg Ala Thr Ser Glu Ser Arg Thr Cys Arg Ser Val
115 120 125

Arg Pro Cys Ile Arg Ala Gly Gly Ser Ser Ala Arg Val Gln Gly Arg
130 135 140

Thr
145

<210> SEQ ID NO 16
<211> LENGTH: 185
<212> TYPE: PRT
<213> ORGANISM: Sorangium cellulosum

<400> SEQUENCE: 16

Val Leu Ala Pro Pro Ala Asp Ile Arg Pro Pro Ala Ala Ala Gln Leu
1 5 10 15

Glu Pro Asp Ser Pro Asp Asp Glu Ala Asp Glu Ala Asp Glu Ala Leu
20 25 30

Arg Pro Phe Arg Asp Ala Ile Ala Ala Tyr Ser Glu Ala Val Arg Trp
35 40 45

Ala Glu Ala Ala Gln Arg Pro Arg Leu Glu Ser Leu Val Arg Leu Ala
50 55 60

Ile Val Arg Leu Gly Lys Ala Leu Asp Lys Val Pro Phe Ala His Thr
65 70 75 80

Thr Ala Gly Val Ser Gln Ile Ala Gly Arg Leu Gln Asn Asp Ala Val
85 90 95

Trp Phe Asp Val Ala Ala Arg Tyr Ala Ser Phe Arg Ala Ala Thr Glu
100 105 110

His Ala Leu Arg Asp Ala Ala Ser Ala Met Glu Ala Leu Ala Ala Gly
115 120 125

Pro Tyr Arg Gly Ser Ser Arg Val Ser Ala Ala Val Gly Glu Phe Arg
130 135 140

Gly Glu Ala Ala Arg Leu His Pro Ala Asp Arg Val Pro Ala Ser Asp
145 150 155 160

Gln Gln Ile Leu Thr Ala Leu Arg Ala Ala Glu Arg Ala Leu Ile Ala
165 170 175

Leu Tyr Thr Ala Phe Ala Arg Glu Glu
180 185

<210> SEQ ID NO 17
<211> LENGTH: 146
<212> TYPE: PRT
<213> ORGANISM: Sorangium cellulosum

<400> SEQUENCE: 17

Met Ala Asp Ala Ala Ser Arg Ser Ala Cys Ser Val Ala Ala Arg Lys
1 5 10 15

Leu Ala Tyr Arg Ala Ala Thr Ser Asn Gln Thr Ala Ser Phe Trp Ser
20 25 30

Leu Pro Ala Ile Trp Glu Thr Pro Ala Val Val Cys Ala Lys Gly Thr
35 40 45

```
Leu Ser Ser Ala Leu Pro Ser Arg Thr Ile Ala Ser Arg Thr Arg Leu
                50              55                  60

Ser Ser Arg Gly Arg Cys Ala Ala Ser Ala His Arg Thr Ala Ser Glu
 65              70                  75                  80

Tyr Ala Ala Ile Ala Ser Arg Asn Gly Arg Ser Ala Ser Ser Ala Ser
                    85                  90                  95

Ser Ala Ser Ser Gly Glu Ser Gly Ser Ser Trp Ala Ala Ala Gly
                100                 105                 110

Gly Arg Met Ser Ala Gly Gly Ala Ser Thr Gly Glu Val Tyr Glu Gln
            115                 120                 125

Ala Pro Arg Leu Arg Leu Ala Gln Ser Val Ala Arg Arg Arg Asp
            130                 135                 140

Pro Thr
145

<210> SEQ ID NO 18
<211> LENGTH: 288
<212> TYPE: PRT
<213> ORGANISM: Sorangium cellulosum

<400> SEQUENCE: 18

Val Thr Val Ser Ser Met Pro Arg Ser Trp Ser Ser Arg Val Arg Thr
 1               5                  10                  15

Val Val Thr Ala Leu Gly Cys Ala Arg Arg Leu Ser Gly Ser Ile Ser
                20                  25                  30

Arg Leu Arg Arg His Pro Glu Ala Gly Arg Ala Pro Arg Ser Arg Leu
            35                  40                  45

Arg Ala Trp Arg Arg Leu Pro Gln His Ile Ser Ser Pro Trp Arg His
 50                  55                  60

Leu Pro Pro Gly Ala Arg Val Gly Thr Ser Cys Pro Ala Asp Arg Arg
 65                  70                  75                  80

Ile Leu Pro Ser His Arg Thr Ala Asp Leu Gly Thr Ser Gly Gly Thr
                85                  90                  95

Leu Val Ala Arg Met Ser Gly His Val Ala Arg Asn Pro His Ala Ala
                100                 105                 110

Val Leu Val Gly Asp Gly Ser Ala Arg Gly Arg Arg Leu Ser Asn
            115                 120                 125

Arg Arg Ala Glu Arg Arg Val Ser Asp Val Thr Cys Arg Glu Gly Gly
130                 135                 140

Glu Ala Met Gln Lys Ile Ala Gly Lys Leu Val Gly Leu Ile Ser
145                 150                 155                 160

Val Ser Gly Met Ser Leu Leu Ala Ala Cys Gly Gly Glu Lys Arg Ser
                165                 170                 175

Gly Gly Glu Ala Gln Thr Pro Gly Gly Ala Gln Gly Glu Ala Pro Val
            180                 185                 190

Pro Val Gly Ser Ala Val Asp Ser Ile Val Ala Ala Arg Cys Asp Arg
        195                 200                 205

Glu Ala Arg Cys Asn Asn Ile Gly Gln Asp Arg Glu Tyr Ser Ser Lys
    210                 215                 220

Asp Ala Cys Ser Asn Lys Ile Arg Ser Glu Trp Arg Asp Glu Leu Thr
225                 230                 235                 240

Phe Gly Glu Cys Pro Gly Gly Ile Asp Ala Lys Gln Leu Asn Glu Cys
                245                 250                 255

Leu Glu Gly Ile Arg Asn Glu Gly Cys Gly Asn Pro Phe Asp Thr Leu
                260                 265                 270
```

```
Gly Arg Val Val Ala Cys Arg Ser Ser Asp Leu Cys Arg Asp Ala Arg
        275                 280                 285

<210> SEQ ID NO 19
<211> LENGTH: 288
<212> TYPE: PRT
<213> ORGANISM: Sorangium cellulosum

<400> SEQUENCE: 19

Val Thr Val Ser Ser Met Pro Arg Ser Trp Ser Arg Val Arg Thr
  1               5                  10                  15

Val Val Thr Ala Leu Gly Cys Ala Arg Arg Leu Ser Gly Ser Ile Ser
                 20                  25                  30

Arg Leu Arg Arg His Pro Glu Ala Gly Arg Ala Pro Arg Ser Arg Leu
         35                  40                  45

Arg Ala Trp Arg Arg Leu Pro Gln His Ile Ser Ser Pro Trp Arg His
     50                  55                  60

Leu Pro Pro Gly Ala Arg Val Gly Thr Ser Cys Pro Ala Asp Arg Arg
 65                  70                  75                  80

Ile Leu Pro Ser His Arg Thr Ala Asp Leu Gly Thr Ser Gly Gly Thr
                 85                  90                  95

Leu Val Ala Arg Met Ser Gly His Val Ala Arg Asn Pro His Ala Ala
                100                 105                 110

Val Leu Val Gly Asp Gly Ser Ala Arg Gly Arg Arg Leu Ser Asn
             115                 120                 125

Arg Arg Ala Glu Arg Arg Val Ser Asp Val Thr Cys Arg Glu Gly Gly
        130                 135                 140

Glu Ala Met Gln Lys Ile Ala Gly Lys Leu Val Val Gly Leu Ile Ser
145                 150                 155                 160

Val Ser Gly Met Ser Leu Leu Ala Ala Cys Gly Gly Glu Lys Arg Ser
                165                 170                 175

Gly Gly Glu Ala Gln Thr Pro Gly Gly Ala Gln Gly Glu Ala Pro Val
            180                 185                 190

Pro Val Gly Ser Ala Val Asp Ser Ile Val Ala Ala Arg Cys Asp Arg
        195                 200                 205

Glu Ala Arg Cys Asn Asn Ile Gly Gln Asp Arg Glu Tyr Ser Ser Lys
    210                 215                 220

Asp Ala Cys Ser Asn Lys Ile Arg Ser Glu Trp Arg Asp Glu Leu Thr
225                 230                 235                 240

Phe Gly Glu Cys Pro Gly Gly Ile Asp Ala Lys Gln Leu Asn Glu Cys
                245                 250                 255

Leu Glu Gly Ile Arg Asn Glu Gly Cys Gly Asn Pro Phe Asp Thr Leu
            260                 265                 270

Gly Arg Val Val Ala Cys Arg Ser Ser Asp Leu Cys Arg Asp Ala Arg
        275                 280                 285

<210> SEQ ID NO 20
<211> LENGTH: 155
<212> TYPE: PRT
<213> ORGANISM: Sorangium cellulosum

<400> SEQUENCE: 20

Met Asp Pro Arg Ala Arg Arg Glu Lys Arg Pro Ser Leu Leu Asp Ser
  1               5                  10                  15

Arg Gly Arg Gln Pro Lys Arg Ser Gln Gln Gly Gly His Met Glu Lys
                 20                  25                  30
```

Pro Ile Gly Arg Thr Arg Trp Ala Ile Ala Glu Gly Tyr Ile Pro Gly
        35                  40                  45

Arg Ser Asn Gly Pro Glu Pro Gln Met Thr Ser His Glu Thr Ala Cys
 50                  55                  60

Leu Leu Asn Ala Ser Asp Arg Asp Ala Gln Val Ala Ile Thr Val Tyr
 65                  70                  75                  80

Phe Ser Asp Arg Asp Pro Ala Gly Pro Tyr Arg Val Thr Val Pro Ala
                85                  90                  95

Arg Arg Thr Arg His Val Arg Phe Asn Asp Leu Thr Glu Pro Glu Pro
                100                 105                 110

Ile Pro Arg Asp Thr Asp Tyr Ala Ser Val Ile Glu Ser Asp Val Pro
            115                 120                 125

Ile Val Val Gln His Thr Arg Leu Asp Ser Arg Gln Ala Glu Asn Ala
130                 135                 140

Leu Ile Ser Thr Ile Ala Tyr Thr Asp Arg Glu
145                 150                 155

<210> SEQ ID NO 21
<211> LENGTH: 156
<212> TYPE: PRT
<213> ORGANISM: Sorangium cellulosum

<400> SEQUENCE: 21

Val Arg Arg Ser Arg Trp Gln Met Lys His Val Asp Thr Gly Arg Arg
 1               5                   10                  15

Val Gly Arg Arg Ile Gly Leu Thr Leu Gly Leu Leu Ala Ser Met Ala
                20                  25                  30

Leu Ala Gly Cys Gly Gly Pro Ser Glu Lys Ile Val Gln Gly Thr Arg
            35                  40                  45

Leu Ala Pro Gly Ala Asp Ala His Val Ala Ala Asp Val Asp Pro Asp
 50                  55                  60

Ala Ala Thr Thr Arg Leu Ala Val Asp Val Val His Leu Ser Pro Pro
 65                  70                  75                  80

Glu Arg Ile Glu Ala Gly Ser Glu Arg Phe Val Val Trp Gln Arg Pro
                85                  90                  95

Ser Ser Glu Ser Pro Trp Gln Arg Val Gly Val Leu Asp Tyr Asn Ala
                100                 105                 110

Ala Ser Arg Arg Gly Lys Leu Ala Glu Thr Thr Val Pro His Ala Asn
            115                 120                 125

Phe Glu Leu Leu Ile Thr Val Glu Lys Gln Ser Ser Pro Gln Ser Pro
130                 135                 140

Ser Ser Ala Ala Val Ile Gly Pro Thr Ser Val Gly
145                 150                 155

<210> SEQ ID NO 22
<211> LENGTH: 305
<212> TYPE: PRT
<213> ORGANISM: Sorangium cellulosum

<400> SEQUENCE: 22

Met Glu Lys Glu Ser Arg Ile Ala Ile Tyr Gly Ala Ile Ala Ala Asn
 1               5                   10                  15

Val Ala Ile Ala Ala Val Lys Phe Ile Ala Ala Ala Val Thr Gly Ser
20 25 30

Ser Ala Met Leu Ser Glu Gly Val His Ser Leu Val Asp Thr Ala Asp
35 40 45

```
Gly Leu Leu Leu Leu Gly Lys His Arg Ser Ala Arg Pro Pro Asp
         50                  55                  60
Ala Glu His Pro Phe Gly His Gly Lys Glu Leu Tyr Phe Trp Thr Leu
 65                  70                  75                  80
Ile Val Ala Ile Met Ile Phe Ala Ala Gly Gly Val Ser Ile Tyr
                 85                  90                  95
Glu Gly Ile Leu His Leu Leu His Pro Arg Gln Ile Glu Asp Pro Thr
                100                 105                 110
Trp Asn Tyr Val Val Leu Gly Ala Ala Val Phe Glu Gly Thr Ser
                115                 120                 125
Leu Ile Ile Ser Ile His Glu Phe Lys Lys Asp Gly Gln Gly Tyr
        130                 135                 140
Leu Ala Ala Met Arg Ser Ser Lys Asp Pro Thr Thr Phe Thr Ile Val
145                 150                 155                 160
Leu Glu Asp Ser Ala Ala Leu Ala Gly Leu Thr Ile Ala Phe Leu Gly
                165                 170                 175
Val Trp Leu Gly His Arg Leu Gly Asn Pro Tyr Leu Asp Gly Ala Ala
                180                 185                 190
Ser Ile Gly Ile Gly Leu Val Leu Ala Ala Val Ala Val Phe Leu Ala
                195                 200                 205
Ser Gln Ser Arg Gly Leu Leu Val Gly Glu Ser Ala Asp Arg Glu Leu
        210                 215                 220
Leu Ala Ala Ile Arg Ala Leu Ala Ser Ala Asp Pro Gly Val Ser Ala
225                 230                 235                 240
Val Gly Arg Pro Leu Thr Met His Phe Gly Pro His Glu Val Leu Val
                245                 250                 255
Val Leu Arg Ile Glu Phe Asp Ala Ala Leu Thr Ala Ser Gly Val Ala
                260                 265                 270
Glu Ala Ile Glu Arg Ile Glu Thr Arg Ile Arg Ser Glu Arg Pro Asp
        275                 280                 285
Val Lys His Ile Tyr Val Glu Ala Arg Ser Leu His Gln Arg Ala Arg
        290                 295                 300
Ala
305

<210> SEQ ID NO 23
<211> LENGTH: 135
<212> TYPE: PRT
<213> ORGANISM: Sorangium cellulosum

<400> SEQUENCE: 23

Val Gln Thr Ser Ser Phe Asp Ala Arg Tyr Ala Gly Cys Lys Ser Ser
  1               5                  10                  15
Arg Arg Ile Ala Arg Ser Gly Ser Ala Gly Ala Arg Ala Gly Arg Ala
                 20                  25                  30
His Glu Gly Ala Ala Ser Ala Gly Phe Glu Gly Gly Asp Val Met Arg
         35                  40                  45
Lys Ala Arg Ala His Gly Ala Met Leu Gly Gly Arg Asp Asp Gly Trp
 50                  55                  60
Arg Arg Gly Leu Pro Gly Ala Gly Ala Leu Arg Ala Leu Gln Arg
 65                  70                  75                  80
Gly Arg Ser Arg Asp Leu Ala Arg Arg Leu Ile Ala Ser Val Ser
                 85                  90                  95
Leu Ala Gly Gly Ala Ser Met Ala Val Val Ser Leu Phe Gln Leu Gly
```

-continued

```
                        100                 105                 110
Ile Ile Glu Arg Leu Pro Asp Pro Pro Leu Pro Gly Phe Asp Ser Ala
            115                 120                 125

Lys Val Thr Ser Ser Asp Ile
    130                 135

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: universal
      reverse primer

<400> SEQUENCE: 24
ggaaacagct atgaccatg                                                          19

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: universal
      forward primer

<400> SEQUENCE: 25
gtaaaacgac ggccagt                                                            17

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: PCR primer
      NH24 end "B"

<400> SEQUENCE: 26
gtgactggcg cctggaatct gcatgagc                                                28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: PCR primer
      NH2 end "A"

<400> SEQUENCE: 27
agcgggagct tgctagacat tctgtttc                                                28

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: PCR primer
      NH2 end "B"

<400> SEQUENCE: 28
gacgcgcctc gggcagcgcc ccaa                                                    24

<210> SEQ ID NO 29
<211> LENGTH: 25
<212> TYPE: DNA
<213> ORGANISM: Artificial Sequence
<220> FEATURE:
```

-continued

```
<223> OTHER INFORMATION: Description of Artificial Sequence: PCR primer
      pEPO15-NH6 end "B"

<400> SEQUENCE: 29
caccgaagcg tcgatctggt ccatc                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: PCR primer
      pEPO15H2.7 end "A"

<400> SEQUENCE: 30
cggtcagatc gacgacgggc tttcc                                          25
```